(12) United States Patent
Han et al.

(10) Patent No.: US 7,598,264 B2
(45) Date of Patent: Oct. 6, 2009

(54) HIV INTEGRASE INHIBITORS

(75) Inventors: Wei Han, West Chester, PA (US);
Melissa Egbertson, Ambler, PA (US);
John S. Wai, Harleysville, PA (US);
Linghang Zhuang, Chalfont, PA (US);
Rowena D. Ruzek, North Wales, PA (US); Debra S. Perlow, East Greenville, PA (US); Mark Cameron, Brick, NJ (US); Bruce S. Foster, Scoth Plains, NJ (US); Ulf H. Dolling, Westfield, NJ (US); R. Scott Hoerrner, Westfield, NJ (US); Philip J. Pye, Guttenberg, NJ (US); Remy Angelaud, Union, NJ (US); Danny E. Mancheno, Rego Park, NY (US); David Askin, Warren, NJ (US)

(73) Assignee: Merck & Co., Inc., Rahway, NJ (US)

( * ) Notice: Subject to any disclaimer, the term of this patent is extended or adjusted under 35 U.S.C. 154(b) by 195 days.

(21) Appl. No.: 10/587,682

(22) PCT Filed: Mar. 9, 2005

(86) PCT No.: PCT/US2005/007772

§ 371 (c)(1),
(2), (4) Date: Jul. 28, 2006

(87) PCT Pub. No.: WO2005/087768

PCT Pub. Date: Sep. 22, 2005

(65) Prior Publication Data

US 2007/0179196 A1    Aug. 2, 2007

Related U.S. Application Data

(60) Provisional application No. 60/551,625, filed on Mar. 9, 2004, provisional application No. 60/633,134, filed on Dec. 3, 2004.

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)
*C07D 513/02* (2006.01)

(52) U.S. Cl. ..................... 514/300; 546/113
(58) Field of Classification Search ................. 546/86, 546/113; 514/300
See application file for complete search history.

(56) References Cited

U.S. PATENT DOCUMENTS

| | | | |
|---|---|---|---|
| 6,262,055 B1 | 7/2001 | Young et al. |
| 6,306,891 B1 | 10/2001 | Selnick et al. |
| 6,380,249 B1 | 4/2002 | Young et al. |
| 6,841,558 B2 | 1/2005 | Anthony et al. |
| 6,919,351 B2 | 7/2005 | Anthony et al. |
| 6,921,759 B2 | 7/2005 | Anthony et al. |
| 7,109,186 B2 | 9/2006 | Walker et al. |
| 7,169,780 B2 | 1/2007 | Crescenzi et al. |
| 7,211,572 B2 | 5/2007 | Miyazaki et al. |
| 7,217,713 B2 | 5/2007 | Crescenzi et al. |
| 7,232,819 B2 | 6/2007 | Di Francesco et al. |
| 7,279,487 B2 | 10/2007 | Egbertson et al. |
| 7,435,734 B2 | 10/2008 | Crescenzi et al. |
| 7,459,452 B2 | 12/2008 | Di Francesco et al. |
| 2003/0055071 A1 | 3/2003 | Anthony et al. |
| 2003/0229079 A1 | 12/2003 | Payne et al. |
| 2004/0229909 A1 | 11/2004 | Kiyama et al. |
| 2005/0010048 A1 | 1/2005 | Zhuang et al. |
| 2005/0054645 A1 | 3/2005 | Miyazaki et al. |
| 2006/0052361 A1 | 3/2006 | Miyazaki et al. |
| 2007/0161639 A1 | 7/2007 | Jones et al. |
| 2008/0009490 A1 | 1/2008 | Williams et al. |

(Continued)

FOREIGN PATENT DOCUMENTS

EP    1422218 A1    5/2004

(Continued)

OTHER PUBLICATIONS

Collins et al., FEBS letters, (Apr. 14, 2000) vol. 471, No. 2-3, pp. 169-172.*

(Continued)

*Primary Examiner*—D. Margaret Seaman
*Assistant Examiner*—Niloofar Rahmani
(74) *Attorney, Agent, or Firm*—Kenneth R. Walton; Sheldon O. Heber

(57) ABSTRACT

Hydroxy (tetra- or hexa-)hydronaphthyridine dione compounds of Formula I are inhibitors of HIV integrase and inhibitors of HIV replication: (I) wherein a, $R^1$, $R^2$, $R^3$, $R^4$ and $R^5$ are defined herein. The compounds are useful in the prevention and treatment of infection by HIV and in the prevention, delay in the onset, and treatment of AIDS. The compounds are employed against HIV infection and AIDS as compounds per se or in the form of pharmaceutically acceptable salts. The compounds and their salts can be employed as ingredients in pharmaceutical compositions, optionally in combination with other antivirals, immunomodulators, antibiotics or vaccines.

(I)

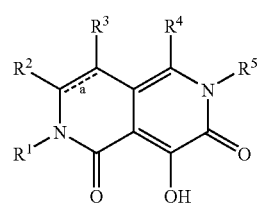

11 Claims, No Drawings

U.S. PATENT DOCUMENTS

2008/0139579 A1    6/2008    Morrissette et al.

FOREIGN PATENT DOCUMENTS

| WO | WO 01/00578 A1 | 1/2001 |
|---|---|---|
| WO | WO 02/30426 A1 | 4/2002 |
| WO | WO 02/36734 A2 | 5/2002 |
| WO | WO 02/55079 A2 | 7/2002 |
| WO | WO 03/035076 A1 | 5/2003 |
| WO | WO 03/035077 A1 | 5/2003 |
| WO | WO 03/062204 A1 | 7/2003 |
| WO | WO 2004/004657 A2 | 1/2004 |
| WO | 2006/121831 A2 | 11/2006 |

OTHER PUBLICATIONS

Office Action mailed Aug. 1, 2007, U.S. Appl. No. 10/587,601, filed Jul. 28, 2006.

Ratner, L., et al., "Complete Nucleotide Sequence of the AIDS Virus, HTLV-III", Nature, vol. 313, pp. 277-284, (1985).

Toh, H., et al., "Close Structural Resemblance Between Putative Polymerase of a Drosphila Transposable Genetic Element 17.6 and Pol Gene Product of Moloney Murine Leukemia Virus", EMBO Journal, vol. 4, No. 5, pp. 1267-1272, (1985).

Power, M.D., et al., "Nucleotide Sequence of SRV-1, a Type D Simian Acquired Immune Deficiency Syndrome Retrovirus", Science, vol. 231, pp. 1567-1572, (1986).

Pearl, L.H., et al., "A Structural Model for the Retroviral Proteases", Nature, vol. 329, pp. 351-354, (1987).

Derwent Abstract No. 2003-300600/29, Abstract of WO 03/016275, "Compositions Containing New and Known Heterocyclic Ketone Compounds Useful as Antiviral Agents Especially for Treating HIV Infections (JPN)".

Derwent Abstract, No. 2005-202383/21, Abstract of WO 05/016927, "New Bicyclic Nitrogen Containing Heterocyclic Dione Compounds are Integrase Inhibitors Used for Treating Viral Infections e.g. HIV Infection (JPN)".

Maurin, C., et al., "Structure-Activity Relationships of HIV-1 Integrase Inhibitors—Enzyme-Ligand Interactions", Current Medicinal Chemistry, vol. 10, pp. 1795-1810 (2003).

Declaration of Interference No. 105,655 between (i) Jones et al., U.S. Appl. No. 10/587,601, filed Jul. 28, 2006, and (ii) Miyazaki et al., US 7,211,572.

LaFemina et al. Requirement of Active Human Immunodeficiency Virus Type 1 Integrase Enzyme for Productive Infection of Human T-Lymphoid Cells, Journal of Virology, 1992, vol. 66, No. 12, pp. 7414-7419.

Fauci et al. "Acquired Immunodeficiency Syndrome: Epidemiologic, Clinical, Immunologic, and Therapeutic Considerations", Annals of Internal Medicine, 1984, vol. 100, No. 1, pp. 92-106.

Dean, et al. "Genetic Restriction of HIV-1 Infection and Progression to AIDS by a Deletion Allele of the CKR5 Structural Gene", Science, 1996, vol. 273, pp. 1856-1862.

Mylonakis et al. "Laboratory Testing for Infection with the Human Immunodeficiency Virus: Established and Novel Approaches", The American Journal of Medicine, 2000, vol. 109, pp. 568-576.

The Medical Letter on Drugs and Therapeutics, "Diagnostic Tests for HIV", 1997, vol. 39, Issue 1008, pp. 81-83.

Constantine "Serologic tests for the retroviruses: approaching a decade of evolution", AIDS, 1993, vol. 7, No. 1, pp. 1-13.

Mellors, et al. "Plasma Viral Load and CD4+ Lymphocytes as Prognostic Markers of HIV-1 Infection", Annals of Internal Medicine, 1997, vol. 126, No. 12, pp. 946-954.

Selected papers from Interference No. 105,655 between U.S. Appl. No. 10/587,601 (Merck) and US 7,211,572 (Japan Tobacco)—Merck Amended Miscellaneous Motion 1 dated Nov. 10, 2008; Interlocutory Order dated Nov. 18, 2008, Granting Merck's Unopposed Revised Miscellaneous Motion 1; Redeclaration of Interference dated Nov. 18, 2008; Judgement dated Dec. 5, 2008.

Preliminary Amendment filed Nov. 7, 2007 in U.S. Appl. No. 11/920,032 (unpublished national phase application of WO 2006/121831).

Preliminary Amendment filed Mar. 24, 2008 in U.S. Appl. No. 11/920,032 (unpublished national phase application of WO 2006/121831).

Second Preliminary Amendment filed Feb. 2, 2009 in U.S. Appl. No. 12/316,027.

Preliminary Amendment filed Dec. 9, 2008 in U.S. Appl. No. 12/316,027.

U.S. Appl. No. 12/316,027, filed Dec. 9, 2008, unpublished application.

* cited by examiner

HIV INTEGRASE INHIBITORS

This application is the National Stage of International Application No. PCT/US2005/007772, filed on Mar. 9, 2005, which claims the benefit of U.S. Provisional Application Nos. 60/551,625 (filed Mar. 9, 2004) and 60/633,134 (filed Dec. 3, 2004), the disclosures of which are hereby incorporated by reference in their entireties.

FIELD OF THE INVENTION

The present invention is directed hydroxy tetrahydro-2,6-naphthyridine dione and hydroxy hexahydro-2,6-naphthyridine dione compounds and pharmaceutically acceptable salts thereof, their synthesis, and their use as inhibitors of the HIV integrase enzyme. The compounds and pharmaceutically acceptable salts thereof of the present invention are useful for preventing or treating infection by HIV and for preventing or treating or delaying the onset of AIDS.

BACKGROUND OF THE INVENTION

A retrovirus designated human immunodeficiency virus (HIV), particularly the strains known as HIV type-1 (HIV-1) virus and type-2 (HIV-2) virus, is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the insertion by virally-encoded integrase of +proviral DNA into the host cell genome, a required step in HIV replication in human T-lymphoid and monocytoid cells. Integration is believed to be mediated by integrase in three steps: assembly of a stable nucleoprotein complex with viral DNA sequences; cleavage of two nucleotides from the 3' termini of the linear proviral DNA; covalent joining of the recessed 3' OH termini of the proviral DNA at a staggered cut made at the host target site. The fourth step in the process, repair synthesis of the resultant gap, may be accomplished by cellular enzymes.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, integrase and an HIV protease [Toh, H. et al., EMBO J. 4, 1267 (1985); Power, M. D. et al., Science, 231, 1567 (1986); Pearl, L. H. et al., Nature, 329, 351 (1987)]. All three enzymes have been shown to be essential for the replication of HIV.

It is known that some antiviral compounds which act as inhibitors of HIV replication are effective agents in the treatment of AIDS and similar diseases, including reverse transcriptase inhibitors such as azidothymidine (AZT) and efavirenz and protease inhibitors such as indinavir and nelfinavir. The compounds of this invention are inhibitors of HIV integrase and inhibitors of HIV replication. The inhibition of integrase in vitro and HIV replication in cells is a direct result of inhibiting the strand transfer reaction catalyzed by the recombinant integrase in vitro in HIV infected cells. The particular advantage of the present invention is highly specific inhibition of HIV integrase and HIV replication.

The following references are of interest as background:

U.S. Pat. Nos. 6,380,249, 6,306,891, and 6,262,055 disclose 2,4-dioxobutyric acids and acid esters useful as HIV integrase inhibitors.

WO 01/00578 discloses 1-(aromatic- or heteroaromatic-substituted)-3-(heteroaromatic substituted)-1,3-propanediones useful as HIV integrase inhibitors.

US 2003/0055071 (corresponding to WO 02/30930), WO 02/30426, and WO 02/55079 each disclose certain 8-hydroxy-1,6-naphthyridine-7-carboxamides as BEIV integrase inhibitors.

WO 02/036734 discloses certain aza- and polyaza-naphthalenyl ketones to be HIV integrase inhibitors.

WO 03/016275 discloses certain compounds having integrase inhibitory activity.

WO 03/35076 discloses certain 5,6-dihydroxypyrimidine-4-carboxamides as HIV integrase inhibitors, and WO 03/35077 discloses certain N-substituted 5-hydroxy-6-oxo-1,6-dihydropyrimidine-4-carboxamides as HIV integrase inhibitors.

WO 03/1062204 discloses certain hydroxynaphthyridinone carboxamides that are useful as HIV integrase inhibitors.

WO 04/004657 discloses certain hydroxypyrrole derivatives that are HIV integrase inhibitors.

WO 2005/016927 discloses certain nitrogenous condensed ring compounds that are HIV integrase inhibitors.

SUMMARY OF THE INVENTION

The present invention is directed to hydroxy polyhydro-2, 6-naphthyridine dione compounds. These compounds are useful in the inhibition of HIV integrase, the prevention of infection by HIV, the treatment of infection by HIV and in the prevention, treatment, and delay in the onset of AIDS and/or ARC, either as compounds or their pharmaceutically acceptable salts or hydrates (when appropriate), or as pharmaceutical composition ingredients, whether or not in combination with other HIV/AIDS antivirals, anti-infectives, immunomodulators, antibiotics or vaccines. More particularly, the present invention includes compounds of Formula I, and pharmaceutically acceptable salts thereof:

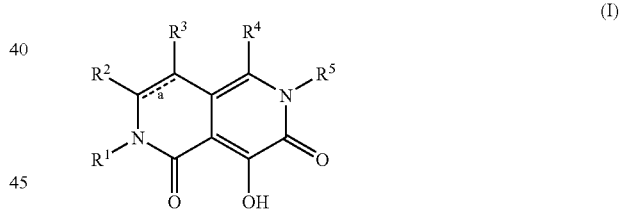

(I)

wherein:
bond

" $\underset{\text{-----}}{a}$ "

in the ring is a single bond or a double bond;
$R^1$ is —$C_{1-6}$ alkyl, $R^J$, or —$C_{1-6}$ alkyl substituted with $R^J$, wherein $R^J$ is:
  (A) (i) aryl or (ii) aryl fused to a 5- or 6-membered heteroaromatic ring containing from 1 to 4 heteroatoms independently selected from N, O and S or (iii) aryl substituted on two adjacent ring carbons with alkylenedioxy, wherein the aryl or fused aryl or alkylenedioxy aryl is:
    (a) optionally substituted with from 1 to 5 substituents each of which is independently:

(1) —$C_{1-6}$ alkyl optionally substituted with —OH, —O—$C_{1-6}$ alkyl, —O—$C_{1-6}$ haloalkyl, —CN, —$NO_2$, —$N(R^a)R^b$, —$C(=O)N(R^a)R^b$, —$C(=O)R^a$, —$CO_2R^a$, —$S(O)_nR^a$, —$SO_2N(R^a)R^b$, —$N(R^a)C(=O)R^b$, —$N(R^a)CO_2R^b$, —$N(R^a)SO_2R^b$, —$N(R^a)SO_2N(R^a)R^b$, —$OC(=O)N(R^a)R^b$, or —$N(R^a)C(=O)N(R^a)R^b$, (2) —O—$C_{1-6}$ alkyl,
(3) —$C_{1-6}$ haloalkyl,
(4) —O—$C_{1-6}$ haloalkyl,
(5) —OH,
(6) halogen,
(7) —CN,
(8) —$NO_2$,
(9) —$N(R^a)R^b$,
(10) —$C(=O)N(R^a)R^b$,
(11) —$C(=O)R^a$,
(12) —$CO_2R^a$,
(13) —$SR^a$,
(14) —$S(=O)R^a$,
(15) —$SO_2R^a$,
(16) —$SO_2N(R^a)R^b$,
(17) —$N(R^a)SO_2R^b$,
(18) —$N(R^a)SO_2N(R^a)R^b$,
(19) —$N(R^a)C(=O)R^b$,
(20) —$N(R^a)C(=O)$—$C(=O)N(R^a)R^b$,
(21) —$N(R^a)CO_2R^b$, or
(22) —$N(R^a)C(=O)N(R^a)R^b$, and (b) optionally substituted with 1 or 2 substituents each of which is independently:

(1) $C_{3-8}$ cycloalkyl which is optionally substituted with from 1 to 4 substituents each of which is independently halogen, CN, $C_{1-6}$ alkyl, OH, O—$C_{1-6}$ alkyl, $C_{1-6}$ haloalkyl, O—$C_{1-6}$ haloalkyl, $C_{1-6}$ alkylene-CN, $C_{1-6}$ alkylene-OH, or $C_{1-6}$ alkylene-O—$C_{1-6}$ alkyl, (2) aryl or $C_{1-6}$ alkyl substituted with aryl, wherein in either case the aryl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $N(R^a)R^b$, $C(O)N(R^a)R^b$, $C(O)R^a$, $C(O)OR^a$, $SR^a$, $S(O)R^a$, $S(O)_2R^a$, $S(O)_2N(R^a)R^b$, $S(O)_2N(R^a)C(O)R^b$, $C_{1-6}$ alkylene-CN, $C_{1-6}$ alkylene-$NO_2$, $C_{1-6}$ alkylene-OH, $C_{1-6}$ alkylene-O—$C_{1-6}$ alkyl, $C_{1-6}$ alkylene-O—$C_{1-6}$ haloalkyl, $C_{1-6}$ alkylene-$N(R^a)R^b$, $C_{1-6}$ alkylene-$C(O)N(R^a)R^b$, $C_{1-6}$ alkylene-$C(O)R^a$, $C_{1-6}$ alkylene-$C(O)OR^a$, $C_{1-6}$ alkylene-$SR^a$, $C_{1-6}$ alkylene-$S(O)R^a$, $C_{1-6}$ alkylene-$S(O)_2R^a$, $C_{1-6}$ alkylene-$S(O)_2N(R^a)R^b$, or $C_{1-6}$ alkylene-$S(O)_2N(R^a)C(O)R^b$, (3) —HetA,
(4) —C(=O)—HetA, or
(5) —HetB;

wherein each HetA is independently a $C_{4-7}$ azacycloalkyl or a $C_{3-6}$ diazacycloalkyl, either of which is optionally substituted with from 1 to 4 substituents each of which is independently halogen, CN, $C_{1-6}$ alkyl, OH, oxo, O—$C_{1-6}$ alkyl, $C_{1-6}$ haloalkyl, $S(O)_2R^a$, $C_{1-6}$ alkylene-CN, $C_{1-6}$ alkylene-OH, or $C_{1-6}$ alkylene-O—$C_{1-6}$ alkyl; and wherein each HetB is independently a 5- or 6-membered heteroaramatic ring containing from 1 to 4 heteroatoms independently selected from N, O and S, wherein the heteroaromatic ring is optionally substituted with from 1 to 4 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $N(R^a)R^b$, $C(O)N(R^a)R^b$, $C(O)R^a$, $C(O)OR^a$, $SR^a$, $S(O)R^a$, $S(O)_2R^a$, $S(O)_2N(R^a)R^b$, $S(O)_2N(R^a)C(O)R^b$, $C_{1-6}$ alkylene-CN, $C_{1-6}$ alkylene-$NO_2$, $C_{1-6}$ alkylene-OH, $C_{1-6}$ alkylene-O—$C_{1-6}$ alkyl, $C_{1-6}$ alkylene-O—$C_{1-6}$ haloalkyl, $C_{1-6}$ alkylene-$N(R^a)R^b$, $C_{1-6}$ alkylene-$C(O)N(R^a)R^b$, $C_{1-6}$ alkylene-$C(O)R^a$, $C_{1-6}$ alkylene-$C(O)OR^a$, $C_{1-6}$ alkylene-$SR^a$, $C_{1-6}$ alkylene-$S(O)R^a$, $C_{1-6}$ alkylene-$S(O)_2R^a$, $C_{1-6}$ alkylene-$S(O)_2N(R^a)R^b$, or $C_{1-6}$ alkylene-$S(O)_2N(R^a)C(O)R^b$; or (B) a 5- or 6-membered heteroaromatic ring containing from 1 to 4 heteroatoms independently selected from N, O and S, wherein the heteroaromatic ring is:

(a) optionally substituted with from 1 to 4 substituents each of which is independently:

(1) —$C_{1-6}$ alkyl optionally substituted with —OH, —O—$C_{1-6}$ alkyl, —O—$C_{1-6}$ haloalkyl, —CN, —$NO_2$, —$N(R^a)R^b$, —$C(=O)N(R^a)R^b$, —$C(=O)R^a$, —$CO_2R^a$, —$S(O)_nR^a$, —$SO_2N(R^a)R^b$, —$N(R^a)C(=O)R^b$, —$N(R^a)CO_2R^b$, —$N(R^a)SO_2R^b$, —$N(R^a)SO_2N(R^a)R^b$, —$OC(=O)N(R^a)R^b$, or —$N(R^a)C(=O)N(R^a)R^b$, (2) —O—$C_{1-6}$ alkyl,
(3) —$C_{1-6}$ haloalkyl,
(4) —O—$C_{1-6}$ haloalkyl,
(5) —OH,
(6) halogen,
(7) —CN,
(8) —$NO_2$,
(9) —$N(R^a)R^b$,
(10) —$C(=O)N(R^a)R^b$,
(11) —$C(=O)R^a$,
(12) —$CO_2R^a$,
(13) —$SR^a$,
(14) —$S(=O)R^a$,
(15) —$SO_2R^a$,
(16) —$SO_2N(R^a)R^b$,
(17) —$N(R^a)SO_2R^b$,
(18) —$N(R^a)SO_2N(R^a)R^b$,
(19) —$N(R^a)C(=O)R^b$,
(20) —$N(R^a)C(=O)$—$C(=O)N(R^a)R^b$,
(21) —$N(R^a)CO_2R^b$, or
(22) —$N(R^a)C(=O)N(R^a)R^b$, and (b) optionally substituted with 1 or 2 substituents each of which is independently:

(1) $C_{3-8}$ cycloalkyl which is optionally substituted with from 1 to 4 substituents each of which is independently halogen, CN, $C_{1-6}$ alkyl, OH, O—$C_{1-6}$ alkyl, $C_{1-6}$ haloalkyl, O—$C_{1-6}$ haloalkyl, $C_{1-6}$ alkylene-CN, $C_{1-6}$ alkylene-OH, or $C_{1-6}$ alkylene-O—$C_{1-6}$ alkyl, (2) aryl or $C_{1-6}$ alkyl substituted with aryl, wherein in either case the aryl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $N(R^a)R^b$, $C(O)N(R^a)R^b$, $C(O)R^a$, $C(O)OR^a$, $SR^a$, $S(O)R^a$, $S(O)_2R^a$, $S(O)_2N(R^a)R^b$, $S(O)_2N(R^a)C(O)R^b$, $C_{1-6}$ alkylene-CN, $C_{1-6}$ alkylene-$NO_2$, $C_{1-6}$ alkylene-OH, $C_{1-6}$ alkylene-O—$C_{1-6}$ alkyl, $C_{1-6}$ alkylene-O—$C_{1-6}$ haloalkyl, $C_{1-6}$ alkylene-$N(R^a)R^b$, $C_{1-6}$ alkylene-$C(O)N(R^a)R^b$, $C_{1-6}$ alkylene-$C(O)R^a$, $C_{1-6}$ alkylene-$C(O)OR^a$, $C_{1-6}$ alkylene-$SR^a$, $C_{1-6}$ alkylene-S(O)$R^a$, $C_{1-6}$ alkylene-S(O)$_2R^a$, $C_{1-6}$ alkylene-S(O)$_2$N($R^a$)$R^b$, or $C_{1-6}$ alkylene-S(O)$_2$N ($R^A$)C(O)$R^b$,
  (3) —HetA,
  (4) —C(=O)—HetA, or
  (5) —HetB;
    wherein HetA and HetB are each independently as defined above;
$R^2$ is —H or —$C_{1-6}$ alkyl;
$R^3$ independently has the same definition as $R^4$, with the proviso that at least one of $R^3$ and $R^4$ is —H or —$C_{1-6}$ alkyl;
or, as an alternative, when bond "------a------"

is a double bond, $R^2$ and $R^3$ together with the carbon atoms to which each is attached form:
  (i) a benzene ring which is optionally substituted with a total of from 1 to 4 substituents wherein (a) from zero to 4 substituents are each independently one of substituents (1) to (22) as defined in part (A)(a) of the definition of $R^1$ and (b) from zero to 2 substituents are each independently one of the substituents (1) to (5) as defined in part (A)(b) of the definition of $R^1$, or
  (ii) a 5- or 6-membered heteroaromatic ring containing from 1 to 4 heteroatoms independently selected from N, O and S, wherein the heteroaromatic ring is optionally substituted with a total of from 1 to 3 substituents wherein (a) from zero to 3 substituents are each independently one of substituents (1) to (22) as defined in part (B)(a) of the definition of $R^1$ and (b) from zero to 2 substituents are each independently one of the substituents (1) to (5) as defined in part (B)(b) of the definition of $R^1$;
$R^4$ is:
  (1) —H,
  (2) —$C_{1-6}$ alkyl,
  (3) —$C_{1-6}$ haloalkyl,
  (4) —$C_{1-6}$ alkyl substituted with —OH, —O—$C_{1-6}$ alkyl, —O—$C_{1-6}$ haloalkyl, —CN, —N($R^a$)$R^b$, —C(=O)N($R^a$)$R^b$, —C(=O)$R^a$, —CO$_2R^a$, —C(=O)—N($R^a$)—$C_{1-6}$ alkylene-O$R^b$ with the proviso that the —N($R^a$)— moiety and the —O$R^b$ moiety are not both attached to the same carbon of the —$C_{1-6}$ alkylene-moiety, —S(O)$_n$$R^a$, —SO$_2$N($R^a$)$R^b$, —N($R^a$)C(=O)—$R^b$, —N($R^a$)CO$_2R^b$, —N($R^a$)SO$_2R^b$, —N($R^a$)SO$_2$N($R^a$)$R^b$, —N($R^a$)C(=O)N($R^a$)$R^b$, or —OC(=O)N($R^a$)$R^b$,
  (5) —C(=O)$R^a$,
  (6) —CO$_2R^a$,
  (7) —C(=O)N($R^a$)$R^b$,
  (8) —C(=O)—N($R^a$)—$C_{1-6}$ alkylene-O$R^b$ with the proviso that the —N($R^a$)— moiety and the —O$R^b$ moiety are not both attached to the same carbon of the —$C_{1-6}$ alkylene-moiety,
  (9) —N($R^a$)—C(=O)—$R^b$,
  (10) —N($R^a$)—C(=O)—C(=O)N($R^a$)$R^b$,
  (11) —N($R^a$)SO$_2R^b$,
  (12) —N($R^a$)SO$_2$N($R^a$)$R^b$,
  (13) —N($R^a$)C(=O)N($R^a$)$R^b$,
  (14) —OC(=O)N($R^a$)$R^b$,
  (15) $R^K$,
  (16) —C(=O)—$R^K$,
  (17) —C(=O)N($R^a$)—$R^K$,
  (18) —C(=O)N($R^a$)—$C_{1-6}$ alkylene-$R^K$,
  (19) —$C_{1-6}$ alkyl substituted with —$R^K$,
  (20) —$C_{1-6}$ alkyl substituted with —C(=O)—$R^K$,
  (21) —$C_{1-6}$ alkyl substituted with —C(=O)N($R^a$)—$R^K$,
  (22) —$C_{1-6}$ alkyl substituted with —C(=O)N($R^a$)—$C_{1-6}$ alkylene-$R^K$,
  (23) —C(=O)N($R^a$)$R^c$,
  (24) —CN,
  (25) halogen,
  (26) —N($R^a$)$R^b$, or
  (27) —N($R^a$)CO$_2R^b$;
    wherein $R^K$ is
    (i) $C_{3-8}$ cycloalkyl which is optionally substituted with from 1 to 4 substituents each of which is independently halogen, CN, $C_{1-6}$ alkyl, OH, O—$C_{1-6}$ alkyl, $C_{1-6}$ haloalkyl, O—$C_{1-6}$ haloalkyl, $C_{1-6}$ alkylene-CN, $C_{1-6}$ alkylene-OH, or $C_{1-6}$ alkylene-O—$C_{1-6}$ alkyl,
    (ii) aryl, which is optionally substituted with from 1 to 5 substituents each of which is independently —$C_{1-6}$ alkyl, —$C_{1-6}$ alkylene-OH, —$C_{1-6}$ alkylene-O—$C_{1-6}$ alkyl, —$C_{1-6}$ alkylene-O—$C_{1-6}$ haloalkyl, —$C_{1-6}$ alkylene-N($R^a$)$R^b$, —$C_{1-6}$ alkylene-C(=O)N($R^a$)$R^b$, —$C_{1-6}$ alkylene-C(=O)$R^a$, —$C_{1-6}$ alkylene-CO$_2R^a$, —$C_{1-6}$ alkylene-S(O)$_n$$R^a$, —O—$C_{1-6}$ alkyl, —$C_{1-6}$ haloalkyl, —O—$C_{1-6}$ haloalkyl, —OH, halogen, —N($R^a$)$R^b$, —C(=O)N($R^a$)$R^b$, —C(=O)$R^a$, —CO$_2R^a$, —S(O)$_n$$R^a$, or —SO$_2$N($R^a$)$R^b$,
    (iii) HetK, which is a 4- to 7-membered saturated heterocyclic ring containing at least one carbon atom and from 1 to 4 heteroatoms independently selected from N, O and S, wherein the heterocyclic ring is:
      (a) optionally substituted with from 1 to 6 substituents each of which is independently halogen, —$C_{1-6}$ alkyl, —$C_{1-6}$ haloalkyl, —O—$C_{1-6}$ alkyl, —O—$C_{1-6}$ haloalkyl, oxo, —C(=O)N($R^a$)$R^b$, —C(=O)C(=O)N($R^a$)$R^b$, —C(=O)$R^a$, —CO$_2R^a$, —S(O)$_n$$R^a$, or —SO$_2$N($R^a$)$R^b$; and
      (b) optionally substituted with:
        (1) $C_{3-8}$ cycloalkyl which is optionally substituted with from 1 to 4 substituents each of which is independently halogen, CN, $C_{1-6}$ alkyl, OH, O—$C_{1-6}$ alkyl, $C_{1-6}$ haloalkyl, Q-$C_{1-6}$ haloalkyl, $C_{1-6}$ alkylene-CN, $C_{1-6}$ alkylene-OH, or $C_{1-6}$ alkylene-O—$C_{1-6}$ alkyl,
        (2) aryl which is optionally substituted with from 1 to 5 substituents each of which is independently halogen, CN, NO$_2$, $C_{1-6}$ alkyl, $C_{1-6}$ haloalkyl, OH, O—$C_{1-6}$ alkyl, O—$C_{1-6}$ haloalkyl, N($R^a$)$R^b$, C(O)N($R^a$)$R^b$, C(O)$R^a$, C(O)O$R^a$, S$R^a$, S(O)$R^a$, S(O)$_2R^a$, S(O)$_2$N($R^a$)$R^b$, S(O)$_2$N($R^a$)C(O)$R^b$, $C_{1-6}$ alkylene-CN, $C_{1-6}$ alkylene-NO$_2$, $C_{1-6}$ alkylene-OH, $C_{1-6}$ alkylene-O—$C_{1-6}$ alkyl, $C_{1-6}$ alkylene-O—$C_{1-6}$ haloalkyl, $C_{1-6}$ alkylene-N($R^a$)$R^b$, $C_{1-6}$ alkylene-C(O)N($R^a$)$R^b$, $C_{1-6}$ alkylene-C(O)$R^a$, $C_{1-6}$ alkylene-C(O)O$R^a$, $C_{1-6}$ alkylene-S$R^a$, $C_{1-6}$ alkylene-S(O)$R^a$, $C_{1-6}$ alkylene-S(O)$_2R^a$, $C_{1-6}$ alkylene-S(O)$_2$N($R^a$)$R^b$, or $C_{1-6}$ alkylene-S(O)$_2$N($R^A$)C(O)$R^b$, or
        (3) HetC,
          wherein HetC is a 5- or 6-membered heteroaromatic ring containing from 1 to 4 heteroatoms independently selected from N, O and S, wherein the heteroaromatic ring is optionally fused with a benzene ring, and the optionally fused heteroaromatic ring is optionally substituted with from 1 to 4 substituents each of which is independently halogen, CN, NO$_2$, $C_{1-6}$ alkyl, $C_{1-6}$ haloalkyl, OH, O—$C_{1-6}$ alkyl, O—$C_{1-6}$ haloalkyl, N(R$^a$)R$^b$, C(O)N(R$^a$)R$^b$, C(O)R$^a$, C(O)OR$^a$, SR$^a$, S(O)R$^a$, S(O)$_2$R$^a$, S(O)$_2$N(R$^a$)R$^b$, S(O)$_2$N(R$^a$)C(O)R$^b$, C$_{1-6}$ alkylene-CN, C$_{1-6}$ alkylene-NO$_2$, C$_{1-6}$ alkylene-OH, C$_{1-6}$ alkylene-O—C$_{1-6}$ alkyl, C$_{1-6}$ alkylene-O—C$_{1-6}$ haloalkyl, C$_{1-6}$ alkylene-N(R$^a$)R$^b$, C$_{1-6}$ alkylene-C(O)N(R$^a$)R$^b$, C$_{1-6}$ alkylene-C(O)R$^a$, C$_{1-6}$ alkylene-C(O)OR$^a$, C$_{1-6}$ alkylene-SR$^a$, C$_{1-6}$ alkylene-S(O)R$^a$, C$_{1-6}$ alkylene-S(O)$_2$R$^a$, C$_{1-6}$ alkylene-S(O)$_2$N(R$^a$)R$^b$, or C$_{1-6}$ alkylene-S(O)$_2$N(R$^a$)C(O)R$^b$, or (iv) —HetL, which is a 5- or 6-membered heteroaromatic ring containing from 1 to 4 heteroatoms independently selected from N, O and S, wherein the heteroaromatic ring is optionally substituted with from 1 to 4 substituents each of which is independently halogen, CN, NO$_2$, C$_{1-6}$ alkyl, C$_{1-6}$ haloalkyl, OH, O—C$_{1-6}$ alkyl, O—C$_{1-6}$ haloalkyl, N(R$^a$)R$^b$, C(O)N(R$^a$)R$^b$, C(O)R$^a$, C(O)OR$^a$, SR$^a$, S(O)R$^a$, S(O)$_2$R$^a$, S(O)$_2$N(R$^a$)R$^b$, S(O)$_2$N(R$^a$)C(O)R$^b$, C$_{1-6}$ alkylene-CN, C$_{1-6}$ alkylene-NO$_2$, C$_{1-6}$ alkylene-OH, C$_{1-6}$ alkylene-O—C$_{1-6}$ alkyl, C$_{1-6}$ alkylene-O—C$_{1-6}$ haloalkyl, C$_{1-6}$ alkylene-N(R$^a$)R$^b$, C$_{1-6}$ alkylene-C(O)N(R$^a$)R$^b$, C$_{1-6}$ alkylene-C(O)R$^a$, C$_{1-6}$ alkylene-C(O)OR$^a$, C$_{1-6}$ alkylene-SR$^a$, C$_{1-6}$ alkylene-S(O)R$^a$, C$_{1-6}$ alkylene-S(O)$_2$R$^a$, C$_{1-6}$ alkylene-S(O)$_2$N(R$^a$)R$^b$, or C$_{1-6}$ alkylene-S(O)$_2$N(R$^a$)C(O)R$^b$;

R$^5$ is:

(1) —H, (2) —C$_{1-6}$ alkyl, (3) —C$_{3-8}$ cycloalkyl optionally substituted with from 1 to 4 substituents each of which is independently halogen, CN, C$_{1-6}$ alkyl, OH, O—C$_{1-6}$ alkyl, C$_{1-6}$ haloalkyl, O—C$_{1-6}$ haloalkyl, C$_{1-6}$ alkylene-CN, C$_{1-6}$ alkylene-OH, or C$_{1-6}$ alkylene-O—C$_{1-6}$ alkyl, (4) —C$_{1-6}$ alkyl substituted with C$_{3-8}$ cycloalkyl, wherein the cycloalkyl is optionally substituted with from 1 to 4 substituents each of which is independently halogen, CN, C$_{1-6}$ alkyl, OH, O—C$_{1-6}$ alkyl, C$_{1-6}$ haloalkyl, O—C$_{1-6}$ haloalkyl, C$_{1-6}$ alkylene-CN, C$_{1-6}$ alkylene-OH, or C$_{1-6}$ alkylene-O—C$_{1-6}$ alkyl, (5) —C$_{1-6}$ alkyl substituted with aryl, wherein the aryl is optionally substituted with from 1 to 5 substituents each of which is independently halogen, CN, NO$_2$, C$_{1-6}$ alkyl, C$_{1-6}$ haloalkyl, OH, O—C$_{1-6}$ alkyl, O—C$_{1-6}$ haloalkyl, N(R$^a$)R$^b$, C(O)N(R$^a$)R$^b$, C(O)R$^a$, C(O)OR$^a$, SR$^a$, S(O)R$^a$, S(O)$_2$R$^a$, S(O)$_2$N(R$^a$)R$^b$, S(O)$_2$N(R$^a$)C(O)R$^b$, C$_{1-6}$ alkylene-CN, C$_{1-6}$ alkylene-NO$_2$, C$_{1-6}$ alkylene-OH, C$_{1-6}$ alkylene-O—C$_{1-6}$ alkyl, C$_{1-6}$ alkylene-O—C$_{1-6}$ haloalkyl, C$_{1-6}$ alkylene-N(R$^a$)R$^b$, C$_{1-6}$ alkylene-C(O)N(R$^a$)R$^b$, C$_{1-6}$ alkylene-C(O)R$^a$, C$_{1-6}$ alkylene-C(O)OR$^a$, C$_{1-6}$ alkylene-SR$^a$, C$_{1-6}$ alkylene-S(O)R$^a$, C$_{1-6}$ alkylene-S(O)$_2$R$^a$, C$_{1-6}$ alkylene-S(O)$_2$N(R$^a$)R$^b$, or C$_{1-6}$ alkylene-S(O)$_2$N(R$^A$)C(O)R$^b$, (6) —C$_{1-6}$ alkyl substituted with HetD, wherein HetD is:

(i) a 4- to 7-membered saturated heterocyclic ring containing at least one carbon atom and from 1 to 4 heteroatoms independently selected from N, O and S, wherein the heterocyclic ring is optionally substituted with from 1 to 5 substituents each of which is independently halogen, —C$_{1-6}$ alkyl, —C$_{1-6}$ haloalkyl, —O—C$_{1-6}$ alkyl, —O—C$_{1-6}$ haloalkyl, oxo, —C(=O)N(R$^a$)R$^b$, —C(=O)C(=O)N(R$^a$)R$^b$, —C(=O)R$^a$, —CO$_2$R$^a$, —S(O)$_n$R$^a$, or —SO$_2$N(R$^a$)R$^b$; or (ii) a 5- or 6-membered heteroaromatic ring containing from 1 to 4 heteroatoms independently selected from N, O and S, wherein the heteroaromatic ring is optionally substituted with from 1 to 4 substituents each of which is independently —C$_{1-6}$ alkyl, —C$_{1-6}$ haloalkyl, —O—C$_{1-6}$ alkyl, —O—C$_{1-6}$ haloalkyl, or hydroxy, (7) aryl, which is optionally substituted with from 1 to 5 substituents each of which is independently —C$_{1-6}$ alkyl, —C$_{1-6}$ alkylene-OH, —C$_{1-6}$ alkylene-O—C$_{1-6}$ alkyl, —C$_{1-6}$ alkylene-O—C$_{1-6}$ haloalkyl, —C$_{1-6}$ alkylene-N(R$^a$)R$^b$, —C$_{1-6}$ alkylene-C(=O)N(R$^a$)R$^b$, —C$_{1-6}$ alkylene-C(=O)R$^a$, —C$_{1-6}$ alkylene-CO$_2$R$^a$, —C$_{1-6}$ alkylene-S(O)$_n$R$^a$, —O—C$_{1-6}$ alkyl, —C$_{1-6}$ haloalkyl, —O—C$_{1-6}$ haloalkyl, —OH, halogen, —CN, —NO$_2$, —N(R$^a$)R$^b$, —N(R$^a$)C(=O)R$^b$, —N(R$^a$)C(=O)—C$_{1-6}$ haloalkyl, —N(R$^a$)C(=O)N(R$^a$)R$^b$, —N(R$^a$)CO$_2$R$^b$, —N(R$^a$)S(O)$_n$R$^b$, —C(=O)N(R$^d$)R$^e$, —C(=O)R$^a$, —CO$_2$R$^a$, —S(O)$_n$R$^a$, or —SO$_2$N(R$^d$)R$^e$, (8) a 5- or 6-membered heteroaromatic ring containing from 1 to 4 heteroatoms independently selected from N, O and S, wherein the heteroaromatic ring is optionally substituted with from 1 to 4 substituents each of which is independently halogen, CN, NO$_2$, C$_{1-6}$ alkyl, C$_{1-6}$ haloalkyl, OH, O—C$_{1-6}$ alkyl, O—C$_{1-6}$ haloalkyl, N(R$^a$)R$^b$, C(O)N(R$^a$)R$^b$, C(O)R$^a$, C(O)OR$^a$, SR$^a$, S(O)R$^a$, S(O)$_2$R$^a$, S(O)$_2$N(R$^a$)R$^b$, S(O)$_2$N(R$^a$)C(O)R$^b$, C$_{1-6}$ alkylene-CN, C$_{1-6}$ alkylene-NO$_2$, C$_{1-6}$ alkylene-OH, C$_{1-6}$ alkylene-O—C$_{1-6}$ alkyl, C$_{1-6}$ alkylene-O—C$_{1-6}$ haloalkyl, C$_{1-6}$ alkylene-N(R$^a$)R$^b$, C$_{1-6}$ alkylene-C(O)N(R$^a$)R$^b$, C$_{1-6}$ alkylene-C(O)R$^a$, C$_{1-6}$ alkylene-C(O)OR$^a$, C$_{1-6}$ alkylene-SR$^a$, C$_{1-6}$ alkylene-S(O)R$^a$, C$_{1-6}$ alkylene-S(O)$_2$R$^a$, C$_{1-6}$ alkylene-S(O)$_2$N(R$^a$)R$^b$, or C$_{1-6}$ alkylene-S(O)$_2$N(R$^a$)C(O)R$^b$, (9) C$_{1-6}$ alkyl substituted with —O—C$_{1-6}$ alkyl, —O—C$_{1-6}$ haloalkyl, —CN, —N(R$^a$)R$^b$, —C(=O)N(R$^a$)R$^b$, —C(=O)R$^a$, —CO$_2$R$^a$, —S(O)$_n$R$^a$, —SO$_2$N(R$^a$)R$^b$, —N(R$^a$)C(=O)—R$^b$, —N(R$^a$)CO$_2$R$^b$, or —N(R$^a$)SO$_2$R$^b$, or

(10) —C$_{1-6}$ haloalkyl;

each aryl is independently (i) phenyl, (ii) a 9- or 10-membered bicyclic, fused carbocylic ring system in which at least one ring is aromatic, or (iii) an 11- to 14-membered tricyclic, fused carbocylic ring system in which at least one ring is aromatic;

each R$^a$ is independently H or C$_{1-6}$ alkyl;

each R$^b$ is independently H or C$_{1-6}$ alkyl;

R$^c$ is C$_{1-6}$ haloalkyl or C$_{1-6}$ alkyl substituted with —C(=O)N(R$^a$)R$^b$, —C(=O)R$^a$, —CO$_2$R$^a$, —S(O)$_n$R$^a$, —SO$_2$N(R$^a$)R$^b$, N(R$^a$)R$^b$, —N(R$^a$)C(=O)—R$^b$, —N(R$^a$)CO$_2$R$^b$, or —N(R$^a$)SO$_2$R$^b$;

each R$^d$ and R$^e$ are independently H or C$_{1-6}$ alkyl, or together with the N atom to which they are attached form a 4- to 7-membered saturated or mono-unsaturated heterocyclic ring optionally containing a heteroatom in addition to the nitrogen attached to R$^d$ and R$^e$ selected from N, O, and S, wherein the S is optionally oxidized to S(O) or S(O)$_2$, and wherein the saturated or mono-unsaturated heterocyclic ring is optionally substituted with from 1 to 4 substituents each of which is independently halogen, —CN, —C$_{1-6}$ alkyl, —OH, oxo, —O—C$_{1-6}$ alkyl, —C$_{1-6}$ haloalkyl, —C(=O)R$^a$, —CO$_2$R$^a$, —S(O)$_n$R$^a$, —SO$_2$N(R$^a$)R$^b$, —N(R$^a$)C(=O)—R$^b$, —N(R$^a$)CO$_2$R$^b$, or —N(R$^a$)SO$_2$R$^b$; and each n is independently an integer equal to zero, 1, or 2.

The present invention also includes pharmaceutical compositions containing a compound of the present invention and methods of preparing such pharmaceutical compositions. The present invention further includes methods of treating AIDS, methods of delaying the onset of AIDS, methods of preventing AIDS, methods of preventing infection by HIV, and methods of treating infection by HIV.

Other embodiments, aspects and features of the present invention are either further described in or will be apparent from the ensuing description, examples and appended claims.

DETAILED DESCRIPTION OF THE INVENTION

The present invention includes compounds of Formula I above, and pharmaceutically acceptable salts thereof. These compounds and their pharmaceutically acceptable salts are HIV integrase inhibitors (e.g., HIV-1 integrase inhibitors).

A first embodiment of the present invention is a compound of Formula I, or a pharmaceutically acceptable salt thereof, wherein:

$R^1$ is —$C_{1-6}$ alkyl substituted with $R^J$, wherein $R^J$ is:
  (A) aryl or aryl fused to a 5- or 6-membered heteroaromatic ring containing from 1 to 4 heteroatoms independently selected from N, O and S, wherein the aryl or fused aryl is:
    (a) optionally substituted with from 1 to 5 substituents each of which is independently:
      (1) —$C_{1-6}$ alkyl optionally substituted with —OH, —O—$C_{1-6}$ alkyl, —O—$C_{1-6}$ haloalkyl, —CN, —$NO_2$, —N($R^a$)$R^b$, —C(=O)N($R^a$)$R^b$, —C(=O)$R^a$, —$CO_2R^a$, —S(O)$_n R^a$, —$SO_2$N($R^a$)$R^b$, —N($R^a$)C(=O)$R^b$, —N($R^a$)$CO_2R^b$, —N($R^a$)$SO_2R^b$, —N($R^a$)$SO_2$N($R^a$)$R^b$, —OC(=O)N($R^a$)$R^b$, or —N($R^a$)C(=O)N($R^a$)$R^b$,
      (2) —O—$C_{1-6}$ alkyl,
      (3) —$C_{1-6}$ haloalkyl,
      (4) —O—$C_{1-6}$ haloalkyl,
      (5) —OH,
      (6) halogen,
      (7) —CN,
      (8) —$NO_2$,
      (9) —N($R^a$)$R^b$,
      (10) —C(=O)N($R^a$)$R^b$,
      (11) —C(=O)$R^a$,
      (12) —$CO_2R^a$,
      (13) —$SR^a$,
      (14) —S(=O)$R^a$,
      (15) —$SO_2R^a$,
      (16) —$SO_2$N($R^a$)$R^b$,
      (17) —N($R^a$)$SO_2R^b$,
      (18) —N($R^a$)$SO_2$N($R^a$)$R^b$,
      (19) —N($R^a$)C(=O)$R^b$,
      (20) —N($R^a$)C(=O)—C(=O)N($R^a$)$R^b$, or
      (21) —N($R^a$)$CO_2R^b$, and
    (b) optionally substituted with 1 or 2 substituents each of which is independently:
      (1) phenyl,
      (2) benzyl,
      (3) —HetA,
      (4) —C(=O)—HetA, or
      (5) —HetB;
        wherein each HetA is independently a $C_{4-7}$ azacycloalkyl or a $C_{3-6}$ diazacycloalkyl, either of which is optionally substituted with from 1 to 4 substituents each of which is independently oxo or $C_{1-6}$ alkyl; and
        wherein each HetB is a 5- or 6-membered heteroaromatic ring containing from 1 to 4 heteroatoms independently selected from N, O and S,
        wherein the heteroaromatic ring is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy; or
  (B) a 5- or 6-membered heteroaromatic ring containing from 1 to 4 heteroatoms independently selected from N, O and S; wherein the heteroaromatic ring is
    (i) optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy; and
    (ii) optionally substituted with 1 or 2 substituents each of which is independently aryl or —$C_{1-6}$ alkyl substituted with aryl;

$R^2$ and $R^3$ are each independently —H or —$C_{1-6}$ alkyl;

$R^4$ is:
  (1) —H,
  (2) —$C_{1-6}$ alkyl,
  (3) —$C_{1-6}$ haloalkyl,
  (4) —$C_{1-6}$ alkyl substituted with —OH, —O—$C_{1-6}$ alkyl, —O—$C_{1-6}$ haloalkyl, —CN, —N($R^a$)$R^b$, —C(=O)N($R^a$)$R^b$, —C(=O)$R^a$, —$CO_2R^a$, —C(=O)—N($R^a$)—$C_{1-6}$ alkylene-$OR^b$ with the proviso that the —N($R^a$) moiety and the —$OR^b$ moiety are not both attached to the same carbon of the —$C_{1-6}$ alkylene-moiety, —S(O)$_n R^a$, —$SO_2$N($R^a$)$R^b$, —N($R^a$)C(=O)—$R^b$, —N($R^a$)$CO_2R^b$, —N($R^a$)$SO_2R^b$, —N($R^a$)$SO_2$N($R^a$)$R^b$, —N($R^a$)C(=O)N($R^a$)$R^b$, or —OC(=O)N($R^a$)$R^b$,
  (5) —C(=O)$R^a$,
  (6) —$CO_2R^a$,
  (7) —C(=O)N($R^a$)$R^b$,
  (8) —C(=O)—N($R^a$)—$C_{1-6}$ alkylene-$OR^b$ with the proviso that the —N($R^a$)— moiety and the —$OR^b$ moiety are not both attached to the same carbon of the —$C_{1-6}$ alkylene-moiety,
  (9) —N($R^a$)—C(=O)—$R^b$,
  (10) —N($R^a$)—C(=O)—C(=O)N($R^a$)$R^b$,
  (11) —N($R^a$)$SO_2R^b$,
  (12) —N($R^a$)$SO_2$N($R^a$)$R^b$,
  (13) —N($R^a$)$SO_2$N($R^a$)$R^b$,
  (14) —N($R^a$)C(=O)N($R^a$)$R^b$,
  (15) —OC(=O)N($R^a$)$R^b$,
  (16) —$R^K$,
  (17) —C(=O)—$R^K$,
  (18) —C(=O)N($R^a$)—$R^K$,
  (19) —C(=O)N($R^a$)—$C_{1-6}$ alkylene-$R^K$,
  (20) —$C_{1-6}$ alkyl substituted with —$R^K$,
  (21) —$C_{1-6}$ alkyl substituted with —C(=O)—$R^K$,
  (22) —$C_{1-6}$ alkyl substituted with —C(=O)N($R^a$)—$R^K$, or
  (23) —$C_{1-6}$ alkyl substituted with —C(=O)N($R^a$)—$C_{1-6}$ alkylene-$R^K$;

wherein $R^K$ is
  (i) $C_{3-8}$ cycloalkyl, which is optionally substituted with from 1 to 4 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl,
  (ii) aryl, which is optionally substituted with from 1 to 5 substituents each of which is independently —$C_{1-6}$ alkyl, —$C_{1-6}$ alkylene-OH, —$C_{1-6}$ alkylene-O—$C_{1-6}$ alkyl, —$C_{1-6}$ alkylene-O—$C_{1-6}$ haloalkyl, —$C_{1-6}$ alkylene-N($R^a$)$R^b$, —$C_{1-6}$ alkylene-C(=O)N($R^a$)$R^b$, —$C_{1-6}$ alkylene-C(=O)$R^a$, —$C_{1-6}$ alkylene-$CO_2R^a$, —$C_{1-6}$ alkylene-S(O)$_n R^a$, —O—$C_{1-6}$ alkyl, —$C_{1-6}$ haloalkyl, —O—$C_{1-6}$ haloalkyl, —OH, halogen, —N(R$^a$)R$^b$, —C(=O)N(R$^a$)R$^b$, —C(=O)R$^a$, —CO$_2$R$^a$, —S(O)$_n$R$^a$, or —SO$_2$N(R$^a$)R$^b$;
  (iii) HetK, which is a 4- to 7-membered saturated heterocyclic ring containing at least one carbon atom and from 1 to 4 heteroatoms independently selected from N, O and S, wherein the heterocyclic ring is:
    (a) optionally substituted with from 1 to 6 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; and
    (b) optionally substituted with aryl or HetC;
      wherein HetC is a 5- or 6-membered heteroaromatic ring containing from 1 to 4 heteroatoms independently selected from N, O and S, wherein the heteroaromatic ring is optionally fused with a benzene ring, and the optionally fused heteroaromatic ring is optionally substituted with from 1 to 4 substituents each of which is independently —C$_{1-6}$ alkyl, —C$_{1-6}$ haloalkyl, —O—C$_{1-6}$ alkyl, —O—C$_{1-6}$ haloalkyl, or hydroxy; or
  (iv) —HetL, which is a 5- or 6-membered heteroaromatic ring containing from 1 to 4 heteroatoms independently selected from N, O and S, wherein the heteroaromatic ring is optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or hydroxy;
R$^5$ is:
  (1) —H,
  (2) —C$_{1-6}$ alkyl,
  (3) —C$_{3-8}$ cycloalkyl optionally substituted with from 1 to 4 substituents each of which is independently halogen, —OH, —C$_{1-6}$ alkyl, —C$_{1-6}$ haloalkyl, —O—C$_{1-6}$ alkyl, or —O—C$_{1-6}$ haloalkyl,
  (4) —C$_{1-6}$ alkyl substituted with C$_{3-8}$ cycloalkyl, wherein the cycloalkyl is optionally substituted with from 1 to 4 substituents each of which is independently halogen, —OH, —C$_{1-6}$ alkyl, —C$_{1-6}$ haloalkyl, —O—C$_{1-6}$ alkyl, or —O—C$_{1-6}$ haloalkyl,
  (5) —C$_{1-6}$ alkyl substituted with aryl, wherein the aryl is optionally substituted with from 1 to 5 substituents each of which is independently —C$_{1-6}$ alkyl, —C$_{1-6}$ alkylene-OH, —C$_{1-6}$ alkylene-O—C$_{1-6}$ alkyl, —C$_{1-6}$ alkylene-O—C$_{1-6}$ haloalkyl, —C$_{1-6}$ alkylene-N(R$^a$)R$^b$, —C$_{1-6}$ alkylene-C(=O)N(R$^a$)R$^b$, —C$_{1-6}$ alkylene-C(=O)R$^a$, —C$_{1-6}$ alkylene-CO$_2$R$^a$, —C$_{1-6}$ alkylene-S(O)$_n$R$^a$, —O—C$_{1-6}$ alkyl, —C$_{1-6}$ haloalkyl, —O—C$_{1-6}$ haloalkyl, —OH, halogen, —N(R$^a$)R$^b$, —C(=O)N(R$^a$)R$^b$, —C(=O)R$^a$, —CO$_2$R$^a$, —S(O)$_n$R$^a$, or —SO$_2$N(R$^a$)R$^b$;
  (6) —C$_{1-6}$ alkyl substituted with HetD, wherein HetD is
    (i) a 4- to 7-membered saturated heterocyclic ring containing at least one carbon atom and from 1 to 4 heteroatoms independently selected from N, O and S, wherein the heterocyclic ring is optionally substituted with from 1 to 5 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; or
    (ii) a 5- or 6-membered heteroaromatic ring containing from 1 to 4 heteroatoms independently selected from N, O and S, wherein the heteroaromatic ring is optionally substituted with from 1 to 4 substituents each of which is independently —C$_{1-6}$ alkyl, —C$_{1-6}$ haloalkyl, —O—C$_{1-6}$ alkyl, —O—C$_{1-6}$ haloalkyl, or hydroxy;
each aryl is independently phenyl, naphthyl, or indenyl;

and all other variables are as originally defined (i.e., as defined in the Summary of the Invention).

A second embodiment of the present invention is a compound of Formula I, or a pharmaceutically acceptable salt thereof, wherein R$^1$ is —C$_{1-6}$ alkyl substituted with R$^J$; and all other variables are as originally defined (i.e., as defined in the Summary of the Invention) or as defined in the first embodiment. In an aspect of this embodiment, R$^1$ is —CH$_2$—R$^J$.

A third embodiment of the present invention is a compound of Formula I, or a pharmaceutically acceptable salt thereof, wherein R$^1$ is R$^J$ or —CH$_2$—R$^J$ (e.g., R$^1$ is —CH$_2$—R$^J$), wherein R$^J$ is phenyl, quinolinyl, isoquinolinyl, cinnolinyl, or quinazolinyl, any of which is:
  (a) optionally substituted with from 1 to 4 substituents each of which is independently:
    (1) —C$_{1-4}$ alkyl,
    (2) —O—C$_{1-4}$ alkyl,
    (3) —C$_{1-4}$ haloalkyl,
    (4) —O—C$_{1-4}$ haloalkyl,
    (5) halogen,
    (6) —CN,
    (7) —N(R$^a$)R$^b$,
    (8) —C(=O)N(R$^a$)R$^b$,
    (9) —S(=O)R$^a$,
    (10) —SO$_2$R$^a$,
    (11) —N(R$^a$)SO$_2$R$^b$,
    (12) —N(R$^a$)SO$_2$N(R$^a$)R$^b$,
    (13) —N(R$^a$)C(=O)R$^b$, or
    (14) —N(R$^a$)C(=O)—C(=O)N(R$^a$)R$^b$, and
  (b) optionally substituted with 1 or 2 substituents each of which is independently:
    (1) —HetA, or
    (2) —C(=O)—HetA;
      wherein each HetA is independently a C$_{4-7}$ azacycloalkyl or a C$_{3-6}$ diazacycloalkyl, either of which is optionally substituted with 1 or 2 substituents each of which is independently oxo or C$_{1-4}$ alkyl; and with the proviso that when HetA is attached to the rest of the compound via the —C(=O)— moiety, the HetA is attached to the —C(=O)— via a ring N atom;

and all other variables are as originally defined or as defined in the first embodiment.

A fourth embodiment of the present invention is a compound of Formula I, or a pharmaceutically acceptable salt thereof, wherein R$^1$ is R$^J$ or —CH$_2$—R$^J$ (e.g., R$^1$ is —CH$_2$—R$^J$), wherein R$^J$ is phenyl optionally substituted with from 1 to 3 substituents each of which is independently:
  (1) —C$_{1-4}$ alkyl,
  (2) —C$_{1-4}$ haloalkyl,
  (3) —O—C$_{1-4}$ alkyl,
  (4) halogen,
  (5) —CN,
  (6) —C(=O)N(R$^a$)R$^b$, or
  (7) —SO$_2$R$^a$;

and all other variables are as originally defined or as defined in the first embodiment.

A fifth embodiment of the present invention is a compound of Formula I, or a pharmaceutically acceptable salt thereof, wherein R$^1$ is:

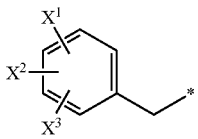

the asterisk * denotes the point of attachment of $R^1$ to the rest of the compound; $X^1$ and $X^2$ are each independently:
(1) —H,
(2) —$C_{1-6}$ alkyl,
(3) —OH
(4) —O—$C_{1-6}$ alkyl,
(5) —$C_{1-6}$ haloalkyl,
(6) —O—$C_{1-6}$ haloalkyl,
(7) halogen,
(8) —CN,
(9) —N($R^a$)$R^b$,
(10) —C(=O)N($R^a$)$R^b$,
(11) —S$R^a$,
(12) —S(O)$R^a$,
(13) SO$_2R^a$,
(14) —N($R^a$)SO$_2R^b$,
(15) —N($R^a$)SO$_2$N($R^a$)$R^b$,
(16) —N($R^a$)C(=O)$R^b$,
(17) —N($R^a$)C(=O)—C(=O)N($R^a$)$R^b$,
(18) —HetA,
(19) —C(=O)—HetA, or
(20) HetB;
  wherein each HetA is independently a $C_{4-5}$ azacycloalkyl or a $C_{3-4}$ diazacycloalkyl, either of which is optionally substituted with 1 or 2 substituents each of which is independently oxo or $C_{1-6}$ alkyl; and with the proviso that when HetA is attached to the rest of the compound via the —C(=O)— moiety, the HetA is attached to the —C(=O)— via a ring N atom; and
  each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy;
or alternatively $X^1$ and $X^2$ are respectively located on adjacent carbons in the phenyl ring and together form methylenedioxy or ethylenedioxy;
$X^3$ is:
(1) —H,
(2) —$C_{1-6}$ alkyl,
(3) —O—$C_{1-6}$ alkyl,
(4) —$C_{1-6}$ haloalkyl,
(5) —O—$C_{1-6}$ haloalkyl, or
(6) halogen;
and all other variables are as originally defined or as defined in the first embodiment.

An aspect of the fifth embodiment is a compound of Formula I, or a pharmaceutically acceptable salt thereof, wherein $X^1$ and $X^2$ in the definition of $R^1$ are each independently: (1) —H, (2) —$C_{1-4}$ alkyl, (3) —$C_{1-4}$ haloalkyl, (4) —OH, (5) —O—$C_{1-4}$ alkyl, (6) halogen, (7) —CN, (8) —C(=O)NH$_2$, (9) —C(=O)NH(—$C_{1-4}$ alkyl), (10) —C(=O)N(—$C_{1-4}$ alkyl)$_2$, or (11) —SO$_2$—$C_{1-4}$ alkyl; or alternatively $X^1$ and $X^2$ are respectively located on adjacent carbons in the phenyl ring and together form methylenedioxy or ethylenedioxy; $X^3$ is —H, halogen, —$C_{1-4}$ alkyl, or —O—$C_{1-4}$ alkyl; and all other variables are as defined in the fifth embodiment.

A sixth embodiment of the present invention is a compound of Formula I, or a pharmaceutically acceptable salt thereof, wherein $R^1$ is:

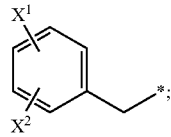

the asterisk * denotes the point of attachment of $R^1$ to the rest of the compound; $X^1$ and $X^2$ are each independently as defined in the fifth embodiment, except that neither $X^1$ nor $X^2$ is —OH; and all other variables are as originally defined or as defined in the first embodiment.

An aspect of the sixth embodiment is a compound of Formula I, or a pharmaceutically acceptable salt thereof, wherein $X^1$ and $X^2$ in the definition of $R^1$ are each independently: (1) —H, (2) —$C_{1-4}$ alkyl, (3) —$C_{1-4}$ haloalkyl, (4) —O—$C_{1-4}$ alkyl, (5) halogen, (6) —CN, (7) —C(=O)NH$_2$, (8) —C(=O)NH(—$C_{1-4}$ alkyl), (9) —C(=O)N(—$C_{1-4}$ alkyl)$_2$, or (10) —SO$_2$—$C_{1-4}$ alkyl; and all other variables are as defined in the sixth embodiment.

Another aspect of the sixth embodiment is a compound of Formula I, or a pharmaceutically acceptable salt thereof, wherein $X^1$ in the definition of $R^1$ is (1) —H, (2) bromo, (3) chloro, (4) fluoro, or (5) methoxy; and $X^2$ in the definition of $R^1$ is (1) —H, (2) bromo, (3) chloro, (4) fluoro, (5) methyl, (6) methoxy, (7) —CF$_3$, or (8) —OCF$_3$.

A seventh embodiment of the present invention is a compound of Formula I, or a pharmaceutically acceptable salt thereof, wherein $R^1$ is:

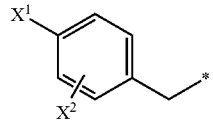

the asterisk * denotes the point of attachment of $R^1$ to the rest of the compound; $X^1$ is: (1) —H, (2) bromo, (3) chloro, (4) fluoro, or (5) methoxy; $X^2$ is: (1) —H, (2) bromo, (3) chloro, (4) fluoro, (5) methoxy, (6) —$C_{1-4}$ alkyl, (7) —CF$_3$, (8) —OCF$_3$, (9) —CN, or (10) —SO$_2$($C_{1-4}$ alkyl); and all other variables are as originally defined, or as defined in the first embodiment.

An aspect of the seventh embodiment is a compound of Formula I, or a pharmaceutically acceptable salt thereof, wherein $X^1$ in the definition of $R^1$ is (1) —H, (2) bromo, (3) chloro, (4) fluoro, or (5) methoxy; and $X^2$ in the definition of $R^1$ is (1) —H, (2) bromo, (3) chloro, (4) fluoro, (5) methyl, (6) methoxy, (7) —CF$_3$, or (8) —OCF$_3$.

An eighth embodiment of the present invention is a compound of Formula I, or a pharmaceutically acceptable salt thereof, wherein $R^1$ is CH$_2$—$R^J$; $R^J$ is 4-fluorophenyl or 3-chloro-4-fluorophenyl; and all other variables are as originally defined or as defined in the first embodiment.

A ninth embodiment of the present invention is a compound of Formula I, or a pharmaceutically acceptable salt thereof, wherein $R^1$ is $CH_2—R^J$; $R^J$ is 4-fluorophenyl; and all other variables are as originally defined or as defined in the first embodiment.

A tenth embodiment of the present invention is a compound of Formula I, or a pharmaceutically acceptable salt thereof, wherein $R^1$ is $CH_2—R^J$; $R^J$ is 3-chloro-4-fluorophenyl; and all other variables are as originally defined or as defined in the first embodiment.

An eleventh embodiment of the present invention is a compound of Formula I, or a pharmaceutically acceptable salt thereof, wherein $R^4$ is:
(1) —H,
(2) —$C_{1-6}$ alkyl,
(3) —$C_{1-6}$ haloalkyl,
(4) —$C_{1-6}$ alkyl substituted with —OH, —O—$C_{1-6}$ alkyl, —O—$C_{1-6}$ haloalkyl, —CN, —N($R^a$)$R^b$, —C(=O)N($R^a$)$R^b$, —C(=O)$R^a$, —$CO_2R^a$, —C(=O)—N($R^a$)—$(CH_2)_{2-3}$—$OR^b$, —S(O)$_n R^a$, —$SO_2N(R^a)R^b$, —N($R^a$)C(=O)—$R^b$, —N($R^a$)$CO_2R^b$, —N($R^a$)$SO_2R^b$, —N($R^a$)$SO_2N(R^a)R^b$, —N($R^a$)C(=O)N($R^a$)$R^b$, or —OC(=O)N($R^a$)$R^b$,
(5) —C(=O)$R^a$,
(6) —$CO_2R^a$,
(7) —C(=O)N($R^a$)$R^b$,
(8) —C(=O)—N($R^a$)—$(CH_2)_{2-3}$—$OR^b$,
(9) —N($R^a$)—C(=O)—$R^b$,
(10) —N($R^a$)—C(=O)—C(=O)N($R^a$)$R^b$,
(11) —N($R^a$)$SO_2R^b$,
(12) —N($R^a$)$SO_2N(R^a)R^b$,
(13) —$R^K$,
(14) —C(=O)—$R^K$,
(15) —C(=O)N($R^a$)—$R^K$,
(16) —C(=O)N($R^a$)—$C_{1-6}$ alkylene-$R^K$,
(17) —$(CH_2)_{1-3}$—$R^K$,
(18) —$(CH_2)_{1-3}$—C(=O)—$R^K$,
(19) —$(CH_2)_{1-3}$—C(=O)N($R^a$)—$R^K$, or
(20) —$(CH_2)_{1-3}$—C(=O)N($R^a$)—$C_{1-6}$ alkylene-$R^K$;

and all other variables are as originally defined or as defined in any one of the preceding embodiments.

A twelfth embodiment of the present invention is a compound of Formula I, or a pharmaceutically acceptable salt thereof, wherein $R^4$ is: (1) —H, (2) —$C_{1-6}$ alkyl, (3) —$C_{1-6}$ fluoroalkyl, (4) —$CO_2R^a$, (5) —C(=O)N($R^a$)$R^b$, (6) —C(=O)—N($R^a$)—$(CH_2)_{2-3}$—$OR^b$, (7) —N($R^a$)—C(=O)$R^b$, (8) —N($R^a$)$SO_2R^b$, (9) —N($R^a$)$SO_2N(R^a)R^b$, (10) —$R^K$, (11) —C(=O)—$R^K$, (12) —C(=O)N($R^a$)—$(CH_2)_{0-2}$—$R^K$ (13) —C(=O)N($R^a$)$R^c$, or (14) halogen; and all other variables are as originally defined or as defined in any one of the preceding embodiments.

A thirteenth embodiment of the present invention is a compound of Formula I, or a pharmaceutically acceptable salt thereof, wherein $R^4$ is: (1) —H, (2) —$C_{1-6}$ alkyl, (3) —$C_{1-6}$ fluoroalkyl, (4) —$CO_2R^a$, (5) —C(=O)N($R^a$)$R^b$, (6) —C(=O)—N($R^a$)—$(CH_2)_{2-3}$—$OR^b$, (7) —N($R^a$)—C(=O)—$R^b$, (8) —N($R^a$)$SO_2R^b$, (9) —N($R^a$)$SO_2N(R^a)R^b$, (10) —$R^K$, (11) —C(=O)—$R^K$, or (12) —C(=O)N($R^a$)—$(CH_2)_{0-2}$—$R^K$; and all other variables are as originally defined or as defined in any one of the preceding embodiments.

An aspect of the eleventh, twelfth, and thirteenth embodiment is a compound of Formula I, or a pharmaceutically acceptable thereof, wherein $R^K$ is:
(i) $C_{3-6}$ cycloalkyl, which is optionally substituted with from 1 to 4 substituents each of which is independently halogen, —OH, —$C_{1-6}$ alkyl, —$C_{1-6}$ haloalkyl, —O—$C_{1-6}$ alkyl, or —O—$C_{1-6}$ haloalkyl, (ii) phenyl, which is optionally substituted with from 1 to 5 substituents each of which is independently —$C_{1-6}$ alkyl, —$C_{1-6}$ alkylene-OH, —$C_{1-6}$ alkylene-O—$C_{1-6}$ alkyl, —$C_{1-6}$ alkylene-O—$C_{1-6}$ haloalkyl, —$C_{1-6}$ alkylene-N($R^a$)$R^b$, —$C_{1-6}$ alkylene-C(=O)N($R^a$)$R^b$, —$C_{1-6}$ alkylene-C(=O)$R^a$, —$C_{1-6}$ alkylene-$CO_2R^a$, —$C_{1-6}$ alkylene-S(O)$_n R^a$, —O—$C_{1-6}$ alkyl, —$C_{1-6}$ haloalkyl, —O—$C_{1-6}$ haloalkyl, —OH, halogen, —N($R^a$)$R^b$, —C(=O)N($R^a$)$R^b$, —C(=O)$R^a$, —$CO_2R^a$, —S(O)$_n R^a$, or —$SO_2N(R^a)R^b$;

(iii) HetK, which is a 5- or 6-membered saturated heterocyclic ring containing at least one carbon atom and a total of from 1 to 4 heteroatoms independently selected from 1 to 4 N atoms, from 0 to 2 O atoms, and from 0 to 2 S atoms, wherein the heterocyclic ring is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or oxo; or (iv) —HetL, which is a 5- or 6-membered heteroaromatic ring containing a total of from 1 to 4 heteroatoms independently selected from 1 to 4 N atoms, from 0 to 2 O atoms, and from 0 to 2 S atoms, wherein the heteroaromatic ring is optionally substituted with from 1 to 3 substituents each of which is independently halogen, —$C_{1-6}$ alkyl, —$C_{1-6}$ haloalkyl, —O—$C_{1-6}$ alkyl, or —O—$C_{1-6}$ haloalkyl;

and all other variables are as defined in the eleventh, twelfth, or thirteenth embodiment.

A fourteenth embodiment of the present invention is a compound of Formula I, or a pharmaceutically acceptable salt thereof, wherein $R^4$ is: (1) —H, (2) —$C_{1-4}$ alkyl, (3) —$CO_2H$, (4) —C(=O)—O—$C_{1-4}$ alkyl, (5) —C(=O)$NH_2$, (6) —C(=O)NH—$C_{1-4}$ alkyl, (7) —C(=O)N($C_{1-4}$ alkyl)$_2$, (8) —C(=O)—NH—$(CH_2)_{2-3}$—O—$C_{1-4}$ alkyl, (9) —C(=O)—N($C_{1-4}$ alkyl)-$(CH_2)_{2-3}$—O—$C_{1-4}$ alkyl, (10) —HetK, (11) —C(=O)—HetK, (12) —C(=O)NH—$(CH_2)_{0-1}$—($C_{3-6}$ cycloalkyl), (13) —C(=O)N($C_{1-4}$ alkyl)-$(CH_2)_{0-1}$—($C_{3-6}$ cycloalkyl) (14) —C(=O)NH—$CH_2$-phenyl, or (15) —C(=O)N($C_{1-4}$ alkyl)-$CH_2$-phenyl; wherein:

HetK is a 5- or 6-membered saturated heterocyclic ring containing at least one carbon atom and a total of from 1 to 4 heteroatoms independently selected from 1 to 4 N atoms, from 0 to 2 O atoms, and from 0 to 2 S atoms, wherein the heterocyclic ring is optionally substituted with from 1 to 3 substituents each of which is independently —$C_{1-4}$ alkyl or oxo; and with the proviso that when HetK is attached to the rest of the compound via the —C(=O)— moiety, the HetK is attached to the —C(=O)— via a ring N atom;

the cycloalkyl in (12) or (13) is optionally substituted with from 1 to 4 substituents each of which is independently halogen, —$C_{1-4}$ alkyl, —$CF_3$, —O—$C_{1-4}$ alkyl, or —$OCF_3$; and the phenyl in (14) or (15) is optionally substituted with from 1 to 4 substituents each of which is independently halogen, —$C_{1-4}$ alkyl, —O—$C_{1-4}$ alkyl, —$CF_3$, or —$OCF_3$;

and all other variables are as originally defined or as defined in any one of the preceding embodiments.

A fifteenth embodiment of the present invention is a compound of Formula I, or a pharmaceutically acceptable salt thereof, wherein $R^4$ is: (1) —$CO_2R^a$, (2) —C(=O)N($R^a$)$R^b$, (3) —C(=O)—N($R^a$)—$(CH_2)_{2-3}$—$OR^b$, (4) —N($R^a$)C(=O)$R^b$, (5) —N($R^a$)$SO_2R^b$, (6) —HetK, (7) —C(=O)—HetK, (8) —C(=O)N($R^a$)—$(CH_2)_{0-1}$—($C_{3-6}$ cycloalkyl), wherein the cycloalkyl is optionally substituted with from 1 to 4 substituents each of which is independently halogen, —C$_{1-6}$ alkyl, —CF$_3$, —O—C$_{1-6}$ alkyl, or —OCF$_3$, or (9) —C(=O)N(R$^a$)—CH$_2$-phenyl, wherein the phenyl is optionally substituted with from 1 to 4 substituents each of which is independently —C$_{1-6}$ alkyl, —O—C$_{1-6}$ alkyl, —CF$_3$, —OCF$_3$, or halogen; and all other variables are as originally defined or as defined in any one of the preceding embodiments.

An aspect of the fifteenth embodiment is a compound of Formula I, or a pharmaceutically acceptable salt thereof, wherein HetK is a 5- or 6-membered saturated heterocyclic ring containing at least one carbon atom and a total of from 1 to 4 heteroatoms independently selected from 1 to 4 N atoms, from 0 to 2 O atoms, and from 0 to 2 S atoms, wherein the heterocyclic ring is optionally substituted with from 1 to 4 substituents each of which is independently —C$_{1-6}$ alkyl or oxo; and with the proviso that when HetK is attached to the rest of the compound via the —C(=O)— moiety, the HetK is attached to the —C(=O)— via a ring N atom; and all other variables are as defined in the fifteenth embodiment.

Another aspect of the fifteenth embodiment is a compound of Formula I, or a pharmaceutically acceptable salt thereof, wherein:

(a) when HetK is directly attached to the rest of the compound, HetK is:

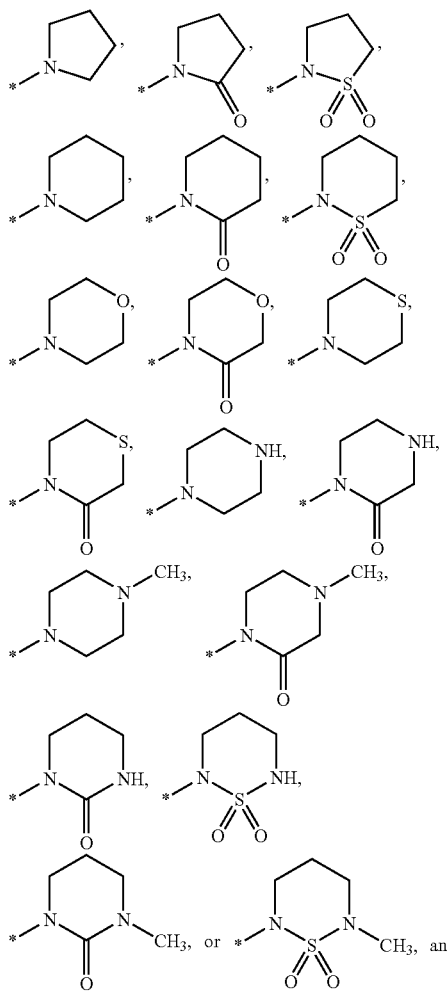

(b) when HetK is attached to the rest of the compound via the —C(=O)— moiety, HetK is:

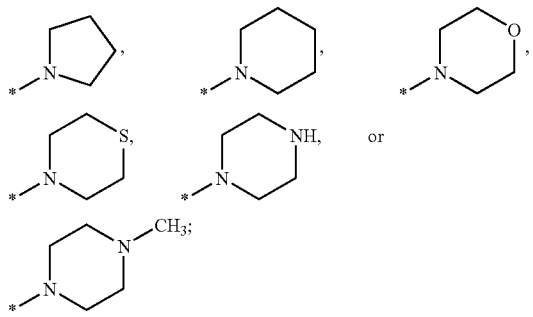

wherein the asterisk * denotes the point of attachment to the rest of the compound; and all other variables are as defined in the fifteenth embodiment.

A sixteenth embodiment of the present invention is a compound of Formula I, or a pharmaceutically acceptable salt thereof, wherein R$^4$ is: (1) —CO$_2$H, (2) —C(=O)—O—C$_{1-4}$ alkyl, (3) —C(=O)NH$_2$, (4) —C(=O)NH—C$_{1-4}$ alkyl, (5) —C(=O)N(C$_{1-4}$ alkyl)$_2$, (6) —C(=O)—NH—(CH$_2$)$_{2-3}$—O—C$_{1-4}$ alkyl, (7) —C(=O)—N(C$_{1-4}$ alkyl)-(CH$_2$)$_{2-3}$—O—C$_{1-4}$ alkyl, (8) —NHC(=O)—C$_{1-4}$ alkyl, (9) —N(C$_{1-4}$ alkyl)C(=O)—C$_{1-4}$ alkyl, (10) —NHSO$_2$—C$_{1-4}$ alkyl, (11) —N(C$_{1-4}$ alkyl)SO$_2$—C$_{1-4}$ alkyl, (12) —C(=O)—HetK, wherein HetK is:

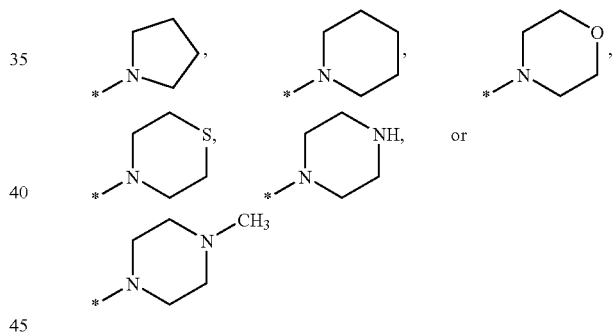

and wherein the asterisk * denotes the point of attachment to the rest of the compound, (13) —C(=O)NH—(CH$_2$)$_{0-1}$—(C$_{3-6}$ cycloalkyl), (14) —C(=O)N(C$_{1-4}$ alkyl)-(CH$_2$)$_{0-1}$—(C$_{3-6}$ cycloalkyl), (15) —C(=)NH—CH$_2$-phenyl, or (16) —C(=O)N(C$_{1-4}$ alkyl)-CH$_2$-phenyl; and all other variables are as originally defined or as defined in any one of the preceding embodiments.

A seventeenth embodiment of the present invention is identical to the sixteenth embodiment, except that HetK is:

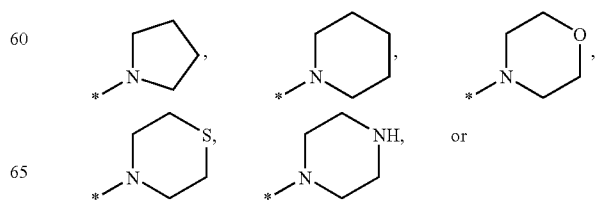

-continued

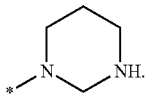

In an aspect of this embodiment, HetK is:

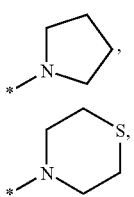 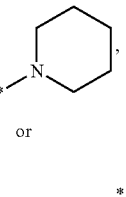 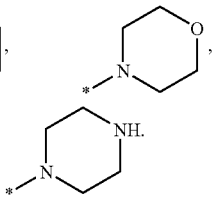

An eighteenth embodiment of the present invention is a compound of Formula I, or a pharmaceutically acceptable salt thereof, wherein $R^4$ is: (1) —C(=O)—O—$C_{1-3}$ alkyl, (2) —C(=O)NH—$C_{1-3}$ alkyl, (3) —C(=O)N($C_{1-3}$ alkyl)$_2$, (4) —C(=O)—N($C_{1-3}$ alkyl)-(CH$_2$)$_2$—O—$C_{1-3}$ alkyl, (5) —N($C_{1-3}$ alkyl)C(=O)—$C_{1-3}$ alkyl, (6) —N($C_{1-3}$ alkyl)SO$_2$—$C_{1-3}$ alkyl, (7) —C(=O)—HetK, wherein HetK is:

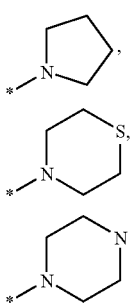 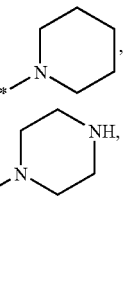 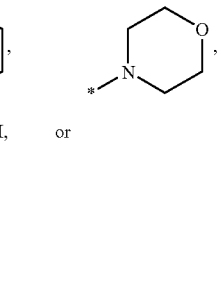

and wherein the asterisk * denotes the point of attachment to the rest of the compound, (8) —C(=O)NH—(CH$_2$)0-1-(cyclopropyl), (9) —C(=O)NH—(CH2)0-1-(cyclobutyl), (10) —C(=O)N(C1-3 alkyl)-(CH$_2$)$_{0-1}$-cyclopropyl, (11) —C(=O)N($C_{1-3}$ alkyl)-(CH$_2$)$_{0-1}$-cyclobutyl, (12) —C(=O)NH—CH$_2$-phenyl, or (13) —C(=O)N($C_{1-3}$ alkyl)-CH$_2$-phenyl; and all other variables are as originally defined or as defined in any one of the preceding embodiments.

A nineteenth embodiment of the present invention is identical to the eighteenth embodiment, except that HetK is:

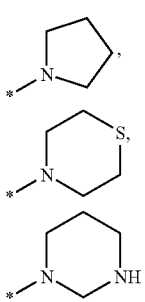 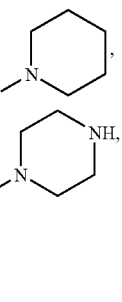 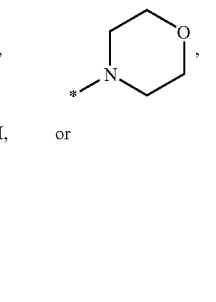

In an aspect of this embodiment, Hetk is:

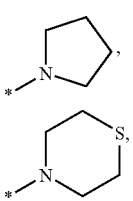 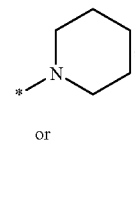 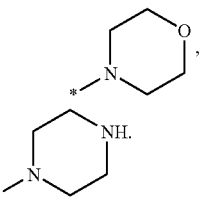

A twentieth embodiment of the present invention is a compound of Formula I, or a pharmaceutically acceptable salt thereof, wherein $R^5$ is:
(1) —H,
(2) —$C_{1-4}$ alkyl,
(3) —$C_{3-6}$ cycloalkyl optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
(4) —(CH$_2$)$_{1-2}$—$C_{3-6}$ cycloalkyl, wherein the cycloalkyl is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
(5) —(CH$_2$)$_{1-2}$-phenyl or —CH(CH$_3$)-phenyl, wherein in either case the phenyl is optionally substituted with from 1 to 4 substituents each of which is independently halogen, —$C_{1-4}$ alkyl, —$C_{1-4}$ alkylene-O—$C_{1-4}$ alkyl, —$C_{1-4}$ haloalkyl, or —O—$C_{1-4}$ haloalkyl,
(6) —(CH$_2$)$_{1-2}$—HetD or —CH(CH$_3$)—HetD, wherein in either case HetD is:
  (i) a 4- to 7-membered saturated heterocyclic ring containing a total of from 1 to 3 heteroatoms independently selected from 1 to 2 N atoms, from zero to 1 O atom and from zero to 1 S atom, wherein heterocyclic ring is attached to the rest of the molecule via a ring N atom, and the heterocyclic ring is optionally substituted with from 1 to 4 substituents each of which is independently —$C_{1-4}$ alkyl, —$C_{1-4}$ haloalkyl, —O—$C_{1-4}$ alkyl, —O—$C_{1-4}$ haloalkyl, oxo, —C(=O)N(R$^a$)R$^b$, —C(=O)R$^a$, —CO$_2$R$^a$, —SO$_2$R$^a$, or —SO$_2$N(R$^a$)R$^b$, or
  (ii) a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-4}$ alkyl, —$C_{1-4}$ haloalkyl, —O—$C_{1-4}$ alkyl, —O—$C_{1-4}$ haloalkyl, or hydroxyl,
(7) phenyl which is optionally substituted with from 1 to 4 substituents each of which is independently —$C_{1-4}$ alkyl, —$C_{1-4}$ haloalkyl, —O—$C_{1-4}$ haloalkyl, —OH, halogen, —CN, —NO$_2$, —N(R$^a$)R$^b$, —N(R$^a$)C(=O)R$^b$, —N(R$^a$)C(=O)—$C_{1-4}$ haloalkyl, —N(R$^a$)C(=O)N(R$^a$)R$^b$, —N(R$^a$)CO$_2$R$^b$, —N(R$^a$)S(O)$_n$R$^b$, —C(=O)N(R$^d$)R$^e$, —C(=O)R$^a$, —CO$_2$R$^a$, —SO$_2$R$^a$, or —SO$_2$N(R$^d$)R$^e$,
(8) a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-4}$ alkyl, —$C_{1-4}$ haloalkyl, —O—$C_{1-4}$ alkyl, —O—$C_{1-4}$ haloalkyl, or hydroxyl,
(9) $C_{1-4}$ alkyl substituted with —O—$C_{1-4}$ alkyl, —CN, —N(R$^a$)R$^b$, —C(=O)N(R$^a$)R$^b$, —C(=O)R$^a$, —$CO_2R^a$, —$SO_2R^a$, —$SO_2N(R^a)R^b$, —$N(R^a)C(=O)$—$R^b$, —$N(R^a)CO_2R^b$, or —$N(R^a)SO_2R^b$, or

(10) —$C_{1-4}$ haloalkyl;

and all other variables are as originally defined or as defined in any one of the preceding embodiments.

A twenty-first embodiment of the present invention is a compound of Formula I, or a pharmaceutically acceptable salt thereof, wherein $R^5$ is:

(1) —H,
(2) —$C_{1-4}$ alkyl,
(3) —$C_{3-6}$ cycloalkyl optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
(4) —$(CH_2)_{1-2}$—$C_{3-6}$ cycloalkyl, wherein the cycloalkyl is optionally substituted with from 1 to 3 substituents each of which is independently halogen, —$C_{1-4}$ alkyl, —$C_{1-4}$ haloalkyl, —O—$C_{1-4}$ alkyl, or —O—$C_{1-4}$ haloalkyl,
(5) —$(CH_2)_{1-2}$-phenyl, wherein the phenyl is optionally substituted with from 1 to 4 substituents each of which is independently halogen, —$C_{1-4}$ alkyl, —$C_{1-4}$ alkylene-O—$C_{1-4}$ alkyl, —$C_{1-4}$ haloalkyl, or —O—$C_{1-4}$ haloalkyl, or
(6) —$(CH_2)_{1-2}$—HetD;

and all other variables are as originally defined or as defined in any one of the preceding embodiments.

An aspect of the twenty-first embodiment is a compound of Formula I, or a pharmaceutically acceptable salt thereof, wherein: HetD is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-4}$ alkyl, —$C_{1-4}$ haloalkyl, —O—$C_{1-4}$ alkyl, —O—$C_{1-4}$ haloalkyl, or hydroxy; and all other variables are as defined in the twenty-first embodiment. In a feature of this aspect, all other variables are as defined in the fifteenth embodiment (or an aspect thereof).

A twenty-second embodiment of the present invention is a compound of Formula I, or a pharmaceutically acceptable salt thereof, wherein $R^5$ is: (1) —H, (2) —$C_{1-4}$ alkyl, (3) —$C_{3-6}$ cycloalkyl, (4) —$CH_2$—$C_{3-6}$ cycloalkyl, or (5) —$CH_2$-phenyl; and all other variables are as originally defined or as defined in any one of the preceding embodiments.

A twenty-third embodiment of the present invention is a compound of Formula I, or a pharmaceutically acceptable salt thereof, wherein $R^5$ is: (1) —H, (2) —$C_{1-4}$ alkyl, (3) cyclopropyl, (4) cyclobutyl, (5) —$CH_2$-cyclopropyl, (6) —$CH_2$-cyclobutyl, or (5) —$CH_2$-phenyl; and all other variables are as originally defined or as defined in any one of the preceding embodiments.

A twenty-fourth embodiment of the present invention is a compound of Formula I, or a pharmaceutically acceptable salt thereof, wherein $R^5$ is —H or —$C_{1-4}$ alkyl; and all other variables are as originally defined or as defined in any one of the preceding embodiments. In an aspect of this embodiment, $R^5$ is —$C_{1-4}$ alkyl. In other aspect of this embodiment, $R^5$ is methyl, isopropyl, or isobutyl.

A twenty-fifth embodiment of the present invention is a compound of Formula I, or a pharmaceutically acceptable salt thereof, wherein $R^5$ is —H; and all other variables are as originally defined or as defined in any one of the preceding embodiments.

A twenty-sixth embodiment of the present invention is a compound of Formula I, or a pharmaceutically acceptable salt thereof, wherein $R^2$ and $R^3$ are each independently —H or —$C_{1-6}$ alkyl; and all other variables are as originally defined or as defined in any one of the preceding embodiments. In an aspect of this embodiment, $R^2$ and $R^3$ are each independently —H or —$C_{1-4}$ alkyl. In another aspect of this embodiment, $R^2$ and $R^3$ are both —H.

A twenty-seventh embodiment of the present invention is a compound of Formula I, wherein each $R^a$ and $R^b$ is independently H or $C_{1-3}$ alkyl; and all other variables are as originally defined or as defined in any one of the preceding embodiments.

A twenty-eighth embodiment of the present invention is a compound of Formula I, wherein each $R^a$ and $R^b$ is independently H or methyl; and all other variables are as originally defined or as defined in any one of the preceding embodiments.

A twenty-ninth embodiment of the present invention is a compound of Formula I, wherein bond "$\underset{a}{-----}$"

in the ring is a single bond; and all other variables are as originally defined or as defined in any one of the preceding embodiments.

A first class of the present invention includes compounds of Formula II, and pharmaceutically acceptable salts thereof:

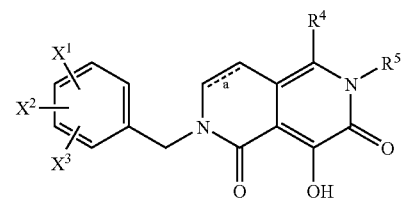

(II)

wherein:
bond

"$\underset{a}{-----}$"

in the ring is a single bond or a double bond (e.g., is a single bond);
$X^1$ and $X^2$ are each independently:
(1) —H,
(2) —$C_{1-6}$ alkyl,
(3) —OH
(4) —O—$C_{1-6}$ alkyl,
(5) —$C_{1-6}$ haloalkyl,
(6) —O—$C_{1-6}$ haloalkyl,
(7) halogen,
(8) —CN,
(9) —$N(R^a)R^b$,
(10) —$C(=O)N(R^a)R^b$,
(11) —$SR^a$,
(12) —$S(O)R^a$,
(13) $SO_2R^a$,
(14) —$N(R^a)SO_2R^b$,
(15) —$N(R^a)SO_2N(R^a)R^b$,
(16) —$N(R^a)C(=O)R^b$,
(17) —$N(R^a)C(=O)$—$C(=O)N(R^a)R^b$,
(18) —HetA,

(19) —C(=O)—HetA, or
(20) HetB;
  wherein each HetA is independently a $C_{4-5}$ azacycloalkyl or a $C_{3-4}$ diazacycloalkyl, either of which is optionally substituted with 1 or 2 substituents each of which is independently oxo or $C_{1-6}$ alkyl; and with the proviso that when HetA is attached to the rest of the compound via the —C(=O)— moiety, the HetA is attached to the —C(=O)— via a ring N atom; and
  each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, —$C_{1-6}$ alkyl, —$C_{1-6}$ haloalkyl, —O—$C_{1-6}$ alkyl, —O—$C_{1-6}$ haloalkyl, or hydroxy;

or alternatively $X^1$ and $X^2$ are respectively located on adjacent carbons in the phenyl ring and together form methylenedioxy or ethylenedioxy;

$X^3$ is:
  (1) —H,
  (2) —$C_{1-6}$ alkyl,
  (3) —O—$C_{1-6}$ alkyl,
  (4) —$C_{1-6}$ haloalkyl,
  (5) —O—$C_{1-6}$ haloalkyl, or
  (6) halogen;

$R^4$ is:
  (1) —$C_{1-6}$ alkyl,
  (2) —$CO_2R^a$,
  (3) —C(=O)N($R^a$)$R^b$,
  (4) —C(=O)—N($R^a$)—(CH$_2$)$_{2-3}$—O$R^b$,
  (5) —N($R^a$)C(=O)$R^b$,
  (6) —N($R^a$)SO$_2R^b$,
  (7) —$C_{3-6}$ cycloalkyl, which is optionally substituted with from 1 to 4 substituents each of which is independently halogen, —$C_{1-6}$ alkyl, —CF$_3$, —O—$C_{1-6}$ alkyl, or —OCF$_3$,
  (8) —HetK,
  (9) —C(=O)—HetK,
  (10) —C(=O)N($R^a$)—HetK,
  (11) —C(=O)N($R^a$)—(CH$_2$)$_{0-2}$—($C_{3-6}$ cycloalkyl), wherein the cycloalkyl is optionally substituted with from 1 to 4 substituents each of which is independently halogen, —$C_{1-6}$ alkyl, —CF$_3$, —O—$C_{1-6}$ alkyl, or —OCF$_3$, or
  (12) —C(=O)N($R^a$)—CH$_2$-phenyl, wherein the phenyl is optionally substituted with from 1 to 4 substituents each of which is independently —$C_{1-6}$ alkyl, —O—$C_{1-6}$ alkyl, —CF$_3$, —OCF$_3$, or halogen;
  (13) —HetL,
  (14) —C(=O)N($R^a$)$R^c$, or
  (15) halogen;
    wherein HetK is a 5- or 6-membered saturated heterocyclic ring containing a total of from 1 to 4 heteroatoms independently selected from 1 to 4 N atoms, from 0 to 2 O atoms, and from 0 to 2 S atoms, wherein the heterocyclic ring is optionally substituted with (i) from 1 to 4 substituents each of which is independently —$C_{1-6}$ alkyl, oxo, halogen, —C(=O)N($R^a$)$R^b$, —C(=O)C(=O)N($R^a$)$R^b$, —C(=O)$R^a$, —CO$_2R^a$, —SO$_2R^a$, or —SO$_2$N($R^a$)$R^b$ and (ii) from zero to 1 $C_{3-6}$ cycloalkyl; and with the proviso that when HetK is attached to the rest of the compound via the —C(=O)— moiety, the HetK is attached to the —C(=O)— via a ring N atom;
    wherein HetL is a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl or —OH;

$R^5$ is:
  (1) —H,
  (2) —$C_{1-6}$ alkyl,
  (3) —$C_{3-6}$ cycloalkyl,
  (4) —(CH$_2$)$_{1-2}$—$C_{3-6}$ cycloalkyl,
  (5) —CH$_2$-phenyl wherein the phenyl is optionally substituted with from 1 to 4 substituents each of which is independently halogen, $C_{1-6}$ alkyl, $C_{1-6}$ haloalkyl, —O—$C_{1-6}$ alkyl, or —O—$C_{1-6}$ haloalkyl,
  (6) —(CH$_2$)$_{1-2}$—HetD, wherein HetD is a 4- to 7-membered saturated heterocyclic ring containing from 1 to 2 heteroatoms independently selected from 1 to 2 N atoms, from zero to 1 O atom and from zero to 1 S atom, wherein the heterocyclic ring is attached to the rest of the molecule via a ring N atom, and the heterocyclic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, oxo, —C(=O)N($R^a$)$R^b$, —C(=O)$R^a$, —CO$_2R^a$, —SO$_2R^a$, or —SO$_2$N($R^a$)$R^b$,
  (7) phenyl which is optionally substituted with from 1 to 4 substituents each of which is independently —$C_{1-6}$ alkyl, —O—$C_{1-6}$ alkyl, —$C_{1-6}$ haloalkyl, —O—$C_{1-6}$ haloalkyl, —OH, halogen, —CN, —NO$_2$, —C(=O)$R^a$, —CO$_2R^a$, —SO$_2R^a$, —N($R^a$)C(=O)—$C_{1-6}$ haloalkyl, —N($R^a$)C(=O)$R^b$, —N($R^a$)C(=O)N($R^a$)$R^b$, —N($R^a$)CO$_2R^b$, —N($R^a$)SO$_2R^b$, —C(=O)N($R^d$)$R^e$, or —SO$_2$N($R^d$)$R^e$;
  (8) a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl, —$C_{1-6}$ haloalkyl, —O—$C_{1-6}$ alkyl, —O—$C_{1-6}$ haloalkyl, or —OH,
  (9) $C_{1-6}$ alkyl substituted with —O—$C_{1-6}$ alkyl, —CN, —N($R^a$)$R^b$, —C(=O)N($R^a$)$R^b$, —C(=O)$R^a$, —CO$_2R^a$, —SO$_2R^a$, or —SO$_2$N($R^a$)$R^b$, or
  (10) —$C_{1-6}$ haloalkyl;

each $R^a$ is independently H or $C_{1-6}$ alkyl;
each $R^b$ is independently H or $C_{1-6}$ alkyl;
$R^c$ is $C_{1-6}$ haloalkyl or $C_{1-6}$ alkyl substituted with —CO$_2R^a$, —SO$_2R^a$, —SO$_2$N($R^a$)$R^b$, or N($R^a$)$R^b$; and
each $R^d$ and $R^e$ are independently H or $C_{1-6}$ alkyl, or together with the N atom to which they are attached form a 4- to 7-membered saturated heterocyclic ring optionally containing a heteroatom in addition to the nitrogen attached to $R^d$ and $R^e$ selected from N, O, and S, wherein the S is optionally oxidized to S(O) or S(O)$_2$, and wherein the saturated heterocyclic ring is optionally substituted with from 1 to 4 substituents each of which is independently halogen, —CN, —$C_{1-6}$ alkyl, —OH, oxo, —O—$C_{1-6}$ alkyl, —$C_{1-6}$ haloalkyl, —C(=O)$R^a$, —CO$_2R^a$, —SO$_2R^a$, or —SO$_2$N($R^a$)$R^b$.

A first sub-class of the first class includes compounds of Formula IIa, and pharmaceutically acceptable salts thereof, wherein

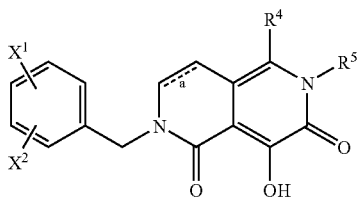

(IIa)

wherein:
X[1] and X[2] are each independently: (1) —H, (2) —$C_{1-6}$ alkyl, (3) —O—$C_{1-6}$ alkyl, (4) —$C_{1-6}$ haloalkyl, (5) —O—$C_{1-6}$ haloalkyl, (6) halogen, (7) —CN, (8) —N($R^a$)$R^b$, (9) —C(=O)N($R^a$)$R^b$, (10) —S(O)$_n R^a$, wherein n is an integer equal to zero, 1, or 2, (11) —N($R^a$)SO$_2 R^b$, (12) —N($R^a$)SO$_2$N($R^a$)$R^b$, (13) —N($R^a$)C(=O)$R^b$, (14) —N($R^a$)C(=O)—C(=O)N($R^a$)$R^b$, (15) —HetA, (16) —C(=O)—HetA, or (17) HetB;

$R^4$ is: (1) —CO$_2 R^a$, (2) —C(=O)N($R^a$)$R^b$, (3) —C(=O)—N($R^a$)—(CH$_2$)$_{2-3}$—OR$^b$, (4) —N($R^a$)C(=O)$R^b$, (5) —N($R^a$)SO$_2 R^b$, (6) —HetK, (7) —C(=O)—HetK, (8) —C(=O)N($R^a$)—(CH$_2$)$_{0-1}$—(C$_{3-6}$ cycloalkyl), wherein the cycloalkyl is optionally substituted with from 1 to 4 substituents each of which is independently halogen, —$C_{1-6}$ alkyl, —CF$_3$, —O—$C_{1-6}$ alkyl, or —OCF$_3$, or (9) —C(=O)N($R^a$)—CH$_2$-phenyl, wherein the phenyl is optionally substituted with from 1 to 4 substituents each of which is independently —$C_{1-6}$ alkyl, —O—$C_{1-6}$ alkyl, —CF$_3$, —OCF$_3$, or halogen;

$R^5$ is: (1) —H, (2) —$C_{1-6}$ alkyl, (3) —$C_{3-6}$ cycloalkyl, (4) —CH$_2$—$C_{3-6}$ cycloalkyl, or (5) —CH$_2$-phenyl;

and all other variables are as originally defined in the first class.

A second sub-class of the first class includes compounds of Formula II, and pharmaceutically acceptable salts thereof, wherein:

bond

" ----ᵃ---- "

in the ring is a single bond or a double bond (e.g., is a single bond);

X[1] and X[2] are each independently:
(1) —H,
(2) —$C_{1-4}$ alkyl,
(3) —$C_{1-4}$ haloalkyl,
(4) —OH,
(5) —O—$C_{1-4}$ alkyl,
(6) halogen,
(7) —CN,
(8) —C(=O)NH$_2$,
(9) —C(=O)NH(—$C_{1-4}$ alkyl),
(10) —C(=O)N(—$C_{1-4}$ alkyl)$_2$, or
(11) —SO$_2$—$C_{1-4}$ alkyl;

or alternatively X[1] and X[2] are respectively located on adjacent carbons in the phenyl ring and together form methylenedioxy or ethylenedioxy;

$X^3$ is —H, halogen, —$C_{1-4}$ alkyl, or —O—$C_{1-4}$ alkyl;

$R^4$ is:
(1) —$C_{1-4}$ alkyl,
(2) —CO$_2$H,
(3) —C(=O)—O—$C_{1-4}$ alkyl,
(4) —C(=O)NH$_2$,
(5) —C(=O)NH—$C_{1-5}$ alkyl,
(6) —C(=O)N(C$_{1-4}$ alkyl)$_2$,
(7) —C(=O)—NH—(CH$_2$)$_{2-3}$—O—$C_{1-4}$ alkyl,
(8) —C(=O)—N(C$_{1-4}$ alkyl)-(CH$_2$)$_{2-3}$—O—$C_{1-4}$ alkyl,
(9) —NHC(=O)—$C_{1-4}$ alkyl,
(10) —N(C$_{1-4}$ alkyl)C(=O)—$C_{1-4}$ alkyl,
(11) —NHSO$_2$—$C_{1-4}$ alkyl,
(12) —N(C$_{1-4}$ alkyl)SO$_2$—$C_{1-4}$ alkyl,
(13) —$C_{3-6}$ cycloalkyl,
(14) —HetK wherein HetK is:

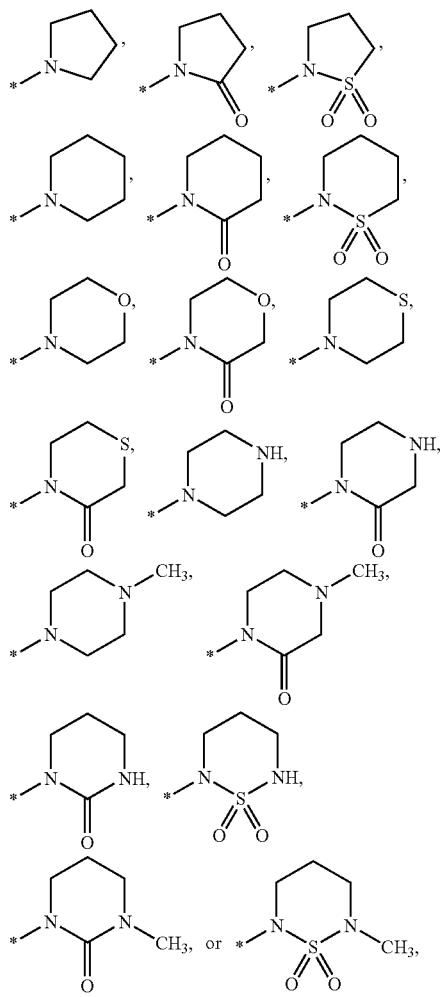

wherein the asterisk * denotes the point of attachment to the rest of the compound,

(15) —C(=O)—HetK, wherein HetK is:

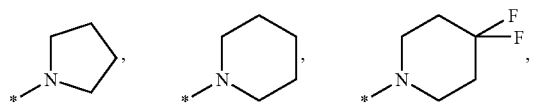

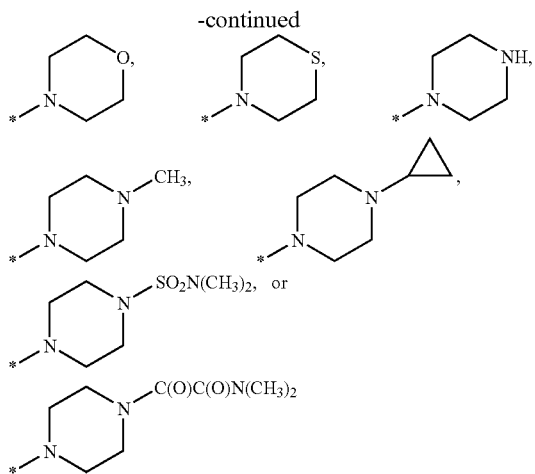

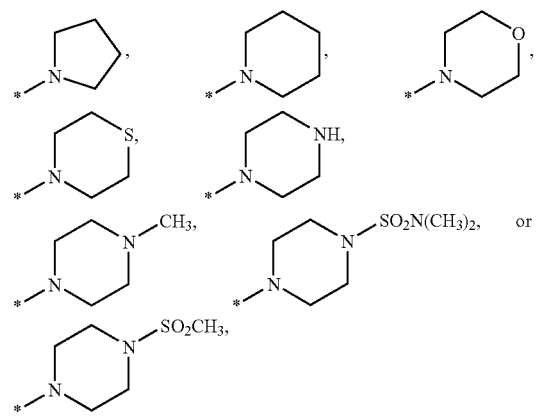

wherein the asterisk * denotes the point of attachment to the rest of the compound,

(16) —C(=O)NH—HetK or —C(=O)N($C_{1-4}$ alkyl)-HetK, wherein HetK is a saturated heterocyclic selected from the group consisting of pyrrolidinyl, piperidinyl, piperazinyl, morpholinyl, and thiomorpholinyl, wherein the saturated heterocyclic is optionally substituted with from 1 to 2 substituents each of which is independently —$C_{1-4}$ alkyl, $SO_2$—$C_{1-4}$ alkyl, or —$SO_2N(C_{1-4}$ alkyl$)_2$,

(17) —C(=O)NH—$(CH_2)_{0-1}$—($C_{3-6}$ cycloalkyl),

(18) —C(=O)N($C_{1-4}$ alkyl)-$(CH_2)_{0-1}$—($C_{3-6}$ cycloalkyl),

(19) —C(=O)NH—$CH_2$-phenyl, wherein the phenyl is optionally substituted with 1 or 2 substituents each of which is independently halogen, —$C_{1-4}$ alkyl, —$CF_3$, —O—$C_{1-4}$ alkyl, or —$OCF_3$,

(20) —C(=O)N($C_{1-4}$ alkyl)-$CH_2$-phenyl, wherein the phenyl is optionally substituted with 1 or 2 substituents each of which is independently halogen, —$C_{1-4}$ alkyl, —$CF_3$, —O—$C_{1-4}$ alkyl, or —$OCF_3$,

(21) —HetL, wherein HetL is a heteroaromatic ring which is pyrrolyl, thienyl, furanyl, imidazolyl, oxazolyl, thiazolyl, isoxazolyl, isothiazolyl, pyrazolyl, triazolyl, tetrazolyl, oxadiazolyl, pyridinyl, pyrimidinyl, or pyrazinyl, wherein the heteroaromatic ring is optionally substituted with from 1 to 4 substituents each of which is independently halogen or —$C_{1-4}$ alkyl,

(22) —C(O)N(H)—$C_{1-4}$ haloalkyl,

(23) —C(O)N($C_{1-4}$ alkyl)-$C_{1-4}$ haloalkyl,

(24) —C(O)N(H)—$(CH_2)_{1-2}SO_2$—$C_{1-4}$ alkyl,

(25) —C(O)N($C_{1-4}$ alkyl)-$(CH_2)_{1-2}SO_2$—$C_{1-4}$ alkyl,

(26) —C(O)N(H)—$(CH_2)_{1-2}N(C_{1-4}$ alkyl$)_2$,

(27) —C(O)N($C_{1-4}$ alkyl)-$(CH_2)_{1-2}N(C_{1-4}$ alkyl$)_2$, or

(28) —Cl or —Br; and $R^5$ is:

(1) —H, (2) —$C_{1-4}$ alkyl, (3) —$C_{3-6}$ cycloalkyl, (4) —$CH_2$—$C_{3-6}$ cycloalkyl, (5) —$CH_2$-phenyl, wherein the phenyl is optionally substituted with from 1 to 3 substituents each of which is independently halogen, —$C_{1-4}$ alkyl, —$CF_3$, —O—$C_{1-4}$ alkyl, or —$OCF_3$, (6) —$(CH_2)_{1-2}$—HetD, wherein HetD is:

wherein the asterisk * denotes the point of attachment to the rest of the compound, (7) phenyl which is optionally substituted with —$C_{1-4}$ alkyl, —O—$C_{1-4}$ alkyl, —$CF_3$, —$OCF_3$, halogen, —CN, —$NO_2$, —C(=O)—$C_{1-4}$ alkyl, —C(=O)—O—$C_{1-4}$ alkyl, —C(O)$NH_2$, —C(O)N(H)—$C_{1-4}$ alkyl, —C(O)N($C_{1-4}$ alkyl$)_2$, —$SO_2$—$C_{1-4}$ alkyl, —$SO_2NH_2$, —$SO_2N(H)$—$C_{1-4}$ alkyl, —$SO_2N(C_{1-4}$ alkyl$)_2$, —N(H)C(=O)—$C_{1-4}$ alkyl, —N($C_{1-4}$ alkyl)C(=O)—$C_{1-4}$ alkyl, —N(H)C(=O)—$CF_3$, —N($C_{1-4}$ alkyl)C(=O)—$CF_3$, —N(H)C(=O)N(H)$C_{1-4}$ alkyl, —N($C_{1-4}$ alkyl)C(=O)N(H)$C_{1-4}$ alkyl, —N(H)C(=O)N($C_{1-4}$ alkyl$)_2$, —N($C_{1-4}$ alkyl)C(=O)N($C_{1-4}$ alkyl$)_2$, —N(H)C(=O)—O—$C_{1-4}$ alkyl, —N($C_{1-4}$ alkyl)C(=O)—O—$C_{1-4}$ alkyl, —N(H)$SO_2$—$C_{1-4}$ alkyl, —N($C_{1-4}$ alkyl)$SO_2$—$C_{1-4}$ alkyl,

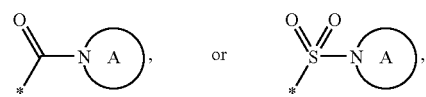

wherein ring A is pyrrolidinyl, piperidinyl, morpholinyl, thiomorpholinyl, or piperazinyl optionally substituted on the other ring nitrogen with methyl or $SO_2$—$CH_3$, (8) a 5- or 6-membered heteroaromatic ring which is pyrrolyl, thienyl, furanyl, imidazolyl, oxazolyl, thiazolyl, isoxazolyl, isothiazolyl, pyrazolyl, triazolyl, tetrazolyl, pyridinyl, pyrimidinyl, or pyrazinyl, wherein the heteroaromatic ring is optionally substituted with from 1 to 2 substituents each of which is independently halogen or —$C_{1-4}$ alkyl, (9) $C_{1-4}$ alkyl substituted with —O—$C_{1-4}$ alkyl, —CN, —$NH_2$, —N(H)—$C_{1-4}$ alkyl, —N($C_{1-4}$ alkyl$)_2$, —C(O)$NH_2$, —C(O)N(H)—$C_{1-4}$ alkyl, —C(O)N($C_{1-4}$ alkyl$)_2$, —C(=O)—$C_{1-4}$ alkyl, —C(=O)—O—$C_{1-4}$ alkyl, —$SO_2$—$C_{1-4}$ alkyl, —$SO_2NH_2$, —$SO_2N(H)$—$C_{1-4}$ alkyl, or —$SO_2N(C_{1-4}$ alkyl$)_2$, or

(10) —$C_{1-4}$ fluoroalkyl.

A third sub-class of the first class includes compounds of Formula IIa, and pharmaceutically acceptable salts thereof, wherein:

bond

" ═ₐ═ "

in the ring is a single bond or a double bond (e.g., is a single bond);

$X^1$ and $X^2$ are each independently: (1) —H, (2) —$C_{1-4}$ alkyl, (3) —$C_{1-4}$ haloalkyl, (4) —O—$C_{1-4}$ alkyl, (5) halogen, (6) —CN, (7) —C(═O)$NH_2$, (8) —C(═O)NH—($C_{1-4}$ alkyl), (9) —C(═O)N(—$C_{1-4}$ alkyl)$_2$, or (10) —$SO_2$—$C_{1-4}$ alkyl;

$R^4$ is: (1) —$CO_2$H, (2) —C(═O)—O—$C_{1-4}$ alkyl, (3) —C(═O)$NH_2$, (4) —C(═O)NH—$C_{1-4}$ alkyl, (5) —C(═O)N($C_{1-4}$ alkyl)$_2$, (6) —C(═O)—NH—($CH_2$)$_{2-3}$—O—$C_{1-4}$ alkyl, (7) —C(═O)—N($C_{1-4}$ alkyl)-($CH_2$)$_{2-3}$—O—$C_{1-4}$ alkyl, (8) —NHC(═O)—$C_{1-4}$ alkyl, (9) —N($C_{1-4}$ alkyl)C(═O)—$C_{1-4}$ alkyl, (10) —$NHSO_2$—$C_{1-4}$ alkyl, (11) —N($C_{1-4}$ alkyl)$SO_2$—$C_{1-4}$ alkyl, (12) —HetK wherein HetK is:

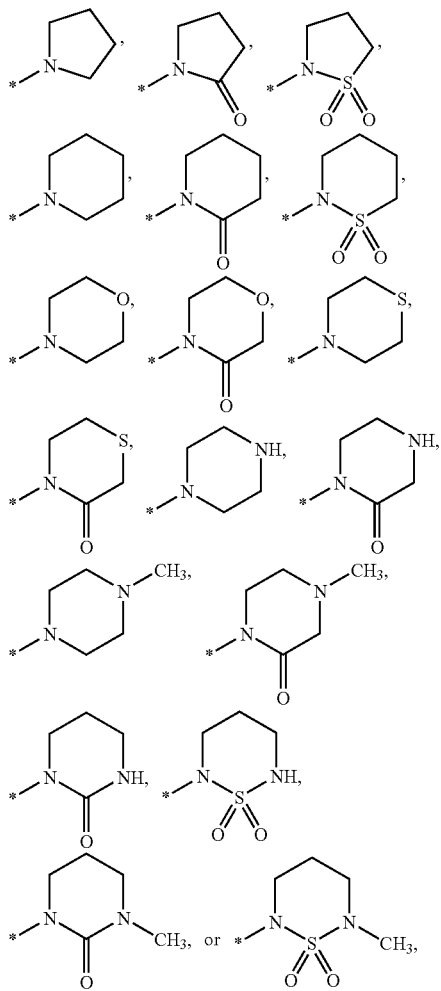

wherein the asterisk * denotes the point of attachment to the rest of the compound, (13) —C(═O)-HetK, wherein HetK is:

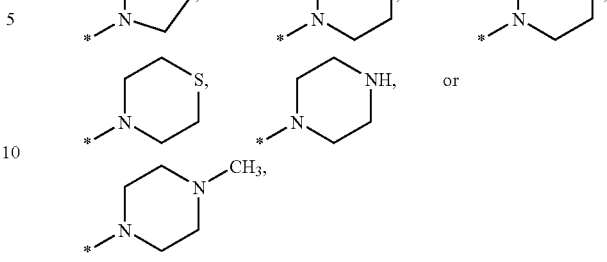

wherein the asterisk * denotes the point of attachment to the rest of the compound, (13) —C(═O)NH—($CH_2$)$_{0-1}$—($C_{3-6}$ cycloalkyl), (14) —C(═O)N($C_{1-4}$ alkyl)-($CH_2$)$_{0-1}$—($C_{3-6}$ cycloalkyl), (15) —C(═O)NH—$CH_2$-phenyl, or (16) —C(═O)N($C_{1-4}$ alkyl)-$CH_2$-phenyl; and $R^5$ is: (1) —H, (2) —$C_{1-4}$ alkyl, (3) —$C_{3-6}$ cycloalkyl, (4) —$CH_2$—$C_{3-6}$ cycloalkyl, or (5) —$CH_2$-phenyl.

A fourth sub-class of the first class is identical to the third sub-class, except that $R^4$ is: (1) —$CO_2$H, (2) —C(═O)—O—$C_{1-4}$ alkyl, (3) —C(═O)$NH_2$, (4) —C(═O)NH—$C_{1-4}$ alkyl, (5) —C(═O)N($C_{1-4}$ alkyl)$_2$, (6) —C(═O)—NH—($CH_2$)$_{2-3}$—O—$C_{1-4}$ alkyl, (7) —C(═O)—N($C_{1-4}$ alkyl)-($CH_2$)$_{2-3}$—O—$C_{1-4}$ alkyl, (8) —NHC(═O)—$C_{1-4}$ alkyl, (9) —N($C_{1-4}$ alkyl)C(═O)—$C_{1-4}$ alkyl, (10) —$NHSO_2$—$C_{1-4}$ alkyl, (11) —N($C_{1-4}$ alkyl)$SO_2$—$C_{1-4}$ alkyl, (12) —C(═O)—HetK, wherein HetK is:

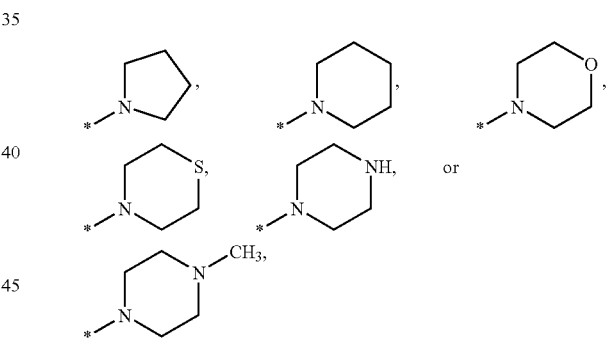

wherein the asterisk * denotes the point of attachment to the rest of the compound, (13) —C(═O)NH—($CH_2$)$_{0-1}$—($C_{3-6}$ cycloalkyl), (14) —C(═O)N($C_{1-4}$ alkyl)-($CH_2$)$_{0-1}$—($C_{3-6}$ cycloalkyl), (15) —C(═O)NH—$CH_2$-phenyl, or (16) —C(═O)N($C_{1-4}$ alkyl)-$CH_2$-phenyl.

A fifth sub-class of the first class is identical to the fourth sub-class, except that HetK is:

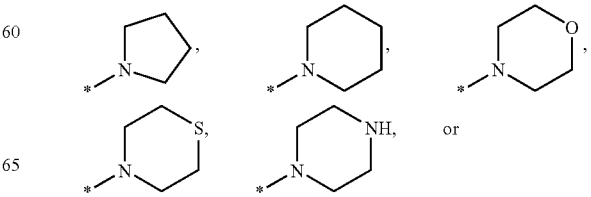

-continued

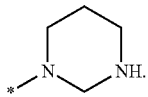

A sixth sub-class of the first class is identical to the fourth sub-class, except that HetK is:

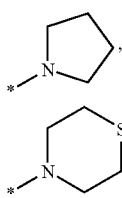 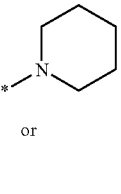 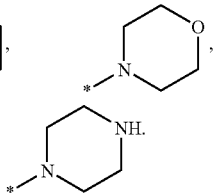

A second class of the present invention includes compounds of Formula III, and pharmaceutically acceptable salts thereof:

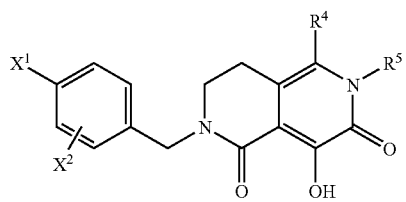

(III)

wherein:

$X^1$ is: (1) —H, (2) bromo, (3) chloro, (4) fluoro, or (5) methoxy;

$X^2$ is: (1) —H, (2) bromo, (3) chloro, (4) fluoro, (5) methoxy, (6) —$C_{1-4}$ alkyl, (7) —$CF_3$, (8) —$OCF_3$, (9) —CN, or (10) —$SO_2(C_{1-4}$ alkyl);

$R^4$ is: (1) —$CO_2H$, (2) —C(=O)—O—$C_{1-4}$ alkyl, (3) —C(=O)$NH_2$, (4) —C(=O)NH—$C_{1-4}$ alkyl, (5) —C(=O)N($C_{1-4}$ alkyl)$_2$, (6) —C(=O)—NH—$(CH_2)_{2-3}$—O—$C_{1-4}$ alkyl, (7) —C(=O)—N($C_{1-4}$ alkyl)-$(CH_2)_{2-3}$—O—$C_{1-4}$ alkyl, (8) —NHC(=O)—$C_{1-4}$ alkyl, (9) —N($C_{1-4}$ alkyl)C(=O)—$C_{1-4}$ alkyl, (10) —$NHSO_2$—$C_{1-4}$ alkyl, (11) —N($C_{1-4}$ alkyl)$SO_2$—$C_{1-4}$ alkyl, (12) —C(=O)—HetK, wherein HetK is:

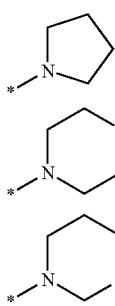 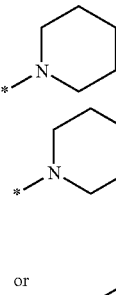 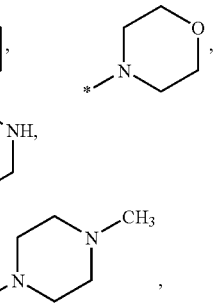

wherein the asterisk * denotes the point of attachment to the rest of the compound, (13) —C(=O)NH—$(CH_2)_{0-1}$—$(C_{3-6}$ cycloalkyl), (14) —C(=O)N($C_{1-4}$ alkyl)-$(CH_2)_{0-1}$—$(C_{3-6}$ cycloalkyl), (15) —C(=O)NH—$CH_2$-phenyl, or (16) —C(=O)N($C_{1-4}$ alkyl)-$CH_2$-phenyl; and $R^5$ is: (1) —H, (2) —$C_{1-4}$ alkyl, (3) cyclopropyl, (4) cyclobutyl, (5) —$CH_2$-cyclopropyl, (6) —$CH_2$-cyclobutyl, or (7) —$CH_2$-phenyl.

A first sub-class of the second class is identical to the second class, except that HetK is:

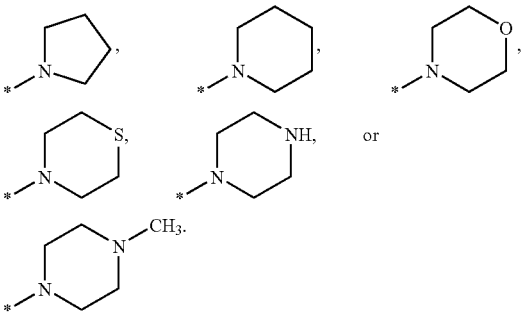

A second sub-class of the second class is identical to the second class, except that HetK is:

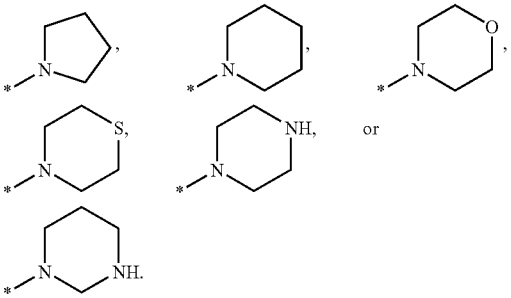

A third sub-class of the second class is identical to the second class, except that HetK is:

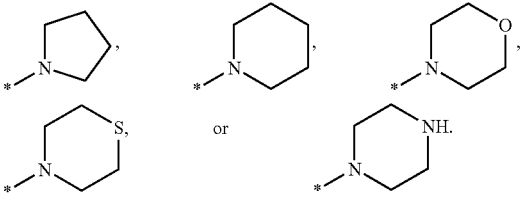

A fourth sub-class of the second class includes compounds of Formula III, and pharmaceutically acceptable salts thereof, wherein:

$X^1$ is fluoro;

$X^2$ is —H or chloro;

$R^4$ is: (1) —C(=O)—O—$C_{1-3}$ alkyl, (2) —C(=O)NH—$C_{1-3}$ alkyl, (3) —C(=O)N($C_{1-3}$ alkyl)$_2$, (4) —C(=O)—N($C_{1-3}$ alkyl)-$(CH_2)_2$—O—$C_{1-3}$ alkyl, (5) —N($C_{1-3}$ alkyl)C(=O)—$C_{1-3}$ alkyl, (6) —N($C_{1-13}$ alkyl)$SO_2$—$C_{1-3}$ alkyl, (7) —C(=O)—HetK, wherein HetK is:

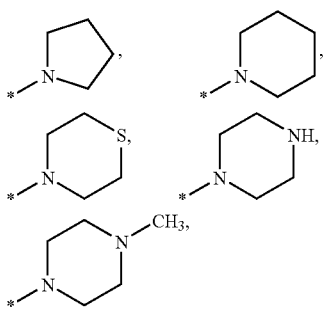

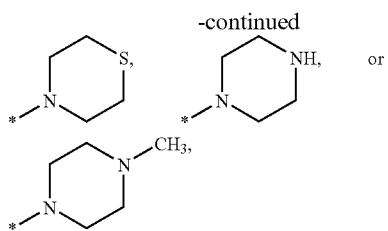

wherein the asterisk * denotes the point of attachment to the rest of the compound, (8) —C(=O)NH—(CH$_2$)$_{0-1}$-(cyclopropyl), (9) —C(=O)NH—(CH$_2$)$_{0-1}$-(cyclobutyl), (10) —C(=O)N(C$_{1-3}$ alkyl)-(CH$_2$)$_{0-1}$-cyclopropyl, (11) —C(=O)N(C$_{1-3}$ alkyl)-(CH$_2$)$_{0-1}$-cyclobutyl, (12) —C(=O)NH—CH$_2$-phenyl, or (13) —C(=O)N(C$_{1-3}$ alkyl)-CH$_2$-phenyl; and R$^5$ is —H or C$_{1-4}$ alkyl.

A fifth sub-class of the second class is identical to the fourth sub-class, except that X$^2$ is —H; R$^5$ is —H; and HetK is:

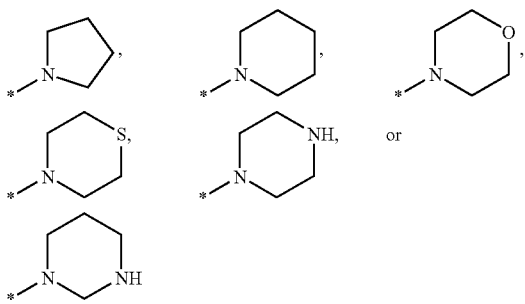

A sixth sub-class of the second class is identical to the fifth sub-class, except that HetK is:

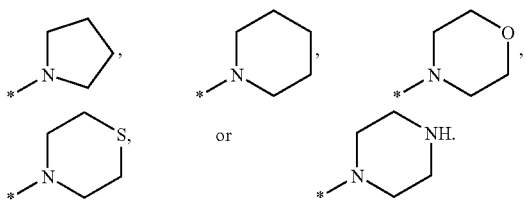

A third class of the present invention includes compounds of Formula III, and pharmaceutically acceptable salts thereof, wherein X$^1$ is fluoro; X$^2$ is —H or chloro; R$^4$ is:

(1) —C(=O)N(C$_{1-3}$ alkyl)$_2$,
(2) —C(=O)—HetK, wherein HetK is:

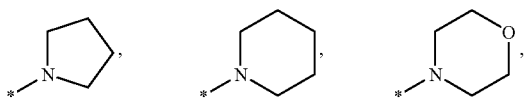

-continued wherein the asterisk * denotes the point of attachment to the rest of the compound, (3) —C(=O)N(C$_{1-3}$ alkyl)-(CH$_2$)$_{0-1}$-cyclopropyl, or
(4) —C(=O)N(C$_{1-3}$ alkyl)-(CH$_2$)$_{0-1}$-cyclobutyl; and R$^5$ is —C$_{1-4}$ alkyl.

A first sub-class of the third class is identical to the third class, except that R$^4$ is —C(=O)N(C$_{1-3}$ alkyl)$_2$.

A second sub-class of the third class is identical to the third class, except that R$^4$ is —C(=O)N(CH$_3$)$_2$.

Another embodiment of the present invention is a compound, or a pharmaceutically acceptable salt thereof, selected from the group consisting of the compounds set forth in Examples 1 to 87 below. An aspect of this embodiment is a compound, or a pharmaceutically acceptable salt thereof, which is the compound set forth in Example 11, 13, or 14. Another aspect of this embodiment is a compound, or a pharmaceutically acceptable salt thereof, which is the compound set forth in Example 11 or Example 13. Another aspect of this embodiment is a compound, or a pharmaceutically acceptable salt thereof, which is the compound set forth in Example 11 (i.e., 6-(3-chloro-4-fluorobenzyl)-4-hydroxy-N,N,2-trimethyl-3,5-dioxo-2,3,5,6,7,8-hexahydro-2,6-naphthyridine-1-carboxamide). Another aspect of this embodiment is a compound, or a pharmaceutically acceptable salt thereof, which is the compound set forth in Example 13 (i.e., 6-(3-chloro-4-fluorobenzyl)-4-hydroxy-2-isopropyl-N,N-dimethyl-3,5-dioxo-2,3,5,6,7,8-hexahydro-2,6-naphthyridine-1-carboxamide).

Other embodiments of the present invention include the following:

(a) A pharmaceutical composition comprising an effective amount of a compound of Formula I and a pharmaceutically acceptable carrier.

(b) A pharmaceutical composition which comprises the product prepared by combining (e.g., mixing) an effective amount of a compound of Formula I and a pharmaceutically acceptable carrier.

(c) The pharmaceutical composition of (a) or (b), further comprising an effective amount of an HIV infection/AIDS treatment agent selected from the group consisting of HIV/AIDS antiviral agents, immunomodulators, and anti-infective agents.

(d) The pharmaceutical composition of (c), wherein the HIV infection/AIDS treatment agent is an antiviral selected from the group consisting of HIV protease inhibitors, non-nucleoside HIV reverse transcriptase inhibitors, and nucleoside HIV reverse transcriptase inhibitors.

(e) A pharmaceutical combination which is (i) a compound of Formula I and (ii) an HIV infection/AIDS treatment agent selected from the group consisting of HIV/AIDS antiviral agents, immunomodulators, and anti-infective agents; wherein the compound of Formula I and the HIV infection/AIDS treatment agent are each employed in an amount that renders the combination effective for inhibiting HIV integrase, for treating or preventing infection by HIV, or for preventing, treating or delaying the onset of AIDS.

(f) The combination of (e), wherein the HIV infection/AIDS treatment agent is an antiviral selected from the group consisting of HIV protease inhibitors, non-nucleoside HIV reverse transcriptase inhibitors and nucleoside HIV reverse transcriptase inhibitors.

(g) A method of inhibiting HIV integrase in a subject in need thereof which comprises administering to the subject an effective amount of a compound of Formula I.

(h) A method of preventing or treating infection by HIV in a subject in need thereof which comprises administering to the subject an effective amount of a compound of Formula I.

(i) The method of (h), wherein the compound of Formula I is administered in combination with an effective amount of at least one antiviral selected from the group consisting of HIV protease inhibitors, non-nucleoside HIV reverse transcriptase inhibitors, and nucleoside HIV reverse transcriptase inhibitors.

j) A method of preventing, treating or delaying the onset of AIDS in a subject in need thereof which comprises administering to the subject an effective amount of a compound of Formula I.

(k) The method of (j), wherein the compound is administered in combination with an effective amount of at least one antiviral selected from the group consisting of HIV protease inhibitors, non-nucleoside HIV reverse transcriptase inhibitors, and nucleoside HIV reverse transcriptase inhibitors (l) A method of inhibiting HIV integrase in a subject in need thereof which comprises administering to the subject the pharmaceutical composition of (a), (b), (c) or (d) or the combination of (e) or (f).

(m) A method of preventing or treating infection by HIV in a subject in need thereof which comprises administering to the subject the pharmaceutical composition of (a), (b), (c) or (d) or the combination of (e) or (f).

(n) A method of preventing, treating or delaying the onset of AIDS in a subject in need thereof which comprises administering to the subject the pharmaceutical composition of (a), (b), (c) or (d) or the combination of (e) or (f).

The present invention also includes a compound of the present invention (i) for use in, (ii) for use as a medicament for, or (iii) for use in the preparation of a medicament for: (a) inhibiting HIV integrase, (b) preventing or treating infection by HIV, or (c) preventing, treating or delaying the onset of AIDS. In these uses, the compounds of the present invention can optionally be employed in combination with one or more HIV/AIDS treatment agents selected from HIV/AIDS antiviral agents, anti-infective agents, and immunomodulators.

Additional embodiments of the invention include the pharmaceutical compositions, combinations and methods set forth in (a)-(n) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—.

The term "alkylenedioxy" refers to —O—R—O— wherein R is $(CH_2)_{1-3}$ in which one of the hydrogens on each methylene is optionally replaced with $C_{1-4}$ alkyl. R is preferably $(CH_2)_{1-2}$ or $CH(CH_3)$, and is more preferably $(CH_2)_{1-2}$.

The terms "C(O)" and "C(=O)" are alternative representations of carbonyl. The terms "$S(O)_2$" and "$SO_2$" are alternative representations of sulfonyl.

The terms "cycloalkyl" refers to any cyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

The term "$C_{4-7}$ azacycloalkyl" (or "$C_4$-$C_7$ azacycloalkyl") means a saturated cyclic ring consisting of one nitrogen and from four to seven carbon atoms (i.e., pyrrolidinyl, piperidinyl, azepanyl, or octahydroazocinyl).

The term "$C_{3-6}$ diazacycloalkyl" (or "$C_3$-$C_6$ diazacycloalkyl") means a saturated cyclic ring consisting of two nitrogens and from three to six carbon atoms (e.g., imidazolidinyl, pyrazolidinyl, or piperazinyl).

Unless expressly stated to the contrary, all ranges cited herein are inclusive. For example, a heterocyclic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, and so forth.

When any variable (e.g., $R^a$, $R^b$, or HetA) occurs more than one time in any constituent or in Formula I or in any other formula depicting and describing compounds of the invention, its definition on each occurrence is independent of its definition at every other occurrence. Also, combinations of substituents and/or variables are permissible only if such combinations result in stable compounds.

The term "substituted" (e.g., as in "is optionally substituted with from 1 to 5 substituents . . . ") includes mono- and poly-substitution by a named substituent to the extent such single and multiple substitution (including multiple substitution at the same site) is chemically allowed. Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound.

Any of the various carbocyclic and heterocyclic rings and ring systems defined herein may be attached to the rest of the compound at any ring atom (i.e., any carbon atom or any heteroatom) provided that a stable compound results. Suitable 5- or 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, and thiadiazolyl. The foregoing are representative of heteroaromatics defined by HetB and HetL, and included in the definitions of HetC and HetD. Suitable heteroaryls consisting of an aryl fused with a 5- or 6-membered heteroaromatic ring include, for example, benzopiperidinyl, benzisoxazolyl, benzoxazolyl, chromenyl, quinolinyl, isoquinolinyl, cinnolinyl, and quinazolinyl. The foregoing are representative of fused bicyclic heteroaryls included in the definition of HetC and of fused aryl in part (A) of the definition of $R^J$. Suitable 4- to 7-membered saturated heterocyclics include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, thiadiazepanyl, dithiazepanyl, azepanyl, diazepanyl, thiadiazinanyl, tetrahydropyranyl, tetrahydrothiopyranyl, and dioxanyl. The foregoing are representative of saturated heterocyclics defined by HetK and included in the definition of HetD.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers, such as the following:

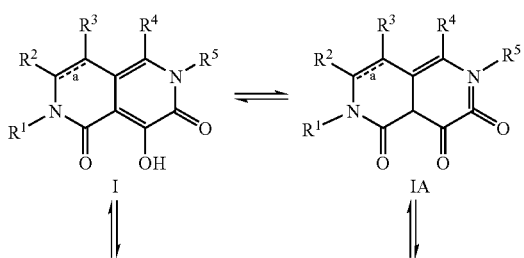

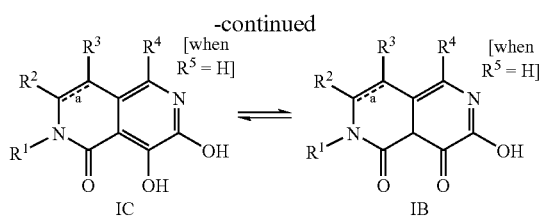

For the purposes of the present invention a reference herein to a compound of Formula I, II, or III is a reference to the compound per se, or to any one of its tautomers per se, or to mixtures of two or more tautomers.

In instances where a hydroxy (—OH) substituent(s) is(are) permitted on a heteroaromatic ring and keto-enol tautomerism is possible, it is understood that the substituent might in fact be present, in whole or in part, in the keto form, as exemplified here for a hydroxypyridinyl substituent:

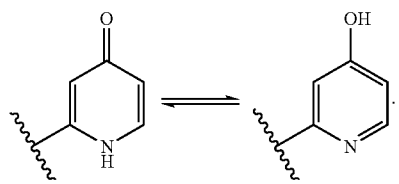

Compounds of the present invention having a hydroxy substituent on a carbon atom of a heteroaromatic ring are understood to include compounds in which only the hydroxy is present, compounds in which only the tautomeric keto form (i.e., an oxo substituent) is present, and compounds in which the keto and enol forms are both present.

Certain of the compounds of the present invention can exhibit a chirality resulting from the presence of bulky substituents that hinder the otherwise free rotation about a bond. These rotational enantiomers are named atropisomers, and the interconversion can be sufficiently slow to allow for their separation and characterization. See, e.g., J. March, *Advanced Organic Chemistry*, 4th Edition, John Wiley & Sons, 1992, pp. 101-102; and Ahmed et al., *Tetrahedron* 1998, 13277. For example, certain of the compounds of the present invention in which $R^4$ is —C(=O)N($R^a$)$R^b$ or —N($R^a$)SO2$R^b$ where at least one of $R^a$ and $R^b$ is alkyl can have sufficiently hindered rotation along the bond linking $R^4$ to the bicyclic core of the molecule when $R^5$ is other than H (e.g., $R^5$=alkyl, cycloalkyl, or aryl) to permit separation of the enantiomers using, e.g., column chromatography on a chiral stationary phase. The present invention includes atropisomers of compounds embraced by Formula I, singly and in mixtures.

The compounds of the present inventions are useful in the inhibition of HIV integrase (e.g., HIV-1 integrase), the prevention or treatment of infection by human immunodeficiency virus (HIV) and the prevention, treatment or the delay in the onset of consequent pathological conditions such as AIDS. Preventing AIDS, treating AIDS, delaying the onset of AIDS, or preventing or treating infection by HIV is defined as including, but not limited to, treatment of a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV integrase, e.g., by competitive inhibition. Thus the compounds of this invention are commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HIV infection or AIDS), "administration" and its variants are each understood to include concurrent and sequential provision of the compound or prodrug and other agents.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV integrase and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HIV integrase, preventing or treating HIV infection or preventing, treating or delaying the onset of AIDS, the compounds of the present invention, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

The compounds of the invention can, for example, be administered orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, $18^{th}$ edition, edited by A. R. Gennaro, Mack Publishing Co., 1990.

The compounds of this invention can be administered orally in a dosage range of about 0.001 to about 1000 mg/kg of mammal (e.g., human) body weight per day in a single dose or in divided doses. One preferred dosage range is about 0.01 to about 500 mg/kg body weight per day orally in a single dose or in divided doses. Another preferred dosage range is about 0.1 to about 100 mg/kg body weight per day orally in single or divided doses. For oral administration, the compositions can be provided in the form of tablets or capsules containing about 1.0 to about 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy. As an example, the title compound of Example 12 below can be administered to adult humans in the form of an amorphous Na salt in a neat drug-filled capsule in an amount of from about 5 mg to about 800 mg (e.g., 400 mg) twice/day. As another example, the crystalline compound of Example 13 or an amorphous Na salt thereof can be administered to adult humans in the same fashion.

As noted above, the present invention is also directed to use of the HIV integrase inhibitor compounds of the present invention with one or more agents useful in the treatment of HIV infection or AIDS. For example, the compounds of this invention may be effectively administered, whether at periods of pre-exposure and/or post-exposure, in combination with effective amounts of one or more HIV/AIDS antivirals, immunomodulators, antiinfectives, or vaccines useful for treating HIV infection or AIDS, such as those disclosed in Table 1 of WO 01/38332 or in the Table in WO 02/30930. Suitable HIV/AIDS antivirals for use in combination with the compounds of the present invention include, for example, HIV protease inhibitors (e.g., indinavir, atazanavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). It will be understood that the scope of combinations of the compounds of this invention with HIV/AIDS antivirals, immunomodulators, anti-infectives or vaccines is not limited to the foregoing substances or to the list in the above-referenced Tables in WO 01/38332 and WO 02/30930, but includes in principle any combination with any pharmaceutical composition useful for the treatment of AIDS. The HIV/AIDS antivirals and other agents will typically be employed in these combinations in their conventional dosage ranges and regimens as reported in the art, including, for example, the dosages described in the *Physicians' Desk Reference*, 57$^{th}$ edition, Thomson PDR, 2003. The dosage ranges for a compound of the invention in these combinations are the same as those set forth above.

Abbreviations used in the instant specification, particularly the in the Schemes and Examples, include the following: Ac=acetyl; AIDS=acquired immunodeficiency syndrome; AIBN=2,2-azobisisobutyronitrile; ARC=AIDS related complex; BOC or Boc=t-butyloxycarbonyl; BOP=benzotriazol-1-yloxytris-(dimethylamino)phosphonium; DABCO=1,4-diazabicyclo[2.2.2]octene; DCM=dichloromethane; DME=1,2-dimethoxyethane; DMF=N,N-dimethylformamide; DMPU=1,3-dimethyl-3,4,5,6-tetrahydro-2(1H)-pyrimidinone (or N,N'-dimethylpropyleneurea); DMSO=dimethylsulfoxide; ES MS=electrospray mass spectroscopy; Et=ethyl; EtOAc=ethyl acetate; HIV=human immunodeficiency virus; HOAc=acetic acid; HOAT=1-hydroxy-7-azabenzotriazole; HPLC=high performance liquid chromatography; HMPA=hexamethylphosphoramide; IPAc=isopropyl acetate; LC=liquid chromatography; LHMDS=lithium hexamethyldisilazide; mCPBA=meta-chloroperbenzoic acid; Me=methyl; MeOH=methanol; Ms=mesylate; MTBE=methyl tert-butyl ether; NBS=N-bromosuccinimide; NMR=nuclear magnetic resonance; t-Bu=tert-butyl; TEA=triethylamine; TFA=trifluoroacetic acid; THF=tetrahydrofuran; Ts=tosyl.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme 1 depicts a method for preparing 5,6,7,8-tetrahydro-2,6-naphthyridine-1-carboxylate intermediates useful for making compounds of the present invention. In the scheme, lactam 1-1 can be alkylated with an appropriate alkyl halide to give 1-2, using methods as described in Jerry March, *Advanced Organic Chemistry*, 3rd edition, John Wiley & Sons, 1985, pp. 377-379. Piperidin-2-one 1-2 can be converted to the corresponding dihydropyridinone compound 1-5 following the two step procedure set forth in Meyers et al., *Tett. Lett.* 1995, 36: 7051-7054, wherein the lactam can be treated with base and methyl benzene sulfinate to give intermediate 1-4, which can then be treated by heating in a high boiling solvent (e.g., toluene) and optionally in the presence of base to effect the elimination to 1-5. Separately, oxazoles of the type 1-9 can readily be prepared by acylating amino acid ester 1-6 with an oxylate ester 1-7 in the presence of base to afford acylated compound 1-8, which can then be cyclized and dehydrated (using, e.g., P$_2$O$_5$) in the manner described in Krapcho et al. *J. Heterocyclic Chem.* 1995, 32, 1693-1702 to afford oxazole 1-9. Diels-Alder reaction of 1-9 and 1-5, optionally in the presence of water or an acid (preferably in the presence of water), will then provide the desired napthyridine intermediate 1-10.

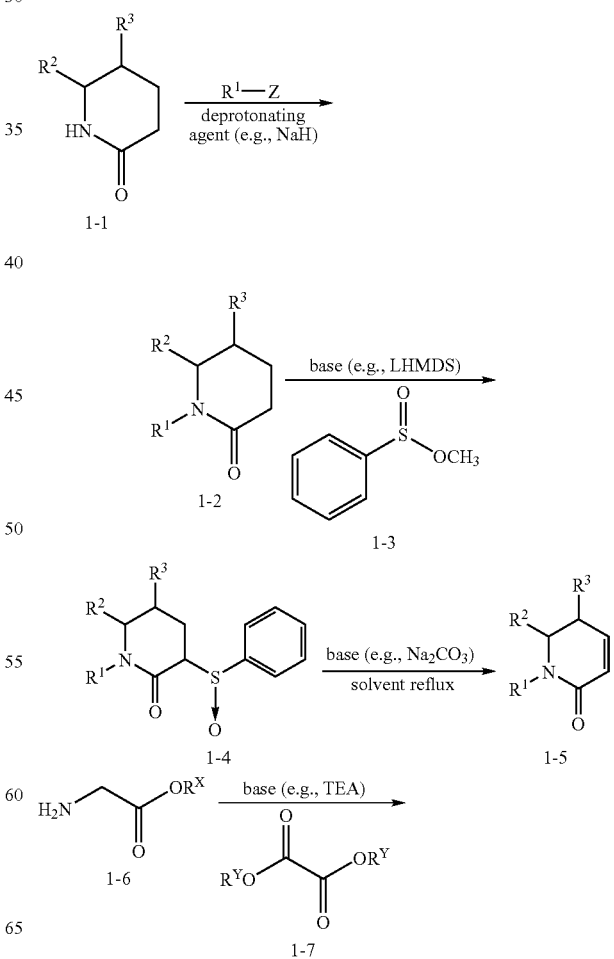

SCHEME 1

-continued

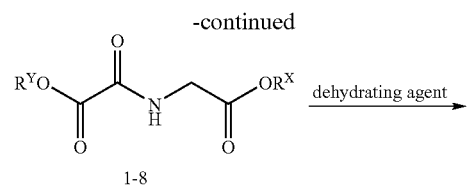

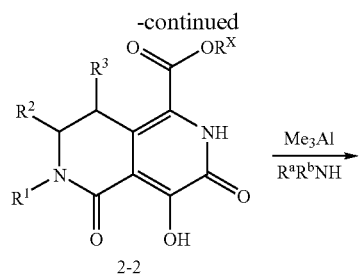

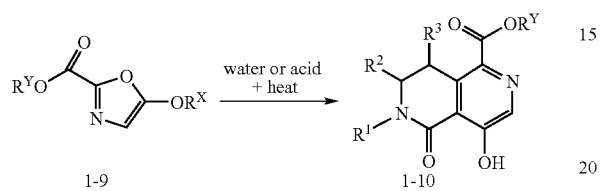

[R$^X$ = H, C$_{1-6}$ alkyl, or
C$_{1-6}$ alkyl substituted with aryl
R$^Y$ = alkyl]

Scheme 2 depicts a method for preparing naphthyridine carboxylates and carboxamides embraced by the present invention from naphthyridine intermediate 1-10, wherein the intermediate 1-10 is contacted with a suitable oxidizing agent (e.g., hydrogen peroxide or mCPBA) to obtain N-oxide 2-1, which can then be treated as described Suzuki et al. *J. Med. Chem.* 1992, 35, 4045-4053 with acetic anhydride to effect the rearrangement to the O-acylated intermediate, and then treated with a nucleophile (e.g., an alkoxide such as NaOMe) to afford the desired dioxohexahydro-2,6-naphthyridine-1-carboxylate 2-2. The alkyl carboxylate 2-2 can then be further treated with an appropriate amine and trimethylaluminum in the manner described in Evans et al., *J. Am. Chem. Soc.* 1990, 112: 7001 to give the desired alkyl carboxamide 2-3.

SCHEME 2

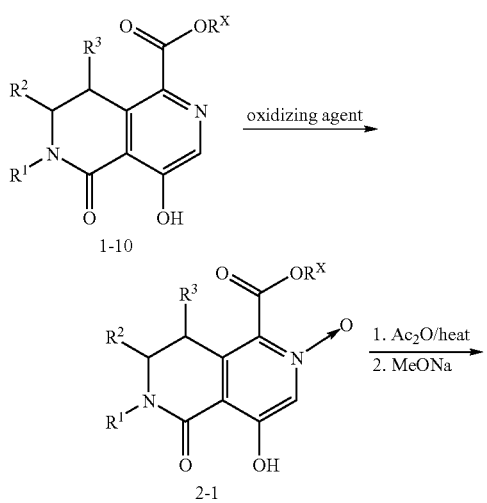

Scheme 3 depicts an alternative method for preparing naphthyridine carboxamides 2-3 and analogs in which the R$^5$ substituent is other than H. The intermediate 2-2 can be alkylated with an alkylating agent (e.g., an alkyl halide or an alkyl sulfate such as dimethyl sulfate) using a suitable base (e.g., (i) an alkali metal carbonate such as K$_2$CO$_3$ or Cs$_2$CO$_3$, (ii) an alkali metal hydride such as NaH, (iii) a metal alkoxide such as Mg(OMe)$_2$, or (iv) the combination of (i) and (iii) in successive steps) to give a mixture of N- and O-alkylated products 3-1 and 3-2. A similar method using alkali metal carbonates is described in T. Ukita et. al., *Chem. Pharm. Bull.* 2000, 48 (4): 589-591. Analogs possessing a non-H R$^5$ substituent can also be prepared by hydrolysis of the N-alkylated product 3-1 with a nucleophile such as hydroxide to afford the acid 3-3, followed by conversion to the acid chloride 3-4 using a suitable agent like thionyl chloride or oxalyl chloride/catalytic DMF, similar to the method described in Jerry March, *Advanced Organic Chemistry*, 3rd edition, John Wiley & Sons, 1985, pp. 388. The acid 3-3 can be coupled with an amine using a peptide coupling reagent such as BOP, or, alternatively, the acid chloride 3-4 can be treated directly with an amine to give the amide. The O-alkylated groups can then be removed under acidic conditions (e.g., using a strong acid like HBr in a suitable solvent like acetic or propionic acid, or using p-toluene sulfonic acid, or a reagent like BBr$_3$) to give 3-5, similar to the method described in Jerry March, *Advanced Organic Chemistry*, 3rd edition, John Wiley & Sons, 1985, pp. 384. A similar sequence of hydrolysis, acid chloride formation, coupling and de-protection, starting from the bis-O-alkylated compound 3-2, can allow the preparation of compounds 2-3.

SCHEME 3

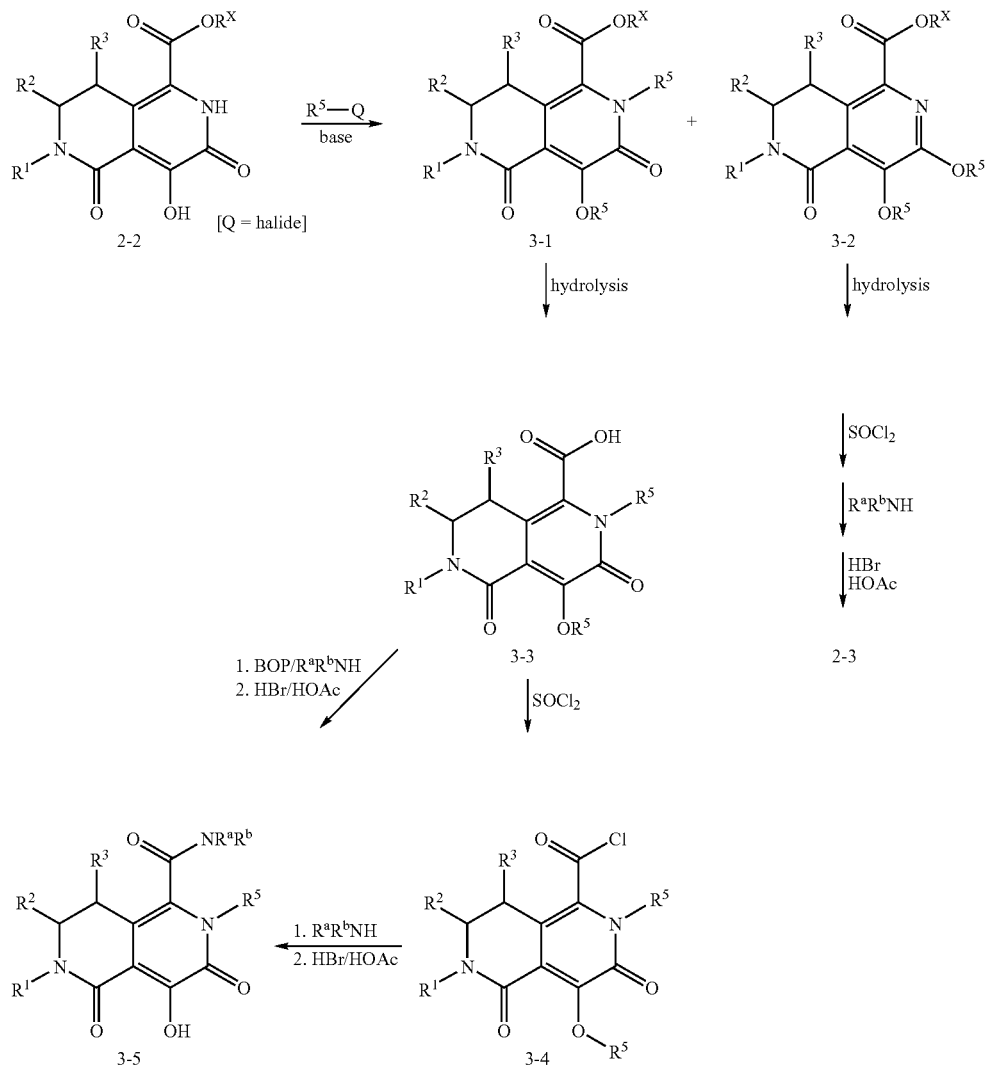

Scheme 4 depicts a method for preparing compounds of the invention in which the $R^4$ group is linked to the parent template via a nitrogen-carbon bond. Acid chloride 34 can be treated with sodium azide to give the acyl azide, which will undergo Curtius rearrangement followed by hydrolysis to the amine 4-2, similar to the method described in R. J. Borchis et. al. *J. Med. Chem.* (1981), 24, 1518-1521. The amine may then be acylated or sulfonylated with the appropriate agent like an acyl or sulfonyl anhydride or acyl or sulfonyl chloride to give the mono or bis N-acyl or N-sulfonylated intermediate, which can then be converted to product 4-3 by using a suitable nucleophile like sodium methoxide or sodium hydroxide. The amine can further be modified by alkylation with a suitable alkyl halide under the influence of a base (e.g., $Cs_2CO_3$ or $K_2CO_3$, using a method similar to that described in A. Nadin, et. al. *J. Org. Chem.* (2003), 68(7), 2844-2852, to give compounds 4-4. The O-alkyl group can then be removed with a strong acid like HBr to give 4-5.

SCHEME 4

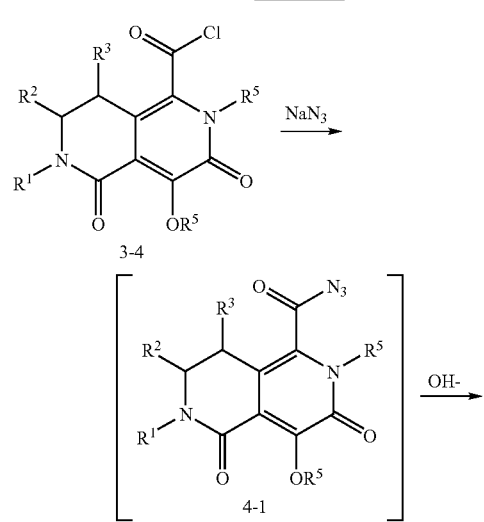

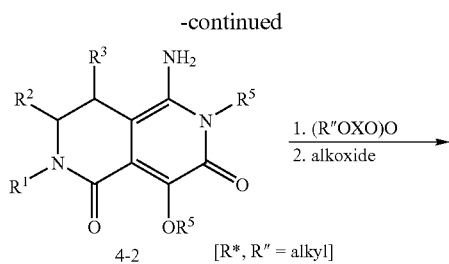
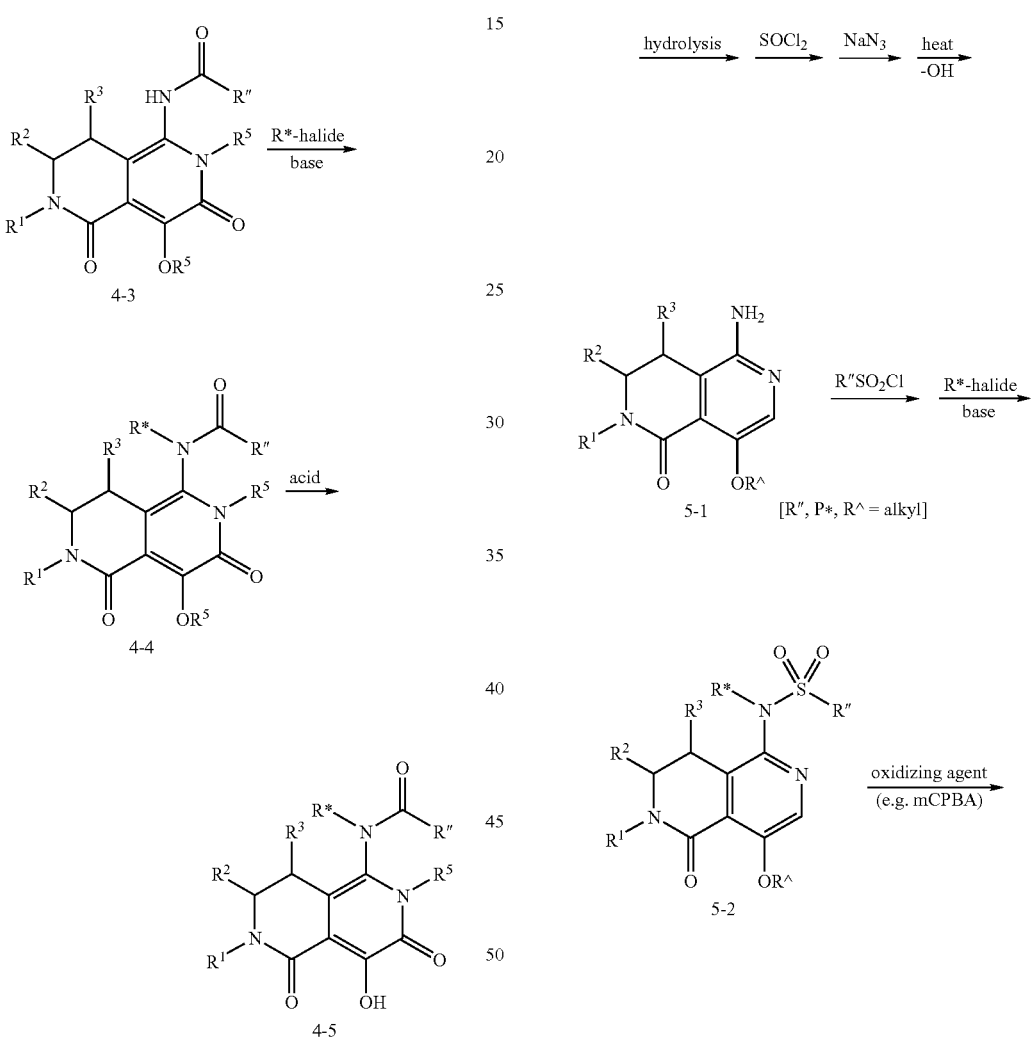

Scheme 5 depicts an alternative sequence of transformations similar to those described in the above schemes. Starting with the intermediate 1-10, O-alkylation, hydrolysis of the ester to the acid, acid chloride formation, acyl azide formation, Curtius rearrangement and hydrolysis give the intermediate 5-1, which can be derivatized with various acyl or sulfonyl halides, and then alkylated to give 5-2. N-oxide formation, similar to that described in M. Adamczyk, *Tetrahedron* (2002) 58, 6951-6963, followed by rearrangement in acetic anhydride and hydrolysis will give 5-4, and cleavage of the O-alkyl group in acid will afford 5-5.

-continued

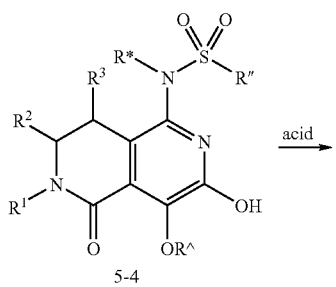

5-4

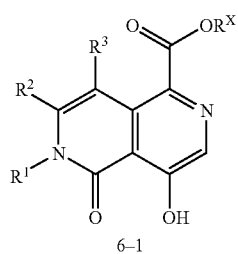

6-1

Scheme 3 or 4 ⇙   ⇘ Scheme 3 or 5

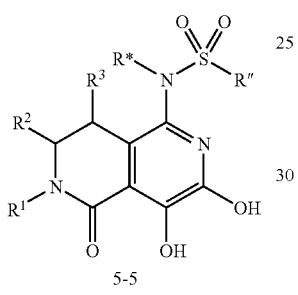

5-5

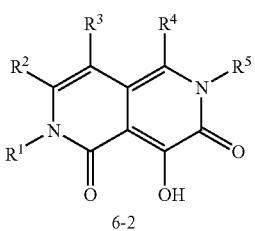 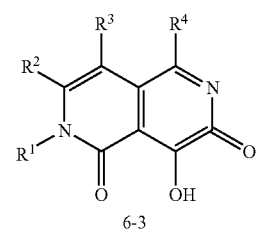

6-2      6-3

Scheme 6 depicts a route to compounds containing a double bond in the "a" position. These analogs can be prepared from treatment of an intermediate like 1-10 with a brominating agent (e.g., NBS) followed by elimination to give the double bond, similar to the method described in Jerry March, *Advanced Organic Chemistry*, 3rd edition, John Wiley & Sons, 1985, pp. 914. The intermediate 6-1 can then be taken through a series of transformations as previously outlined to give products 6-2 and 6-3.

Scheme 7 shows methods that can be used to prepare analogs in which $R^4$ is attached by a carbon-carbon bond. The amine 4-2 or 5-1 can be converted to the halide 7-1, using methods described in A. Bouillon et. al. *Tetrahedron* 58 (14) 2885-2890 (2002), which will allow for carbon-carbon bond formation. Treatment of the halide with a palladium catalyst and vinyl halide, for example, using methods developed by R. F. Heck (M. Schlosser, *Organometallics in Synthesis, a Manual* $2^{nd}$ ed. John Wiley and Sons, Ltd. N.Y. 2002, pp 1169) can provide intermediate 7-2, which can be reduced to the alkyl analog 7-3. Similarly, treatment of the halide with an organometallic catalyst such as zinc or palladium and an aryl or heteroaryl boronic acid, an aryl or heteroaryl tin reagent, or an aryl and heteroaryl halide will afford the product 7-4 Such transformations are well known in the art and are described, for example, in J. J. Li, G. W. Gribble *Palladium in Heterocyclic Chemistry*, Pergamon Press NY 2000. Compounds 7-3 and 7-4 can then be taken through the sequence of steps elaborated in previous schemes to afford additional compounds of the present invention.

SCHEME 6

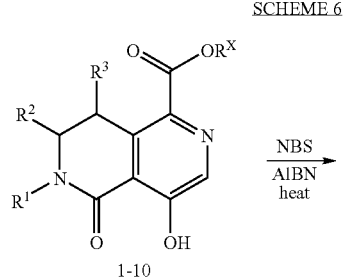

1-10

SCHEME 7

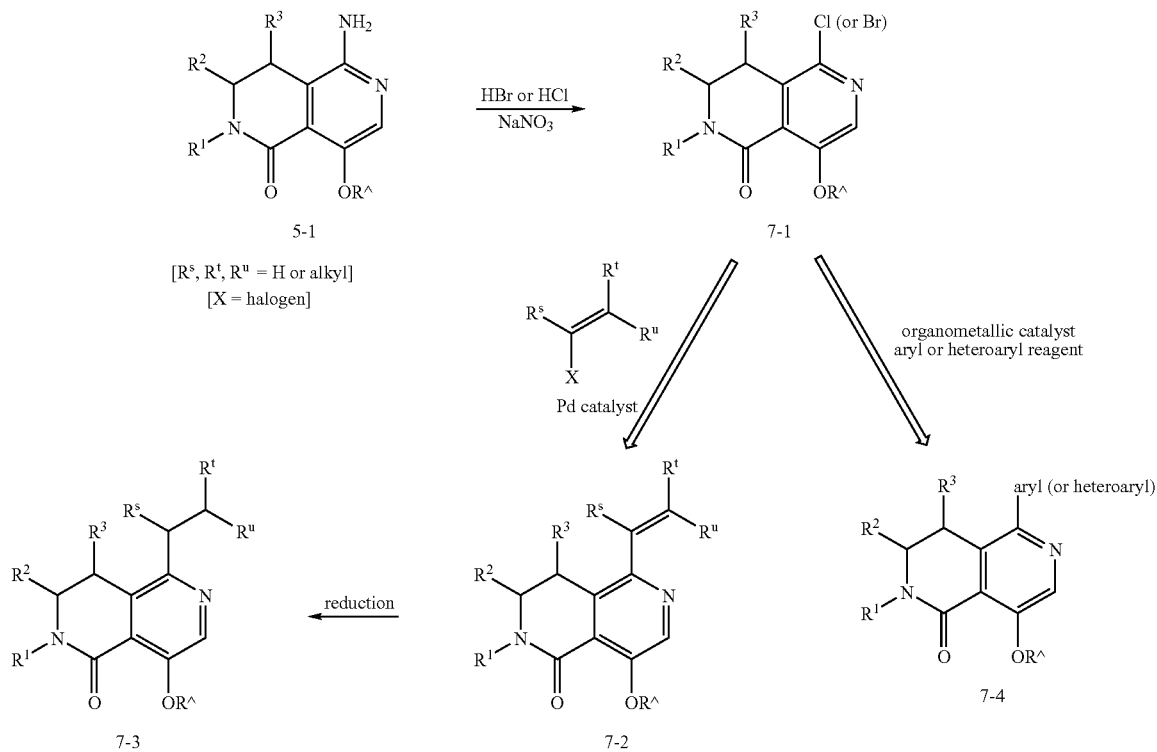

Scheme 8 depicts a method for preparing analogs with R¹ substituents from starting substrate 8-1 with a removable R* group. Substrate 8-1, containing an R* functional group (i.e., a group which is readily removable from an amide moiety, such as p-methoxybenzyl, 3,4- or 2,4-bismethoxybenzyl, allyl, or tosyl), can be prepared by coupling a suitable acid 3-3 or acid chloride 3-4 with an amine (see Scheme 3), and can be de-protected with a strong acid like p-toluene sulfonic acid in a manner similar to the method described in W. M. Kan et. al., Tetrahedron 2000, 44: 1039-1041 to give intermediate 8-2. Deprotected compound 8-2 can then be bis-alkylated with a suitable alkyl halide using a base (e.g., NaH) to give the N,O-alkylated intermediate 8-3. Removal of the O-alkyl group with strong acid (e.g., HBR in a solvent such as acetic or propionic acid) will then afford the product 8-4.

-continued

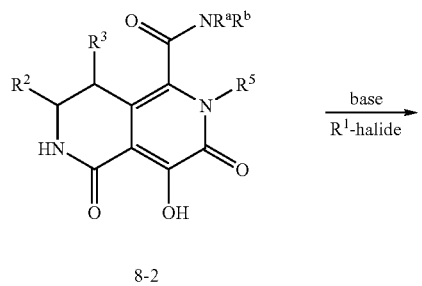

8-2

SCHEME 8

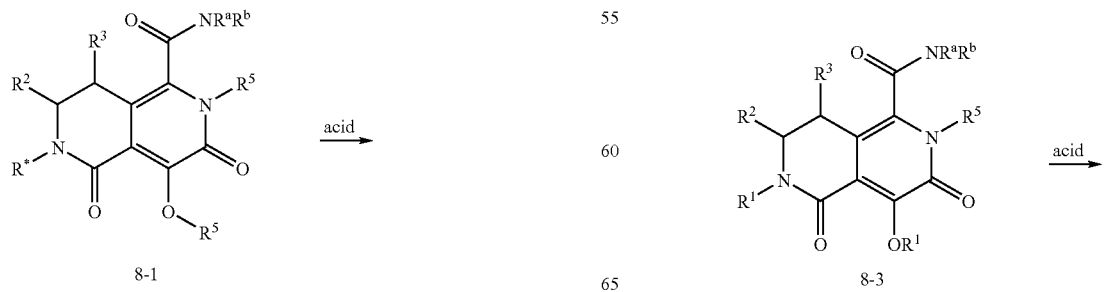

-continued

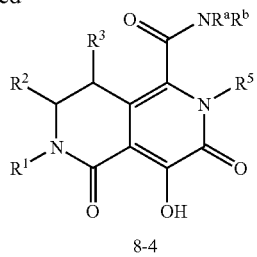

8-4

Scheme 9 depicts an alternative method for preparing naphthyridine carboxamide analog intermediate 8-1 embraced by the present invention in which the amide substituent is incorporated early in the reaction scheme, and in which the R* substituent (defined in Scheme 8) is used to allow variation of $R^1$ at a late stage in the synthesis. Starting material 9-1 can be prepared in a manner similar to that used for 1-10, incorporating the removable group in the initial alkylation step as described for 1-2. The phenolic group in 9-1 can be protected with a suitable alkyl protecting group (e.g., an $R^5$ group as defined herein other than H) followed by hydrolysis with a nucleophile such as hydroxide to afford 9-2. Protection can be accomplished, for example, by treatment with a diazomethane reagent (e.g., TMS diazomethane) in solvent (e.g., chloroform) or by alkylation with an alkylating agent (e.g., by contact with an alkyl halide or an alkyl sulfate such as dimethyl sulfate) in the presence of a suitable base (e.g., an alkali metal carbonate such as $K_2CO_3$ or $Cs_2CO_3$ or an alkali metal hydride such as NaH) in a solvent such as DMSO or methylene chloride. The acid 9-2 can be coupled with an amine using a peptide coupling reagent such as EDC to obtain 9-3. The intermediate 9-3 can then be treated with a suitable oxidizing agent (e.g., mCPBA or peracetic acid) to obtain the N-oxide, which can then be treated as described Suzuki et al. *J. Med. Chem.* 1992, 35, 4045-4053 with acetic anhydride to effect the rearrangement to the O-acylated intermediate, and then treated with a nucleophile (e.g., an alkoxide such as NaOMe) to afford the dioxohexahydro-2,6-naphthyridine-1-carboxylate 9-4. Intermediate 9-4 can be alkylated with an alkylating agent (e.g., an alkyl halide or an alkyl sulfate such as dimethyl sulfate) using a suitable base (e.g., an alkali metal carbonate such as $K_2CO_3$ or $Cs_2CO_3$, an alkali metal hydride such as NaH, or a metal alkoxide such as $Mg(OMe)_2$) in a solvent like DMSO to give a mixture of N- and O-alkylated products 8-1 and 9-5. A similar use of alkali metal carbonates is described in T. Ukita, et. al. *Chem. Pharm. Bull.* 2000, 48 (4) 589-591.

When R* is a benzyl analog containing a chloro in the benzyl ring the chloro can be removed via catalytic dechlorination (e.g., in the presence of 10% palladium on charcoal in methanol) under an atmosphere of hydrogen using conditions similar to those described in M. Freifelder, *Catalytic Hydrogenation in Organic Synthesis Procedures and Commentary*, John Wiley & Sons, 1978, pp. 121. See, e.g., Examples 69 and 70.

When R* is a benzyl analog, the benzyl can be iodinated with a suitable iodinating reagent (e.g., N-iodosuccinimide) in the presence of an acid (e.g., trifluoromethanesulfonic acid or TFA) in a manner similar to that described in Olah et al., *J. Org. Chem.* 1999, 3194, or Castanet et al., *Tetrahedron. Lett.* 2002, 5047. See, e.g., Examples 71 and 72.

SCHEME 9

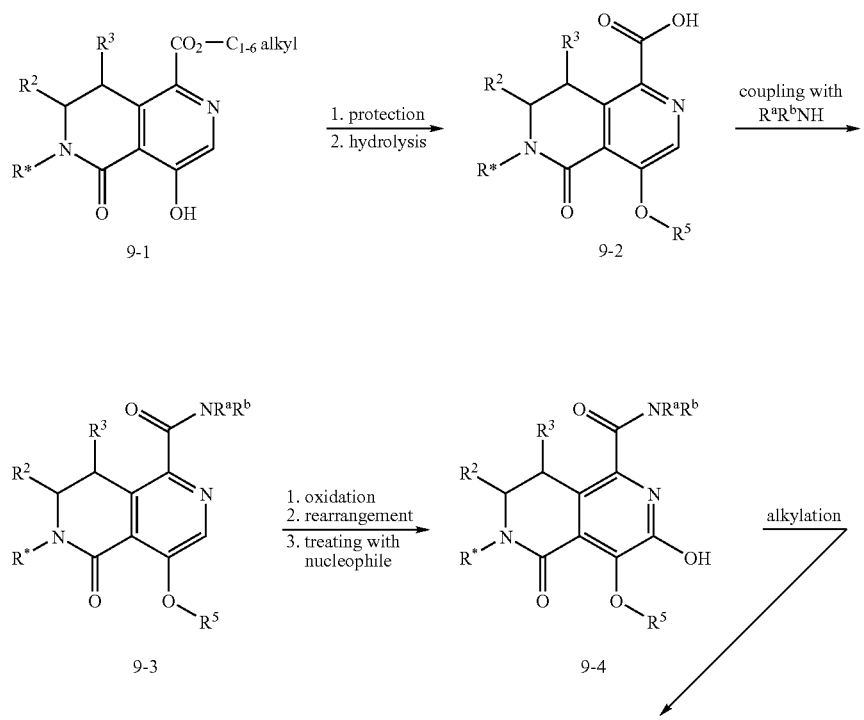

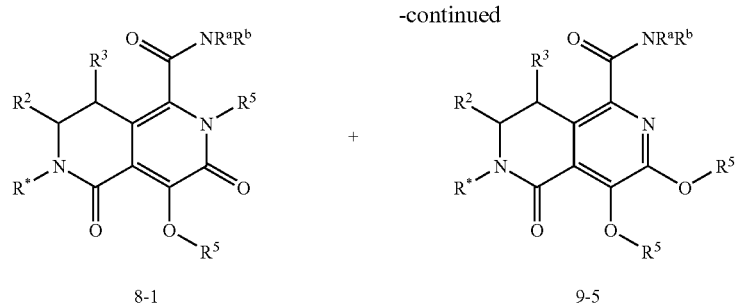

8-1    9-5

Scheme 10 depicts an alternative method for preparing naphthyridine carboxamide analogs embraced by the present invention in which the $R^5$ substituent is other than H, starting from naphthyridine intermediate 10-1. Hydrolysis of the pyridine 10-1 with a nucleophile such as hydroxide can afford the acid 10-2, which can be coupled with an amine using a peptide coupling reagent such as BOP to afford amide 10-3. Alternatively, 10-2 can be converted to the acid chloride using a suitable agent like thionyl chloride or oxalyl chloride/catalytic DMF, similar to the method described in Jerry March, *Advanced Organic Chemistry,* 3rd edition, John Wiley & Sons, 1985, pp. 388, and the acid chloride treated directly with an amine to give the amide 10-3. The intermediate 10-3 can then be treated with a suitable oxidizing agent (e.g., mCPBA or peracetic acid) to obtain the N-oxide 10-4, which can then be treated as described Suzuki et al. *J. Med. Chem.* 1992, 35, 40454053 with acetic anhydride to effect the rearrangement to the O-acylated intermediate, and then treated with a nucleophile (e.g., an alkoxide such as NaOMe) to afford the desired dioxohexahydro-2,6-naphthyridine-1-carboxylate 10-5. Intermediate 10-5 can be alkylated with an alkylating agent (e.g., an alkyl halide or an alkyl sulfate such as dimethyl sulfate) using a suitable base (e.g., an alkali metal carbonate such as $K_2CO_3$ or $Cs_2CO_3$, an alkali metal hydride such as NaH, or a metal alkoxide such as $Mg(OMe)_2$) in a solvent like DMSO to give a mixture of N- and O-alkylated products 10-6 and 10-7. A similar use of alkali metal carbonates is described in T. Ukita, et. al. *Chem. Pharm. Bull.* 2000, 48 (4) 589-591.

SCHEME 10

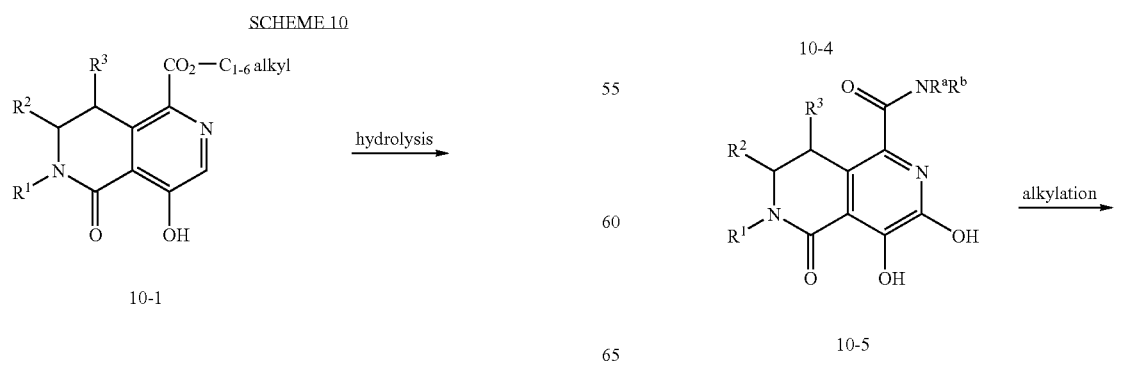

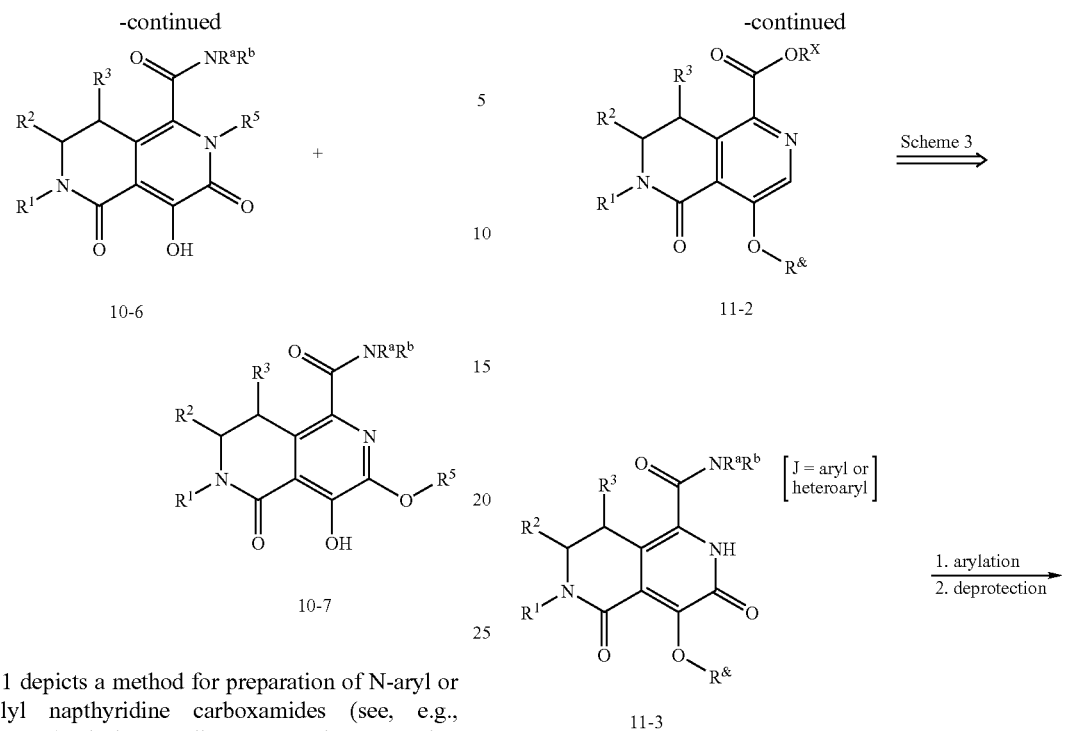

Scheme 11 depicts a method for preparation of N-aryl or N-heterocyclyl napthyridine carboxamides (see, e.g., Examples 25 to 53). The intermediate 11-1 can be prepared as described in Scheme 3 (see also Steps 1 to 6 of Example 12). The hydroxyl group on 11-1 can be protected as alkyl ether by treatment with a base (e.g., cesium carbonate, sodium hydride, or sodium bis(trimethyl)silylamide), followed by reaction with an alkylating reagent such as methyl iodide, benzyl bromide, using methods similar to those described in T. W. Greene & P. G. M. Wuts, *Protective Groups in Organic Synthesis,* 3rd edition, John Wiley & Sons, 1999, p. 246. The resultant napthyridine intermediate 11-2 can then be converted to the corresponding napthyridinone intermediate 11-3 in a sequence similar to that described in Steps 1 to 5 of Example 13. Napthyridinone 11-3 can then be N-arylated with an appropriate aryl or heterocyclyl boronic acid in the presence of a catalyst such as copper(II) acetate (see Lam et al, *Tetrahedron Lett.* 1998, p. 2941, and references cited therein) and the resulting N-arylated compound treated with HBr in acetic acid or boron tribromide (see Scheme 2) to remove the ether protecting group and thereby provide 11-4.

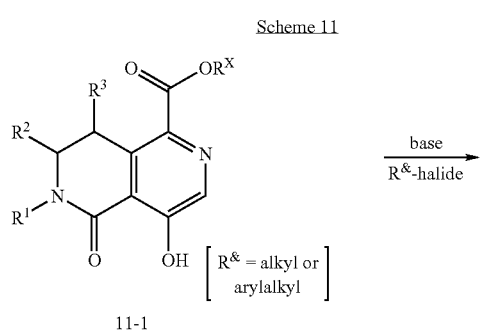

Scheme 12 depicts a method for the preparation of N-aminoethyl napthyridine carboxamides (see, e.g., Examples 66 to 68). The intermediate 12-1 can be alkylated with a dihaloalkane (exemplified by bromo-2-chloroethane in the scheme) using established alkylation conditions (e.g., in DMSO in the presence of magnesium methoxide as described in of Scheme 10) to provide the intermediate alkylation product 12-2a. Treatment of 12-2a with a suitable secondary amine in the presence of sodium iodide provides 12-3. Similarly, 12-1 can be reacted with a Boc-protected haloalkyl secondary amine (exemplified by 1-bromo-2-N-Boc-N-alkyl-aminoethane in the scheme) to provide 12-2b, which can be treated with acid (e.g., HCl in dioxane) to provide the desired 12-4 (see T. W. Greene & P. G. M. Wuts, *Protective Groups in Organic Synthesis,* 3rd edition, John Wiley & Sons, 1999, p. 520).

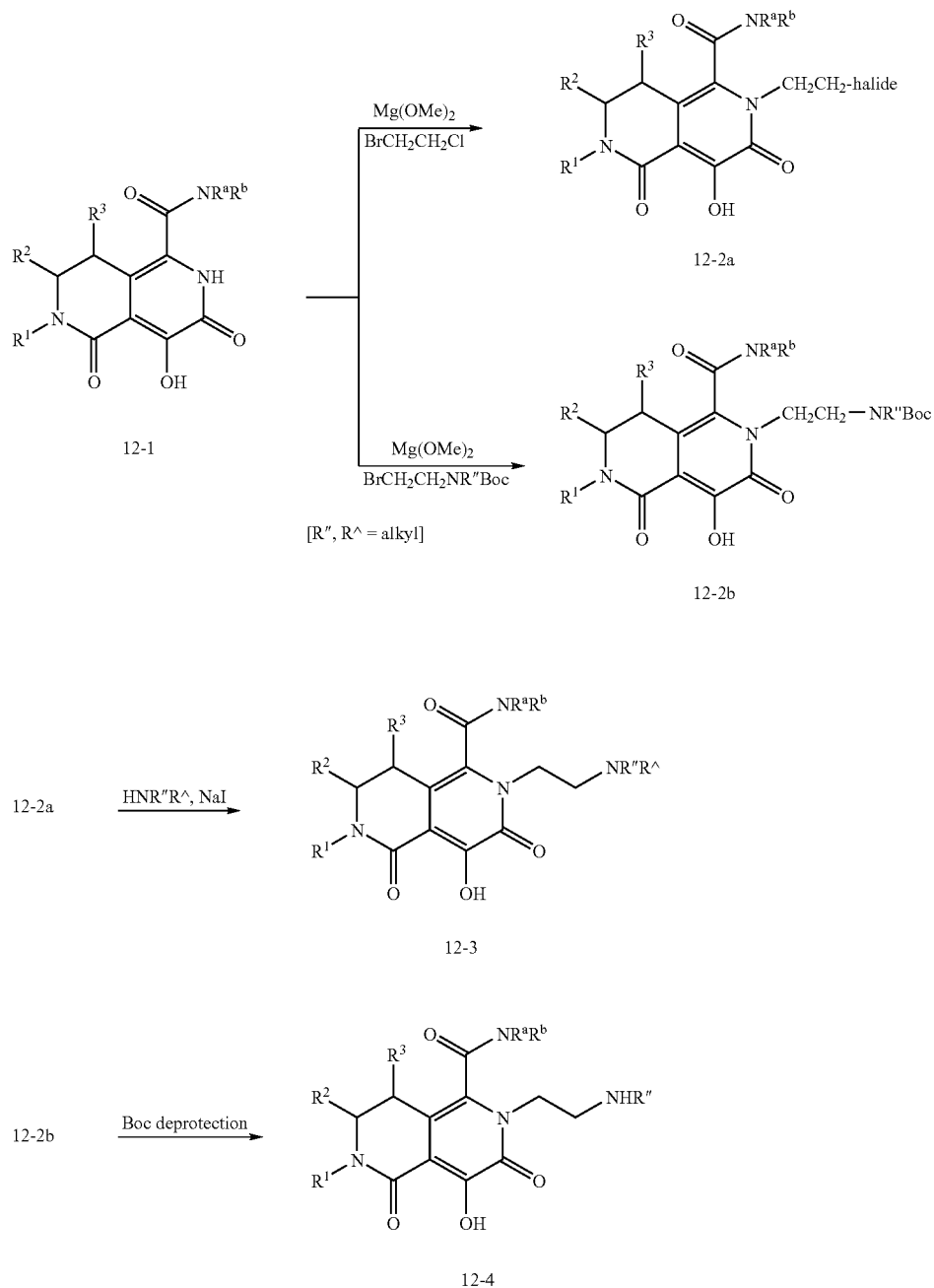

Scheme 13 depicts a method for preparation of napthyridine sulfonamides (see, e.g., Examples 73 to 76). The carboxylic group in intermediate 13-1, which can be prepared as described in Scheme 3, can be converted to the corresponding tert-butyl carbamate 13-2 via a Curtius rearrangement in the manner described in J. March, *Advanced Organic Chemistry*, 3rd edition, John Wiley & Sons, 1992, p. 1091 (e.g., acid 13-1 can be treated with diphenylphosphoryl azide in the presence of anhydrous tert-butanol to afford carbamate 13-2). Carbamate 13-2 can then be treated with base (e.g., as sodium hydride or sodium bis(trimethyl)silylamide), followed by contact with a sulfonylation reagent (e.g., an alkane sulfonyl chloride) to provide an intermediate sulfonylated carbamate, which can be transformed to the corresponding sulfonamide 13-3 by treatment with acid (e.g., TFA) in a manner similar to the conditions described in T. W. Greene & P. G. M. Wuts, *Protective Groups in Organic Synthesis*, 3rd edition, John Wiley & Sons, 1999, p. 520. Treatment of 13-3 with a base (e.g., sodium hydride or sodium bis(trimethyl)silyl-amide), followed by alkylation with a suitable reagent (e.g., an alkyl halide such as methyl iodide) and then by removal of the ether protecting group (see Schemes 2 and 11) to afford the desired 13-4.

Scheme 13

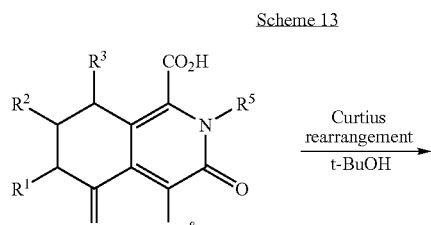

13-1

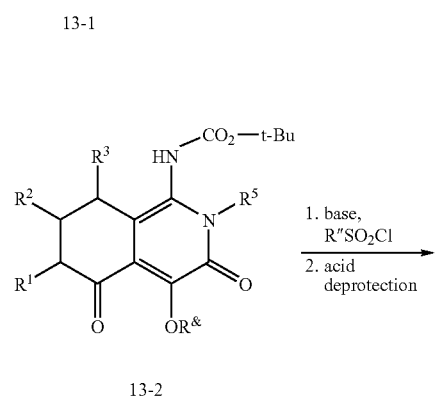

13-2

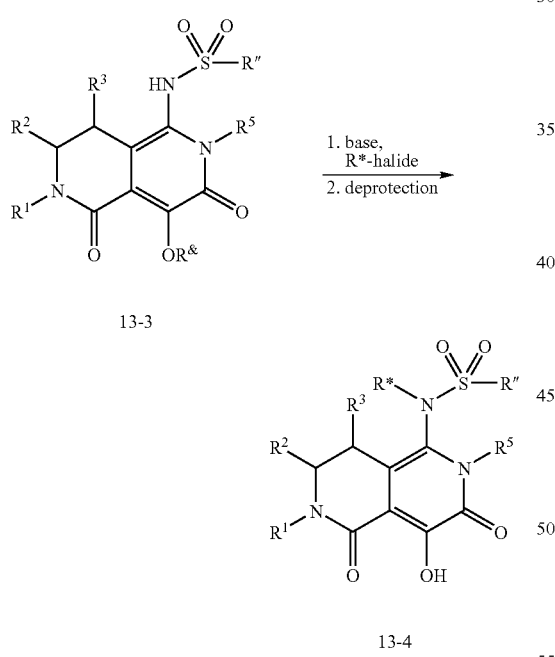

13-3

13-4

Scheme 14

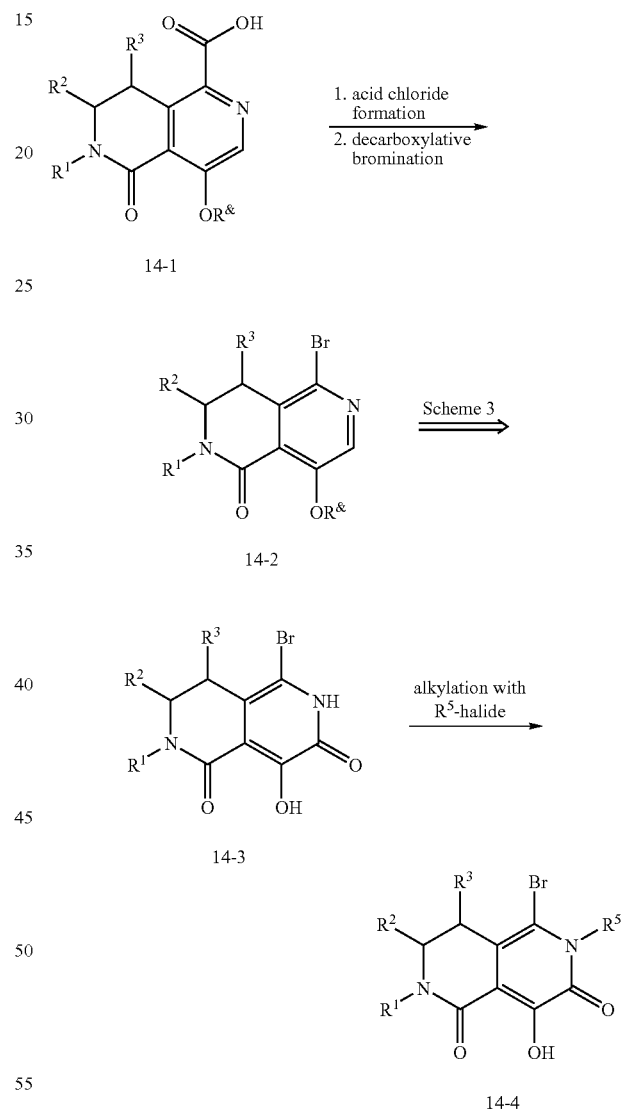

14-1

14-2

14-3

14-4

Scheme 14 depicts the preparation of bromo compounds of the invention, wherein the carboxylic acid intermediate 14-1 (Scheme 9) is converted to the corresponding acid chloride by treatment with a suitable agent (e.g., oxalyl chloride or thionyl chloride) and the resulting acid chloride is converted to the corresponding bromide 14-2 via a Barton decarboxylative bromination as described in Barton et al, *Tetrahedron Lett.* 1985, 5939 (e.g., with a mixture of bromotrichloro-methane and 2-pyridinethiol-N-oxide in the presence of AIBN). The bromide 14-2 can then be converted to the corresponding napthyridinone intermediate in a sequence similar to that described in Scheme 3. Subsequent removal of the ether protecting group (see description in Scheme 2 or Scheme 11) affords the desired 14-3. N-alkylation of 14-3 provides 14-4. Catalytic debromination of 14-3 and 14-4 (e.g., in the presence of 10% palladium on charcoal in methanol under an atmosphere of hydrogen similar to conditions described in M. Freifelder, *Catalytic Hydrogenation in Organic Synthesis Procedures and Commentary*, John Wiley & Sons, 1978, p. 121) will afford analogs without a substituent in the 5-position of the naphthyridine ring.

Scheme 15 depicts the preparation of alkylated products from a starting bromide, wherein bromide 14-4 is treated with an appropriate vinyl stannane in the presence of a palladium catalyst to provide the corresponding vinyl napthyridine intermediate 15-1. Hydrogenation or cyclopropanation of this intermediate, followed by removal of the ether protecting group, will afford the corresponding desired alkyl substituted napthyridine 15-2 and cyclopropane substituted napthyridine 15-3.

Scheme 15

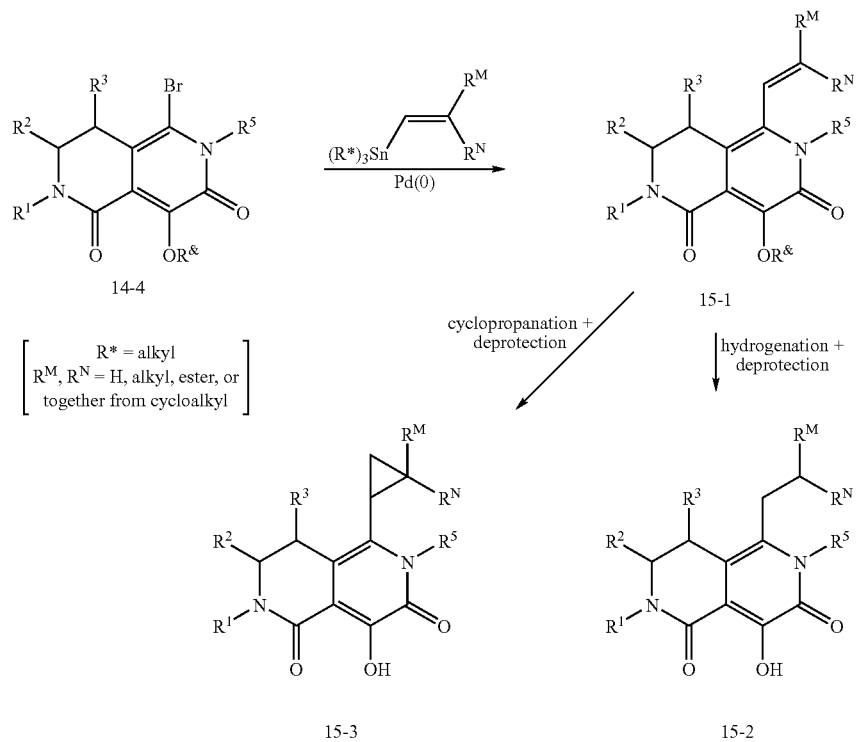

Compounds of the present invention having aryl, heteroaryl, or saturated heterocyclyl groups in the naphthyridine ring can be prepared by treatment of 14-4 with a saturated heterocycle or with an aryl/heteroaryl boronic acid or ester in the presence of a suitable ligand-complexed metal catalyst. Scheme 16 is illustrative, wherein the desired arylated analog 16-1 is obtained by treating 14-4 with an aryl boronic acid in the presence of a palladium catalyst (e.g., tetrakis(triphenylphosphine)-palladium(0)). Suitable chemistries are described in *Angew Chem. Intl.* 2004, 1871; *Org. Lett.* 2003, 793; and *Tetrahedron Lett.* 2004, 3305.

Scheme 16

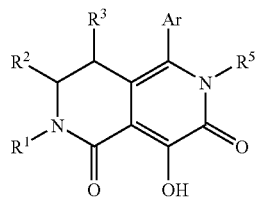

-continued 16-1

The present invention also includes a process (alternatively referred to herein as "Process P1" or the "P1 process") for preparing a compound of Formula IV:

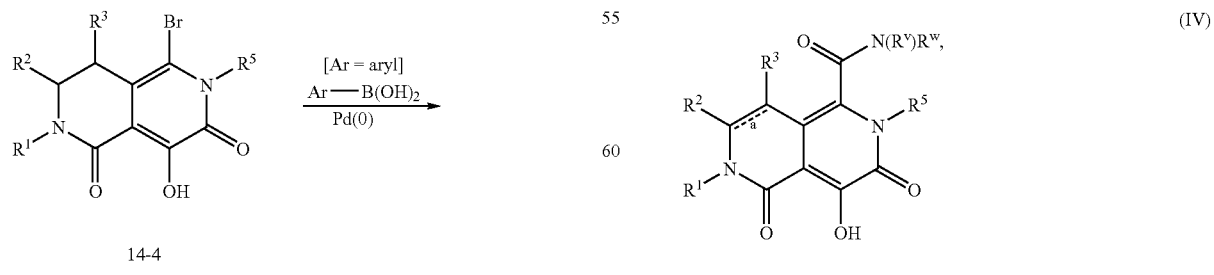

(IV)

which comprises:
(B) contacting a compound of Formula V:

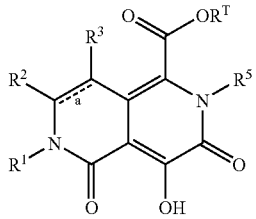 (V)

with a Grignard salt of an amine of Formula VI:

HN(R$^V$)R$^W$ (VI)

to obtain Compound IV; wherein:
bond

in the ring is a single bond or a double bond;
R$^1$ is —C$_{1-6}$ alkyl substituted with R$^J$, wherein R$^J$ is:
(A) aryl or aryl fused to a 5- or 6-membered heteroaromatic ring containing from 1 to 4 heteroatoms independently selected from N, O and S, wherein the aryl or fused aryl is:
(a) optionally substituted with from 1 to 5 substituents each of which is independently:
(1) —C$_{1-6}$ alkyl,
(2) —C$_{1-6}$ alkyl substituted with —O—C$_{1-6}$ alkyl, —O—C$_{1-6}$ haloalkyl, —NO$_2$, —N(R$^a$)R$^b$, or —S(O)$_n$R$^a$,
(3) —C$_{1-6}$ haloalkyl,
(4) —O—C$_{1-6}$ alkyl,
(5) halogen,
(6) —C(=O)N(R$^a$)R$^b$, or
(7) —SO$_2$R$^a$, and
(b) optionally substituted with 1 or 2 substituents each of which is independently:
(1) phenyl,
(2) benzyl, or
(3) —HetB;
wherein each HetB is a 5- or 6-membered heteroaromatic ring containing from 1 to 4 heteroatoms independently selected from N, O and S, wherein the heteroaromatic ring is optionally substituted with from 1 to 4 substituents each of which is independently halogen, —C$_{1-6}$ alkyl, —C$_{1-6}$ haloalkyl, —O—C$_{1-6}$ alkyl, or —O—C$_{1-6}$ haloalkyl; or
(B) a 5- or 6-membered heteroaromatic ring containing from 1 to 4 heteroatoms independently selected from N, O and S; wherein the heteroaromatic ring is
(i) optionally substituted with from 1 to 4 substituents each of which is independently halogen, —C$_{1-6}$ alkyl, —C$_{1-6}$ haloalkyl, —O—C$_{1-6}$ alkyl, or —O—C$_{1-6}$ haloalkyl, and
(ii) optionally substituted with 1 or 2 substituents each of which is independently aryl or —C$_{1-6}$ alkyl substituted with aryl;

R$^2$ and R$^3$ are each independently —H or —C$_{1-6}$ alkyl;
R$^5$ is:
(1) —C$_{1-6}$ alkyl,
(2) —C$_{3-8}$ cycloalkyl optionally substituted with from 1 to 4 substituents each of which is independently —C$_{1-6}$ alkyl or —O—C$_{1-6}$ alkyl,
(3) —C$_{1-6}$ alkyl substituted with C$_{3-8}$ cycloalkyl, wherein the cycloalkyl is optionally substituted with from 1 to 4 substituents each of which is independently —C$_{1-6}$ alkyl or —O—C$_{1-6}$ alkyl,
(4) —C$_{1-6}$ alkyl substituted with aryl, wherein the aryl is optionally substituted with from 1 to 5 substituents each of which is independently —C$_{1-6}$ alkyl, —C$_{1-6}$ alkylene-O—C$_{1-6}$ alkyl, or halogen, or
(5) —C$_{1-6}$ alkyl substituted with a 5- or 6-membered heteroaromatic ring containing from 1 to 4 heteroatoms independently selected from N, O and S, wherein the heteroaromatic ring is optionally substituted with from 1 to 4 substituents each of which is independently —C$_{1-6}$ alkyl;
R$^T$ is —C$_{1-6}$ alkyl;
R$^V$ and R$^W$ are each independently —C$_{1-6}$ alkyl or R$^V$ and R$^W$ together with the N atom to which they are both attached form a 4- to 6-membered saturated heterocyclic ring optionally containing a heteroatom in addition to the nitrogen attached to R$^V$ and R$^W$ selected from N, O, and S, where the S is optionally oxidized to S(O) or S(O)$_2$, and wherein the saturated heterocyclic ring is optionally substituted with 1 or 2 substituents each of which is independently a C$_{1-6}$ alkyl group;
each aryl is independently phenyl, naphthyl, or indenyl;
each R$^a$ is independently H or C$_{1-6}$ alkyl; and
each R$^b$ is independently H or C$_{1-6}$ alkyl.

Process P1 can produce Compound IV from Compound V in good yield without protecting the 4-hydroxy group. The P1 process is exemplified in Step 8 of Example 91, wherein the protection and deprotection steps included in the process set forth in Example 12 are avoided.

The Grignard salt employed in the P1 process is typically a halomagnesium salt of amine VI. The halomagnesium salt of amine VI is preferably a chloromagnesium salt or a bromomagnesium salt of amine VI, and is more preferably a chloromagnesium salt of amine VI (i.e., ClMgN(R$^V$)R$^W$).

Representative amines of Formula VI which can be employed in the P1 process include dimethylamine, diethylamine, isopropylethylamine, azetidine, pyrrolidine, piperidine, piperazine, 4-methylpiperazine, morpholine, and thiomorpholine.

The contacting step B of the P1 process is suitably conducted in an aprotic solvent. As used herein, the term "solvent" refers to an organic substance which is a chemically inert liquid under the reaction conditions and which will dissolve or suspend the reactants in such a manner as to bring the reactants into contact and permit the reaction to proceed.

Aprotic solvents suitable for use in the present invention include those selected from the group consisting of alkanes, cycloalkanes, halogenated alkanes, halogenated cycloalkanes, aromatic hydrocarbons, alkylated aromatic hydrocarbons, halogenated aromatic hydrocarbons, alkylated and halogenated aromatic hydrocarbons, ethers, polyalkylphosphoramides, N,N'-dialkylalkyleneureas, and mixtures thereof. In this context, a "halogenated" compound or substance is a compound or substance containing one or more C—H bonds wherein one or more of the hydrogens have been replaced with halogen. A class of solvents suitable for use in the P1 process consists of the solvents selected from the group consisting of C$_{1-10}$ linear and branched alkanes, C$_{1-10}$ linear and branched halogenated alkanes, $C_{5-10}$ cycloalkanes, halogenated $C_{5-10}$ cycloalkanes, benzene, naphthalene, mono- and di- and tri-$C_{1-6}$ alkyl substituted benzenes, halogenated benzenes, halogenated mono- and di- and tri-$C_{1-6}$ alkyl substituted benzenes, dialkyl ethers wherein each alkyl is independently a $C_{1-6}$ alkyl, $C_{1-6}$ linear and branched alkanes substituted with two —O—$C_{1-6}$ alkyl groups (which are the same or different), $C_4$-$C_8$ cyclic ethers and diethers, phenyl $C_{1-4}$ alkyl ethers, diethylene glycol di($C_{1-4}$ alkyl)ethers, hexa ($C_{1-6}$ alkyl)phosphoramides, N,N'-di-($C_{1-6}$ alkyl)ethyleneureas, and N,N'-di-($C_{1-6}$ alkyl)propyleneureas.

Representative examples of aprotic solvents suitable for use as a solvent in the P1 process include the following: pentane (individual isomers and mixtures thereof), hexane (individual isomers and mixtures thereof), heptane (individual isomers and mixtures thereof), cyclopentane, cyclohexane, cycloheptane, carbon tetrachloride, chloroform, methylene chloride, 1,2-dichloroethane, 1,1,2-trichloroethane, 1,1,2,2-tetrachloroethane, chlorocyclopentane, chlorocyclohexane, benzene, toluene, o- and m- and p-xylene, xylene mixtures, ethylbenzene, chlorobenzene, bromobenzene, o-chlorotoluene, 2,4-dichlorotoluene, 2,4,6-trichlorotoluene, ethyl ether, MTBE, THF, dioxane, 1,2-dimethoxyethane, HMPA, and DMPU.

In one embodiment of the P1 process, the contacting comprises adding Compound V to the Grignard salt of amine VI dissolved or suspended in the aprotic solvent to form a reaction mixture and ageing the reaction mixture. The Grignard salt can be prepared, for example, by adding amine VI dissolved or suspended in a first aprotic solvent to a solution of an alkylmagnesium halide (e.g., a $C_{1-4}$ alkylmagnesium chloride or bromide) in a second aprotic solvent that is the same or different from the first aprotic solvent. The addition can suitably be conducted with agitation (e.g., stirring) at a temperature at or below about 0° C. (e.g., from about −50 to about 0° C., or from about −10 to about 0° C.). The resulting admixture (either a solution or suspension) can then be aged with agitation for a time sufficient to effect formation of the amine salt, after which Compound V, typically dissolved or suspended in a third aprotic solvent that is the same or different from the first and second solvents, can be charged to the admixture (either maintained at a temperature below about 0° C.—e.g., from about −10 to about 0° C.—or warmed to a temperature in a range of from about 0 to about 25° C.) to provide a reaction mixture, and the resulting reaction mixture is aged until the desired degree of conversion of Compound V is achieved or until conversion is complete.

As used herein, the term "ageing" and variants thereof (e.g., "aged") refer to maintaining the reactants in a given reaction or treatment step in contact for a time and under conditions effective for achieving the desired degree of conversion.

Process P1 can be conducted at any temperature at which the reaction forming Compound IV can be detected. The reaction (i.e., the contacting) can suitably be conducted at a temperature in a range of from about −40 to about 40° C., is typically conducted at a temperature in a range of from about −20 to about 25° C., and is more typically conducted at a temperature in a range of from about −10 to about 0° C.

The Grignard salt of amine VI can be employed in any proportion with respect to Compound V which results in the formation of at least some of the desired compound of Formula IV, but the Grignard salt is typically employed in a proportion which, under the reaction conditions (e.g., temperature) employed, can optimize conversion of Compound V to Compound IV. The Grignard salt is suitably employed in an amount in a range of at least about 2 equivalents (e.g., from about 2 to about 10 equivalents) per equivalent of Compound V, is typically employed in an amount in a range of from about 3 to about 6 equivalents per equivalent of Compound V, and is more typically employed in an amount in a range of from about 4 to about 5 equivalents per equivalent of Compound V.

An embodiment of the P1 process is the process as originally defined above, wherein the compound of Formula IV is a compound of Formula IV-A:

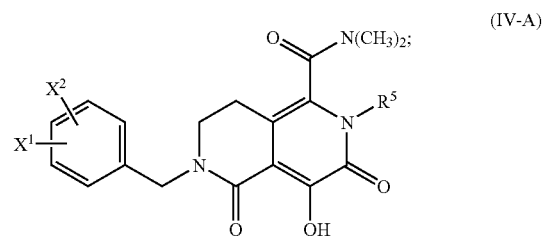

the compound of Formula V is a compound of Formula V-A:

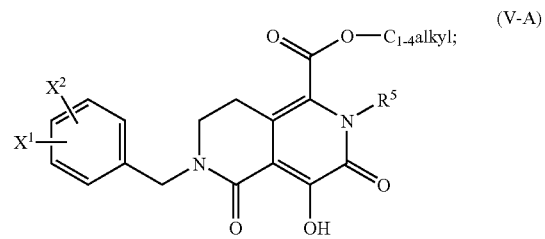

the Grignard salt is a Grignard salt of dimethylamine; $X^1$ is: (1) —H, (2) bromo, (3) chloro, (4) fluoro, or (5) methoxy; $X^2$ is: (1) —H, (2) bromo, (3) chloro, (4) fluoro, (5) methyl, (6) methoxy, (7) —$CF_3$, or (8) —$OCF_3$; and $R^5$ is —$C_{1-4}$ alkyl.

Additional embodiments of the P1 process include the process as just described in the preceding embodiment incorporating one or more of the features (i) to (v) as follows:

(i) Compound IV-A is

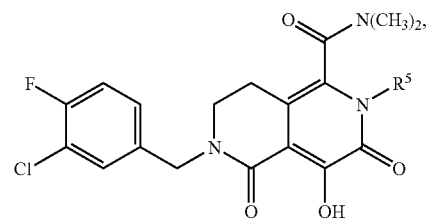

and Compound V-A is

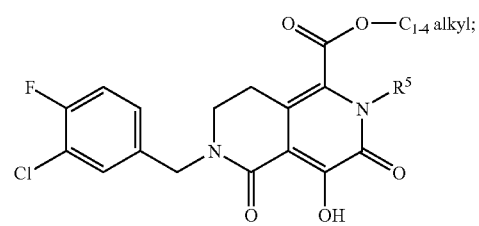

(ii) the contacting is conducted in an aprotic solvent selected from the group consisting of an alkane, a cycloalkane, a halogenated alkane, a halogenated cycloalkane, an aromatic hydrocarbon, an alkylated aromatic hydrocarbon, a halogenated aromatic hydrocarbon, an alkylated and halogenated aromatic hydrocarbon, an ether, a polyalkyl phosphoramide, an N,N'-dialkylalkyleneurea, and mixtures thereof;

(iii) the Grignard salt is $ClMg(CH_3)_2$;

(iv) the contacting is conducted at a temperature in a range of from about −20 to about 25° C. (e.g., in a range of from about −10 to about 0° C.); and (v) the Grignard salt is employed in an amount of at least about 2 equivalents (e.g., in an amount in a range of from about 2 to about 10 equivalents, or from about 3 to about 6 equivalents, or from about 4 to about 5 equivalents) per equivalent of Compound V-A.

Another embodiment of Process P1 is the process as originally set forth above or as described in a preceding embodiment, which further comprises: (C) recovering Compound IV from the reaction medium. Compound IV can be recovered, for example, by quenching the reaction mixture with an aqueous solution of a mineral acid (e.g., aqueous HCl), separating the resulting organic layer (i.e., the aprotic solvent medium containing the desired product), and removing in whole or in part the volatile solvent from the organic layer using heat or a vacuum or both to obtain Compound IV either directly or by precipitation from the concentrated organic layer and separation of the precipitate by filtration.

Still another embodiment of the P1 Process is the process as originally set forth above which further comprises:

(A) treating a compound of Formula IX:

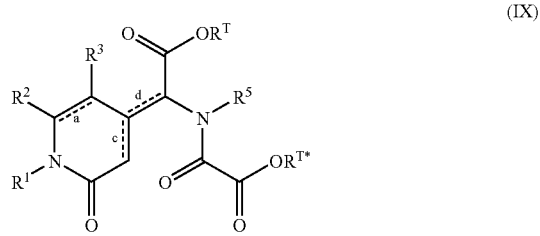

(IX)

with (i) a tertiary amine base in the presence of a lithium salt or (ii) an alkoxide base, to obtain a compound of Formula V; wherein one of bonds " $\underset{\text{-----}}{c}$ "

and

" $\underset{\text{-----}}{d}$ "

is a single bond and the other is a double bond; $R^{T*}$ is $C_{1-6}$ alkyl (where $R^T$ and $R^{T*}$ can be the same or different alkyl groups); and all other variables are as originally defined in the P1 process. In an aspect of this embodiment, Compound IX is a compound of Formula IX-A:

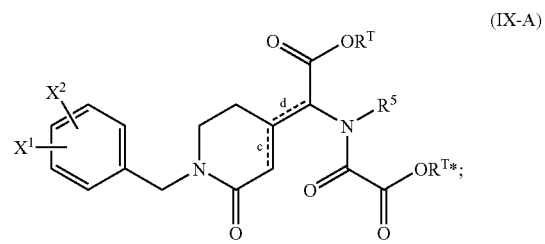

(IX-A)

Compound V is a compound of Formula V-A as defined above; $R^T$ and $R^{T*}$ are each independently $C_{1-4}$ alkyl; and $R^5$, $X^1$ and $X^2$ are each as defined in Compound V-A above. This embodiment of the P1 process (i.e., the embodiment including Steps A and B) is alternatively referred to herein as "Process P1a" or the "P1a process".

The tertiary amine bases suitable for use in the P1a process include trimethylamine, triethylamine, tri-n-butylamine, ethyl-diisopropylamine, N,N-dimethylaniline, N,N-dimethyl-benzylamine, pyridine, picoline, N-methylpiperidine, N-methylmorpholine, 4-N,N-dimethylaminopyridine (DMAP), 1,4-diazabicyclo[2.2.2]octane (DABCO), 1,5-diazabicyclo[4.3.0]nonene (DBN), and 1,8-diazabicyclo[5.4.0]undec-7-ene (DBU).

Lithium salts suitable for use in the P1a process include halide salts and sulfonate salts, such as LiBr, LiCl, LiI, LiOTs, and LiOMs. A class of suitable lithium salts is the lithium halide salts, and a sub-class of suitable lithium halide salts is LiBr, LiCl, and LiI.

Alkoxide bases suitable for use in the P1a process include the alkali metal alkoxides such as the $C_{1-4}$ alkoxides of lithium, sodium and potassium. The alkoxide base can be, for example, LiOMe, NaOMe, NaOEt, KOMe, KOEt, t-BuONa, or t-BuOK.

Treating in Step A of the P1a process can suitably be conducted in an organic solvent. The organic solvent can be an aprotic solvent, wherein the aprotic solvent is suitably an ether, a tertiary amide, an N-alkylpyrrolidone, a sulfoxide, or an aromatic hydrocarbon. The solvent can be, for example, THF, MTBE, DME, dioxane, DMF, DMAC, N-methylpyrrolidone, N-ethylpyrrolidone, DMSO, or toluene. A class of suitable solvents is the ethers (e.g., THF).

The treating in Step A of the P1a process can be conducted at any temperature at which the reaction forming Compound V can be detected. The treating can suitably be conducted at a temperature in a range of from about −20 to about 60° C., is typically conducted at a temperature in a range of from about 0 to about 30° C., and is more typically conducted at a temperature in a range of from about 15 to about 25° C.

The tertiary amine base (e.g., DABCO) or alkoxide base can be employed in Step A in any proportion with respect to Compound IX which results in the formation of at least some of the desired compound of Formula V, but the base is typically employed in a proportion which, under the reaction conditions (e.g., temperature) employed, can optimize conversion of Compound IX to Compound V. The base is suitably employed in an amount in a range of at least about 0.1 equivalent (e.g., from about 0.1 to about 5 equivalents) per equivalent of Compound IX, is typically employed in an amount in a range of from about 1 to about 5 equivalents per equivalent of Compound IX, and is more typically employed in an amount in a range of from about 2 to about 4 equivalents per equivalent of Compound IX.

The lithium salt (e.g., LiBr) used in combination with the tertiary amine base can be employed in Step A in any proportion with respect to Compound IX which results in the formation of at least some of the desired compound of Formula V, but salt is typically employed in a proportion which, under the reaction conditions (e.g., temperature) employed, can optimize conversion of Compound IX to Compound V. The Li salt is suitably employed in an amount in a range of at least about 0.1 equivalent (e.g., from about 0.1 to about 5 equivalents) per equivalent of Compound IX, is typically employed in an amount in a range of from about 1 to about 5 equivalents per equivalent of Compound IX, and is more typically employed in an amount in a range of from about 2 to about 4 equivalents per equivalent of Compound IX.

The treatment time can vary widely depending upon, inter alia, the scale of the treatment (e.g., laboratory bench v. pilot plant), the treatment temperature and the choice and relative amounts of reactants and reagents, but the reaction time is typically in a range of from about 15 minutes to about 24 hours.

In one embodiment, Step A of Process P1a comprises adding the Li salt (e.g., LiBr) to Compound IX dissolved or suspended in an organic solvent (e.g., an ether such as THF), and then adding the tertiary amine base (e.g., DABCO) to form a reaction mixture, and then ageing the resulting mixture to obtain Compound V. The additions of Li salt and amine base can be conducted with agitation (e.g., stirring). The reaction mixture is aged at a suitable reaction temperature as set forth above and optionally with agitation until the desired degree of conversion of Compound IX is achieved or until conversion is complete. The addition of the Li salt and amine base to Compound IX can be done at the desired reaction temperature which is then maintained during ageing, or the addition of the Li salt and amine base can be done below the desired reaction temperature and the mixture brought to the desired temperature for ageing. The ageing can be quenched by addition of an acid. The desired Compound V can be recovered by extraction with a suitable organic solvent, followed by evaporative removal of the solvent.

The present invention also includes a process (alternatively referred to herein as "Process P2" or the "P2 process") for preparing a compound of Formula VII:

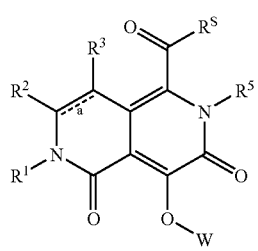

(VII)

which comprises reacting an alkylating agent of formula $R^5$-Z with a compound of Formula VIII:

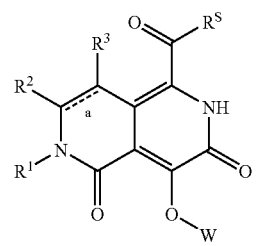

(VIII)

in a polar aprotic solvent and in the presence of a base selected from a magnesium base and a calcium base; wherein:
bond " ⁻⁻a⁻⁻ "

in the ring is a single bond or a double bond;
W is —H or —$C_{1-6}$ alkyl;
Z is halogen or —$SO_3$-Q wherein Q is (i) $C_{1-6}$ alkyl or (ii) phenyl optionally substituted with 1 or 2 substituents each of which is independently a $C_{1-6}$ alkyl;
$R^S$ is —O—$C_{1-6}$ alkyl or N($R^V$)$R^W$ wherein $R^V$ and $R^W$ are each independently —$C_{1-6}$ alkyl or $R^V$ and $R^W$ together with the N atom to which they are both attached form a 4- to 6-membered saturated heterocyclic ring optionally containing a heteroatom in addition to the nitrogen attached to $R^V$ and $R^W$ selected from N, O, and S, where the S is optionally oxidized to S(O) or S(O)$_2$, and wherein the saturated heterocyclic ring is optionally substituted with 1 or 2 substituents each of which is independently a $C_{1-6}$ alkyl group;
$R^5$ is:
(1) —$C_{1-6}$ alkyl,
(2) —$C_{3-8}$ cycloalkyl optionally substituted with from 1 to 4 substituents each of which is independently —$C_{1-6}$ alkyl or —O—$C_{1-6}$ alkyl,
(3) —$C_{1-6}$ alkyl substituted with $C_{3-8}$ cycloalkyl, wherein the cycloalkyl is optionally substituted with from 1 to 4 substituents each of which is independently —$C_{1-6}$ alkyl or —O—$C_{1-6}$ alkyl,
(4) —$C_{1-6}$ alkyl substituted with aryl, wherein the aryl is optionally substituted with from 1 to 5 substituents each of which is independently —$C_{1-6}$ alkyl, —$C_{1-6}$ alkylene-O—$C_{1-6}$ alkyl, or halogen, or
(5) —$C_{1-6}$ alkyl substituted with a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl;

and $R^1$, $R^2$, and $R^3$ are each independently as originally defined above.

Compounds embraced by Formula VIII include compounds of the present invention (i.e., when W is H) and compounds which can be used as intermediates (i.e., when W is $C_{1-6}$ alkyl) in the preparation of compounds of the present invention. The use of a magnesium base or a calcium base (preferably a magnesium base) can favor the desired N-alkylation over O-alkylation; e.g., the formation of a compound of Formula VII over the formation of the following compound:

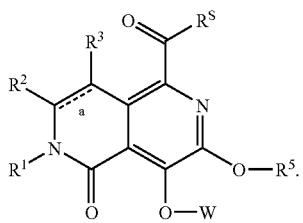

The base employed in Process P2 can be a magnesium-containing base or a calcium-containing base. Magnesium and calcium bases suitable for use in the process include those of formula $M(R^x)_2$, wherein M is Mg or Ca, and each $R^x$ is independently H or —O—$C_{1-6}$ alkyl. Exemplary bases include $MgH_2$, $Mg(OMe)_2$, $Mg(OH)_2$, $Mg(OEt)_2$, MgHOMe, MgHOEt, $CaH_2$, $Ca(OMe)_2$ and $Ca(OEt)_2$. The base is preferably a magnesium base. In one embodiment, the P2 process is as originally set forth above, wherein the base comprises a magnesium base of formula $Mg(R^x)_2$ where $R^x$ is as defined above. In an aspect of this embodiment, the base is a $Mg(O—C_{1-4}\text{-alkyl})_2$. In another aspect of this embodiment, the base is $Mg(OMe)_2$.

The base can be employed in any proportion with respect to Compound VIII and alkylating agent (e.g., alkyl halide) which results in the formation of at least some of the desired N-alkylated compound of Formula VII, but the base is typically employed in a proportion which, under the reaction conditions (e.g., temperature) employed, can optimize conversion of Compound VIII to Compound VII. The base is suitably employed in an amount in a range of from about 0.5 to about 10 equivalents per equivalent of Compound VIII, is typically employed in an amount in a range of from about 1 to about 10 equivalents per equivalent of Compound VIII, and is more typically employed in an amount in a range of from about 1 to about 5 equivalents (e.g., from about 1.5 to about 2 equivalents) per equivalent of Compound VIII.

The alkylating agent employed in Process P2 is of formula $R^5$-Z, wherein $R^5$ is as defined above and Z is halogen (i.e., F, Cl, Br, or I) or —$SO_3$-Q wherein Q is (i) $C_{1-6}$ alkyl or (ii) phenyl optionally substituted with 1 or 2 substituents each of which is independently a $C_{1-6}$ alkyl. In one embodiment, the P2 process is as originally set forth above or as set forth in a preceding embodiment, wherein the alkylating agent is of formula $R^5$-Z, wherein $R^5$ is $C_{1-6}$ alkyl and Z is chloride, bromide, iodide, mesylate, or tosylate. In an aspect of this embodiment, Z is iodide or tosylate. In another aspect of this embodiment, the alkylating agent is MeI or methyl tosylate, and in a feature of this aspect the alkylating agent is methyl tosylate.

The alkylating agent can be employed in any proportion with respect to the base and Compound VIII which results in the formation of at least some of the desired N-alkylated compound of Formula VII, but the alkylating agent is typically employed in a proportion which, under the reaction conditions (e.g., temperature) employed will optimize conversion of Compound VIII to Compound VII. The alkylating agent is suitably employed in an amount in a range of from about 0.5 to about 20 equivalents per equivalent of Compound VIII, and is typically employed in an amount in a range of from about 1 to about 20 equivalents per equivalent of Compound VIII. The alkylating agent (e.g., alkyl halide) is more typically employed in an amount in a range of from about 1 to about 10 equivalents (e.g., from about 1 to 5 equivalents) per equivalent of Compound VIII. The alkylating agent is preferably employed in excess with respect to Compound VIII, such as in an amount in a range of from about 2 to about 6 equivalents (e.g., from about 3 to about 5 equivalents, or about 4 equivalents) per equivalent of Compound VIII.

The solvent employed in Process P2 can be any polar aprotic solvent which under the conditions employed is in the liquid phase, is chemically inert, and will dissolve, suspend, and/or disperse the reactants so as to bring them into contact and permit the formation of the desired Compound VII. The solvent is preferably one which under the conditions employed in the process favors N-alkylation to the desired Compound VII over O-alkylation to an O-alkylated by-product. The polar aprotic solvent is suitably a halogenated alkane, an ether, an ester, a tertiary amide, an N-alkylpyrrolidone, a sulfoxide, or a nitrile; and is typically a tertiary amide, an N-alkylpyrrolidone, or a sulfoxide. In one embodiment, the P2 process is as originally set forth above or as set forth in a preceding embodiment, wherein the polar aprotic solvent comprises a N,N-di-($C_{1-6}$ alkyl)-$C_{1-6}$ alkylamide, a N—($C_{1-6}$ alkyl)pyrrolidone, or a di-($C_{1-6}$ alkyl)sulfoxide. In an aspect of this embodiment, the polar aprotic solvent comprises a N,N-di-($C_{1-3}$ alkyl)-$C_{1-3}$ alkylamide, a N—($C_{1-3}$ alkyl)pyrrolidone, or a di-($C_{1-3}$ alkyl)sulfoxide. In another aspect of this embodiment, the polar aprotic solvent is DMF, DMAC, N-methylpyrrolidone, N-ethylpyrrolidone, or DMSO. In a feature of this aspect, the polar aprotic solvent is DMF.

Process P2 can be conducted at any temperature at which the reaction (N-alkylation) forming Compound VII can be detected. The reaction can suitably be conducted at a temperature in a range of from about −20 to about 100° C., is typically conducted at a temperature in a range of from about 0 to about 100° C., and is more typically conducted at a temperature in a range of from about 15 to about 80° C. In one embodiment of the P2 process the temperature is in a range of from about 20 to about 60° C., wherein the process step is initially conducted at about 20° C. and subsequently heated to a temperature of about 60° C.

An embodiment of the P2 process is the process for preparing a compound of Formula VII-A:

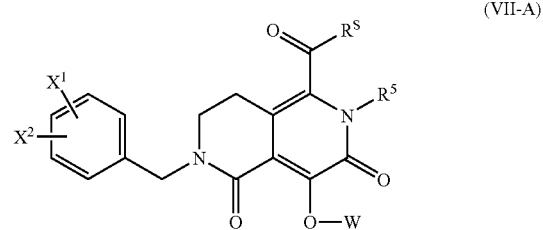

which comprises reacting an alkylating agent of formula $R^5$-Z with a compound of Formula VIII-A:

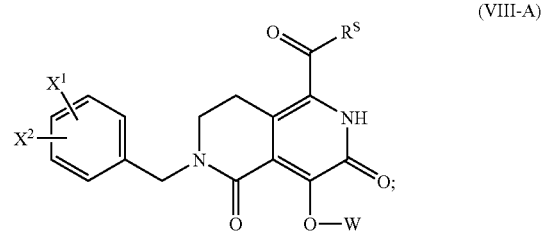

in a polar aprotic solvent and in the presence of a magnesium base; wherein:

W is —H or —$C_{1-6}$ alkyl;

$X^1$ and $X^2$ are each independently:
- (1) —H,
- (2) —$C_{1-4}$ alkyl,
- (3) —$C_{1-4}$ haloalkyl,
- (4) —O—$C_{1-4}$ alkyl,
- (5) halogen,
- (6) —CN,
- (7) —C(=O)$NH_2$,
- (8) —C(=O)NH(—$C_{1-4}$ alkyl),
- (9) —C(=O)N(—$C_{1-4}$ alkyl)$_2$, or
- (10) —$SO_2$—$C_{1-4}$ alkyl;

Z is —Cl, —Br, —I, or tosylate;

$R^S$ is —O—$C_{1-6}$ alkyl or N($R^V$)$R^W$ wherein $R^V$ and $R^W$ are each independently —$C_{1-6}$ alkyl; and $R^5$ is —$C_{1-6}$ alkyl.

Additional embodiments of the P2 process include the process as just described in the preceding embodiment incorporating one or more of the features (i) to (vi) as follows:

(i) the magnesium base comprises $MgH_2$ or Mg(O—$C_{1-3}$ alkyl)$_2$ (or is Mg(OMe)$_2$);

(ii) the polar aprotic solvent is a N,N-di-($C_{1-3}$ alkyl)-$C_{1-3}$ alkylamide, a N—($C_{1-3}$ alkyl)pyrrolidone, or a di-($C_{1-3}$ alkyl) sulfoxide (e.g., the solvent is DMF, DMAC, N-methylpyrrolidone, N-ethylpyrrolidone, or DMSO; or the solvent is DMF);

(iii) the reaction is conducted at a temperature in a range of from about 0 to about 100° C. (or from about 20 to about 60° C.);

(iv) the alkylating agent $R^5$-Z is a $C_{1-4}$ alkyl iodide or a $C_{1-4}$ alkyl tosylate (or is MeI or methyl tosylate);

(v) the alkylating agent $R^5$-Z is employed in an amount in a range of from about 1 to about 5 equivalents (or from about 3 to about 5 equivalents) per equivalent of Compound VIII-A; and (vi) the magnesium base is employed in an amount in a range of from about 1 to about 5 equivalents (or from about 1.5 to about 2 equivalents) per equivalent of Compound VIII-A).

Another embodiment of Process P2 is the process as originally set forth above or as described in a preceding embodiment, which further comprises recovering Compound VII from the reaction medium. Process P2 can result in the formation of O-alkylated by-product, which can be separated from the desired N-alkylated product (i.e., Compound VII) by methods known in the art such as washing the precipitated solids with suitable solvents or via chromatography.

The present invention also includes a process (alternatively referred to herein as "Process P3" or the "P3 process") for preparing a compound of Formula IV as defined above, which comprises treating a compound of Formula X:

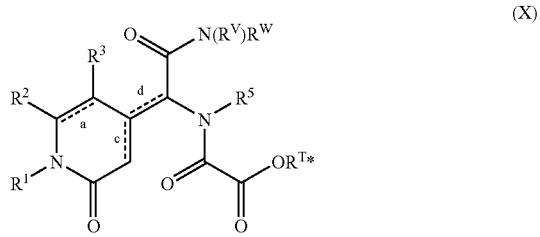

(X)

with (i) a tertiary amine base in the presence of a lithium salt or (ii) an alkoxide base, to obtain a compound of Formula IV, wherein bonds "--c--"

and

"--d--"

and $R^{T*}$ are each as defined above in the P1a process; and all of the variables in Formula X are as originally defined above in the P1 process. An embodiment of the P3 process is the process as just defined, wherein the compound of Formula X is a compound of Formula X-A:

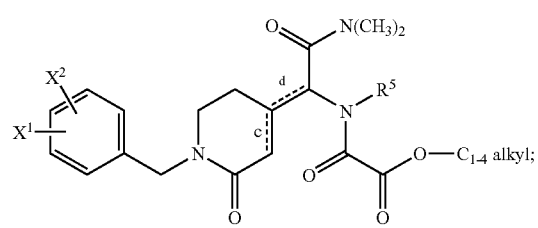

(X-A)

the compound of Formula IV is a compound of Formula IV-A; and $R^5$, $X^1$ and $X^2$ are each as defined in Compound IV-A above. The description of the choice and amounts of base (i.e., tertiary amine base or alkoxide base) and lithium salt, the treatment temperature, the treatment time, the choice and use of organic solvents, methods of quenching and recovery, etc. set forth above for Step A of Process P1a applies to Process P3 as well and is considered part of the description of Process P3.

Process P2 is an alkylation process in which the $R^5$ substituent is added to the ring nitrogen to provide the desired N-alkylated compound. Process P3, on the other hand, is a process in which cyclization of the ring affords the desired N-alkylated compound, the $R^5$ substituent having been attached to the N atom prior to ring closure. (The $R^5$ group can, for example, be introduced onto the N atom prior to cyclization by reductive amination with the appropriate aldehyde or ketone in the presence of a reducing agent such as a borohydride—see, e.g., Step 2 of Example 92.) When $R^5$ is a bulky group (e.g., a branched alkyl group such as isopropyl or isobutyl), alkylation of the ring N can be sterically hindered resulting in relatively low yields of the desired compound VII in Process P2. In such cases (and where $R^S$ is N($R^V$)$R^W$), Process P3 can be preferred, because the cyclization is comparatively unaffected by the size of the $R^5$ group and because methods for introducing $R^5$ into the uncyclized precursor (e.g., reductive amination) can be more efficient relative to the post-cyclization alkylation of the P2 process.

It is understood that tautomers can exist for Compound IV in Process P1 and P3, Compound V in Process P1, and Compound VII and Compound VIII in Process P2 as a result of keto-enol tautomerism. The P1 and P2 and P3 processes encompass all tautomeric forms, individually and in mixtures.

The progress of any reaction step of any chemical process set forth herein, including processes P1 and P2 and P3, can be followed by monitoring the disappearance of a reactant (e.g., Compound VIII) and/or the appearance of the desired product (e.g., Compound VII) using such analytical techniques as TLC, HPLC, IR, NMR or GC.

Unless a contrary meaning is clear from the context, a reference herein to "equivalent" or "equivalents" means molar equivalent(s).

The following examples serve only to illustrate the invention and its practice. The examples are not to be construed as limitations on the scope or spirit of the invention. In the following examples "MS (M+1)" refers to the mass of the molecular ion plus 1 of the subject compound as determined by mass spectroscopy.

EXAMPLE 1

Methyl 6-(4-fluorobenzyl)-4-hydroxy-3,5-dioxo-2,3,5,6,7,8-hexahydro-2,6-naphthyridine-1-carboxylate

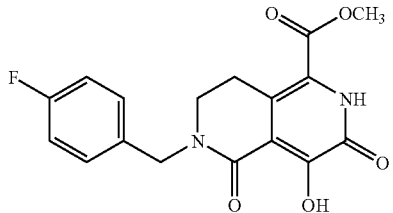

Step 1: 1-(4-Fluorobenzyl)piperidine-2-one

To a suspension of sodium hydride (2.4 g, 0.1 mol) in anhydrous THF (400 mL) was added piperidine-2-one (9.0 g, 90 mmol) in anhydrous THF (20 mL) over 10 minutes. After 20 minutes, the resultant thick slurry was treated with 4-fluorobenzyl bromide (18.9 g, 99.9 mmol). The reaction mixture was refluxed overnight. The resultant mixture was cooled to 0° C. and treated with H$_2$O (10 mL) cautiously. The mixture was stirred for 10 minutes and concentrated under vacuum. The residue was partitioned between ethyl acetate (300 mL) and H$_2$O. The organic extract was washed with brine, dried with MgSO$_4$, filtered, and concentrated under vacuum. The residual oil was subjected to column chromatography on silica gel eluting with 50%-70% ethyl acetate in hexanes. The appropriate fractions were combined and concentrated to afford the benzylated piperidinone as a white solid.

$^1$HNMR (400 MHz, CDCl$_3$) δ 7.23 (dd, J=8.7 Hz, 5.4 Hz, 2H), 7.00 (t, J=8.7 Hz, 2H), 4.56 (s, 2H), 3.18 (t, J=6 Hz, 2H), 2.46 (t, J=6 Hz, 2H), 1.79 (m, 4H).

Step 2: 1-(4-Fluorobenzyl)-3-(phenylsulfinyl)piperidin-2-one

To a cooled (0° C.) solution of 1-(4-fluorobenzyl)piperidine (5.0 g, 24.1 mmol) in anhydrous THF (100 mL) was added lithium bis(trimethylsilyl)amide (1.0 M in THF, 53 mL, 53 mmol) dropwise, and the solution was stirred for one half hour. The solution was treated with methyl benzene sulfinate (5.65 g, 36.1 mmol) in anhydrous THF (3 mL) dropwise. After 30 minutes at 0° C., the resultant mixture was quenched with water and partitioned between 10% KHSO$_4$ and CHCl$_3$, the layers separated and the aqueous extracted several more times with CHCl$_3$. The organic extract was dried with Na$_2$SO$_4$, filtered, and concentrated under vacuum to afford 1-(4-fluorobenzyl)-3-(phenylsulfinyl)piperidin-2-one as a waxy solid that was taken on to the next step. ES MS M+1=332

Step 3: 1-(4-Fluorobenzyl)-5,6-dihydropyridin-2-(1H)-one

To a solution of 1-(4-fluorobenzyl)-3-(phenylsulfinyl)piperidin-2-one (0.37 g, 1.11 mmol) in toluene (15 mL) was added solid Na$_2$CO$_3$ (2 g, 18.8 mmol). The reaction mixture was refluxed for about 6 hours. The resultant solution was filtered and concentrated under vacuum and the residue chromatographed on silica eluting with a gradient of 040% EtOAc/Hexanes to give the product as colorless glass.

$^1$HNMR (400 MHz, CDCl$_3$) δ 7.26 (m, 2H), 7.01 (m, 2H), 6.56 (dt, J=9.9 Hz, 4.2 Hz, 1H), 6.00 (dt, J=9.7 Hz, 1.8 Hz, 1H), 4.59 (s, 2H), 3.32 (t, J=7.2 Hz, 2H), 2.33 (m, 2H).

Step 4: Methyl[(2-methoxy-2-oxoethyl)amino](oxo)acetate

To a cooled (0° C.) solution of the glycine methyl ester HCl salt (30.0 g, 0.24 mol) in methylene chloride (500 mL) was added triethylamine (50.8 g, 0.50 mol). Methyl oxalyl chloride (29.3 g, 0.24 mol) was carefully added dropwise. The reaction solution warmed to room temperature and stirred overnight. The product mixture was partitioned between H$_2$O and methylene chloride. The organic extract was dried with Na$_2$SO$_4$ and concentrated under vacuum to afford the title compound as a brown oil.

$^1$HNMR (400 MHz, CDCl$_3$) δ 7.59 (br, 1H), 4.14 (d, J=5.6 Hz, 2H), 3.93 (s, 3H), 3.79 (s, 3H). ES MS M+1=176

Step 5: Methyl 5-methoxy-1,3-oxazole-2-carboxylate

To a warm (35-40° C.) suspension of phosphorous pentoxide (77.7 g, 109 mmol) in anhydrous acetonitrile (200 mL) was added methyl[(2-methoxy-2-oxoethyl)amino](oxo)acetate (19.19 g, 109.6 mmol). The reaction mixture was heated to 65° C., then stirred overnight at room temperature. The product mixture was cooled to 0° C. and carefully quenched with ice and brine keeping the reaction from generating an unsuitable exotherm. The resultant mixture was extracted with ethyl acetate (600 mL). The organic extract was washed with brine, dried with Na$_2$SO$_4$, then concentrated under vacuum. The residue was subjected to column chromatography on silica gel eluting with 100% CH$_2$Cl$_2$. The appropriate fractions were combined and concentrated to afford the title compound as a light yellow solid that was used without further purification.

$^1$H NMR (400 MHz, CDCl$_3$) δ 6.36 (s, 1H), 4.01 (s, 3H), 3.96 (s, 3H). ES MS M+1=158

Step 6: Methyl 6-(4-fluorobenzyl)-4-hydroxy-5-oxo-5,6,7,8-tetrahydro-2,6-naphthyridine-1-carboxylate In a sealed tube, 1-(4-fluorobenzyl)-5,6-dihydropyridin-2-(1H)-one (3.84 g, 18.7 mmol), and methyl 5-methoxy-1,3-oxazole-2-carboxylate prepared in Step 5 (2.94 g, 18.7 mmol), were combined. The reaction mixture was heated at 120° C. After 24 hours, the resultant mixture was cooled and methanol saturated with HCl (2 mL) was added. The product mixture stirred at room temperature for 40 minutes, then was concentrated under vacuum. The residual crude material was diluted with DMSO (6.0 mL) and filtered to give the title compound.

¹H NMR (400 MHz, DMSO-d₆) δ 12.96 (br, 1H), 8.39 (s, 1H), 7.31 (m, 2H), 7.06 (t, J=8.5 Hz, 2H), 4.72 (s, 2H), 3.94 (s, 3H), 3.50 (m, 4H). ES MS M+1=331

Step 7: Methyl 6-(4-fluorobenzyl)-4-hydroxy-5-oxo-5,6,7,8-tetrahydro-2,6-naphthyridine-1-carboxylate 2-oxide To a solution of methyl 6-(4-fluorobenzyl)-4-hydroxy-5-oxo-5,6,7,8-tetrahydro-2,6-naphthyridine-1-carboxylate (0.509 g, 1.541 mmol) in acetic acid (2 mL) was added hydrogen peroxide (35% wt % in H₂O, 0.262 g, 7.705 mmol). The reaction mixture was heated to 100° C. for 1 hour. The product mixture was concentrated under vacuum and purified by reverse phase HPLC eluting with 5%-95% acetonitrile (0.1% TFA) in H₂O (0.1% TFA) to afford the title compound as a yellow solid.

¹HNMR (400 MHz, CD₃OD) δ 7.95 (s, 1H), 7.38 (dd, J=5.3 Hz, 8.6 Hz, 2H), 7.08 (t, J=8.8 Hz, 2H), 4.71 (s, 2H), 3.93 (s, 3H), 3.56 (t, J=6.7 Hz, 2H), 2.89 (t, J=6.7 Hz, 2H). ES MS M+1=347

Step 8: Methyl 6-(4-fluorobenzyl)-4-hydroxy-3,5-dioxo-2,3,5,6,7,8-hexahydro-2,6-naphthyridine-1-carboxylate To methyl 6-(4-fluorobenzyl)-4-hydroxy-5-oxo-5,6,7,8-tetrahydro-2,6-naphthyridine-1-carboxylate 2-oxide (0.178 g, 0.514 mmol) was added acetic anhydride (0.157 g, 1.542 mmol) and refluxed. After 1 hour, the reaction mixture was concentrated under vacuum, then sodium methoxide (30 wt. % in methanol, 0.083 g, 1.540 mmol) was added. After stirring at room temperature for 1 hour, the product mixture was concentrated under vacuum. The residue was purified by reverse phase HPLC eluting with 5%-95% acetonitrile (0.1% TFA) in H₂O (0.1% TFA) to afford the title compound as a pale yellow solid.

¹HNMR (400 MHz, CDCl₃) δ 7.30 (dd, J=5.3 Hz, 8.4 Hz, 2h), 7.06 (t, J=8.5 Hz, 2H), 4.71 (s, 2H), 3.93 (s, 3H), 3.46 (t, J=6.5 Hz, 2H), 3.32 (t, J=6.5 Hz, 2H).
ES MS M+1=347

EXAMPLE 2

6-(4-Fluorobenzyl)-4-hydroxy-N,N-dimethyl-3,5-dioxo-2,3,5,6,7,8-hexahydro-2,6-naphthyridine-1-carboxamide

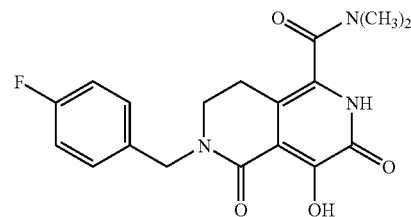

To a cooled (−10° C.) solution of dimethylamine (2M in THF, 0.002 g, 0.035 mmol) was slowly added trimethylaluminum (2M in toluene, 0.002 g, 0.035 mmol) and stirred for 30 minutes at room temperature. The reaction mixture was cooled to −10° C. and methyl 6-(4-fluorobenzyl)-4-hydroxy-3,5-dioxo-2,3,5,6,7,8-hexahydro-2,6-naphthyridine-1-carboxylate (0.004 g, 0.012 mmol, Example 1, Step 8) in THF (5 mL) was added. The reaction stirred at room temperature for 2 hours, then transferred via syringe to a solution of 1:1 CH₂Cl₂:0.5 N aq. HCl at 0° C. and stirred for 1 hour. The product mixture was separated, and the aqueous was extracted three times with CH₂Cl₂. The aqueous layer was treated with saturated Na₂CO₃ solution to pH 5 and extracted three times with CH₂Cl₂ again. The organic combined extracts were dried with Na₂SO₄ and concentrated under vacuum. The residue was purified by reverse phase HPLC eluting with 5%-95% acetonitrile (0.1% TFA) in H₂O (0.1% TFA) to afford the title compound as a light yellow solid.

¹H NMR (400 MHz, CD₃OD) δ 7.39 (dd, J=5.3 Hz, 8.6 Hz, 2H), 7.09 (t, J=8.8 Hz, 2H), 4.74 (s, 2H), 3.50 (t, J=6.4 Hz, 2H), 3.05 (s, 3H), 2.96 (s, 3H), 2.67 (t, J=6.4 Hz, 2H) ppm. ES MS M+1=360

EXAMPLES 3-6

The compounds in the following table were prepared in accordance with the procedure set forth in Example 2 using the appropriate analogous starting materials.

| Example | Compound | Data |
|---|---|---|
| 3 | N-Cyclohexyl-6-(4-fluorobenzyl)-4-hydroxy-3,5-dioxo-2,3,5,6,7,8-hexahydro-2,6-naphthyridine-1-carboxamide | ¹HNMR (400 MHz, CD₃OD) δ 7.39 (dd, J=5.6 Hz, 8.7 Hz, 2H), 7.09 (t, J=8.7 Hz, 2H), 4.74 (s, 2H), 4.39 (p, J=7.9 Hz, 1H), 3.49 (t, J=6.1 Hz, 2H), 3.06 (t, J=6.1 Hz, 2H), 2.32 (m, 2H), 2.04 (m, 2H), 1.78 (m, 2H) ppm. ES MS M + 1 = 386 |

-continued

| Example | Compound | Data |
|---|---|---|
| 4 | N-Cyclopropyl-6-(4-fluorobenzyl)-4-hydroxy-3,5-dioxo-2,3,5,6,7,8-hexahydro-2,6-naphthyridine-1-carboxamide | $^1$HNMR (400 MHz, CDCl$_3$) δ 13.53 (br, 1H), 7.63 (br, 1H), 7.30 (dd, J=5.6 Hz, 8.5 Hz, 2H), 7.06 (t, J=8.5 Hz, 2H), 4.71 (s, 2H), 3.51 (m, 2H), 3.46 (m, 2H), 2.86 (m, 1H), 1.88 (br, 1H), 0.83 (q, J=5.9 Hz, 2H), 0.71 (m, 2H) ppm. ES MS M + 1 = 372 |
| 5 | 6-(4-Fluorobenzyl)-4-hydroxy-N-isopropyl-3,5-dioxo-2,3,5,6,7,8-hexahydro-2,6-naphthyridine-1-carboxamide | $^1$HNMR (400 MHz, CDCl$_3$) δ 7.30 (dd, J=5.7 Hz, 8.8 Hz, 2H), 7.06 (t, J=8.8 Hz, 2H), 6.89 (d, J=7.3 Hz, 1H), 4.82 (br, 1H), 4.71 (s, 2H), 4.17 (m, 1H), 3.47 (t, J=6.3 Hz, 2H), 3.35 (t, J=6.3 Hz, 2H), 1.26 (d, J=6.1 Hz, 6H) ppm. ES MS M + 1 = 374 |
| 6 | 6-(4-fluorobenzyl)-4-hydroxy-N-methyl-3,5-dioxo-2,3,5,6,7,8-hexahydro-2,6-naphthyridine-1-carboxamide | $^1$H NMR (400 MHz, CD$_3$OD) δ 7.38 (m, 2H), 7.08 (m, 2H), 4.73 (s, 2H), 3.48 (t, J=6.6 Hz, 2H), 3.08 (t, J=6.5 Hz, 2H), 2.85 (s, 3H) ppm. MS m/z 346.3 (M + 1). |

EXAMPLE 7

6-(4-fluorobenzyl)-4-hydroxy-3,5-dioxo-2,3,5,6,7,8-hexahydro-2,6-naphthyridine-1-carboxylic acid

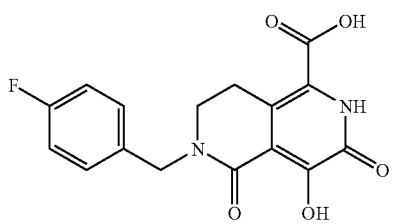

To methyl 6-(4-fluorobenzyl)-4-hydroxy-3,5-dioxo-5,6,7,8-tetrahydro-2,6-naphthyridine-1-carboxylate (0.178 g, 0.514 mmol) in wet methanol was added N,N-dimethylamine in MeOH (4.0 eq.). The reaction mixture was put in a microwave reactor where it was heated at 130° C. for 1.5 hours, after which the reaction mixture was concentrated under vacuum. The residue was purified by reverse phase HPLC eluting with 5%-95% acetonitrile (0.1% TFA) in H$_2$O (0.1% TFA) to afford the title compound as a solid. Alternatively, the starting material can be treated with LiOH in 1:1:1 THF/MeOH/H$_2$O to give the product.

$^1$HNMR (400 MHz, CD$_3$OD) δ 7.38 (m, 2H), 7.06 (m, 2H), 4.74 (s, 2H), 3.48 (m, 2H), 3.32 (m, 2H). ES MS M+1=333

EXAMPLE 8

N-[6-(4-fluorobenzyl)-3,4-dihydroxy-5-oxo-5,6,7,8-tetrahydro-2,6-naphthyridin-1-yl]-N-methylmethane-sulfonamide

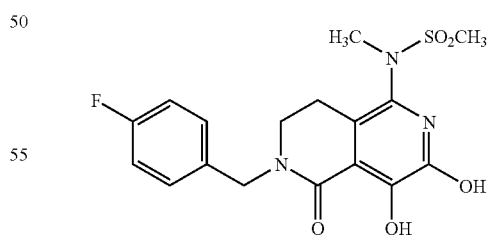

Step 1: 1-(glycyloxy)butane chloride

To a suspension of glycine hydrochloride (10 g, 89.6 mmol) in 250 mL butanol under nitrogen was added thionyl chloride (45.7 mL, 627 mmol) dropwise. After the addition was complete, the solution was heated at 70° C. overnight. The volatile components were removed on the roto-evaporator and the residue was suspended and evaporated from toluene three times. The resulting crude gum was dissolved in an equal weight of toluene for easy transfer and was used as is in the next reaction.

$^1$H NMR (400 MHz, CDCl$_3$) δ 8.5 (bs, 3H), 4.18 (t, J=6.7 Hz, 2H), 4.0 (bs, 2H), 1.62 (m, 2H), 1.38 (m, 2H), 0.92 (t, J=7.4 Hz, 3H) ppm. ES MS M+1=132.

Step 2: Butyl N-[ethoxy(oxo)acetyl]glycinate

A 1:1 by weight solution of 1-(glycyloxy)butane chloride (10 g, 59.6 mmol) in toluene (10 g) was treated with EtOH (100 mL), then Triethylamine (10 mL, 71.6 mmol) and diethyloxalate (16.2 mL, 119.3 mmol) and heated to 50° C. for three hours. The volatile components were removed on the roto-evaporator and the residue was dissolved in CHCl$_3$, washed two times with 10% KHSO$_4$, the aqueous layer was washed two times with CHCl$_3$, the organic layers were combined, dried over Na$_2$SO$_4$, filtered and evaporated to give the crude oil, which was chromatographed on silica eluting first with 20% EtOAc/hexanes and then with 50% EtOAc/hexanes to give clean product.

$^1$H NMR (400 MHz, CDCl$_3$) δ 7.56 (bs, 1H), 4.37 (q, J=7.2 Hz, 2H), 4.2 (t, J=6.6 Hz, 2H), 4.12 (d, J=5.5 Hz, 2H), 1.64 (p, J=6.8 Hz, 2H), 1.39 (t, J=7.15 Hz, 3H), 1.37 (m, buried, 2H), 0.94 (t, J=7.4 Hz, 3H) ppm. ES MS M+1=232

Step 3: Ethyl 5-butoxy-1,3-oxazole-2-carboxylate

A suspension of P$_2$O$_5$ (22 g, 155.6 mmol) in CH$_3$CN (50 mL) under nitrogen was warmed to 50° C. and treated with butyl N-[ethoxy(oxo)acetyl]glycinate (6 g, 25.9 mmol) dissolved in 10 mL CH$_3$CN. The mixture was heated to 65° C. for 1.5 hours, then cooled in an ice bath. Ice and brine were added to the reaction mixture, then EtOAc was added and the mixture transferred to a separatory funnel. CHCl$_3$ was added to dissolve solids and the organic layer was isolated. The aqueous layer was washed repeatedly with CHCl$_3$ and EtOAc, the organic layers were combined and dried with Na$_2$SO$_4$, then concentrated. The residue was chromatographed on silica eluting with a gradient of 0-30% EtOAc/Hexanes to give the product as a clear, colorless oil.

$^1$H NMR (400 MHz, CDCl$_3$) δ 6.33 (s, 1H), 4.42 (q, J=7.15 Hz, 2H), 4.18 (t, J=6.4 Hz, 2H), 1.8 (p, J=6.4 Hz, 2H), 1.47 (p, J=7.4 Hz, 2H), 1.41 (t, J=7.15 Hz, 3H), 0.97 (t, J=7.4 Hz, 3H) ppm. ES MS M+1=214.

Step 4: Ethyl 6-(4-fluorobenzyl)-4-hydroxy-5-oxo-5,6,7,8-tetrahydro-2,6-naphthyridine-1-carboxylate In a heavy walled round bottom flask with screw top were combined ethyl 5-butoxy-1,3-oxazole-2-carboxylate (2.53 g, 11.88 mmol) and 1-(4-fluorobenzyl)-5,6-dihydropyridin-2-(1H)-one (1.22 g, 5.94 mmol; see Example 1, Step 3) and trifluoroacetic acid (0.46 mL, 5.94 mmol). The vessel was sealed and placed in an oil bath heated to 130° C. The reaction mixture was stirred for 3 days. The dark brown reaction mixture was cooled and a crystalline precipitate formed. The mixture was diluted with ether and the solids collected by filtration and washed with ether to give the product as tan shiny plates. Further product can be obtained by evaporating the mother liquor, adding more trifluoroacetic acid and re-heating the mixture.

$^1$H NMR (400 MHz, CDCl$_3$) δ 12.9 (s, 1H), 8.42 (s, 1H), 7.31 (dd, J=5.3, 8.8 Hz, 2H), 7.06 (t, J=8.6 Hz, 2H), 4.72 (s, 2H), 4.41 (q, J=7.15 Hz, 2H), 3.50 (m, 4H), 1.41 (t, J=7.15 Hz, 3H) ppm. ES MS M+1=345.

Step 5: Ethyl 6-(4-fluorobenzyl)-4-methoxy-5-oxo-5,6,7,8-tetrahydro-2,6-naphthyridine-1-carboxylate To a solution of chloroform (10 mL) and methanol (10 mL) was added trimethylsilyl diazomethane (2.0 M in hexanes, 5 mL, 0.01 mole). After stirring for 10 minutes at room temperature, ethyl 6-(4-fluorobenzyl)-4-hydroxy-5-oxo-5,6,7,8-tetrahydro-2,6-naphthyridine-1-carboxylate (1.6 g, 3.5 mmol) in chloroform was added. After 7 hours, methanol (5 mL) and trimethylsilyl diazomethane (2.5 mL, 0.005 mole) was added to the reaction mixture. After 1 hour, glacial acetic acid (3 mL) was added with gas evolution observed. The solution was stirred for 0.5 hour. The product mixture was concentrated under vacuum. The residual material was subjected to column chromatography on silica gel eluting with 0-100% ethyl acetate in hexanes. The appropriate fractions were combined and concentrated to afford the title compound as a foam.

$^1$H NMR (400 MHz, CDCl$_3$) δ 8.47 (s, 1H), 7.32 (dd, J=5.3, 8.5 Hz, 2H), 7.03 (t, J=8.6 Hz, 2H), 4.73 (s, 2H), 4.45 (q, J=7.14 Hz, 2H), 4.11 (s, 3H), 3.43 (t, J=6 Hz, 2H), 3.29 (t, J=6 Hz, 2H), 1.42 (t, J=7.2 Hz, 3H) ppm. ES MS M+1=359

Step 6: 6-(4-Fluorobenzyl)-4-methoxy-5-oxo-5,6,7,8-tetrahydro-2,6-naphthyridine-1-carboxylic acid To a solution of ethyl 6-(4-fluorobenzyl)-4-methoxy-5-oxo-5,6,7,8-tetrahydro-2,6-naphthyridine-1-carboxylate (1.21 g, 3.38 mmol) in methanol (5 mL) and water (5 mL) and THF (5 mL) was added lithium hydroxide (0.425 g, 10.13 mmol). After 5 minutes, 1N HCl (3 equiv.) was added to the product mixture, which was then dried under vacuum to provide the crude title compound.

$^1$H NMR (400 MHz, CDCl$_3$) δ 11.29 (br, 1H), 8.35 (s, 1H), 7.27 (m, 2H), 7.03 (m, 2H), 4.73 (s, 2H), 4.15 (s, 3H), 3.55 (m, 4H) ppm. ES MS M+1=331

Step 7: 6-(4-Fluorobenzyl)-4-methoxy-5-oxo-5,6,7,8-tetrahydro-2,6-naphthyridine-1-carbonyl chloride A solution of 6-(4-fluorobenzyl)-4-methoxy-5-oxo-5,6,7,8-tetrahydro-2,6-naphthyridine-1-carboxylic acid (1.11 g, 3.36 mmol) in thionyl chloride (0.4 g, 3.36 mmol) was heated to 110° C. After 0.5 hours, the product mixture was concentrated under vacuum. The residue was suspended in toluene, evaporated, then suspended in chloroform and evaporated to give the title compound. The product was assayed by quenching in methanol solution to produce the methyl ester. ES MS M+1=345 (methyl ester forms after quench in methanol)

Step 8: 5-Amino-2-(4-fluorobenzyl)-8-methoxy-3,4-dihydro-2,6-naphthyridin-1(2H)-one To a solution of sodium azide (0.24 g, 3.69 mmol) in water (2.5 mL) was added 6-(4-fluorobenzyl)-4-methoxy-5-oxo-5,6,7,8-tetrahydro-2,6-naphthyridine-1-carbonyl chloride (1.17 g, 3.36 mmol) in acetone (15 mL). After 20 minutes, the product mixture was concentrated under vacuum to provide 6-(4-fluorobenzyl)-4-methoxy-5-oxo-5,6,7,8-tetrahydro-2,6-naphthyridine-1-carbonyl azide. The crude azide (1.19 g, 3.35 mmol) in DMF (20 mL) was heated to 110° C. After 20 minutes, the product mixture was cooled for 10 minutes, then 1N NaOH (3.3 mL) was added. After 20 minutes, the mixture was concentrated under vacuum, re-dissolved in toluene and CHCl$_3$ and evaporated. The residue was partitioned between CHCl$_3$ and saturated sodium bicarbonate. The organic extract was dried with Na$_2$SO$_4$, filtered, and concentrated under vacuum to provide the title compound.

$^1$H NMR (400 MHz, CDCl$_3$) δ 7.88 (s, 1H), 7.32 (m, 2H), 7.03 (t, J=9 Hz, 2H), 4.71 (s, 2H), 4.17 (s, 2H), 3.94 (s, 3H), 3.47 (t, J=6 Hz, 2H), 2.58 (t, J=6 Hz, 2H) ppm. ES MS (M+1)=302.

Step 9: N-[6-(4-Fluorobenzyl)-4-methoxy-5-oxo-5,6,7,8-tetrahydro-2,6-naphthyridin-1-yl]methanesulfonamide To a solution of 5-amino-2-(4-fluorobenzyl)-8-methoxy-3,4-dihydro-2,6-naphthyridin-1(2H)-one (0.889 g, 2.95 mmol) in pyridine (5 mL) was added dropwise methanesulfonyl chloride (0.575 g, 5.016 mmol). After stirring for an hour at room temperature, the product mixture was quenched with pH 7 buffer, then concentrated under vacuum. The residue was dissolved in CHCl$_3$ and pH 7 buffer, the pH of the aqueous layer was adjusted to pH 5 with 1N NaOH and the layers separated. Several more extractions with CHCl$_3$ were performed. The organic extracts were dried with Na$_2$SO$_4$, filtered, and concentrated under vacuum, then dissolved in toluene and CHCl$_3$ and evaporated to provide the title compound.

$^1$H NMR (400 MHz, CDCl$_3$) δ 7.33 (m, 2H), 7.04 (t, J=9 Hz, 2H), 4.70 (s, 2H), 4.03 (s, 3H), 3.44 (t, J=6.5 Hz, 2H), 3.21 (s, 3H), 2.89 (t, J=6.4 Hz, 2H) ppm. ES MS (M+1)=380.

Step 10: N-[6-(4-Fluorobenzyl)-4-methoxy-5-oxo-5,6,7,8-tetrahydro-2,6-naphthyridin-1-yl]-N-methylmethanesulfonamide To a solution of N-[6-(4-fluorobenzyl)-4-methoxy-5-oxo-5,6,7,8-tetrahydro-2,6-naphthyridin-1-yl]methanesulfonamide (0.097 g, 0.256 mmol) in DMF (2 mL) was added Cs$_2$CO$_3$ (0.083 g, 0.256 mmol) and MeI (0.04 g, 0.28 mmol, dissolved in DMF). After stirring for 2 hours, additional MeI (0.02 g, 0.14 mmol) was added. The product mixture was concentrated. The residue was partitioned between CHCl$_3$ and pH 7 buffer. The organic extract was dried with Na$_2$SO$_4$, filtered, and concentrated under vacuum to provide the title compound.

$^1$H NMR (400 MHz, CDCl$_3$) δ 8.20 (s, 1H), 7.26 (m, 2H), 7.04 (t, J=9 Hz, 2H), 4.70 (s, 2H), 4.06 (s, 3H), 3.43 (t, J=7 Hz, 2H), 3.21 (s, 3H), 3.03 (m, 5H) ppm. ES MS (M+1)=394.

Step 11: N-[6-(4-Fluorobenzyl)-4-methoxy-2-oxido-5-oxo-5,6,7,8-tetrahydro-2,6-naphthyridin-1-yl]-N-methylmethanesulfonamide To a solution of N-[6-(4-fluorobenzyl)-4-methoxy-5-oxo-5,6,7,8-tetrahydro-2,6-naphthyridin-1-yl]-N-methylmethanesulfonamide (0.35 g, 0.89 mmol) in CH$_2$Cl$_2$ (10 mL) was added mCPBA (1.08 g, 6.23 mmol) in portions. After stirring for 3.5 hours at reflux, the product mixture was cooled to room temperature, 1 mL of ethanol was added, and the solution was concentrated. The residue was partitioned between CHCl$_3$ and saturated Na$_2$SO$_3$. The organic layer was extracted repeatedly with saturated sodium bicarbonate. The organic extract was dried with Na$_2$SO$_4$, filtered, and concentrated under vacuum to provide the crude title compound.

$^1$H NMR (400 MHz, CDCl$_3$) δ 8.06 (s, 1H), 7.30 (m, 2H), 7.03 (t, J=7 Hz, 2H), 4.72 (d, J=14.6 Hz, 1H), 4.65 (d, J=14.6 Hz, 1H), 4.01 (s, 3H), 3.45 (m, 2H), 3.29 (s, 3H), 3.20 (s, 3H), 3.18 (m, 1H), 2.87 (m, 1H) ppm. ES MS (M+1)=410.

Step 12: N-[6-(4-Fluorobenzyl)-3-hydroxy-4-methoxy-5-oxo-5,6,7,8-tetrahydro-2,6-naphthyridin-1-yl]-N-methylmethanesulfonamide A solution of N-[6-(4-fluorobenzyl)-4-methoxy-2-oxido-5-oxo-5,6,7,8-tetrahydro-2,6-naphthyridin-1-yl]-N-methylmethanesulfonamide (0.36 g, 0.889 mmol) in acetic anhydride (10 mL) was heated to 110° C. for 3 hours, then evaporated to dryness to give the intermediate 6-(4-fluorobenzyl)-4-methoxy-1-[methyl(methylsulfonyl)amino]-5-oxo-5,6,7,8-tetrahydro-2,6-naphthyridin-3-yl acetate (ES MS (M+1)=452). The crude material was dissolved in methanol (6 mL) and treated with sodium methoxide (30% by weight in methanol, 0.5 mL, 2.6 mmol). After 1 hour, the product mixture was neutralized with 6 N HCl, then concentrated. The residue was partitioned between CHCl$_3$ and 10% KHSO$_4$. The organic extract was dried with Na$_2$SO$_4$, filtered, and concentrated under vacuum to provide the title compound.

$^1$H NMR (400 MHz, CDCl$_3$) δ 7.29 (m, 2H), 7.03 (t, J=9 Hz, 2H), 4.71 (bs, 2H), 4.06 (s, 3H), 3.41 (t, J=6 Hz, 2H), 3.28 (s, 3H), 3.11 (s, 3H), 2.8 (m, 2H) ppm. ES MS (M+1)=410.

Step 13: N-[6-(4-fluorobenzyl)-3,4-dihydroxy-5-oxo-5,6,7,8-tetrahydro-2,6-naphthyridin-1-yl]-N-methylmethanesulfonamide To a solution of N-[6-(4-fluorobenzyl)-3-hydroxy-4-methoxy-5-oxo-5,6,7,8-tetrahydro-2,6-naphthyridin-1-yl]-N-methylmethanesulfonamide (0.0207 g, 0.506 mmol) in CH$_2$Cl$_2$ (6 mL) was added 30% by weight HBr in propionic acid (0.196 g HBr, 2.42 mmol). Alternatively, 30% HBr in acetic acid can be used. After 1.5 hours, the product mixture was evaporated and the residue partitioned between CHCl$_3$ and 10% KHSO$_4$. The organic extract was dried with Na$_2$SO$_4$, filtered, and concentrated under vacuum. The residual material was purified using reverse phase HPLC eluting with 5%-95% acetonitrile (0.1% TFA) in H$_2$O (0.1% TFA) to afford the title compound.

$^1$H NMR (400 MHz, CDCl$_3$) δ 12.97 (br, 1H), 7.28 (m, 2H), 7.04 (t, J=9 Hz, 2H), 4.69 (s, 2H), 3.46 (t, J=7 Hz, 2H), 3.24 (s, 3H), 3.09 (s, 3H), 2.98 (m, 2H) ppm. ES MS (M+1)=396.

EXAMPLE 9

N-[6-(4-fluorobenzyl)-4-hydroxy-2-methyl-3,5-dioxo-2,3,5,6,7,8-hexahydro-2,6-naphthyridin-1-yl]-N-methylacetamide

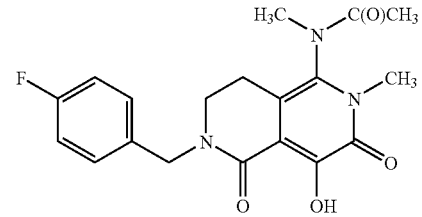

Step 1: Ethyl 6-(4-fluorobenzyl)-4-hydroxy-5-oxo-5,6,7,8-tetrahydro-2,6-naphthyridine-1-carboxylate 2-oxide To ethyl 6-(4-fluorobenzyl)-4-hydroxy-5-oxo-5,6,7,8-tetrahydro-2,6-naphthyridine-1-carboxylate (0.5 gm, 1.09 mmol; see Example 8, Step 4) in glacial acetic acid (25 mL) at room temperature under nitrogen was added, with stirring, aqueous peroxide (30% by wt) (1.24 mL, 10.9 mmol). The reaction was warmed to 100° C. and stirred for 1.5 hours. The reaction was allowed to cool, ethanol (1 mL) was added and volatile components were removed under reduced pressure. The resulting oil was placed under high vacuum for 16 hours, then used as is. Alternatively, after cooling, water can be added and the volatile components removed under reduced pressure. The residue can be partitioned between $CHCl_3$ and saturated $Na_2SO_3$. The organic extract can be dried with $Na_2SO_4$, filtered, and concentrated under vacuum to provide the title compound.

$^1$H NMR (400 MHz, $CDCl_3$) δ 12.8 (br, 1H), 7.90 (s, 1H), 7.28 (dd, J=5.3, 8.5 Hz, 2H), 7.04 (t, J=8.6 Hz, 2H), 4.69 (s, 2H), 4.43 (q, J=7.14 Hz, 2H), 3.50 (t, J=6.8 Hz, 2H), 2.87 (t, J=6.8 Hz, 2H), 1.37 (t, J=7.14 Hz, 3H) ppm. ES MS (M+1) =361.

Step 2: Sodium 1-(ethoxycarbonyl)-6-(4-fluorobenzyl)-3,5-dioxo-2,3,5,6,7,8-hexahydro-2,6-naphthyridin-4-olate To ethyl 6-(4-fluorobenzyl)-4-hydroxy-5-oxo-5,6,7,8-tetrahydro-2,6-naphthyridine-1-carboxylate 2-oxide (2.3 gm, 6.38 mmol) in neat acetic anhydride (24 mL) was stirred under nitrogen at 100° C. for 1 hour. The reaction was concentrated to an oil under reduced pressure and dry methanol (20 mL) was added followed by a methanolic sodium methoxide solution (30% by wt) (4.54 mL, 25.2 mmol). The reaction was stirred at room temperature for 1 hour. The reaction was then concentrated to an oil under reduced pressure and crystallized from a small amount of methanol (~5 mL). The crystals were collected by filtration, washed an additional 10 mL of methanol and dried in vacuo to give the desired product.

$^1$H NMR (400 MHz, $CDCl_3$) δ 9.49 (br, 1H), 7.30 (m, 2H), 7.06 (t, J=9 Hz, 2H), 4.71 (s, 2H), 4.36 (q, J=7 Hz, 2H), 3.44 (t, J=6 Hz, 2H), 3.33 (t, J=6 Hz, 2H), 1.38 (t, J=7 Hz, 3H) ppm. ES MS M+1=361.

Step 3: Ethyl 6-(4-fluorobenzyl)-4-methoxy-2-methyl-3,5-dioxo-2,3,5,6,7,8-hexahydro-2,6-naphthyridine-1-carboxylate To a solution of sodium 1-(ethoxycarbonyl)-6-(4-fluorobenzyl)-3,5-dioxo-2,3,5,6,7,8-hexahydro-2,6-naphthyridin-4-olate (1.45 g, 3.79 mmol) in DMF (20 mL) was added cesium carbonate (4.94 g, 15.1 mmol). After 5 minutes, methyl iodide (2.15 g, 15.1 mmol) was added. The reaction mixture was stirred at room temperature. After 24 hours, the product mixture was concentrated under vacuum. The residual material was subjected to column chromatography on silica gel eluting with 0-3% methanol in $CH_2Cl_2$. The appropriate fractions were combined and concentrated to afford the N- and O-methylated compounds separately.

N-methylated compound: Ethyl 6-(4-fluorobenzyl)-4-methoxy-2-methyl-3,5-dioxo-2,3,5,6,7,8-hexahydro-2,6-naphthyridine-1-carboxylate $^1$H NMR (400 MHz, $CDCl_3$) δ 7.27 (m, 2H), 7.02 (t, J=9 Hz, 2H), 4.69 (s, 2H), 4.39 (q, J=7 Hz, 2H), 4.13 (s, 3H), 3.51 (s, 3H), 3.53 (t, J=6 Hz, 2H), 2.59 (t, J=6 Hz, 2H), 1.38 (t, J=7 Hz, 3H) ppm. ES MS M+1=389.

O-methylated compound: Ethyl 6-(4-fluorobenzyl)-3,4-dimethoxy-5-oxo-5,6,7,8-tetrahydro-2,6-naphthyridine-1-carboxylate $^1$H NMR (400 MHz, $CDCl_3$) δ 7.31 (m, 2H), 7.03 (t, J=9 Hz, 2H), 4.73 (s, 2H), 4.37 (q, J=7 Hz, 2H), 4.05 (m, 6H), 3.38 (t, J=6 Hz, 2H), 3.14 (t, J=6 Hz, 2H), 1.39 (t, J=7 Hz, 3H) ppm. ES MS M+1=389.

Step 4: 6-(4-fluorobenzyl)-4-methoxy-2-methyl-3,5-dioxo-2,3,5,6,7,8-hexahydro-2,6-naphthyridine-1-carboxylic acid To a solution of ethyl 6-(4-fluorobenzyl)-4-methoxy-2-methyl-3,5-dioxo-2,3,5,6,7,8-hexahydro-2,6-naphthyridine-1-carboxylate (1.15 g, 2.96 mmol) in 1:1:1 $MeOH/H_2O/THF$ (15 mL) was added LiOH (0.37 g, 8.88 mmol) and the solution was stirred for 2 hours. A solution of 1 N HCl (8.9 mL) was added, the solution was concentrated and $CHCl_3$ and 10% $KHSO_4$ were added. The layers were separated and the aqueous was extracted repeatedly. The combined organic layers were filtered and the solid collected. The remaining organic was dried over $Na_2SO_4$, filtered, combined with the collected solid and evaporated to give the crude product.

$^1$H NMR (400 MHz, DMSO-$d_6$) δ 7.32 (dd, J=5.6, 8.6 Hz, 2H), 7.16 (t, J=8.8 Hz, 2H), 4.64 (s, 2H), 3.84 (s, 3H), 3.42 (s, 3H), 3.4 (t, J=6 Hz, 2H), 2.6 (t, J=6 Hz, 2H) ppm. ES MS M+1=361.

Step 5: 6-(4-fluorobenzyl)-4-methoxy-2-methyl-3,5-dioxo-2,3,5,6,7,8-hexahydro-2,6-naphthyridine-1-carbonyl chloride To 6-(4-fluorobenzyl)-4-methoxy-2-methyl-3,5-dioxo-2,3,5,6,7,8-hexahydro-2,6-naphthyridine-1-carboxylic acid (0.213 g, 0.6 mmol) was added thionyl chloride (5 mL) and the mixture was heated to reflux for 2 hours, then evaporated to dryness, suspended in toluene and evaporated three times to give the crude product.

$^1$H NMR (400 MHz, $CDCl_3$) δ 7.30 (dd, J=5.3, 8.6 Hz, 2H), 7.03 (t, J=8.8 Hz, 2H), 4.7 (s, 2H), 4.18 (s, 3H), 3.58 (s, 3H), 3.39 (t, J=6 Hz, 2H), 2.65 (t, J=6 Hz, 2H)ppm.
ES MS M+1=379.

Step 6: 5-amino-2-(4-fluorobenzyl)-8-methoxy-6-methyl-2,3,4,6-tetrahydro-2,6-naphthyridine-1,7-dione To a solution of sodium azide (0.091 g, 1.4 mmol) in 2 mL water cooled to 0° C. was add 6-(4-fluorobenzyl)-4-methoxy-2-methyl-3,5-dioxo-2,3,5,6,7,8-hexahydro-2,6-naphthyridine-1-carbonyl chloride (0.48 g, 1.28 mmol) in acetone (8 mL). The solution was stirred for 30 minutes, then evaporated. The residue was partitioned between $CHCl_3$ and saturated Na bicarbonate, dried with $Na_2SO_4$, filtered and evaporated to give the crude product, which was chromatographed on silica eluting with 5% $MeOH/CHCl_3$ saturated with $NH_3$.

$^1$H NMR (400 MHz, $CDCl_3$) δ 7.29 (dd, J=5.5, 8.4 Hz, 2H), 7.01 (t, J=8.6 Hz, 2H), 4.7 (s, 2H), 4.05 (bs, 2H), 3.96 (s, 3H), 3.56 (s, 3H), 3.37 (t, J=6 Hz, 2H), 2.42 (t, J=6 Hz, 2H) ppm. ES MS M+1=332.

Step 7: N-acetyl-N-[6-(4-fluorobenzyl)-4-methoxy-2-methyl-3,5-dioxo-2,3,5,6,7,8-hexahydro-2,6-naphthyridin-1-yl]acetamide To 5-amino-2-(4-fluorobenzyl)-8-methoxy-6-methyl-2,3,4,6-tetrahydro-2,6-naphthyridine-1,7-dione (0.1 19 mg, 0.36 mmol) in a sealable microwave tube was added acetic anhydride (3.5 mL) and the solution was heated to 150° C. for 25 minutes in a microwave. The solution was evaporated to dryness to give the crude product.

$^1$H NMR (400 MHz, CDCl$_3$) δ 7.29 (m, 2H), 7.02 (t, J=8.6 Hz, 2H), 4.69 (s, 2H), 4.14 (s, 3H), 3.37 (s, 3H), 3.35 (t, J=6 Hz, 2H), 2.37 (t, J=6 Hz, 2H), 2.32 (s, 6H)ppm.

ES MS M+1=416.

Step 8: N-[6-(4-fluorobenzyl)-4-methoxy-2-methyl-3,5-dioxo-2,3,5,6,7,8-hexahydro-2,6-naphthyridin-1-yl]acetamide To N-acetyl-N-[6-(4-fluorobenzyl)-4-methoxy-2-methyl-3,5-dioxo-2,3,5,6,7,8-hexahydro-2,6-naphthyridin-1-yl]acetamide (0.149 g, 0.36 mmol) in MeOH (5 mL) cooled to 0° C. was added 30% weight solution NaOMe in MeOH (0.2 mL, 1.07 mmol). The reaction was warmed to room temperature for 40 minutes, then 1 N HCl was added (1.07 mL) and the reaction was concentrated, and CHCl$_3$ and 10% KHSO$_4$ were added. The layers were separated and the aqueous was extracted repeatedly. The organic layer was dried over Na$_2$SO$_4$, filtered, combined with the collected solid and evaporated to give the crude product.

$^1$H NMR (400 MHz, CDCl$_3$) δ 8.46 (bs, 1H), 7.26 (m, 2H), 7.01 (t, J=8.6 Hz, 2H), 4.65 (bs, 2H), 3.96 (s, 3H), 3.39 (s, 3H), 3.33 (t, J=6 Hz, 2H), 2.45 (bs, 2H), 2.23 (s, 3H)ppm. ES MS M+1=374.

Step 9: N-[6-(4-fluorobenzyl)-4-methoxy-2-methyl-3,5-dioxo-2,3,5,6,7,8-hexahydro-2,6-naphthyridin-1-yl]-N-methylacetamide To N-[6-(4-fluorobenzyl)-4-methoxy-2-methyl-3,5-dioxo-2,3,5,6,7,8-hexahydro-2,6-naphthyridin-1-yl]acetamide (0.073 g, 0.196 mmol) in 2 mL DMF was added Cs$_2$CO$_3$ (0.084 g, 0.25 mmol) and methyl iodide (0.044 mL, 0.7 mmole) and the reaction was stirred overnight at room temperature. The solvent was removed and the residue was partitioned between CHCl$_3$ and 10% KHSO$_4$, the organic was dried with Na$_2$SO$_4$, filtered and evaporated to give the crude product.

$^1$H NMR (400 MHz, CDCl$_3$) δ 7.30 (dd, J=5.4, 8.5 Hz, 2H), 7.03 (t, J=8.6 Hz, 2H), 4.70 (s, 2H), 4.14 (s, 3H), 3.43 (s, 3H), 3.37 (m, 2H), 3.08 (s, 3H), 2.48 (m, 2H), 1.87 (s, 3H) ppm. ES MS M+1=388.

Step 10: N-[6-(4-fluorobenzyl)-4-hydroxy-2-methyl-3,5-dioxo-2,3,5,6,7,8-hexahydro-2,6-naphthyridin-1-yl]-N-methylacetamide To N-[6-(4-fluorobenzyl)-4-methoxy-2-methyl-3,5-dioxo-2,3,5,6,7,8-hexahydro-2,6-naphthyridin-1-yl]-N-methylacetamide (0.070 g, 0.181 mmol) was dissolved in 1 mL glacial acetic acid and 0.75 mL 30% by weight HBr in acetic acid solution was added. The reaction was stirred for 1.5 hours, water was added and the reaction evaporated to dryness under vacuum. The residue was purified on reverse phase and the fractions collected and evaporated. The residue was dissolved in dioxane, from which crystals formed and were collected. The crystals were dried under vacuum with heat to give the product.

$^1$H NMR (400 MHz, CDCl$_3$) δ 13.17 (s, 1H), 7.30 (dd, J=5.3, 8.7 Hz, 2H), 7.03 (t, J=8.7 Hz, 2H), 4.73 (d, J=14.6 Hz, 1H), 4.66 (d, J=14.6 Hz, 1H), 3.44 (s, 3H), 3.41 (m, 2H), 3.08 (s, 3H), 2.61 (m, 2H), 1.86 (s, 3H) ppm.

ES MS M+1=374.

EXAMPLE 10

6-(4-Fluorobenzyl)-4-hydroxy-N,N, 2-trimethyl-3,5-dioxo-2,3,5,6,7,8-hexahydro-2,6-naphthyridine-1-carboxamide

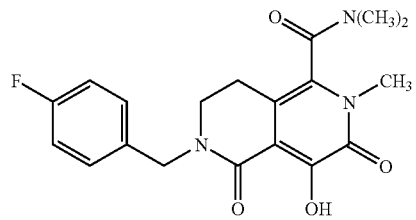

Step 1: Methyl 6-(4-fluorobenzyl)-4-methoxy-2-methyl-3,5-dioxo-2,3,5,6,7,8-hexahydro-2,6-naphthyridine-1-carboxylate To a solution of methyl 6-(4-fluorobenzyl)-4-hydroxy-3,5-dioxo-2,3,5,6,7,8-hexahydro-2,6-naphthyridine-1-carboxylate (0.28 g, 0.81 mmol) in DMF (3.0 mL) was added Cs$_2$CO$_3$ (0.81 g, 2.47 mmol) at room temperature. After 10 minutes, CH$_3$I (0.597 g, 4.21 mmol) was added and the warmed to 40° C. After 2.5 hours, the product mixture was partitioned between EtOAc and 1 N HCl. The organic extract was washed with brine, dried with Na$_2$SO$_4$, filtered, and concentrated under vacuum to give a mixture of N,O- and O,O-alkylated products. The residual material was subjected to column chromatography on silica gel eluting with 0-3% methanol in CH$_2$Cl$_2$. The appropriate fractions were combined and concentrated to afford the title compound.

$^1$HNMR (400 MHz, CDCl$_3$) δ 7.29 (m, 2h), 7.02 (t, J=9 Hz, 2H), 4.68 (s, 2H), 4.12 (s, 3H), 3.91 (s, 3H), 3.48 (s, 3H), 3.32 (t, J=6 Hz, 2H), 2.56 (t, J=6.5 Hz, 2H) ppm. ES MS M+1=375.

Step 2: 6-(4-Fluorobenzyl)-4-methoxy-2-methyl-3,5-dioxo-2,3,5,6,7,8-hexahydro-2,6-naphthyridine-1-carboxylic acid To a solution of methyl 6-(4-fluorobenzyl)-4-methoxy-2-methyl-3,5-dioxo-2,3,5,6,7,8-hexahydro-2,6-naphthyridine-1-carboxylate (0.575 g, 1.536 mmol) in methanol was added LiOH (0.11 g, 4.61 mmol) in water. The reaction mixture was heated to reflux. After 0.5 hours, the product mixture cooled to room temperature and concentrated under vacuum. The residual material was partitioned between EtOAc and 1 N HCl. The organic extract was washed with brine, dried with Na$_2$SO$_4$, filtered, and concentrated under vacuum to provide the title compound.

$^1$HNMR (400 MHz, CDCl$_3$) δ 7.27 (m, 2h), 7.03 (t, J=9 Hz, 2H), 4.66 (s, 2H), 3.95 (s, 3H), 3.49 (s, 3H), 3.35 (t, J=6 Hz, 2H), 2.68 (t, J=6 Hz, 2H) ppm. ES MS M+1=361.

Step 3: 6-(4-Fluorobenzyl)-4-hydroxy-N,N, 2-trimethyl-3,5-dioxo-2,3,5,6,7,8-hexahydro-2,6-naphthyridine-1-carboxamide To a solution of 6-(4-fluorobenzyl)-4-methoxy-2-methyl-3,5-dioxo-2,3,5,6,7,8-hexahydro-2,6-naphthyridine-1-carboxylic acid (0.14 g, 0.40 mol) in DMF was added BOP (0.515 g, 1.167 mmol) and the dimethylamine (2.0 M in THF)

(0.035 g, 0.778 mmol). After 24 hours, the product mixture was concentrated under vacuum. The residual material was purified using reverse phase HPLC eluting with 5-95% acetonitrile (0.1% TFA) in H$_2$O (0.1% TFA) to give 6-(4-fluorobenzyl)-4-methoxy-N,N, 2-trimethyl-3,5-dioxo-2,3,5,6,7,8-hexahydro-2,6-naphthyridine-1-carboxamide (ES MS M+1=388). A solution of this product (0.1 g, 0.3 mmol) in CH$_2$Cl$_2$ was treated with HBr (30 wt % in acetic acid) (0.104 g, 1.29 mmol) and after stirring at room temperature for 24 hours, concentrated under vacuum. The residual material was purified using reverse phase HPLC eluting with 5%-95% acetonitrile (0.1% TFA) in H$_2$O (0.1% TFA) to afford the title compound.

$^1$HNMR (400 MHz, CD$_3$OD) δ 7.38 (m, 2H), 7.04 (t, J=9 Hz, 2H), 4.81 (d, J=14.8 Hz, 1H), 4.56 (d, J=14.8 Hz, 1H), 3.49 (t, J=6 Hz, 2H), 3.43 (s, 3H), 3.08 (s, 3H), 2.93 (s, 3H), 2.59 (t, J=6 Hz, 2H) ppm.

ES MS M+1=374.

The compounds in the following table were prepared in accordance with the procedure set forth in Example 10, using the appropriate amine in place of the dimethylamine employed in Step 3 of Example 10. When the compound was prepared as a salt, the identity of the salt is included in parentheses following the compound name for the free base.

| Example | R$^G$ | Name | ES MS (M + 1) |
|---|---|---|---|
| 10-2 | HN—cyclobutyl | N-cyclobutyl-6-(4-fluorobenzyl)-4-hydroxy-2-methyl-3,5-dioxo-2,3,5,6,7,8-hexahydro-2,6-naphthyridine-1-carboxamide | 400.2 |
| 10-3 | HN—cyclopropyl | N-cyclopropyl-6-(4-fluorobenzyl)-4-hydroxy-2-methyl-3,5-dioxo-2,3,5,6,7,8-hexahydro-2,6-naphthyridine-1-carboxamide | 386.1 |
| 10-4 | HN—CH(CH$_3$)$_2$ | 6-(4-fluorobenzyl)-4-hydroxy-N-isopropyl-2-methyl-3,5-dioxo-2,3,5,6,7,8-hexahydro-2,6-naphthyridine-1-carboxamide | 388.1 |
| 10-5 | HN—CH$_2$CF$_3$ | 6-(4-fluorobenzyl)-4-hydroxy-2-methyl-3,5-dioxo-N-(2,2,2-trifluoroethyl)-2,3,5,6,7,8-hexahydro-2,6-naphthyridine-1-carboxamide | 428.1 |
| 10-6 | HN—CH$_2$CH$_2$SO$_2$CH$_3$ | 6-(4-fluorobenzyl)-4-hydroxy-2-methyl-N-[2-(methylsulfonyl)ethyl]-3,5-dioxo-2,3,5,6,7,8-hexahydro-2,6-naphthyridine-1-carboxamide | 452.2 |
| 10-7 | *—NH—CH$_2$—C$_6$H$_4$—F | N,6-bis(4-fluorobenzyl)-4-hydroxy-2-methyl-3,5-dioxo-2,3,5,6,7,8-hexahydro-2,6-naphthyridine-1-carboxamide | 454.2 |
| 10-8 | piperidin-1-yl | 2-(4-fluorobenzyl)-8-hydroxy-6-methyl-5-(piperidin-1-ylcarbonyl)-2,3,4,6-tetrahydro-2,6-naphthyridine-1,7-dione | 414.1 |
| 10-9 | HN—CH$_2$C(CH$_3$)$_3$ | 6-(4-fluorobenzyl)-4-hydroxy-2-methyl-N-neopentyl-3,5-dioxo-2,3,5,6,7,8-hexahydro-2,6-naphthyridine-1-carboxamide | 416.1 |
| 10-10 | thiomorpholin-4-yl | 2-(4-fluorobenzyl)-8-hydroxy-5-(thiomorpholin-4-ylcarbonyl)-2,3,4,6-tetrahydro-2,6-naphthyridine-1,7-dione | 418.3 |
| 10-11 | piperazin-1-yl | 2-(4-fluorobenzyl)-8-hydroxy-5-(piperazin-1-ylcarbonyl)-2,3,4,6-tetrahydro-2,6-naphthyridine-1,7-dione (TFA salt) | 401.1 |

-continued

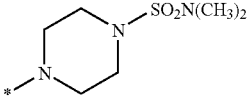

| Example | R<sup>G</sup> | Name | ES MS (M + 1) |
|---|---|---|---|
| 10-12[1] | 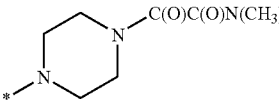 | 4-{[6-(4-fluorobenzyl)-4-hydroxy-3,5-dioxo-2,3,5,6,7,8-hexahydro-2,6-naphthyridin-1-yl]carbonyl}-N,N-dimethylpiperazine-1-sulfonamide | 508.0 |
| 10-13[2] | 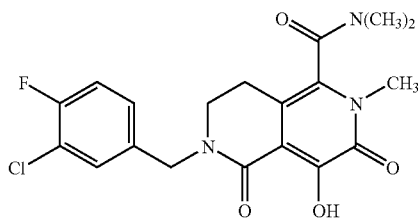 | 2-(4-{[6-(4-fluorobenzyl)-4-hydroxy-3,5-dioxo-2,3,5,6,7,8-hexahydro-2,6-naphthyridin-1-yl]carbonyl}piperazin-1-yl)-N,N-dimethyl-2-oxoacetamide | 500.1 |

[1] Example 10-12 can also be prepared via sulfonylation of Example 10-11 with dimethylaminosulfonyl chloride prior to deprotection with HBr.
[2] Example 10-13 can also be prepared via acylation of Example 10-11 with dimethylaminooxalylchloride prior to deprotection with HBr.

EXAMPLE 11

6-(3-Chloro-4-fluorobenzyl)-4-hydroxy-N,N,2-trimethyl-3,5-dioxo-2,3,5,6,7,8-hexahydro-2,6-naphthyridine-1-carboxamide Step 1: 6-(4-methoxybenzyl)-4-methoxy-N,N, 2-trimethyl-3,5-dioxo-2,3,5,6,7,8-hexahydro-2,6-naphthyridine-1-carboxamide In a manner similar to that described for 6-(4-fluorobenzyl)-4-methoxy-N,N, 2-trimethyl-3,5-dioxo-2,3,5,6,7,8-hexahydro-2,6-naphthyridine-1-carboxamide (Example 10, Step 3), 6-(4-methoxybenzyl)-4-methoxy-N,N, 2-trimethyl-3,5-dioxo-2,3,5,6,7,8-hexahydro-2,6-naphthyridine 1-carboxamide was prepared starting from p-methoxybenzyl chloride, and the material was purified using reverse phase HPLC eluting with 5%-95% acetonitrile (0.1% TFA) in H$_2$O (0.1% TFA).

$^1$HNMR (400 MHz, CDCl$_3$) δ 7.22 (d, J=8.6 Hz, 2H), 6.84 (d, J=8.6 Hz, 2H), 4.82 (d, J=14.5 Hz, 1H), 4.46 (d, J=14.5 Hz, 1H), 4.07 (s, 3H), 3.78 (s, 3H), 3.45 (s, 3H), 3.40 (m, 1H), 3.30 (m, 1H), 3.09 (s, 3H), 2.90 (s, 3H), 2.51 (m, 1H), 2.35 (m, 1H) ppm. (ES MS M+1=400.1)

Step 2: 4-hydroxy-N,N,2-trimethyl-3,5-dioxo-2,3,5, 6,7,8-hexahydro-2,6-naphthyridine-1-carboxamide A solution of 6-(4-methoxybenzyl)-4-methoxy-N,N, 2-trimethyl-3,5-dioxo-2,3,5,6,7,8-hexahydro-2,6-naphthyridine-1-carboxamide (0.18 g, 0.45 mmol) in toluene (about 3 mL) was treated with p-toluene sulfonic acid (0.34 g, 1.8 mmol). The mixture was heated to 110° C. for 4 hours, then cooled and concentrated under vacuum. The residue was partitioned between water and EtOAc, the aqueous layer concentrated, and the residue purified by reverse phase chromatography to give the title product.

$^1$HNMR (400 MHz, CD$_3$OD) δ 3.44 (m, 5H), 3.10 (s, 3H), 2.97 (s, 3H), 2.60 (t, J=6.6 Hz, 2H) ppm.
(ES MS M+1=266.2)

Step 3: 6-(3-chloro-4-fluorobenzyl)-4-hydroxy-N,N, 2-trimethyl-3,5-dioxo-2,3,5,6,7,8-hexahydro-2,6-naphthyridine-1-carboxamide A solution of 4-hydroxy-N,N,2-trimethyl-3,5-dioxo-2,3,5, 6,7,8-hexahydro-2,6-naphthyridine-1-carboxamide (0.018 g, 0.068 mmol) in DMF (2 mL) was treated with Cs$_2$CO$_3$ (0.066 g, 0.2 mmol) and 3-chloro-4-fluoro benzyl bromide (0.045 g, 0.2 mmol) and heated to 40° C. The reaction mixture was then cooled to 0 degrees C., a suspension of NaH (95% dispersion in oil, 0.2 mmol) was added and the reaction was warmed to room temperature. After 1 hr the reaction was partitioned between ice water and EtOAc, the organic layer was dried with brine and Na$_2$SO$_4$, filtered and evaporated to give 6-(3-chloro-4-fluorobenzyl)$_4$-[(3-chloro-4-fluorobenzyl)oxy]-N, N,2-trimethyl-3,5-dioxo-2,3,5,6,7,8-hexahydro-2,6-naphthyridine-1-carboxamide (ES MS M+1=549.9). This material was then dissolved in CH$_2$Cl$_2$ (3 mL) and treated with 4 drops of a 30% by weight solution of HBr in propionic acid at room temperature. After 20 minutes the solution was concentrated and purified by reverse phase chromatography to give the product.

¹HNMR (400 MHz, CD₃OD) δ 7.48 (m, 1H), 7.32 (m, 1H), 7.22 (t, J=8.5 Hz, 1H), 4.76 (d, J=14.8 Hz, 1H), 4.63 (d, J=14.8 Hz, 1H), 3.50 (t, J=6.4 Hz, 2H), 3.44 (s, 3H), 3.08 (s, 3H), 2.95 (s, 3H), 2.61 (t, J=6.2 Hz, 2H) ppm. (ES MS M+1=407.9)

EXAMPLE 12

6-(3-Chloro-4-fluorobenzyl)-4-hydroxy-N,N,2-trimethyl-3,5-dioxo-2,3,5,6,7,8-hexahydro-2,6-naphthyridine-1-carboxamide

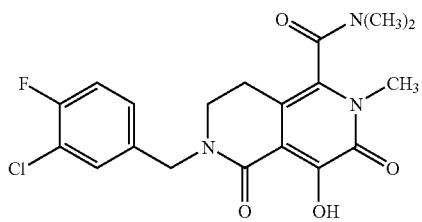

Step 1: 1-(3-Chloro-4-fluorobenzyl)piperidin-2-one

Valerolactam (153.3 g, 1.54 mol) was dissolved in NMP (3.5 L) and cooled to 0° C. NaH (67.7 g, 1.69 mol, 60% dispersion in oil) was added in portions over 5 minutes keeping the temperature at 0° C. The reaction was stirred for 30 minutes, and 3-chloro-4-fluorobenzylbromide (345.5 g, 1.54 mol) dissolved in 200 mL NMP was added over 30 minutes, again keeping the internal temperature at 0° C. The reaction was aged for 1 hour at 0° C., and allowed to warm to room temperature overnight. LCMS showed the reaction complete. The reaction mixture was quenched with 5 L distilled H₂O, extracted with 3 portions of CH₂Cl₂ (2 L, 1 L, 1 L) and the organic layers combined and washed with three 4 L portions of water. The organic layer was concentrated and was found to contain NMP. The residual oil was dissolved in EtOAc (4 L), and extracted with three 2 L portions of water. The organic layer was concentrated to give the product that solidified upon standing.

¹H NMR (400 MHz, CDCl₃) δ 7.24 (m, 2H), 7.0 (m, 2H), 7.1 (m, 1H), 4.56 (s, 2H), 3.19 (t, J=4.9, 2H), 2.46 (t, J=6.4, 2H), 1.8-1.75 (m, 4H) ppm.

Step 2: 1-(3-Chloro-4-fluorobenzyl)-5,6-dihydropyridin-2(1H)-one 1-(3-Chloro-4-fluorobenzyl)piperidin-2-one (340 g, 1.41 mol) was dissolved in THF (5 L) and cooled to −20° C. under nitrogen. LHMDS (3.09 L, 3.09 mol, 1M in THF) was added over 40 minutes keeping the temperature at −20° C. and aged for 1 hr at −20° C. The methyl benzene sulfonate (231 mL, 1.69 mol) was added over 30 minutes, again keeping the internal temperature at −20° C. The reaction was aged for 30 minutes at −20° C. and LCMS showed the reaction complete. The reaction mixture was diluted with 4 L EtOAc and washed with four 2 L portions of distilled H₂O. The organic layer was concentrated and the residue was dissolved in 4 L toluene. Na₂CO₃ (500 g) was added and the reaction heated to 100° C. for 1 hour. LCMS showed the reaction complete. The residue was diluted with 4 L EtOAc and washed with four 2 L portions of distilled water. The organic layer was concentrated and the residue purified by flash chromatography on silica eluting with a gradient of 0-60% EtOAc/heptane. The product was isolated as an oil.

¹H NMR (400 MHz, CDCl₃) δ 7.3 (m, 1H), 7.15 (m, 1H), 7.1 (t, 1H), 6.6 (m, 1H), 6.0 (m, 1H), 4.55 (s, 2H), 3.33 (t, 2H), 1.38 (m, 2H) ppm. (ES MS M+1=240.13)

Step 3

2-Butoxy-2-oxoethanaminium chloride

Glycine hydrochloride (400 g, 3.58 mol) was suspended in 8 L of n-butanol and thionyl chloride (1.37 L, 18.84 mol) was added slowly dropwise (exotherm). After addition was complete, the reaction was heated to 70° C. overnight. The reaction could be followed by spotting directly on TLC, pumping off the volatiles, eluting with 10% MeOH/CHCl₃ saturated with NH₃, and staining in ninhydrin. The next day the reaction was stripped to dryness under vacuum and the residue was triturated with heptane/EtOAc to give the product as a white solid after drying on a filter under Nitrogen.

¹H NMR (400 MHz, CDCl₃) δ 8.5 (bs, 3H), 4.18 (t, J=6.7 Hz, 2H), 4.0 (bs, 2H), 1.62 (m, 2H), 1.38 (m, 2H), 0.92 (t, J=7.4 Hz, 3H) ppm. ES MS M+1=132.

Step 4

Butyl N-[ethoxy(oxo)acetyl]glycinate

2-Butoxy-2-oxoethanaminium chloride (573.5 g, 3.42 mol) was suspended in 7 L of ethanol and triethylamine (415 g, 4.1 mol) was added. Diethyloxalate (1.0 Kg, 6.8 mol) was added and the reaction warmed to 50° C. for 3 hours. The reaction was cooled, the volatiles were removed under vacuum and the residue was dissolved in methylene chloride and washed with two 4 L portions of water and dried over MgSO₄. The next day the reaction was filtered, evaporated to give ~1.2 Kg of an oil that was chromatographed on silica eluting with Heptane/EtOAc to give product.

¹H NMR (400 MHz, CDCl₃) δ 7.56 (bs, 1H), 4.37 (q, J=7.2 Hz, 2H), 4.2 (t, J=6.6 Hz, 2H), 4.12 (d, J=5.5 Hz, 2H), 1.64 (p, J=6.8 Hz, 2H), 1.39 (t, J=7.15 Hz, 3H), 1.37 (m, buried, 2H), 0.94 (t, J=7.4 Hz, 3H) ppm. ES MS M+1=232.

Step 5

Ethyl 5-butoxy-1,3-oxazole-2-carboxylate

Butyl N-[ethoxy(oxo)acetyl]glycinate (783 g, 3.38 mol) was dissolved in 8 L of acetonitrile in a 50 L Chemglass reactor with overhead stirrer and P₂O₅ (415 g, 2.92 mol) was added in large portions, watching for exotherm. The reaction was heated to 60° C. for 1 hour and LCMS showed the reaction done. After cooling, water (8 L) was added at 20° C. and the reaction was transferred to a 50 L flask. Methylene chloride (8 L) was added, the layers split and the aqueous layer was extracted with three 2 L volumes of methylene chloride. The combined organic layers were washed with two 4 L portions of saturated aqueous NaHCO₃, then dried with MgSO₄ and evaporated to give an oil that was purified on silica eluting with 0-30% EtOAc/heptane to give the product as an oil.

¹H NMR (400 MHz, CDCl₃) δ 6.33 (s, 1H), 4.42 (q, J=7.15 Hz, 2H), 4.18 (t, J=6.4 Hz, 2H), 1.8 (p, J=6.4 Hz, 2H), 1.47 (p, J=7.4 Hz, 2H), 1.41 (t, J=7.15 Hz, 3H), 0.97 (t, J=7.4 Hz, 3H) ppm. ES MS M+1=214.

Step 6

Ethyl 6-(3-chloro-4-fluorobenzyl)-4-hydroxy-5-oxo-5,6,7,8-tetrahydro-2,6-naphthyridine-1-carboxylate Ethyl 5-butoxy-1,3-oxazole-2-carboxylate (44.5 g, 208.6 mmol) and 1-(3-chloro-4-fluorobenzyl)-5,6-dihydropyridin-2(1H)-one (25 g, 104.3 mmol) were placed in a heavy walled round bottom flask equipped with a screw top and acid resistant O-ring and a stir bar. The mixture was stirred and water (2.82 mL, 156.7 mmol) was added. The reaction was sealed and placed in an oil bath pre-heated to 130° C. The reaction was aged for 72 hours, when LCMS showed much of the lactam had been consumed. The reaction was allowed to cool and sit until the mass had solidified. The mass was taken up in ether and the solids collected by filtration to give the product as a tan solid. The product was further purified by crystallization from EtOAc.

$^1$H NMR (400 MHz, CDCl$_3$) δ 12.79 (s, 1H), 8.42 (s, 1H), 7.4 (dd, J=2, 7 Hz, 1H), 7.2 (m, 1H), 7.15 (t, J=8.6 Hz, 1H), 4.7 (s, 2H), 4.4 (q, J=7 Hz, 2H), 3.5 (m, 4H), 1.4 (t, J=7 Hz, 3H) ppm. (ES MS M+1=379.0)

Step 7

Ethyl 6-(3-chloro-4-fluorobenzyl)-4-hydroxy-5-oxo-5,6,7,8-tetrahydro-2,6-naphthyridine-1-carboxylate 2-oxide Ethyl 6-(3-chloro-4-fluorobenzyl)-4-hydroxy-5-oxo-5,6,7,8-tetrahydro-2,6-naphthyridine-1-carboxylate (22 g, 58 mmol) was dissolved in 500 mL glacial acetic acid and H$_2$O$_2$ (30% by weight in water, 65.8 mL) was added. The reaction was warmed to 100° C. and aged for four hours at which time LCMS showed the reaction done. The solution was cooled in an ice bath to 25° C. and treated with saturated Na$_2$SO$_3$ solution, keeping the temperature below 40° C. When starch paper test showed no peroxides present, the solution was concentrated by ⅓, the pH was adjusted to ~3 with aqueous HCl and the solution extracted with CH$_2$Cl$_2$ several times. The organic layers were dried over Na$_2$SO$_4$, filtered and evaporated to give product as an oil.

$^1$H NMR (400 MHz, CDCl$_3$) δ 12.65 (s, 1H), 7.9 (s, 1H), 7.38 (dd, J=2, 7 Hz, 1H), 7.27-7.1 (m, 2H), 4.66 (s, 2H), 4.44 (q, J=7 Hz, 2H), 3.52 (t, J=7 Hz, 2H), 2.90 (t, J=7 Hz, 2H), 1.38 (t, J=7 Hz, 3H) ppm. (ES MS M+1=395.0)

Step 8

Ethyl 3,4-bis(acetyloxy)-6-(3-chloro-4-fluorobenzyl)-5-oxo-5,6,7,8-tetrahydro-2,6-naphthyridine-1-carboxylate Ethyl 6-(3-chloro-4-fluorobenzyl)-4-hydroxy-5-oxo-5,6,7,8-tetrahydro-2,6-naphthyridine-1-carboxylate 2-oxide (23 g, 58 mmol) was dissolved in 400 mL acetic anhydride and heated with stirring under nitrogen to 100° C. for 1 hour. By LCMS, the starting material and product are very close in retention time. To check that the reaction was done, an aliquot was treated with NaOMe in water and CH$_3$CN. The resulting hydrolyzed product elutes at an earlier retention time and allows distinguishing between remaining N-oxide and rearranged product. The reaction was evaporated to give the crude product as an oily residue that was taken on to the next step.

$^1$H NMR (400 MHz, CDCl$_3$) δ 7.36 (m, 1H), 7.2-7.1 (m, 1H), 7.12 (t, J=8 Hz, 1H), 4.68 (s, 2H), 4.4 (q, J=7 Hz, 2H), 3.48 (m, 2H), 3.35 (m, 2H), 2.38 (bs, 6H), 1.4 (t, J=7 Hz, 3H) ppm. (ES MS M+1=394.9)

Step 9

Methyl 6-(3-chloro-4-fluorobenzyl)-3,4-dihydroxy-5-oxo-5,6,7,8-tetrahydro-2,6-naphthyridine-1-carboxylate Ethyl 3,4-bis(acetyloxy)-6-(3-chloro-4-fluorobenzyl)-5-oxo-5,6,7,8-tetrahydro-2,6-naphthyridine-1-carboxylate (27.8 g, 58 mmol) was dissolved in 300 mL MeOH and treated with a 30% by weight solution of NaOMe in MeOH (41.8 mL, 232 mmol, 4 equivalents was sufficient to get the pH of the reaction to 9) for 5 hours at 40° C. LCMS showed the cleavage of the acetate groups was complete, a little transesterification was observed as well. The volume was reduced by half under vacuum and the mixture was diluted with THF (400 mL) and an additional 33 mL of NaOMe was added. The reaction was stirred at room temperature overnight and then warmed to 50° C. for four hours, when LCMS showed transesterification completed. The reaction was neutralized with 1N HCl and allowed to sit at room temperature overnight, then later acidified to pH 3 and extracted with CHCl$_3$ several times. The organic layer was dried over Na$_2$SO$_4$ and evaporated to give a black oil.

$^1$H NMR (400 MHz, CDCl$_3$) δ 10.0-8.2 (bs, 1H), 7.38 (dd, J=6.8.2 Hz, 1H), 7.2 (m, 1H), 7.13 (t, J=8.4 Hz, 1H), 4.68 (s, 2H), 3.92 (s, 3H), 3.46 (t, J=6.4 Hz, 2H), 3.34 (t, J=6.4 Hz, 2H) ppm. (ES MS M+1=380.9)

Step 10

Methyl 6-(3-chloro-4-fluorobenzyl)-4-hydroxy-2-methyl-3,5-dioxo-2,3,5,6,7,8-hexahydro-2,6-naphthyridine-1-carboxylate To a solution of methyl 6-(3-chloro-4-fluorobenzyl)-3,4-dihydroxy-5-oxo-5,6,7,8-tetrahydro-2,6-naphthyridine-1-carboxylate (18.00 g, 47 mmol) in DMF (200 mL) was added magnesium methylate (96.08 mL, 95 mmol), and the reaction was warmed for 1 hour and cooled. The reaction was treated with iodomethane (17.66 mL, 283 mmol) and stirred at 45° C. overnight. At this time, LCMS showed the reaction incomplete, and an additional equivalent of iodomethane (2.95 mL, 48 mmol) was added. The reaction was again stirred for 4 hours. The solvent was removed in vacuo, and the resulting oil was partitioned between chloroform and 1N HCl. The aqueous layer was washed twice more with chloroform. The organic fractions were extracted with 10% sodium bisulfite, and the bisulfite layer was washed twice with chloroform. The combined organic layers were washed with 5% aqueous HCl and brine, dried over sodium sulfate and concentrated in vacuo to afford the product as a black oil. This material appears quite clean by NMR and HPLC, but is highly colored.

$^1$H NMR (400 MHz, CDCl$_3$) δ 13.37 (s, 1H), 7.35 (dd, J=2.4, 6.9 Hz, 1H), 7.22-7.18 (m, 1H), 7.13 (t, J=8.4 Hz, 1H), 4.67 (s, 2H), 3.92 (s, 3H), 3.54 (s, 3H), 3.43 (t, J=6.4 Hz, 2H), 2.81 (t, J=6.4 Hz, 2H) ppm. (ES MS M+1=395.0)

Step 11

Methyl 6-(3-chloro-4-fluorobenzyl)-4-methoxy-2-methyl-3,5-dioxo-2,3,5,6,7,8-hexahydro-2,6-naphthyridine-1-carboxylate To a solution of methyl 6-(3-chloro-4-fluorobenzyl)-4-hydroxy-2-methyl-3,5-dioxo-2,3,5,6,7,8-hexahydro-2,6-naphthyridine-1-carboxylate (7.25 g, 18 mmol) in anhydrous DMF (75 mL) was added cesium carbonate (5.98 g, 18 mmol)

and iodomethane (2.86 mL, 46 mmol). The reaction was stirred at room temperature overnight, and LCMS showed 70% completion. The reaction was heated to 50° C. for 7 hours and then allowed to stir at room temperature again overnight. LCMS indicated completion. The reaction was concentrated to dryness, and the resulting residue was dissolved in chloroform. The solution was extracted twice with saturated $Na_2SO_3$ solution, dried over sodium sulfate, filtered, and evaporated to afford a dark brown oil.

$^1$H NMR (400 MHz, $CDCl_3$) δ 7.34 (dd, J=2.1, 7.0 Hz, 1H), 7.19 (m, 1H), 7.11 (m, 1H), 4.65 (s, 2H), 4.12 (s, 3H), 3.92 (s, 3H), 3.49 (s, 3H), 3.34 (m, 2H), 2.59 (m, 2H) ppm. (ES MS M+1=409.0)

Step 12

6-(3-Chloro-4-fluorobenzyl)-4-methoxy-2-methyl-3,5-dioxo-2,3,5,6,7,8-hexahydro-2,6-naphthyridine-1-carboxylic acid To a solution of methyl 6-(3-chloro-4-fluorobenzyl)-4-methoxy-2-methyl-3,5-dioxo-2,3,5,6,7,8-hexahydro-2,6-naphthyridine-1-carboxylate (14.3 g, 35 mmol) in THF (1501 mL) and MeOH (150 mL) was added LiOH (2.74 g, 114 mmol) dissolved in 114 mL water and the reaction was heated to 50° C. for 45 minutes. HPLC showed completion. The reaction was neutralized with 1N HCl and cooled to room temperature. THF was removed in vacuo, and the resulting slurry was partitioned between $CHCl_3$ and 5% aqueous HCl. The aqueous was washed with additional $CHCl_3$. The combined organics were dried over sodium sulfate, filtered, and concentrated to dryness to afford the desired product as a pale yellow foam. The material was crystallized from ethyl acetate to give a light yellow solid.

$^1$H NMR (400 MHz, $CD_3OD$) δ 7.49 (dd, J=2.0, 6.8 Hz, 1H), 7.34-7.30 (m, 1H), 7.25-7.20 (m, 1H), 4.71 (s, 2H), 3.98 (s, 3H), 3.58 (s, 3H), 3.50 (m, 2H), 2.77-2.74 (m, 2H) ppm. (ES MS M+1=395.0)

Step 13

6-(3-Chloro-4-fluorobenzyl)-4-methoxy-N,N,2-trimethyl-3,5-dioxo-2,3,5,6,7,8-hexahydro-2,6-naphthyridine-1-carboxamide To a suspension of 6-(3-chloro-4-fluorobenzyl)-4-methoxy-2-methyl-3,5-dioxo-2,3,5,6,7,8-hexahydro-2,6-naphthyridine-1-carboxylic acid (8.50 g, 22 mmol) in methylene chloride (300 mL) at 0° C. was added oxalyl chloride (2.25 mL, 26 mmol) and 1 drop of anhydrous DMF. The reaction was stirred at 0° C. for 15 minutes during which time no bubbling was observed. The reaction was then allowed to warm to room temperature and stirred for 40 minutes. At this time bubbling had ceased, and all material was in solution. An aliquot of the solution was quenched with dimethylamine and checked by LCMS to confirm completion. To the solution of the acid chloride starting material at 0° C. was added dimethylamine in THF (43.56 mL, 87 mmol, 2.0 M). The green/yellow reaction was allowed to stir at room temperature overnight although the reaction appeared to proceed immediately by LCMS. The solvent was removed in vacuo, and the resulting residue was dissolved in chloroform. The solution was washed with water and 5% aqueous HCl solution and back extracted to recover the product. The combined organic layers were washed with brine, dried over sodium sulfate, filtered and concentrated in vacuo. The resulting iridescent green/yellow residue was examined in several TLC solvent systems (95:5 $CH_2Cl_2$:MeOH, 2:1 acetone:hexanes, 1:1 EtOAc:hexanes) with the most efficient separation of some early running impurities achieved in the $CH_2Cl_2$:MeOH system. The material was purified by silica gel flash column chromatography, loaded as a solution in methylene chloride onto a 330 g RediSep column. Gradient elution consisted of 1.5 L each of neat $CH_2Cl_2$, 1% MeOH:$CH_2Cl_2$, 2% MeOH:$CH_2Cl_2$, 3% MeOH:$CH_2Cl_2$, 4% MeOH:$CH_2Cl_2$, and 5% MeOH:$CH_2Cl_2$, in sequential order. The desired material began to elute with 3% and was pushed off the column with 4% and 5%, yielding two sets of fraction. The earlier set afforded of the desired product plus a fluorescent green contaminant. The later set afforded clean material.

$^1$H NMR (400 MHz, $CD_3OD$) δ 7.49 (dd, J=2.0, 7.2 Hz, 1H), 7.34-7.31 (m, 1H), 7.22 (t, J=8.8 Hz, 1H), 4.77 (d, J=15.2 Hz, 1H), 4.65 (d, J=15.2 Hz, 1H), 3.97 (s, 3H), 3.52-3.48 (m, 2H), 3.45 (s, 3H), 3.11 (s, 3H), 2.97 (s, 3H), 2.57-2.54 (m, 2H) ppm. (ES MS M+1=422.0)

Step 14

6-(3-Chloro-4-fluorobenzyl)-4-hydroxy-N,N,2-trimethyl-3,5-dioxo-2,3,5,6,7,8-hexahydro-2,6-naphthyridine-1-carboxamide To 6-(3-chloro-4-fluorobenzyl)-4-methoxy-N,N,2-trimethyl-3,5-dioxo-2,3,5,6,7,8-hexahydro-2,6-naphthyridine-1-carboxamide (5.43 g, 13 mmol) was added 33% HBr in acetic acid (20 mL, 129 mmol), and the mixture was heated to 50° C. for 15 minutes to give a thick, pale brown/orange solution. By LCMS, the reaction was complete, and the acetic acid was removed in vacuo. The resulting residue was partitioned between chloroform and water, and the organic layer was then washed with aqueous sodium sulfite solution and brine. The combined organic extracts were dried over sodium sulfate, filtered, and concentrated in vacuo to afford a pale yellow foam. The foam was dissolved in hot isopropanol and crystallized quickly, and the crystals were collected by filtration. The material was then taken up in hot acetone which did not afford a complete solution, so the mixture was hot filtered. The resulting filtrate was allowed to cool causing crystals to form. The insoluble material from the hot acetone filtration was dissolved in hot ethanol and re-filtered. This resulting filtrate also produced large, slowly grown crystals over the course of one day. The crystals compound free base from both filtrates were collected, combined, dried for 4 hours, milled, and re-dried overnight without heat to give product.

$^1$H NMR (400 MHz, $CD_3OD$) δ 7.51 (dd, J=2.1, 7.2 Hz, 1H), 7.36-7.33 (m, 1H), 7.23 (t, J=8.9 Hz, 1H), 4.79 (d, J=14.8 Hz, 1H), 4.65 (d, J=14.8 Hz, 1H), 3.52 (t, J=6.8 Hz, 2H), 3.46 (s, 3H), 3.10 (s, 3H), 2.97 (s, 3H), 2.64 (t, J=6.8 Hz, 2H) ppm. (ES MS exact mass=408.1113)

Step 15

6-(3-Chloro-4-fluorobenzyl)-4-hydroxy-N,N,2-trimethyl-3,5-dioxo-2,3,5,6,7,8-hexahydro-2,6-naphthyridine-1-carboxamide sodium salt To 6-(3-chloro-4-fluorobenzyl)-4-hydroxy-N,N,2-trimethyl-3,5-dioxo-2,3,5,6,7,8-hexahydro-2,6-naphthyridine-1-carboxamide (1.08 g, 2.65 mmol) in a freeze drying flask was added acetonitrile (5 mL) at room temperature. The flask was placed in an ultrasonic bath at room temp for 1 minute. Some crystals remained. Water was added (5 mL) followed by the 1 N NaOH (2.65 mL, 2.65 mmol). The total was placed in the ultrasonic bath for 1 minute. An additional 1 mL of acetonitrile was added and placed in the ultrasonic bath for an additional minute. All material was now dissolved. More water (30 mL) was added to the flask and all stayed soluble. The contents of the flask were frozen with spinning in a −78° C. acetone/dry ice bath and placed on the freeze drier for 40 hours to give the product as a dry fluffy solid.

$^1$H NMR (400 MHz, CD$_3$OD) δ 7.46 (dd, J=2.2, 7.14 Hz, 1H), 7.33-7.29 (m, 1H), 7.17 (t, J=9.0 Hz, 1H), 4.72 (d, J=14.8 Hz, 1H), 4.65 (d, J=14.8 Hz, 1H), 3.35 (s, 3H), 3.33-3.96 (m, 2H), 3.07 (s, 3H), 2.97 (s, 3H), 2.47 (dd, J=5.68, 11.36 Hz, 2H) ppm. (ES MS M+1=408.0)

EXAMPLE 13

6-(3-Chloro-4-fluorobenzyl)-4-hydroxy-2-isopropyl-N,N-dimethyl-3,5-dioxo-2,3,5,6,7,8-hexahydro-2,6-naphthyridine-1-carboxamide

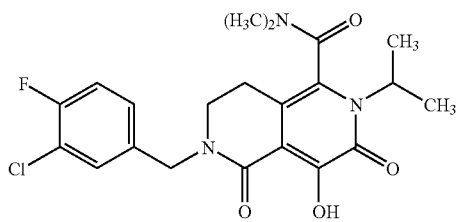

Step 1

6-(3-Chloro-4-fluorobenzyl)-4-hydroxy-5-oxo-5,6,7,8-tetrahydro-2,6-naphthyridine-1-carboxylic acid To a solution of ethyl 6-(3-chloro-4-fluorobenzyl)-4-hydroxy-5-oxo-5,6,7,8-tetrahydro-2,6-naphthyridine-1-carboxylate (27.0 g, 71 mmol) in THF (333 mL) and MeOH (166 mL) was added LiOH (5.21 g, 214 mmol) dissolved in enough water to make a 1N solution (total volume 213 mL) and the reaction was heated to 60° C. overnight. HPLC showed completion. A white precipitate was observed. The reaction was neutralized with 1N HCl and the more volatile solvents removed, leaving the water solution. 300 mL water was added the solution was acidified to pH 1 with 1 N HCl. A large amount of solids had precipitated. The resulting slurry was stirred vigorously with 100 mL CHCl$_3$. Most of the solid had precipitated from the partitioning and the entire mix was filtered and dried over the weekend to give product. Additional less pure product was recovered from extraction of the filtrate.

$^1$H NMR (400 MHz, CD$_3$OD) δ 8.25 (s, 1H), 7.53 (dd, J=2.2, 6.9 Hz, 1H), 7.36 (m, 1H), 7.23 (t, J=8.9 Hz, 1H), 4.74 (s, 2H), 3.61 (bt, J=6.4 Hz, 1H), 3.50 (bt, J=6.4 Hz, 1H) ppm. (ES MS M+1=351.0)

Step 2

6-(3-Chloro-4-fluorobenzyl)-4-hydroxy-N,N-dimethyl-5-oxo-5,6,7,8-tetrahydro-2,6-naphthyridine-1-carboxamide To a suspension of 6-(3-chloro-4-fluorobenzyl)-4-hydroxy-5-oxo-5,6,7,8-tetrahydro-2,6-naphthyridine-1-carboxylic acid (25.0 g, 71.3 mmol) in methylene chloride (1000 mL) at 0° C. was added oxalyl chloride (12.4 mL, 143 mmol) and 8 drops of anhydrous DMF. The reaction was stirred at 0° C. for 15 minutes. during which time no bubbling was observed. The reaction was then allowed to warm to room temperature and stirred for 40 minutes. At this time bubbling had ceased. An aliquot of the solution was quenched with dimethylamine and checked by LCMS. The reaction was incomplete. An additional 0.5 equivalent of oxalyl chloride was added and the reaction stirred an additional 40 minutes. The reaction never attained complete solution but was complete by LCMS. To the suspension of the acid chloride cooled to 0° C. was slowly added 2M dimethylamine in THF (140.8 mL, 281 mmol). The rate of addition was adjusted to avoid a large exotherm. The pH of the solution was found to be about 9. The yellow reaction was allowed to stir at room temperature overnight although the reaction appeared to proceed immediately by LCMS. The solvent was removed in vacuo, and the resulting residue was dissolved in chloroform. The solution was washed with water and 5% aqueous HCl solution and the aqueous layer back extracted to recover the product. The combined organic layers were washed with brine, dried over sodium sulfate, filtered and concentrated in vacuo to give a brown/yellow waxy solid. The initial NMR shows an excessive number of methyl group peaks, perhaps as a result of oxalyl chloride reacting with dimethylamine. A small sample was purified by reverse phase chromatography eluting with 95:5-5:95 water/acetonitrile 0.1% TFA to give clean material for NMR.

$^1$H NMR (400 MHz, CDCl$_3$) δ 12.35 (bs, 1H), 10.9 (bs, 1H), 8.32 (s, 1H), 7.38 (dd, J=2.0, 6.7 Hz, 1H), 7.22 (m, 1H), 7.14 (t, J=8.5 Hz, 1H), 4.69 (s, 2H), 3.54 (t, J=6.8 Hz, 2H), 3.14 (s, 3H), 3.05 (t, J=6.8 Hz, 2H), 2.95 (s, 3H) ppm. (ES MS M+1=378.1)

Step 3

6-(3-Chloro-4-fluorobenzyl)-4-hydroxy-N,N-dimethyl-5-oxo-5,6,7,8-tetrahydro-2,6-naphthyridine-1-carboxamide 2-oxide 6-(3-Chloro-4-fluorobenzyl)-4-hydroxy-N,N-dimethyl-5-oxo-5,6,7,8-tetrahydro-2,6-naphthyridine-1-carboxamide (24 g, 63.5 mmol) was dissolved in 1000 mL glacial acetic acid and per-acetic acid (32% by weight in acetic acid, 151 mL, 635 mmol) and sodium acetate (2.6 g, 31.7 mmol) was added. The reaction was warmed to 50° C. and aged overnight at which time LCMS showed the reaction done. The solution reduced in volume to ⅓ on the rotoevaporator, cooled in an ice bath and quenched slowly with 10% Na$_2$SO$_3$ solution until no peroxide was detected by a starch paper test. The reaction was transferred to a separatory funnel and water (500 mL) and chloroform was added. The layers were separated and the water extracted with CHCl$_3$ several times. The combined organic layers were washed with slightly acidic water, brine and dried over Na$_2$SO$_4$, filtered and evaporated to give the product as an oil. The initial NMR shows an excessive number of methyl group peaks, perhaps as a result of oxalyl chloride reacting with dimethylamine in the second step and this impurity being carried through. A small sample was purified by reverse phase chromatography eluting with 95:5-5:95 water/acetonitrile 0.1% TFA to give clean material for NMR.

$^1$H NMR (400 MHz, CDCl$_3$) δ 12.75 (bs, 1H), 8.4 (bs, 2H), 8.1 (s, 1H), 7.37 (dd, J=1.9, 6.9 Hz, 1H), 7.20 (m, 1H), 7.15 (t, J=8.5 Hz, 1H), 4.84 (d, J=14.7 Hz, 1H), 4.51 (d, J=14.7 Hz,

1H), 3.61 (m, 1H), 3.59 (m, 1H), 3.15 (s, 3H), 3.05 (m, 1H), 2.93 (s, 3H), 2.74 (m, 1H) ppm. (ES MS M+1=394.1)

Step 4

6-(3-Chloro-4-fluorobenzyl)-1-[(dimethylamino) carbonyl]-5-oxo-5,6,7,8-tetrahydro-2,6-naphthyridine-3,4-diyl diacetate 6-(3-Chloro-4-fluorobenzyl)-4-hydroxy-N,N-dimethyl-5-oxo-5,6,7,8-tetrahydro-2,6-naphthyridine-1-carboxamide 2-oxide (25 g, 63.5 mmol) was dissolved in 24 mL acetic anhydride and heated with stirring under nitrogen to 100° C. for 16 hours. By LCMS, the starting material and product are close in retention time and appear as the same molecular weight. To check that the reaction was done, an aliquot was treated with NaOMe in water and $CH_3CN$. The resulting hydrolyzed product elutes at an earlier retention time and allows distinguishing between remaining N-oxide and rearranged product. The reaction was evaporated and the residue was partitioned between chloroform and water and the water layer was back-extracted with more chloroform. The aqueous layer was checked by LCMS for product and no longer contained any. The organic layers were combined, dried over $Na_2SO_4$, filtered and evaporated to give an oil. (ES MS M+1 of NaOMe treated aliquot=394.0)

Step 5

6-(3-Chloro-4-fluorobenzyl)-3,4-dihydroxy-N,N-dimethyl-5-oxo-5,6,7,8-tetrahydro-2,6-naphthyridine-1-carboxamide 6-(3-Chloro-4-fluorobenzyl)-1-[(dimethylamino)carbonyl]-5-oxo-5,6,7,8-tetrahydro-2,6-naphthyridine-3,4-diyl diacetate (30 g, 62.7 mmol) was dissolved in 500 mL MeOH and treated with a 30% by weight solution of NaOMe in MeOH (45.2 mL, 251 mmol 4 equivalents was sufficient to get the pH of the reaction to 9) for 1 hour at 40° C. LCMS showed the cleavage of the acetate groups was complete. The reaction was neutralized with 1N HCl and the volume reduced to remove the MeOH and the residue was diluted with water and acidified to pH 3. The cloudy aqueous layer was diluted with an equal volume (800 mL) of chloroform. After shaking, the product began to crystallize out of the solutions and gathered at the miniscus. The total contents of the funnel were filtered and the collected solids were washed with water until no more salts appeared to remain. The solid was dried in vacuo for 16 hours to give a cinnamon colored solid. The organic layer from the filtered extraction was collected, washed with water and dried over $Na_2SO_4$, filtered and evaporated. The residue was crystallized from methanol to give product. The crude material was quite insoluble but was crystallized from DMF, then boiled in MeOH, filtered and dried under vacuum to give product.

$^1$H NMR (400 MHz, DMSO) δ 13.0 (s, 1H), 11.9 (s, 1H), 7.58 (d, J=6.9 Hz, 1H), 7.38 (m, 2H), 4.69 (bs, 2H), 3.49 (m, 2H), 2.91 (s, 3H), 2.84 (s, 3H), 2.56 (bs, 2H), ppm. (ES MS M+1=394.0)

Step 6

6-(3-Chloro-4-fluorobenzyl)$_{64}$-hydroxy-2-isopropyl-N,N-dimethyl-3,5-dioxo-2,3,5,6,7,8-hexahydro-2,6-naphthyridine-1-carboxamide To a solution of 6-(3-chloro-4-fluorobenzyl)-3,4-dihydroxy-N,N-dimethyl-5-oxo-5,6,7,8-tetrahydro-2,6-naphthyridine-1-carboxamide (3.00 g, 7.62 mmol) in DMSO (86 mL) was added magnesium methylate (42.75 mL of a 6-10% methanol solution, 24.4 mmol), and the reaction was heated to 60° C. for 0.75 hour. The reaction mixture was reduced on a rotoevaporator to remove all of the MeOH over 45 minutes. The heat gun was used to drive all MeOH from the bump bulb. The reaction was treated with 2-iodopropane (2.84 mL, 38.1 mmol) and allowed to stir at 60° C. for 3 hours. LCMS showed 11% starting material remaining and over 70% conversion to N- and O-alkylated products (typically 2:1). The reaction was diluted with 350 mL EtOAc to which 125 mL 1N HCl was added, and the phases were separated. The aqueous layer was washed once with methylene chloride (100 mL). The combined organic layers were washed with 1N HCl twice more and the organic layer was isolated. The organic layer was washed with 10% aqueous solution of $NaHSO_3$ (3×100 mL) followed by brine. The organic layer was dried over sodium sulfate and concentrated in vacuo to afford a yellow-orange foam residue. The solid combined with additional crude material from other reactions, dissolved in DMSO and Methanol and purified via reverse phase chromatography using a Biotage 75 L canister and a Varian Metaflash 75 L C-18 column, eluting with a gradient of 70:30 to 35:65 A:B where A=0.05% TFA in water and B=0.05% TFA in acetonitrile (flowrate=300 mL/minute, detection at 214 and 254 nM). Evaporation of the fractions afforded pure oil by HPLC/LCMS and NMR. Crystallization from EtOAc:hexane afforded white, analytically pure product.

$^1$H NMR (400 MHz, $CD_3OD$) δ 7.50 (dd, J=1.9, 7.2 Hz, 1H), 7.32 (m, 1H), 7.22 (t, J=8.8 Hz, 1H), 4.78 (d, J=14.9 Hz, 1H), 4.63 (d, J=14.9 Hz, 1H), 4.02 (m, 1H), 3.50 (t, J=6.4 Hz, 2H), 3.09 (s, 3H), 3.00 (s, 3H), 2.59 (t, J=6.4 Hz, 2H), 1.64 (d, J=6.8 Hz, 3H), 1.57 (d, J=6.7 Hz, 3H) ppm. (ES MS exact mass M+1=436.144)

EXAMPLE 14

6-(3-Chloro-4-fluorobenzyl)-4-hydroxy-2-isobutyl-N,N-dimethyl-3,5-dioxo-2,3,5,6,7,8-hexahydro-2,6-naphthyridine-1-carboxamide

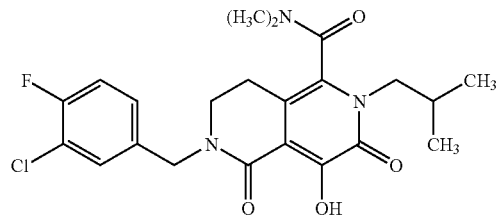

Step 1

4-Amino-6-(3-chloro-4-fluorobenzyl)-2-isobutyl-N,N-dimethyl-3,5-dioxo-2,3,5,6,7,8-hexahydro-2,6-naphthyridine-1-carboxamide To a solution of 6-(3-chloro-4-fluorobenzyl)-3,4-dihydroxy-N,N-dimethyl-5-oxo-5,6,7,8-tetrahydro-2,6-naphthyridine-1-carboxamide (0.5 g, 1.27 mmol) in DMSO (10 mL) was added magnesium methylate (5.48 mL of a 6-10% methanol solution, 30.8 mmol), and the reaction was heated to 60° C. for 0.5 hour. The reaction mixture was rotavapped to remove all of the MeOH. The heat gun was used to drive all MeOH from the bump bulb. The reaction was treated with 1-iodo-2-methylpropane (0.73 mL, 6.35 mmol) and allowed to stir at 60° C. for 40 minutes. LCMS showed trace starting material remaining and mostly N-alklated product formed (O-alkylated products~3%). The reaction was diluted with 1 mL MeOH then 1 N HCl was added until a precipitate began to form. A 10 mL portion of 10% sodium bisulfite was added and the brown mixture turned green. Water was added and the mixture stirred for 1 hr, then the liquid was decanted off the solids. The solids were partitioned with chloroform 20 mL and 1 N HCl 20 mL. The organic layer was washed 2 times more with 1 N HCl and then with brine, dried over $Na_2SO_4$, filtered and evaporated to an oil that smelled strongly of alkylating agent. The residue was diluted with toluene and evaporated and pumped on for 4 hours. The residue would not crystallize from ethyl acetate and methanol. The residue was passed through a Gilson reverse phase column eluting from 95:5 to 5:95 to give an oil after concentration. Crystallization from EtOAc:hexane afforded white, analytically pure product.

$^1$H NMR (400 MHz, DMSO) δ 13.0 (s, 1H), 7.60 (d, J=4.8 Hz, 1H), 7.40 (t, J=8.6 Hz, 1H), 7.38 (m, 1H), 4.77 (d, J=14.7 Hz, 1H), 4.58 (d, J=14.7 Hz, 1H), 3.90 (dd, J=7.7, 13.2 Hz, 1H), 3.50 (m, 3H), 2.97 (s, 3H), 2.04 (s, 3H), 2.54 (m, buried), 2.02 (m, 1H), 0.81 (t, J=6.22 Hz, 6H), ppm. (ES MS exact mass M+1=450.151)

EXAMPLE 14-2

6-(3-chloro-4-fluorobenzyl)-4-hydroxy-2-isobutyl-N-methyl-3,5-dioxo-2,3,5,6,7,8-hexahydro-2,6-naphthyridine-1-carboxamide

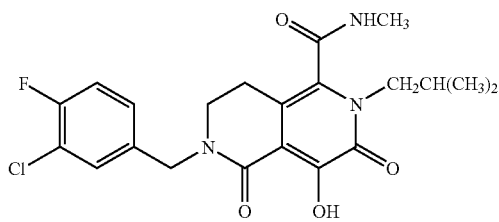

The title compound was prepared in accordance with the procedure set forth in Example 14, using the appropriate naphthyridine carboxamide penultimate. MS (M+1)=436.1.

EXAMPLE 15

6-(3-Chloro-4-fluorobenzyl)-4-hydroxy-N,N,2-trimethyl-3,5-dioxo-2,3,5,6,7,8-hexahydro-2,6-naphthyridine-1-carboxamide

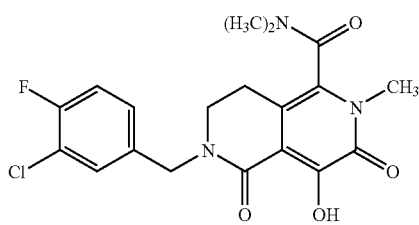

Step 1

6-(3-Chloro-4-fluorobenzyl)-4-hydroxy-N,N,2-trimethyl-3,5-dioxo-2,3,5,6,7,8-hexahydro-2,6-naphthyridine-1-carboxamide To a solution of 6-(3-chloro-4-fluorobenzyl)-3,4-dihydroxy-N,N-dimethyl-5-oxo-5,6,7,8-tetrahydro-2,6-naphthyridine-1-carboxamide (0.1 g, 0.254 mmol) in dry DMSO (5 mL) was added magnesium methylate (1.097 mL of a 6-10% methanol solution, 0.792 mmol), and the reaction was heated to 60° C. for 0.5 hour. The reaction mixture was rotavapped to remove all of the MeOH. The heat gun was used to drive all MeOH from the bump bulb. The reaction was treated with methyl iodide (0.079 mL, 6.35 mmol) and allowed to stir at 60° C. overnight. LCMS showed trace starting material remaining and mostly N-alklated product formed (O-alkylated products minor). The reaction was diluted with 0.5 mL MeOH then 1 N HCl was added until a precipitate began to form. A 5 mL portion of 10% sodium bisulfite was added and the brown mixture turned green. Water was added and the mixture stirred for 1 hr, then the mixture was partitioned with chloroform 20 mL and 1 N HCl 20 mL. The organic layer was washed 2 times more with 1 N HCl and then with brine, dried over $Na_2SO_4$, filtered and evaporated to an oil. The residue was passed through a Gilson reverse phase column eluting from 95:5 to 5:95 to give an oil after concentration.

$^1$H NMR (400 MHz, CD$_3$OD) δ 7.5 (dd, J=2.0, 7.1 Hz, 1H), 7.34 (m, 1H), 7.22 (t, J=8.8 Hz, 1H), 4.78 (d, J=14.8 Hz, 1H), 4.64 (d, J=14.8 Hz, 1H), 3.52 (t, J=6.5 Hz, 2H), 3.45 (s, 3H), 3.10 (s, 3H), 2.97 (s, 3H), 2.64 (t, J=6.4 Hz, 2H) ppm.

EXAMPLE 16

6-(4-fluorobenzyl)-4-hydroxy-N,N,2-trimethyl-3,5-dioxo-2,3,5,6-tetrahydro-2,6-naphthyridine-1-carboxamide

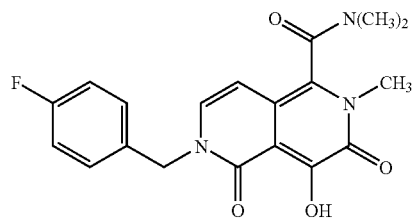

Step 1

Ethyl 6-(4-fluorobenzyl)-4-hydroxy-5-oxo-2,3,5,6-tetrahydro-2,6-naphthyridine-1-carboxamide To solution of 5-(ethoxycarbonyl)-2-(4-fluorobenzyl)-8-hydroxy-1-oxo-1,2,3,4-tetrahydro-2,6-naphthyridin-6-ium trifluoroacetate (0.020 g, 0.045 mmol; see Example 8, Step 4) in CCl$_4$ (2 mL) is added N-bromo succinimide (0.017 g, 0.095 mmol) and AIBN (catalytic). The reaction is heated to 80° C. for 1 hour, then concentrated and chromatographed on reverse phase to give the product.

Step 2

6-(4-fluorobenzyl)-4-hydroxy-N,N,2-trimethyl-3,5-dioxo-2,3,5,6-tetrahydro-2,6-naphthyridine-1-carboxamide The title compound can be prepared using a sequence of transformations similar to those described for Examples 9 and 10.

EXAMPLE 17

6-(3-chloro-4-fluorobenzyl)-N,N-diethyl-4-hydroxy-2-methyl-3,5-dioxo-2,3,5,6,7,8-hexahydro-2,6-naphthyridine-1-carboxamide

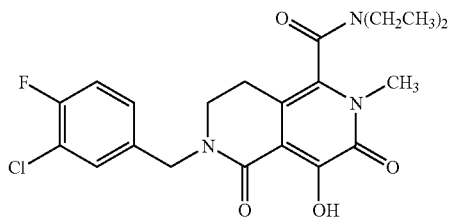

Step 1

Methyl 6-(3-chloro-4-fluorobenzyl)-4-methoxy-2-methyl-3,5-dioxo-2,3,5,6,7,8-hexahydro-2,6-naphthyridine-1-carboxylate Methyl 6-(3-chloro-4-fluorobenzyl)-3,4-dihydroxy-5-oxo-5,6,7,8-tetrahydro-2,6-naphthyridine-1-carboxylate which was prepared as described in Example 12, Steps 1-9 was converted in a manner similar to Example 10, Step 1 for methyl 6-(4-fluorobenzyl)-4-methoxy-2-methyl-3,5-dioxo-2,3,5,6,7,8-hexahydro-2,6-naphthyridine-1-carboxylate to obtain the title compound from preparative silica gel chromatography eluting with 0-3% methanol in methylene chloride.

Step 2

6-(3-chloro-4-fluorobenzyl)-N,N-diethyl-4-hydroxy-2-methyl-3,5-dioxo-2,3,5,6,7,8-hexahydro-2,6-naphthyridine-1-carboxamide The title compound was prepared from methyl 6-(3-chloro-4-fluorobenzyl)-4-methoxy-2-methyl-3,5-dioxo-2,3,5,6,7,8-hexahydro-2,6-naphthyridine-1-carboxylate in a manner similar to that described in Example 12, Steps 12, 13 and 14, using diethyl amine in place of dimethylamine in the step corresponding to Step 13 of Example 12.

$^1$H NMR (400 MHz, CD$_3$OD) δ 7.50 (dd, J=2.1, 7.1 Hz, 1H), 7.36-7.32 (m, 1H), 7.23 (t, J=8.7 Hz, 1H), 4.75 (d, J=14.8 Hz, 1H), 4.67 (d, J=14.6 Hz, 1H), 3.60-3.55 (m, 2H), 3.54-3.51 (m, 2H), 3.46 (s, 3H), 3.36-3.33 (m, 2H), 2.68-2.61 (m, 2H), 1.25 (t, J=6.7 Hz, 3H), 1.13 (t, J=6.7 Hz, 3H) ppm.

ES MS M+1=436.0

The compounds in the following table were prepared in accordance with the procedure set forth in Example 17, using the appropriate amine in place of the diethylamine employed in Step 2 of Example 17. When the compound was prepared as a salt, the identity of the salt is included in parentheses following the compound name for the free base.

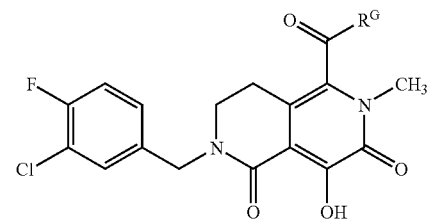

| Example | R$^G$ | Name | ES MS (M + 1) |
|---|---|---|---|
| 17-2 | ![piperazine-CH3] | 2-(3-chloro-4-fluorobenzyl)-8-hydroxy-6-methyl-5-[(4-methylpiperazin-4-yl)carbonyl]-2,3,4,6-tetrahydro-2,6-naphthyridine-1,7-dione (TFA salt) | 463.0 |
| 17-3 | ![thiomorpholine] | 2-(3-chloro-4-fluorobenzyl)-8-hydroxy-6-methyl-5-(thiomorpholin-4-ylcarbonyl)-2,3,4,6-tetrahydro-2,6-naphthyridine-1,7-dione | 465.9 |
| 17-4 | ![piperidine] | 2-(3-chloro-4-fluorobenzyl)-8-hydroxy-6-methyl-5-(piperidin-1-ylcarbonyl)-2,3,4,6-tetrahydro-2,6-naphthyridine-1,7-dione | 448.1 |

-continued

| Example | R^G | Name | ES MS (M + 1) |
|---|---|---|---|
| 17-5 | *NH-CH2-cyclopropyl | 6-(3-chloro-4-fluorobenzyl)-N-(cyclopropylmethyl)-4-hydroxy-2-methyl-3,5-dioxo-2,3,5,6,7,8-hexahydro-2,6-naphthyridine-1-carboxamide | 434.1 |
| 17-6 | HN-cyclopropyl | 6-(3-chloro-4-fluorobenzyl)-N-cyclopropyl-4-hydroxy-2-methyl-3,5-dioxo-2,3,5,6,7,8-hexahydro-2,6-naphthyridine-1-carboxamide | 420.1 |
| 17-7 | N(CH3)CH2CH3 | 6-(3-chloro-4-fluorobenzyl)-N-ethyl-4-hydroxy-N,2-dimethyl-3,5-dioxo-2,3,5,6,7,8-hexahydro-2,6-naphthyridine-1-carboxamide | 422.1 |
| 17-8 | N(CH3)CH(CH3)2 | 6-(3-chloro-4-fluorobenzyl)-4-hydroxy-N-isopropyl-N,2-dimethyl-3,5-dioxo-2,3,5,6,7,8-hexahydro-2,6-naphthyridine-1-carboxamide | 436.1 |
| 17-9 | 4,4-difluoropiperidin-1-yl | 2-(3-chloro-4-fluorobenzyl)-5-[(4,4-difluoropiperidin-1-yl)carbonyl]-8-hydroxy-6-methyl-2,3,4,6-tetrahydro-2,6-naphthyridine-1,7-dione | 484.1 |
| 17-10 | morpholin-4-yl | 2-(3-chloro-4-fluorobenzyl)-8-hydroxy-6-methyl-5-(morpholin-4-ylcarbonyl)-2,3,4,6-tetrahydro-2,6-naphthyridine-1,7-dione | 450.1 |
| 17-11 | HN—CH3 | 6-(3-chloro-4-fluorobenzyl)-4-hydroxy-N,2-dimethyl-3,5-dioxo-2,3,5,6,7,8-hexahydro-2-naphthyridine-1-carboxamide | 394.1 |
| 17-12 | 4-cyclopropylpiperazin-1-yl | 2-(3-chloro-4-fluorobenzyl)-8-hydroxy-6-methyl-5-[(4-cyclopropylpiperazin-4-yl)carbonyl]-2,3,4,6-tetrahydro-2,6-naphthyridine-1,7-dione (TFA salt) | 489.2 |

EXAMPLE 18

N,N-diethyl-6-(4-fluorobenzyl)-4-hydroxy-2-methyl-3,5-dioxo-2,3,5,6,7,8-hexahydro-2,6-naphthyridine-1-carboxamide

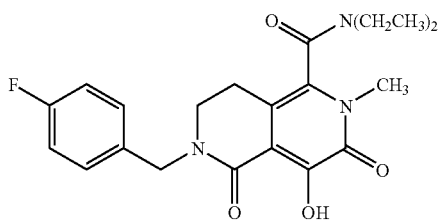

Step 1

Ethyl 6-(4-fluorobenzyl)-4-hydroxy-5-oxo-5,6,7,8-tetrahydro-2,6-naphthyridine-1-carboxylate The title compound was prepared using the procedure described in Steps 14 of Example 8.

Step 2

Methyl 6-(4-fluorobenzyl)-4-hydroxy-3,5-dioxo-2,3,5,6,7,8-hexahydro-2,6-naphthyridine-1-carboxylate The title compound was be prepared in a manner similar to that described for methyl 6-(3-chloro-4-fluorobenzyl)-3,4- dihydroxy-5-oxo-5,6,7,8-tetrahydro-2,6-naphthyridine-1-carboxylate shown in Example 12, Steps 7, 8, 9.

Step 3

Methyl 6-(4-fluorobenzyl)-3,4-dimethoxy-5-oxo-5,6,7,8-tetrahydro-2,6-naphthyridine-1-carboxylate The title compound was prepared in the manner described in Example 10, Step 1, where the desired compound, the N-methyl O-methoxy analog, was isolated as the second major product from the mixture of N,O- and O,O-alkylated products via silica gel chromatography eluting with 0-3% methanol in methylene chloride.

Step 4

6-(4-Fluorobenzyl)-3,4-dimethoxy-5-oxo-5,6,7,8-tetrahydro-2,6-naphthyridine-1-carboxylic acid The title compound was prepared in a similar manner to that described in Example 10, Step 2.

Step 5

N,N-diethyl-6-(4-fluorobenzyl)-4-hydroxy-2-methyl-3,5-dioxo-2,3,5,6,7,8-hexahydro-2,6-naphthyridine-1-carboxamide The title compound was prepared in a manner similar to that described in Example 12, Steps 13 and 14.

$^1$HNMR (400 MHz, CD$_3$OD) δ 7.41-7.37 (m, 2H), 7.10-7.06 (m, 2H), 4.76 (d, J=14.6 Hz, 1H), 4.72 (d, J=14.6 Hz, 1H), 3.57 (q, J=7.14 Hz, 2H), 3.50 (m, 2H), 3.45 (s, 3H), 3.37 (m, 2H)2.64 (m, 2H), 1.27-1.23 (m, 3H), 1.15-1.11 (m, 3H) ppm.

ES MS M+1=402.2

The compounds in the following table were prepared in accordance with the procedure set forth in Example 18, using the appropriate amine in place of the diethylamine employed in Step 5 of Example 18.

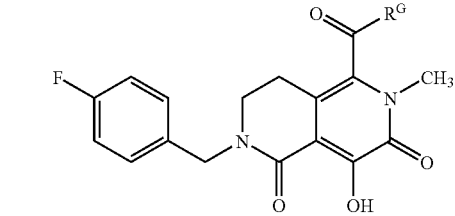

| Example | R$^G$ | Name | ES MS (M + 1) |
|---|---|---|---|
| 18-2 | *—N(CH$_3$)CH$_2$CH$_2$N(CH$_3$)$_2$ | N-[2-(dimethylamino)ethyl]-6-(4-fluorobenzyl)-4-hydroxy-N,2-dimethyl-3,5-dioxo-2,3,5,6,7,8-hexahydro-2,6-naphthyridine-1-carboxamide | 431.3 |
| 18-3 | 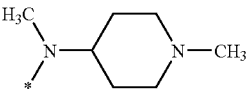 | 6-(4-fluorobenzyl)-4-hydroxy-N,2-dimethyl-N-(1-methylpiperidin-4-yl)-3,5-dioxo-2,3,5,6,7,8-hexahydro-2,6-naphthyridine-1-carboxamide | 457.3 |
| 18-4 | 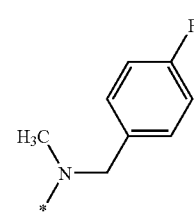 | N,6-bis(4-fluorobenzyl)-4-hydroxy-N,2-dimethyl-3,5-dioxo-2,3,5,6,7,8-hexahydro-2,6-naphthyridine-1-carboxamide | 468.3 |

EXAMPLE 19

N,N-diethyl-6-(4-fluorobenzyl)-3,4-dihydroxy-5-oxo-5,6,7,8-tetrahydro-2,6-naphthyridine-1-carboxamide

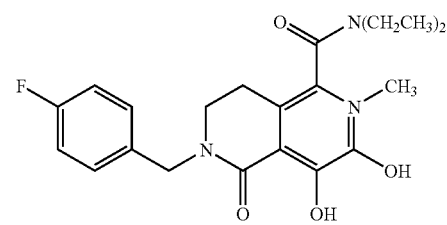

The title compound was prepared using the procedure set forth above in Example 18, except that in the methylation step the O,O alkylated product was isolated and used (first major product eluted off with 0-3% methanol/CH$_2$Cl$_2$).

¹H NMR (400 MHz, CD₃OD) δ 7.38 (m, 2H), 7.09 (m, 2H), 4.73 (bs, 2H), 3.62 (m, 2H), 3.50 (m, 2H), 3.41 (m, 2H), 2.64 (bs, 2H), 1.22 (m, 3H), 1.14 (m, 3H), ppm.
ES MS M+1=388.2

The compounds in the following table were prepared in accordance with the procedure set forth in Example 19, using the appropriate amine in place of the diethylamine.

¹H NMR (400 MHz, CDCl₃) δ 1.39-1.42 (m, J=7.1 Hz, 3H), 3.42-3.52 (m, 4H), 3.8 (s, 3H), 4.37-4.43 (q, J=7.1 Hz, 2H), 4.69 (s, 2H), 6.88-6.90 (dd, J=2, 6.8 Hz, 2H), 7.24-7.26 (m, 2H), 8.42 (s, 1H), 13.05 (br s, 1H) ppm.

LRMS (M+1)=357.0

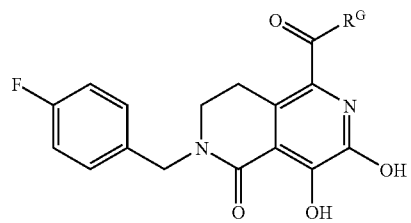

| Example | R$^G$ | Name | ES MS (M + 1) |
|---|---|---|---|
| 19-2 | *⁓N(CH₃)CH₂CH(CH₃)₂ | 6-(4-fluorobenzyl)-3,4-dihydroxy-N-isobutyl-N-methyl-5-oxo-5,6,7,8-tetrahydro-2,6-naphthyridine-1-carboxamide | 402.2 |
| 19-3 | *⁓N(CH₃)CH₂CH₃ | N-ethyl-6-(4-fluorobenzyl)-3,4-dihydroxy-N-methyl-5-oxo-5,6,7,8-tetrahydro-2,6-naphthyridine-1-carboxamide | 374.2 |
| 19-4 | *⁓N(CH₃)CH₂CH₂CH₃ | 6-(4-fluorobenzyl)-3,4-dihydroxy-N-methyl-5-oxo-N-propyl-5,6,7,8-tetrahydro-2,6-naphthyridine-1-carboxamide | 388.2 |
| 19-5 | *⁓N(CH₃)CH(CH₃)₂ | 6-(4-fluorobenzyl)-3,4-dihydroxy-N-isopropyl-N-methyl-5-oxo-5,6,7,8-tetrahydro-2,6-naphthyridine-1-carboxamide | 388.2 |
| 19-6 | pyrrolidine | 2-(4-fluorobenzyl)-7,8-dihydroxy-5-(pyrrolidin-1-ylcarbonyl)-3,4-dihydro-2,6-naphthyridin-1(2H)-one | 386.2 |
| 19-7 | morpholine | 2-(4-fluorobenzyl)-7,8-dihydroxy-5-(morpholin-4-ylcarbonyl)-3,4-dihydro-2,6-naphthyridin-1(2H)-one | 402.2 |

EXAMPLE 20

6-(3-chloro-4-fluorobenzyl)-4-hydroxy-N,N,2-trimethyl-3,5-dioxo-2,3,5,6,7,8-hexahydro-2,6-naphthyridine-1-carboxamide

Step 1

Ethyl 4-hydroxy-6-(4-methoxybenzyl)-5-oxo-5,6,7,8-tetrahydro-2,6-naphthyridine-1-carboxylate Ethyl 4-hydroxy-6-(4-methoxybenzyl)-5-oxo-5,6,7,8-tetrahydro-2,6-naphthyridine-1-carboxylate was prepared in a manner similar to that described in Example 8, Steps 1-4 starting with 4-methoxybenzyl chloride instead of 4-fluorobenzyl bromide, and also in a manner similar to that described in Example 12, Steps 1-6, starting with 4-methoxybenzyl chloride or 3-chloro-4-fluorobenzyl bromide.

Step 2

Ethyl 4-methoxy-6-(4-methoxybenzyl)-5-oxo-5,6,7,8-tetrahydro-2,6-naphthyridine-1-carboxylate The title product was prepared by treating ethyl 4-hydroxy-6-(4-methoxybenzyl)-5-oxo-5,6,7,8-tetrahydro-2,6-naphthyridine-1-carboxylate with TMS-diazomethane, using a method set forth in Step 5 of Example 8 for the preparation of ethyl 6-(4-fluorobenzyl)-4-methoxy-5-oxo-5,6,7,8-tetrahydro-2,6-naphthyridine-1-carboxylate, except that after quenching with HOAc the reaction was concentrated in vacuo and partitioned between sat aq NaHCO₃ and CHCl₃. LRMS (M+1)=371.0

Step 3

4-methoxy-6-(4-methoxybenzyl)-5-oxo-5,6,7,8-tetrahydro-2,6-naphthyridine-1-carboxylic acid To a solution of ethyl 4-methoxy-6-(4-methoxybenzyl)-5-oxo-5,6,7,8-tetrahydro-2,6-naphthyridine-1-carboxylate (15.2 g) in THF (150 mL) was added LiOH monohydrate (5.16 g) and sufficient water to dissolve the solids. The reac tion was allowed to stir at room temperature for 1.5 hours. The reaction was neutralized with 125 mL of 1N HCl and the THF was removed in vacuo. The resulting slurry was partitioned between $CHCl_3$ and 10% aqueous $KHSO_4$. The combined organics were dried over sodium sulfate, filtered, and concentrated to dryness to afford the desired product as a pale tan foam. LRMS (M+1)=343.0

Step 4

4-methoxy-6-(4-methoxybenzyl)-N,N-dimethyl-5-oxo-5,6,7,8-tetrahydro-2,6-naphthyridine-1-carboxamide A 250 mL THF suspension of 4-methoxy-6-(4-methoxybenzyl)-5-oxo-5,6,7,8-tetrahydro-2,6-naphthyridine-1-carboxylic acid (11.0 g), 8.0 g EDC, 5.7 g HOAT, and 11.2 mL TEA was stirred at room temperature for 20 minutes, followed by addition of 45 mL of a 2M THF solution of dimethylamine and then stirring for 1.5 hours. The reaction was quenched with 200 mL of 1N aq HCl and stirred vigorously for 30 minutes. After concentrating in vacuo until an oil formed on the water layer, 200 mL chloroform was added. The water layer was washed again with chloroform then the combined organic layers were washed with brine, dried over sodium sulfate, filtered and concentrated in vacuo to pure product by HPLC/MS and NMR.

HPLC/MS (M+1)=370.1

Step 5

4-methoxy-6-(4-methoxybenzyl)-N,N-dimethyl-5-oxo-5,6,7,8-tetrahydro-2,6-naphthyridine-1-carboxamide 2-oxide A 100 ml $CH_2Cl_2$ solution of 12 g 4-methoxy-6-(4-methoxybenzyl)-N,N-dimethyl-5-oxo-5,6,7,8-tetrahydro-2,6-naphthyridine-1-carboxamide and 16.8 g mCPBA (maximum 77% purity) was allowed to stir at room temperature until the starting material was consumed (5 hours). The reaction was washed four times with 100 mL sat aqueous $NaHCO_3$ then the organic layer was concentrated. The crude reaction was dissolved in 250 mL $CH_2Cl_2$ and the excess mCPBA was then quenched by vigorous stirring with a sat aq sodium sulfite solution for 30 minutes (both organic and aqueous layers were cloudy initially but then turned transparent). The layers were separated and the organic washed twice with sat aqueous $NaHCO_3$. The organic layer was dried over sodium sulfate and concentrated to pure product by HPLC/MS and NMR.

HPLC/MS (M+1)=386.2

Step 6

1-[(dimethylamino)carbonyl]-4-methoxy-6-(4-methoxybenzyl)-5-oxo-5,6,7,8-tetrahydro-2,6-naphthyridin-3-yl acetate 4-methoxy-6-(4-methoxybenzyl)-N,N-dimethyl-5-oxo-5,6,7,8-tetrahydro-2,6-naphthyridine-1-carboxamide 2-oxide (10.3 g) was dissolved in 30 ml acetic anhydride and transferred to a 50 mL heavy walled pressure flask and sealed. The reaction was heated in a 100° C. oil bath overnight. The reaction was concentrated in vacuo. The remaining oil was dissolved in 5 mL EtOAc and purified on an Isco automated system affixed with a Biotage Flash 40 (L) (120 g silica) cartridge eluted with 0-10% MeOH in EtOAc over 20 minutes and hold at 10% for 40 minutes. The product eluted pure by HPLC/MS and NMR.

LRMS (M+1)=428.3

Step 7

3-hydroxy-4-methoxy-6-(4-methoxybenzyl)-N,N-dimethyl-5-oxo-5,6,7,8-tetrahydro-2,6-naphthyridine-1-carboxamide 1-[(dimethylamino)carbonyl]-4-methoxy-6-(4-methoxybenzyl)-5-oxo-5,6,7,8-tetrahydro-2,6-naphthyridin-3-yl acetate (7.55 g) was dissolved in 50 mL MeOH and treated with 6.65 mL of a 30% by weight solution of NaOMe in MeOH at room temperature for 30 minutes. The reaction was concentrated and the remaining solid partitioned between 10% $KHSO_4$ and chloroform. The organic layer was washed with brine, dried over $Na_2SO_4$, and then concentrated to pure product by HPLC/MS and NMR.

LRMS (M+1)=386.3

Step 8

4-methoxy-6-(4-methoxybenzyl)-N,N,2-trimethyl-3,5-dioxo-2,3,5,6,7,8-hexahydro-2,6-naphthyridine-1-carboxamide To a solution of 3-hydroxy-4-methoxy-6-(4-methoxybenzyl)-N,N-dimethyl-5-oxo-5,6,7,8-tetrahydro-2,6-naphthyridine-1-carboxamide (5.00 g) in DMF (50 mL) was added magnesium methylate (14.3 mL of a 6-10% methanol solution), and the reaction was heated to 50° C. for 1 hour. The reaction was treated with iodomethane (17.66 mL) and allowed to stir at 50 degrees for 1.5 hours. The reaction was quenched with 15 mL 10% aq $KHSO_4$ and concentrated in vacuo to remove the methanol. The mixture was diluted with 300 mL chloroform and the phases were separated. The aqueous layer was washed twice more with chloroform. The combined organic layers were washed with brine, dried over sodium sulfate and concentrated in vacuo. The remaining solid was purified on an Isco automated system affixed with a Biotage Flash 40 (L) (120 g) cartridge eluted with 0-10% MeOH in EtOAc over 20 minutes and hold at 10% MeOH for 45 minutes. The product eluted last, pure by HPLC/MS and NMR.

LRMS (M+1)=400.3

Step 9

4-hydroxy-N,N,2-trimethyl-3,5-dioxo-2,3,5,6,7,8-hexahydro-2,6-naphthyridine-1-carboxamide In a 50 mL heavy walled glass pressure flask 4-methoxy-6-(4-methoxybenzyl)-N,N,2-trimethyl-3,5-dioxo-2,3,5,6,7,8-hexahydro-2,6-naphthyridine-1-carboxamide (3.9 g) and 15 ml of (commercial) 33% HBr in HOAc were mixed. The flask was sealed, heated to 75° C. and allowed to stir overnight. The solvent was removed in vacuo. The remaining oil was dissolved in $CH_3CN$ and purified by reverse phase on a Biotage KPCM 250 compression module containing a 10 cm×60 cm Kiloprep cartridge. The product elutes at 13% $CH_3CN$ in water containing 0.1% TFA.

LRMS (M+1)=266.2.

Step 10

6-(3-chloro-4-fluorobenzyl)-4-hydroxy-N,N,2-trimethyl-3,5-dioxo-2,3,5,6,7,8-hexahydro-2,6-naphthyridine-1-carboxamide 4-Hydroxy-N,N,2-trimethyl-3,5-dioxo-2,3,5,6,7,8-hexahydro-2,6-naphthyridine-1-carboxamide (0.43 g, 0.0016 mol) was dissolved in 10 mL dry DMF and 100 mg NaH was added. The mixture was allowed to stir until the bubbles ceased, then 3-chloro-4-fluoro benzyl bromide (0.362 g, 0.0016 mole) was added. The reaction was quenched with 30 mL of a 10% aq KHSO₄ solution and diluted with 100 mL chloroform. The reaction was further diluted with 100 mL brine and allowed to stir vigorously for 30 minutes. The layers were separated and the aqueous layer was washed with chloroform. The organic fractions were combined and dried over NaSO₄, filtered and concentrated under high vacuum to remove the DMF (yield 0.5 g, 75%). HPLC analysis showed 85% purity. The solid product was crystallized first from isopropanol, then from ethanol.

$^1$H NMR (400 MHz, CDCl$_3$) δ 2.49-2.57 (m, 1H), 2.67-2.74 (m, 1H), 2.9 (s, 3H), 3.1 (s, 3H), 3.34-3.46 (m, 1H), 3.47 (s, 1H), 3.48-3.53 (m, 1H), 4.48-4.52 (d, J=15, 1H), 4.79-4.83 (d, J=15, 1H), 7.11-7.21 (m, 2H), 7.34-7.36 (m, 2H), 12.94 (s, 1H).

LRMS (M+1) 408.2.

The compounds in the following table were prepared in accordance with the procedure set forth in Example 20, using the appropriate benzyl bromide in place of 3-chloro-4-fluorobenzyl bromide.

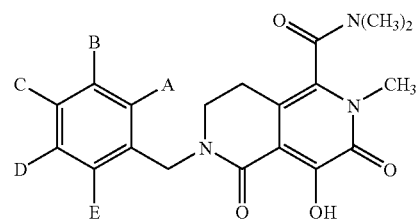

| Example | A | B | C | D | E | Name | ES MS (M + 1) |
|---|---|---|---|---|---|---|---|
| 21-1 | H | CF₃ | H | H | H | 4-hydroxy-N,N,2-trimethyl-3,5-dioxo-6-[3-(trifluoromethyl)benzyl]-2,3,5,6,7,8-hexahydro-2,6-naphthyridine-1-carboxamide | 424.1 |
| 21-2 | H | CF₃ | F | H | H | 4-hydroxy-N,N,2-trimethyl-3,5-dioxo-6-[4-fluoro-3-(trifluoromethyl)benzyl]-2,3,5,6,7,8-hexahydro-2,6-naphthyridine-1-carboxamide | 442.1 |
| 21-3 | A + B together form methylenedioxy | | | H | H | 6-(1,3-benzodioxol-4-ylmethyl)-4-hydroxy-N,N,2-trimethyl-3,5-dioxo-2,3,5,6,7,8-hexahydro-2,6-naphthyridine-1-carboxamide | 400.2 |
| 21-4 | H | B + C together form methylenedioxy | | H | H | 6-(1,3-benzodioxol-5-ylmethyl)-4-hydroxy-N,N,2-trimethyl-3,5-dioxo-2,3,5,6,7,8-hexahydro-2,6-naphthyridine-1-carboxamide | 400.2 |
| 21-5 | OCH₃ | H | H | H | H | 4-hydroxy-6-(2-methoxybenzyl)-N,N,2-trimethyl-3,5-dioxo-2,3,5,6,7,8-hexahydro-2,6-naphthyridine-1-carboxamide | 386.2 |
| 21-6 | H | OCH₃ | H | H | H | 4-hydroxy-6-(3-methoxybenzyl)-N,N,2-trimethyl-3,5-dioxo-2,3,5,6,7,8-hexahydro-2,6-naphthyridine-1-carboxamide | 386.2 |
| 21-7 | H | CH₃ | H | H | H | 4-hydroxy-6-(3-methylbenzyl)-N,N,2-trimethyl-3,5-dioxo-2,3,5,6,7,8-hexahydro-2,6-naphthyridine-1-carboxamide | 370.2 |
| 21-8 | H | CH₃ | CH₃ | H | H | 6-(3,4-dimethylbenzyl)-4-hydroxy-N,N,2-trimethyl-3,5-dioxo-2,3,5,6,7,8-hexahydro-2,6-naphthyridine-1-carboxamide | 384.2 |
| 21-9 | Cl | Cl | H | H | H | 6-(2,3-dichlorobenzyl)-4-hydroxy-N,N,2-trimethyl-3,5-dioxo-2,3,5,6,7,8-hexahydro- | 424.1 |

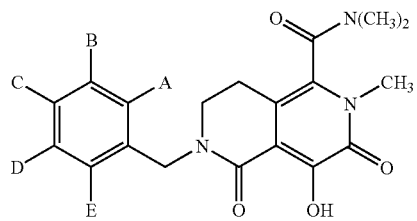

| Example | A | B | C | D | E | Name | ES MS (M + 1) |
|---|---|---|---|---|---|---|---|
| 21-10 | F | H | F | H | H | 6-(2,4-difluorobenzyl)-4-hydroxy-N,N,2-trimethyl-3,5-dioxo-2,3,5,6,7,8-hexahydro-2,6-naphthyridine-1-carboxamide | 392.1 |
| 21-11 | H | OCF$_3$ | H | H | H | 4-hydroxy-N,N,2-trimethyl-3,5-dioxo-6-[3-(trifluoromethoxy)benzyl]-2,3,5,6,7,8-hexahydro-2,6-naphthyridine-1-carboxamide | 440.1 |
| 21-12 | H | F | H | H | H | 6-(3-fluorobenzyl)-4-hydroxy-N,N,2-trimethyl-3,5-dioxo-2,3,5,6,7,8-hexahydro-2,6-naphthyridine-1-carboxamide | 374.2 |
| 21-13 | H | CH$_3$ | F | H | H | 6-(4-fluoro-3-methylbenzyl)-4-hydroxy-N,N,2-trimethyl-3,5-dioxo-2,3,5,6,7,8-hexahydro-2,6-naphthyridine-1-carboxamide | 388.2 |
| 21-14 | Br | Cl | F | H | H | 6-(2-bromo-3-chloro-4-fluorobenzyl)-4-hydroxy-N,N,2-trimethyl-3,5-dioxo-2,3,5,6,7,8-hexahydro-2,6-naphthyridine-1-carboxamide | 485.8 |
| 21-16 | CH$_3$ | H | H | H | H | 4-hydroxy-6-(2-methylbenzyl)-N,N,2-trimethyl-3,5-dioxo-2,3,5,6,7,8-hexahydro-2,6-naphthyridine-1-carboxamide | 370.2 |
| 21-17 | F | H | H | H | H | 6-(2-fluorobenzyl)-4-hydroxy-N,N,2-trimethyl-3,5-dioxo-2,3,5,6,7,8-hexahydro-2,6-naphthyridine-1-carboxamide | 374.2 |
| 21-18 | H | H | CH$_3$ | H | H | 4-hydroxy-6-(4-methylbenzyl)-N,N,2-trimethyl-3,5-dioxo-2,3,5,6,7,8-hexahydro-2,6-naphthyridine-1-carboxamide | 370.2 |
| 21-19 | H | H | Cl | H | H | 6-(4-chlorobenzyl)-4-hydroxy-N,N,2-trimethyl-3,5-dioxo-2,3,5,6,7,8-hexahydro-2,6-naphthyridine-1-carboxamide | 390.1 |
| 21-20 | H | H | OCH$_3$ | H | H | 4-hydroxy-6-(4-methoxybenzyl)-N,N,2-trimethyl-3,5-dioxo-2,3,5,6,7,8-hexahydro-2,6-naphthyridine-1-carboxamide | 386.2 |
| 21-21 | H | Cl | H | Cl | H | 6-(3,5-dichlorobenzyl)-4-hydroxy-N,N,2-trimethyl-3,5-dioxo-2,3,5,6,7,8-hexahydro-2,6-naphthyridine-1-carboxamide | 424.1 |
| 21-22 | H | Cl | Cl | H | H | 6-(3,4-dichlorobenzyl)-4-hydroxy-N,N,2-trimethyl-3,5-dioxo-2,3,5,6,7,8-hexahydro-2,6-naphthyridine-1-carboxamide | 424.1 |
| 21-23 | H | F | H | F | H | 6-(3,5-difluorobenzyl)-4-hydroxy-N,N,2-trimethyl-3,5-dioxo-2,3,5,6,7,8-hexahydro-2,6-naphthyridine-1-carboxamide | 392.1 |

-continued

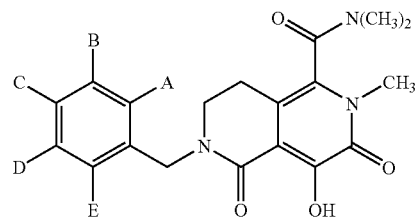

| Example | A | B | C | D | E | Name | ES MS (M + 1) |
|---|---|---|---|---|---|---|---|
| 21-24 | H | OCH₃ | H | OCH₃ | H | 6-(3,5-dimethoxybenzyl)-4-hydroxy-N,N,2-trimethyl-3,5-dioxo-2,3,5,6,7,8-hexahydro-2,6-naphthyridine-1-carboxamide | 416.2 |
| 21-25 | H | Cl | CH₃ | H | H | 6-(3-chloro-4-methylbenzyl)-4-hydroxy-N,N,2-trimethyl-3,5-dioxo-2,3,5,6,7,8-hexahydro-2,6-naphthyridine-1-carboxamide | 404.1 |
| 21-26 | H | F | CH₃ | H | H | 6-(3-fluoro-4-methylbenzyl)-4-hydroxy-N,N,2-trimethyl-3,5-dioxo-2,3,5,6,7,8-hexahydro-2,6-naphthyridine-1-carboxamide | 388.2 |
| 21-27 | F | H | H | F | H | 6-(2,5-difluorobenzyl)-4-hydroxy-N,N,2-trimethyl-3,5-dioxo-2,3,5,6,7,8-hexahydro-2,6-naphthyridine-1-carboxamide | 392.1 |
| 21-28 | F | Cl | H | H | H | 6-(3-chloro-2-fluorobenzyl)-4-hydroxy-N,N,2-trimethyl-3,5-dioxo-2,3,5,6,7,8-hexahydro-2,6-naphthyridine-1-carboxamide | 408.1 |
| 21-29 | F | H | Cl | H | H | 6-(4-chloro-2-fluorobenzyl)-4-hydroxy-N,N,2-trimethyl-3,5-dioxo-2,3,5,6,7,8-hexahydro-2,6-naphthyridine-1-carboxamide | 408.1 |
| 21-30 | F | H | H | Cl | H | 6-(5-chloro-2-fluorobenzyl)-4-hydroxy-N,N,2-trimethyl-3,5-dioxo-2,3,5,6,7,8-hexahydro-2,6-naphthyridine-1-carboxamide | 408.1 |
| 21-31 | F | CH₃ | H | H | H | 6-(2-fluoro-3-methylbenzyl)-4-hydroxy-N,N,2-trimethyl-3,5-dioxo-2,3,5,6,7,8-hexahydro-2,6-naphthyridine-1-carboxamide | 388.2 |
| 21-32 | CH₃ | H | H | F | H | 6-(5-fluoro-2-methylbenzyl)-4-hydroxy-N,N,2-trimethyl-3,5-dioxo-2,3,5,6,7,8-hexahydro-2,6-naphthyridine-1-carboxamide | 388.2 |
| 21-33 | H | CH₃ | H | CH₃ | H | 6-(3,5-dimethylbenzyl)-4-hydroxy-N,N,2-trimethyl-3,5-dioxo-2,3,5,6,7,8-hexahydro-2,6-naphthyridine-1-carboxamide | 384.3 |
| 21-34 | H | H | OH | H | H | 4-hydroxy-6-(4-hydroxybenzyl)-N,N,2-trimethyl-3,5-dioxo-2,3,5,6,7,8-hexahydro-2,6-naphthyridine-1-carboxamide | 372.2 |
| 21-35 | H | B + C together form ethylenedioxy | | H | H | 6-(2,3-dihydro-1,4-benzodioxin-6-ylmethyl)-4-hydroxy-N,N,2-trimethyl-3,5-dioxo-2,3,5,6,7,8-hexahydro-2,6-naphthyridine-1-carboxamide | 414.2 |
| 21-36 | H | OCH₃ | F | H | H | 6-(4-fluoro-3-methoxybenzyl)-4-hydroxy-N,N,2-trimethyl-3,5-dioxo-2,3,5,6,7,8- | 404.2 |

-continued

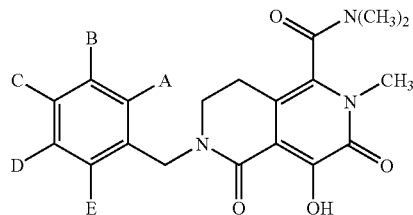

| Example | A | B | C | D | E | Name | ES MS (M + 1) |
|---|---|---|---|---|---|---|---|
| 21-37 | H | Cl | OCH$_3$ | H | H | 6-(3-chloro-4-methoxybenzyl)-4-hydroxy-N,N,2-trimethyl-3,5-dioxo-2,3,5,6,7,8-hexahydro-2,6-naphthyridine-1-carboxamide | 420.1 |
| 21-38 | H | CH$_3$ | Cl | H | H | 6-(4-chloro-3-methylbenzyl)-4-hydroxy-N,N,2-trimethyl-3,5-dioxo-2,3,5,6,7,8-hexahydro-2,6-naphthyridine-1-carboxamide | 404.1 |
| 21-39 | H | F | F | H | H | 6-(3,4-difluorobenzyl)-4-hydroxy-N,N,2-trimethyl-3,5-dioxo-2,3,5,6,7,8-hexahydro-2,6-naphthyridine-1-carboxamide | 392.4 |
| 21-40 | Cl | H | F | H | H | 6-(2-chloro-4-fluorobenzyl)-4-hydroxy-N,N,2-trimethyl-3,5-dioxo-2,3,5,6,7,8-hexahydro-2,6-naphthyridine-1-carboxamide | 408.0 |
| 21-41 | H | Cl | H | H | H | 6-(3-chlorobenzyl)-4-hydroxy-N,N,2-trimethyl-3,5-dioxo-2,3,5,6,7,8-hexahydro-2,6-naphthyridine-1-carboxamide | 390.0 |

EXAMPLE 22

8-hydroxy-2-(4-methoxybenzyl)-6-methyl-5-(pyrrolidin-1-ylcarbonyl)-2,3,4,6-tetrahydro-2,6-naphthyridine-1,7-dione

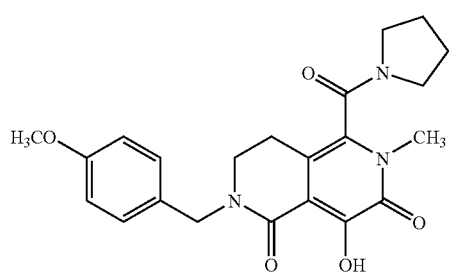

The title compound was prepared using a procedure similar to that set forth above in Example 20, Steps 1 to 4, except that the N-oxidation, rearrangement and alkyation steps were done before the amide was formed, and wherein pyrrolidine was employed instead of dimethylamine. LCMS (M+1) =412.2

EXAMPLE 23

4-hydroxy-6-(4-methoxybenzyl)-N,2-dimethyl-3,5-dioxo-2,3,5,6,7,8-hexahydro-2,6-naphthyridine-1-carboxamide

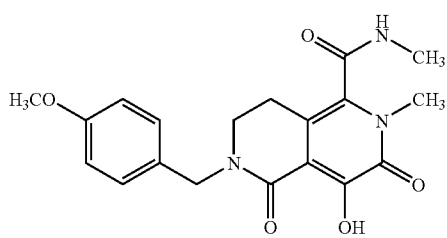

The title compound was prepared was prepared in a manner similar to that described for Example 22, wherein methylamine was employed in place of pyrrolidine. LCMS (M+1) =372.2

EXAMPLE 24

Methyl 6-(1,3-benzodioxol-5-ylmethyl)-4-hydroxy-2-methyl-3,5-dioxo-2,3,5,6,7,8-hexahydro-2,6-naphthyridine-1-carboxylate

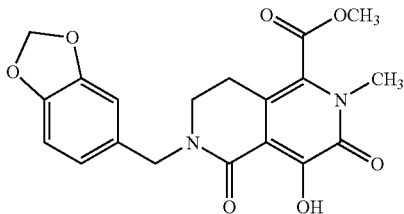

The title compound was prepared from methyl 4-hydroxy-6-(4-methoxybenzyl)-2-methyl-3,5-dioxo-2,3,5,6,7,8-hexahydro-2,6-naphthyridine-1-carboxylate, which was prepared in a manner similar to that described for Example 20, step 8, except that under longer reaction time the O-methyl group is lost. This intermediate was treated as described for Example 20, steps 9 and 10 to give the title compound. LCMS (M+1)=387.1

EXAMPLE 25

6-(3-Chloro-4-fluorobenzyl)-4-hydroxy-N,N-dimethyl-2-(4-methylphenyl)-3,5-dioxo-2,3,5,6,7,8-hexahydro-2,6-naphthyridine-1-carboxamide

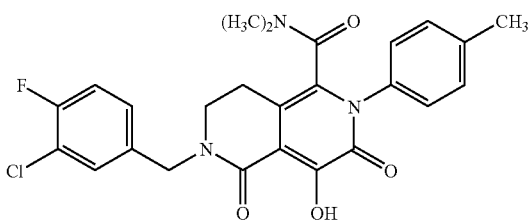

Step 1

Ethyl 6-(3-chloro-4-fluorobenzyl)-4-methoxy-5-oxo-5,6,7,8-hexahydro-2,6-naphthyridine-1-carboxylate A mixture of ethyl 6-(3-chloro-4-fluorobenzyl)-4-hydroxy-5-oxo-5,6,7,8-hexahydro-2,6-naphthyridine-1-carboxylate (1.00 g, 2.64 mmol; Example 12, step 6), cesium carbonate (1.12 g, 3.43 mmol), methyl iodide (0.41 g, 2.90 mmol) in DMF (30 mL) was stirred at room temperature overnight. The reaction mixture was filtered and the filtrate concentrated under vacuum. The residue was partitioned between ethyl acetate and brine. The organic extract was dried over anhydrous sodium sulfate, filtered and concentrated under vacuum to provide the titled ester.

$^1$H NMR (400 MHz, CDCl$_3$) δ 8.48 (s, 1H), 7.41 (dd, J=6.9, 2.2 Hz, 1H), 7.21-7.26 (m, 1H), 7.11 (t, J=8.6 Hz, 1H), 4.70 (s, 2H), 4.43 (q, J=7.2 Hz, 2H), 4.12 (s, 3H), 3.46 (t, J=6.4 Hz, 2H), 3.32 (t, J=6.4 Hz, 2H), 1.43 (t, J=7.1 Hz, 3H). (ES MS M+1=393.01)

Step 2

6-(3-Chloro-4-fluorobenzyl)-4-methoxy-N,N-dimethyl-3,5-dioxo-2,3,5,6,7,8-hexahydro-2,6-naphthyridine-1-carboxamide In a manner similar to that described for 6-(3-chloro-4-fluorobenzyl)-4-hydroxy-N,N-dimethyl-3,5-dioxo-2,3,5,6,7,8-hexahydro-2,6-naphthyridine-1-carboxamide (Example 13, steps 1 to 5), the title compound was prepared.

$^1$H NMR (400 MHz, CDCl$_{3.1}$) 7.38 (dd, J=6.9, 2.0 Hz, 1H), 7.19-7.24 (m, 1H), 7.11 (t, J=8.6 Hz, 1H), 4.67 (s, 2H), 4.11 (s, 3H), 3.38-3.44 (m, 3H), 3.06 (br s, 3H), 2.96 (br s, 3H), 2.58 (t, J=6.0 Hz, 2H).
(ES MS M+1=408.05)

Step 3

6-(3-Chloro-4-fluorobenzyl)-4-methoxy-N,N-dimethyl-2-(4-methyl-phenyl)-3,5-dioxo-2,3,5,6,7,8-hexahydro-2,6-naphthyridine-1-carboxamide A mixture of 6-(3-chloro-4-fluorobenzyl)-4-methoxy-N,N-dimethyl-3,5-dioxo-2,3,5,6,7,8-hexahydro-2,6-naphthyridine-1-carboxamide (0.10 g, 0.25 mmol), p-tolylboronic acid (0.13 g, 0.98 mmol), copper (II) acetate (67 mg, 0.37 mmol), activated molecular sieves type 4A (1 g), and pyridine (40 mg, 0.50 mmol) in dichloromethane (12 mL) was stirred at room temperature overnight. The reaction mixture was treated with a mixture of aqueous NH$_4$OH (1 mL, 1M) and methanol (3 mL). After stirring at room temperature for 15 minutes, the slurry was filtered, and the filtrate concentrated under vacuum. The residue was subjected to column chromatography on silica gel eluting with a gradient of 0 to 15% of methanol in chloroform. Collection and concentration of appropriate fractions provided the title compound.

$^1$HNMR (400 MHz, CDCl$_3$) δ 7.40 (dd, J=6.9, 2.0 Hz, 1H), 7.20-7.30 (m, 4H), 7.06-7.14 (m, 2H), 4.86 (d, J=14.8 Hz, 1H), 4.52 (d, J=14.8 Hz, 1H), 4.14 (s, 3H), 3.48-3.55 (m, 1H), 3.31-3.39 (m, 1H), 2.81 (s, 3H), 2.66 (s, 3H), 2.61-2.69 (m, 1H), 2.38-2.47 (m, 1H), 2.38 (s, 3H). (ES MS M+1=498.03)

Step 4

6-(3-Chloro-4-fluorobenzyl)-4-hydroxy-N,N-dimethyl-2-(4-methyl-phenyl)-3,5-dioxo-2,3,5,6,7,8-hexahydro-2,6-naphthyridine-1-carboxamide A solution of 6-(3-chloro-4-fluorobenzyl)-4-methoxy-N,N-dimethyl-2-(4-methyl-phenyl)-3,5-dioxo-2,3,5,6,7,8-hexahydro-2,6-naphthyridine-1-carboxamide (0.054 g, 0.108 mmol) in anhydrous dichloromethane (10 mL) was treated with a solution of boron tribromide (0.3 mL, 1M) in dichloromethane. The reaction mixture was stirred at room temperature for 3 hours. The product mixture was concentrated under vacuum, and the residue subject to preparative reverse phase HPLC purification. Collection and lyophilization of appropriate fractions provide the titled compound.

$^1$HNMR (400 MHz, DMSO-d$_6$) δ 13.20 (br s, 1H), 7.60 (dd, J=6.9, 1.8 Hz, 1H), 7.37-7.45 (m, 2H), 7.04-7.28 (m, 4H), 4.81 (d, J=14.9 Hz, 1H), 4.62 (d, J=14.9 Hz, 1H), 3.48-3.60 (m, 2H), 2.83 (s, 3H), 2.55-2.59 (m, 2H), 2.54 (s, 3H), 2.34 (s, 3H). (ES MS M+1=483.99)

The compounds in the following table were prepared in accordance with the procedure set forth in Example 25, using the appropriate boronic acid in place of p-tolylboronic acid.

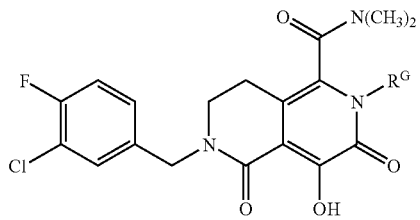

| Example | R^G | Name | ES MS (M + 1) |
|---|---|---|---|
| 26 | phenyl | 6-(3-chloro-4-fluorobenzyl)-4-hydroxy-N,N-dimethyl-2-phenyl-3,5-dioxo-2,3,5,6,7,8-hexahydro-2,6-naphthyridine-1-carboxamide | 470 |
| 27 | 3-thienyl | 6-(3-chloro-4-fluorobenzyl)-4-hydroxy-N,N-dimethyl-2-(3-thienyl)-3,5-dioxo-2,3,5,6,7,8-hexahydro-2,6-naphthyridine-1-carboxamide | 476 |
| 28 | pyridin-3-yl | 6-(3-chloro-4-fluorobenzyl)-4-hydroxy-N,N-dimethyl-2-pyridin-3-yl-3,5-dioxo-2,3,5,6,7,8-hexahydro-2,6-naphthyridine-1-carboxamide | 471 |
| 29 | 4-CO₂CH₃-phenyl | 6-(3-chloro-4-fluorobenzyl)-4-hydroxy-N,N-dimethyl-2-{4-[methoxycarbonyl]-phenyl}-3,5-dioxo-2,3,5,6,7,8-hexahydro-2,6-naphthyridine-1-carboxamide | 528 |
| 30 | 4-C(O)NH₂-phenyl | 6-(3-chloro-4-fluorobenzyl)-4-hydroxy-N,N-dimethyl-2-[4-(amino)carbonyl-phenyl]-3,5-dioxo-2,3,5,6,7,8-hexahydro-2,6-naphthyridine-1-carboxamide | 513 |
| 31 | 4-C(O)N(H)CH₃-phenyl | 6-(3-chloro-4-fluorobenzyl)-4-hydroxy-N,N-dimethyl-2-{4-[(methylamino)carbonyl]-phenyl}-3,5-dioxo-2,3,5,6,7,8-hexahydro-2,6-naphthyridine-1-carboxamide | 527 |
| 32 | 4-C(O)N(H)CH₂CH₃-phenyl | 6-(3-chloro-4-fluorobenzyl)-4-hydroxy-N,N-dimethyl-2-{4-[(ethylamino)carbonyl]-phenyl}-3,5-dioxo-2,3,5,6,7,8-hexahydro-2,6-naphthyridine-1-carboxamide | 541 |
| 33 | 4-C(O)N(H)CH(CH₃)₂-phenyl | 6-(3-chloro-4-fluorobenzyl)-4-hydroxy-N,N-dimethyl-2-{4-[(isopropylamino)carbonyl]-phenyl}-3,5-dioxo-2,3,5,6,7,8-hexahydro-2,6-naphthyridine-1-carboxamide | 555 |
| 34 | 4-C(O)N(CH₃)₂-phenyl | 6-(3-chloro-4-fluorobenzyl)-4-hydroxy-N,N-dimethyl-2-{4-[(dimethylamino)carbonyl]-phenyl}-3,5-dioxo-2,3,5,6,7,8-hexahydro-2,6-naphthyridine-1-carboxamide | 541 |
| 35 | 4-C(O)N(CH₂CH₃)₂-phenyl | 6-(3-chloro-4-fluorobenzyl)-4-hydroxy-N,N-dimethyl-2-{4-[(diethylamino)carbonyl]-phenyl}-3,5-dioxo-2,3,5,6,7,8-hexahydro-2,6-naphthyridine-1-carboxamide | 569 |
| 36 | 3-C(O)N(CH₃)₂-phenyl | 6-(3-chloro-4-fluorobenzyl)-4-hydroxy-N,N-dimethyl-2-{3-[(dimethylamino)carbonyl]-phenyl}-3,5-dioxo-2,3,5,6,7,8-hexahydro-2,6-naphthyridine-1-carboxamide | 541 |

-continued

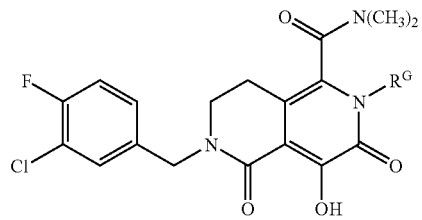

| Example | R^G | Name | ES MS (M + 1) |
|---|---|---|---|
| 37 | 4-NO2-phenyl | 6-(3-chloro-4-fluorobenzyl)-4-hydroxy-N,N-dimethyl-2-(4-nitrophenyl)-3,5-dioxo-2,3,5,6,7,8-hexahydro-2,6-naphthyridine-1-carboxamide | 515 |
| 38 | 4-NHC(O)CH3-phenyl | 6-(3-chloro-4-fluorobenzyl)-4-hydroxy-N,N-dimethyl-2-[4-(acetylamino)phenyl]-3,5-dioxo-2,3,5,6,7,8-hexahydro-2,6-naphthyridine-1-carboxamide | 527 |
| 39 | 4-N(CH3)C(O)CH3-phenyl | 6-(3-chloro-4-fluorobenzyl)-4-hydroxy-N,N-dimethyl-2-[4-(acetylmethylamino)phenyl]-3,5-dioxo-2,3,5,6,7,8-hexahydro-2,6-naphthyridine-1-carboxamide | 541 |
| 40 | 4-N(CH3)C(O)CF3-phenyl | 6-(3-chloro-4-fluorobenzyl)-4-hydroxy-N,N-dimethyl-2-[4-methyl(trifluoroacetyl)-aminophenyl]-3,5-dioxo-2,3,5,6,7,8-hexahydro-2,6-naphthyridine-1-carboxamide | 595 |
| 41 | 4-N(CH3)C(O)N(H)CH3-phenyl | 6-(3-chloro-4-fluorobenzyl)-4-hydroxy-N,N-dimethyl-2-{4-[(methylaminocarbonyl)-methylamino]phenyl}-3,5-dioxo-2,3,5,6,7,8-hexahydro-2,6-naphthyridine-1-carboxamide | 556 |
| 42 | 4-N(CH3)C(O)N(CH3)2-phenyl | 6-(3-chloro-4-fluorobenzyl)-4-hydroxy-N,N-dimethyl-2-{4-[(dimethylaminocarbonyl)-methylamino]phenyl}-3,5-dioxo-2,3,5,6,7,8-hexahydro-2,6-naphthyridine-1-carboxamide | 570 |
| 43 | 4-NHCO2CH3-phenyl | 6-(3-chloro-4-fluorobenzyl)-4-hydroxy-N,N-dimethyl-2-{4-[(methoxycarbonyl)-amino]phenyl}-3,5-dioxo-2,3,5,6,7,8-hexahydro-2,6-naphthyridine-1-carboxamide | 543 |
| 44 | 4-N(CH3)CO2CH3-phenyl | 6-(3-chloro-4-fluorobenzyl)-4-hydroxy-N,N-dimethyl-2-{4-[(methoxycarbonyl)methyl-amino]phenyl}-3,5-dioxo-2,3,5,6,7,8-hexahydro-2,6-naphthyridine-1-carboxamide | 557 |
| 45 | 4-NHSO2CH3-phenyl | 6-(3-chloro-4-fluorobenzyl)-4-hydroxy-N,N-dimethyl-2-{4-[(methylsulfonyl)-amino]phenyl}-3,5-dioxo-2,3,5,6,7,8-hexahydro-2,6-naphthyridine-1-carboxamide | 563 |
| 46 | 4-N(CH3)SO2CH3-phenyl | 6-(3-chloro-4-fluorobenzyl)-4-hydroxy-N,N-dimethyl-2-{4-[methyl(methyl-sulfonyl)amino]phenyl}-3,5-dioxo-2,3,5,6,7,8-hexahydro-2,6-naphthyridine-1-carboxamide | 577 |
| 47 | 4-SO2NH2-phenyl | 6-(3-chloro-4-fluorobenzyl)-4-hydroxy-N,N-dimethyl-2-[4-(aminosulfonyl)phenyl]-3,5-dioxo-2,3,5,6,7,8-hexahydro-2,6-naphthyridine-1-carboxamide | 549 |

-continued

| Example | R$^G$ | Name | ES MS (M + 1) |
|---|---|---|---|
| 48 | 4-(SO$_2$NHCH$_3$)phenyl | 6-(3-chloro-4-fluorobenzyl)-4-hydroxy-N,N-dimethyl-2-[4-(methylaminosulfonyl)-phenyl]-3,5-dioxo-2,3,5,6,7,8-hexahydro-2,6-naphthyridine-1-carboxamide | 563 |
| 49 | 4-(morpholin-4-ylsulfonyl)phenyl | 6-(3-chloro-4-fluorobenzyl)-4-hydroxy-N,N-dimethyl-2-[4-(morpholin-4-ylsulfonyl)-phenyl]-3,5-dioxo-2,3,5,6,7,8-hexahydro-2,6-naphthyridine-1-carboxamide | 619 |
| 50 | 4-(SO$_2$CH$_3$)phenyl | 6-(3-chloro-4-fluorobenzyl)-4-hydroxy-N,N-dimethyl-2-[4-(methylsulfonyl)-phenyl]-3,5-dioxo-2,3,5,6,7,8-hexahydro-2,6-naphthyridine-1-carboxamide | 548 |
| 51 | 3-cyanophenyl | 6-(3-chloro-4-fluorobenzyl)-4-hydroxy-N,N-dimethyl-2-(3-cyanophenyl)-3,5-dioxo-2,3,5,6,7,8-hexahydro-2,6-naphthyridine-1-carboxamide | 495 |
| 52 | 4-cyanophenyl | 6-(3-chloro-4-fluorobenzyl)-4-hydroxy-N,N-dimethyl-2-(4-cyanophenyl)-3,5-dioxo-2,3,5,6,7,8-hexahydro-2,6-naphthyridine-1-carboxamide | 495 |
| 53 | 4-C(O)CH$_3$ phenyl | 6-(3-chloro-4-fluorobenzyl)-4-hydroxy-N,N-dimethyl-2-(4-acetylphenyl)-3,5-dioxo-2,3,5,6,7,8-hexahydro-2,6-naphthyridine-1-carboxamide | 512 |

EXAMPLE 54

6-(3-Chloro-4-fluorobenzyl)-4-hydroxy-N,N-dimethyl-2-(cyanomethyl)-3,5-dioxo-2,3,5,6,7,8-hexahydro-2,6-naphthyridine-1-carboxamide

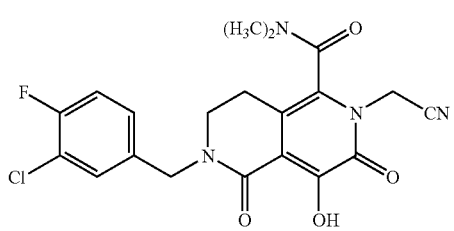

The title compound was prepared in a manner similar to that described for 6-(3-chloro-4-fluorobenzyl)-4-hydroxy-N,N-dimethyl-3,5-dioxo-2,3,5,6,7,8-hexahydro-2,6-naphthyridine-1-carboxamide (Example 13, step 6), wherein bromoacetonitrile was employed in place of 2-iodopropane.

$^1$H NMR (400 MHz, CD$_3$OD) δ 7.51 (dd, J=2.2, 6.9 Hz, 1H), 7.37-7.33 (m, 1H), 7.23 (t, J=9.0 Hz, 1H), 5.06 (d, J=17.6 Hz, 1H), 4.83 (d, J=17.6 Hz, 1H), 4.78 (d, J=15.0 Hz, 1H), 4.64 (d, J=15.0 Hz, 1H), 3.54 (t, J=6.4 Hz, 2H), 3.12 (s, 3H), 3.03 (s, 3H), 2.72-2.61 (m, 2H). (ES MS M+1=433)

The compounds in the following table were prepared in accordance with the procedure n Example 54, using the appropriate halide reagent in place of bromoacetonitrile.

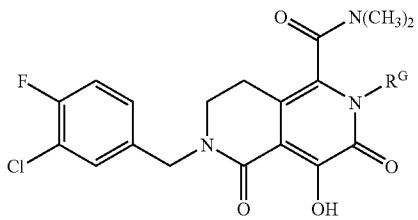

| Example | R<sup>G</sup> (halide reagent) | Name | ES MS (M + 1) |
|---|---|---|---|
| 55 | CH₃ / *—CN (2-bromopropionitrile) | 6-(3-chloro-4-fluorobenzyl)-4-hydroxy-N,N-dimethyl-2-(1-cyanoethyl)-3,5-dioxo-2,3,5,6,7,8-hexahydro-2,6-naphthyridine-1-carboxamide | 447 |
| 56 | *—CH₂—C(O)NH₂ (iodoacetamide) | 6-(3-chloro-4-fluorobenzyl)-4-hydroxy-N,N-dimethyl-2-(2-amino-2-oxoethyl)-3,5-dioxo-2,3,5,6,7,8-hexahydro-2,6-naphthyridine-1-carboxamide | 451 |
| 57 | CH₃ / *—C(O)NH₂ (2-bromoproprionamide) | 6-(3-chloro-4-fluorobenzyl)-4-hydroxy-N,N-dimethyl-2-(2-amino-1-methyl-2-oxoethyl)-3,5-dioxo-2,3,5,6,7,8-hexahydro-2,6-naphthyridine-1-carboxamide | 465 |
| 58 | *—CH₂—cyclopropyl (cyclopropylmethyl bromide) | 6-(3-chloro-4-fluorobenzyl)-4-hydroxy-N,N-dimethyl-2-(cyclopropylmethyl)-3,5-dioxo-2,3,5,6,7,8-hexahydro-2,6-naphthyridine-1-carboxamide | 448 |
| 59 | *—CH₂—cyclobutyl (cyclobutylmethyl bromide) | 6-(3-chloro-4-fluorobenzyl)-4-hydroxy-N,N-dimethyl-2-(cyclobutylmethyl)-3,5-dioxo-2,3,5,6,7,8-hexahydro-2,6-naphthyridine-1-carboxamide | 462 |
| 60 | *—CH₂—cyclohexyl (cyclohexylmethyl bromide) | 6-(3-chloro-4-fluorobenzyl)-4-hydroxy-N,N-dimethyl-2-(cyclohexylmethyl)-3,5-dioxo-2,3,5,6,7,8-hexahydro-2,6-naphthyridine-1-carboxamide | 490 |
| 61 | *—CH₂—CH₂OCH₃ (methoxyethyl bromide) | 6-(3-chloro-4-fluorobenzyl)-4-hydroxy-N,N-dimethyl-2-(2-methoxyethyl)-3,5-dioxo-2,3,5,6,7,8-hexahydro-2,6-naphthyridine-1-carboxamide | 452 |
| 62 | *—CH₂—CF₃ (2,2,2-trifluoroethyl iodide) | 6-(3-chloro-4-fluorobenzyl)-4-hydroxy-N,N-dimethyl-2-(2,2,2-trifluoroethyl)-3,5-dioxo-2,3,5,6,7,8-hexahydro-2,6-naphthyridine-1-carboxamide | 476 |
| 63 | *—CH₂—Ph (benzyl bromide) | 6-(3-chloro-4-fluorobenzyl)-4-hydroxy-N,N-dimethyl-2-benzyl-3,5-dioxo-2,3,5,6,7,8-hexahydro-2,6-naphthyridine-1-carboxamide | 484 |

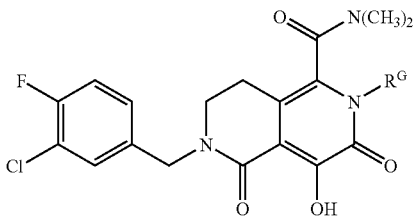

| Example | $R^G$ (halide reagent) | Name | ES MS (M + 1) |
|---|---|---|---|
| 64 | (4-fluorobenzyl bromide) | 6-(3-chloro-4-fluorobenzyl)-4-hydroxy-N,N-dimethyl-2-(4-fluorobenzyl)-3,5-dioxo-2,3,5,6,7,8-hexahydro-2,6-naphthyridine-1-carboxamide | 502 |
| 65 | (3-chloro-4-fluorobenzyl bromide) | 6-(3-chloro-4-fluorobenzyl)-4-hydroxy-N,N-dimethyl-2-(3-chloro-4-fluorobenzyl)-3,5-dioxo-2,3,5,6,7,8-hexahydro-2,6-naphthyridine-1-carboxamide | 536 |

EXAMPLE 66

6-(3-Chloro-4-fluorobenzyl)-4-hydroxy-N,N-dimethyl-2-(2-pyrrolidin-1-ylethyl)-3,5-dioxo-2,3,5,6,7,8-hexahydro-2,6-naphthyridine-1-carboxamide

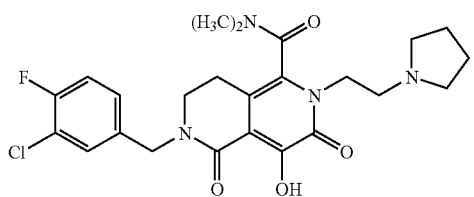

A mixture of 6-(3-chloro-4-fluorobenzyl)-3,4-dihydroxy-N,N-dimethyl-5-oxo-5,6,7,8-tetrahydro-2,6-naphthyridine-1-carboxamide (0.075 g, 0.19 mmol; Example 13, step 5) and magnesium methoxide in methanol (0.06 mL, 6-10% methanol solution available from Aldrich) in DMSO (2 mL) was heated at 60° C. for 30 minutes. Methanol was exhaustively removed under vacuum over 45 minutes. The residual DMSO solution was treated with 1-bromo-2-chloroethane (0.136 g, 0.95 mmol) and stirred at 60° C. under an atmosphere of nitrogen overnight. The product mixture was treated with pyrrolidine (0.27 g, 3.8 mmol) and sodium iodide (0.14 g, 0.95 mmol) and heated at 60° C. overnight. The reaction was partitioned between methylene chloride and aqueous sodium bisulfate. The organic extract was dried over anhydrous sodium sulfate, filtered, and concentrated under vacuum. The residue was subjected to preparative HPLC purification on C-18 reverse stationary phase column eluting with a gradient of water—acetonitrile in the presence of 0.1% trifluoroacetic acid. Collection and lyophilization of appropriate fractions provided the titled compound.

$^1$H NMR (400 MHz, CD$_3$OD) δ 7.50 (dd, J=1.9, 7.2 Hz, 1H), 7.32 (m, 1H), 7.22 (t, J=8.8 Hz, 1H), 4.80-4.70 (m), 4.52 (d, J=14.6 Hz, 1H), 3.97-3.67 (m), 3.54 (t, J=6.3 Hz, 2H), 3.13 (s, 3H), 3.01 (s, 3H), 2.65 (t, J=6.3 Hz, 2H), 2.2-2.0 (m). (ES MS exact mass M+1=491.1863)

EXAMPLE 67

6-(3-Chloro-4-fluorobenzyl)-4-hydroxy-N,N-dimethyl-2-(2-morpholin-4-ylethyl)-3,5-dioxo-2,3,5,6,7,8-hexahydro-2,6-naphthyridine-1-carboxamide

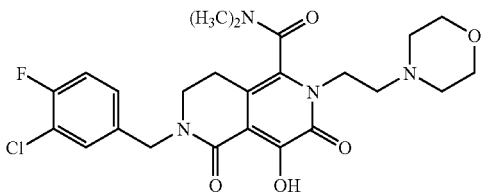

The title compound was prepared in a manner similar to that described for 6-(3-chloro-4-fluorobenzyl)-4-hydroxy-N,N-dimethyl-2-(2-pyrrolidin-1-ylethyl)-3,5-dioxo-2,3,5,6,7,8-hexahydro-2,6-naphthyridine-1-carboxamide (Example 66), substituting pyrrolidine with morpholine. (ES MS M+1=507)

EXAMPLE 68

6-(3-Chloro-4-fluorobenzyl)-4-hydroxy-N,N-dimethyl-2-(2-aminoethyl)-3,5-dioxo-2,3,5,6,7,8-hexahydro-2,6-naphthyridine-1-carboxamide

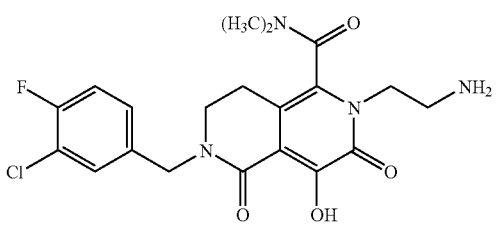

The title compound was prepared in a manner similar to that described for 6-(3-chloro-4-fluorobenzyl)-4-hydroxy-N,N-dimethyl-2-(2-pyrrolidin-1-ylethyl)-3,5-dioxo-2,3,5,6,7,8-hexahydro-2,6-naphthyridine-1-carboxamide (Example 66), substituting 1-bromo-2-chloroethane with 1-bromo-2-N-Boc-aminoethane. The alkylation product mixture was partitioned between chloroform and aqueous sodium bisulfite. The organic extract was washed with brine, dried over anhydrous sodium sulfate, filtered, and concentrated under vacuum. The residue was subjected to preparative HPLC purification on C-18 reverse stationary phase column eluting with a gradient of water—acetonitrile in the presence of 0.1% trifluoroacetic acid. Collection and lyophilization of appropriate fractions provided the N-Boc aminoethylated intermediate. A cold (0° C.) solution of the above N-Boc amino intermediate (36 mg, 0.07 mmol) in dioxane (2 mL) was treated with a solution of anhydrous HCl in dioxane (0.17 mL, 4M). The reaction mixture was stirred at 0° C. for 1 hour and concentrated under vacuum. The residue was triturated with anhydrous diethyl ether to provide the title compound as hydrogen chloride salt.

$^1$H NMR (400 MHz, CD$_3$OD) δ 7.50 (dd, J=1.9, 7.2 Hz, 1H), 7.32 (m, 1H), 7.24 (t, J=8.4 Hz, 1H), 4.90-4.80 (m), 4.68 (d, J=14.1 Hz, 1H), 3.6-2.5 (m), 3.31 (s, 6H). (ES MS exact mass M+1=437.1391)

EXAMPLE 69

6-(4-Fluorobenzyl)-4-hydroxy-N,N-dimethyl-2-isopropyl-3,5-dioxo-2,3,5,6,7,8-hexahydro-2,6-naphthyridine-1-carboxamide

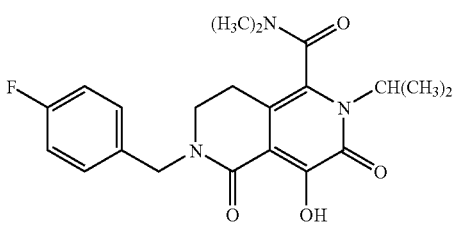

A mixture of 6-(3-chloro-4-fluorobenzyl)-4-hydroxy-N,N-dimethyl-2-isopropyl-3,5-dioxo-2,3,5,6,7,8-hexahydro-2,6-naphthyridine-1-carboxamide (95 mg, 0.22 mmol; Example 13) and 10% palladium on charcoal (0.11 g) in methanol (5 mL) was stirred under a balloon of hydrogen gas at room temperature overnight. The reaction mixture was filtered, and the filtrate concentrated under vacuum. The residue was subjected to preparative HPLC purification on C-18 reverse stationary phase column eluting with a gradient of water—acetonitrile in the presence of 0.1% trifluoroacetic acid. Collection and lyophilization of appropriate fractions provided the titled compound.

$^1$H NMR (400 MHz, CD$_3$OD) δ 7.37 (dd, J=5.5, 8.6 Hz, 2H), 7.08 (t, J=8.6 Hz, 2H), 4.77 (d, J=14.7 Hz, 1H), 4.66 (d, J=14.7 Hz, 1H), 4.03 (m, 1H), 3.48 (t, J=6.4 Hz, 2H), 3.09 (s, 3H), 3.00 (s, 3H), 2.57 (t, J=6.4 Hz, 2H), 1.64 (d, J=6.8 Hz, 3H), 1.57 (d, J=6.6 Hz, 3H). (ES MS exact mass M+1=402.1853)

EXAMPLE 70

6-(4-Fluorobenzyl)-4-hydroxy-N,N-dimethyl-2-isobutyl-3,5-dioxo-2,3,5,6,7,8-hexahydro-2,6-naphthyridine-1-carboxamide

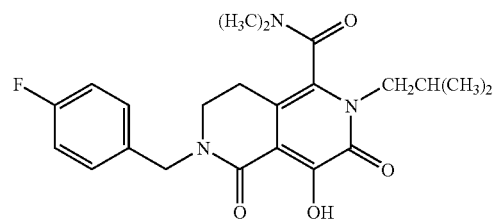

The title compound was prepared in a manner similar to that described for 6-(4-fluorobenzyl)-4-hydroxy-N,N-dimethyl-2-isopropyl-3,5-dioxo-2,3,5,6,7,8-hexahydro-2,6-naphthyridine-1-carboxamide (Example 69), using 6-(3-chloro-4-fluorobenzyl)-4-hydroxy-N,N-dimethyl-2-isobutyl-3,5-dioxo-2,3,5,6,7,8-hexahydro-2,6-naphthyridine-1-carboxamide (Example 14). (ES MS M+1=416)

EXAMPLE 71

6-(5-Chloro-4-fluoro-2-iodobenzyl)-4-hydroxy-N,N-dimethyl-2-isopropyl-3,5-dioxo-2,3,5,6,7,8-hexahydro-2,6-naphthyridine-1-carboxamide

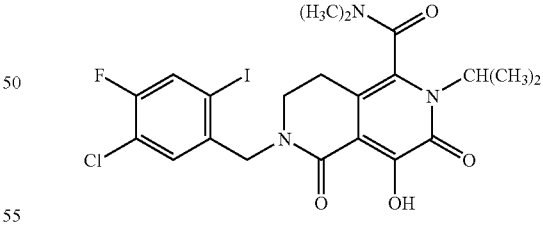

A mixture of 6-(3-chloro-4-fluorobenzyl)-4-hydroxy-N,N-dimethyl-2-isopropyl-3,5-dioxo-2,3,5,6,7,8-hexahydro-2,6-naphthyridine-1-carboxamide (43 mg, 0.10 mmol; Example 13) and N-iodosuccinamide (22 mg, 0.1 mmol) in trifluoromethanesulfonic acid at 0° C. was stirred for 10 minutes. The mixture was diluted with methanol and subjected to preparative HPLC purification on C-18 reverse stationary phase column eluting with a gradient of water—acetonitrile in the presence of 0.1% trifluoroacetic acid. Collection and lyophilization of appropriate fractions provided the titled compound.

¹H NMR (400 MHz, CD₃OD) δ 7.82 (d, J=8.4 Hz, 1H), 7.42 (d, J=7.3 Hz, 1H), 4.79 (d, J=15.6 Hz, 1H), 4.70 (d, J=15.6 Hz, 1H), 4.05 (m, 1H), 3.52 (t, J=6.4 Hz, 2H), 3.10 (s, 3H), 3.03 (s, 3H), 2.64 (t, J=6.4 Hz, 2H), 1.65 (d, J=6.8 Hz, 3H), 1.59 (d, J=6.6 Hz, 3H). (ES MS exact mass M+1=562.0383)

EXAMPLE 72

6-(5-Chloro-4-Fluoro-2-iodobenzyl)-4-hydroxy-N,N-dimethyl-2-isobutyl-3,5-dioxo-2,3,5,6,7,8-hexahydro-2,6-naphthyridine-1-carboxamide

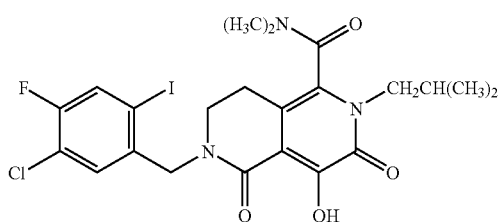

The title compound was prepared in a manner similar to that described for 6-(4-fluorobenzyl)-4-hydroxy-N,N-dimethyl-2-isopropyl-3,5-dioxo-2,3,5,6,7,8-hexahydro-2,6-naphthyridine-1-carboxamide (Example 71), using 6-(3-chloro-4-fluorobenzyl)-4-hydroxy-N,N-dimethyl-2-isobutyl-3,5-dioxo-2,3,5,6,7,8-hexahydro-2,6-naphthyridine-1-carboxamide (Example 14). (ES MS M+1=576)

EXAMPLE 73

N-[6-(3-Chloro-4-fluorobenzyl)-4-hydroxy-2-methyl-3,5-dioxo-2,3,5,6,7,8-hexahydro-2,6-naphthyridin-1-yl]-N-methylmethanesulfonamide

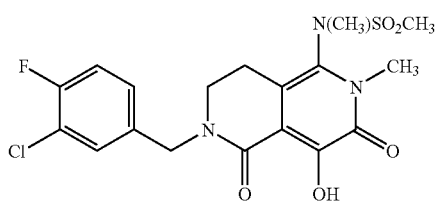

Step 1 tert-Butyl-[6-(3-chloro-4-fluorobenzyl)-4-methoxy-2-methyl-3,5-dioxo-2,3,5,6,7,8-hexahydro-2,6-naphthyridin-1-yl]carbamate A solution of ethyl 6-(3-chloro-4-fluorobenzyl)-4-methoxy-3,5-dioxo-2,3,5,6,7,8-hexahydro-2,6-naphthyridine-1-carboxylic acid (1.2 g, 3.04 mmol; Example 12, step 12), diisopropylethylamine (0.37 g, 3.65 mmol), and diphenylphosphoryl azide (1.00 g, 3.65 mmol) in a 1:1 mixture of dioxane and tert-butanol (30 mL) was heated in an oil bath 90° C. for 3 hours. The reaction mixture was concentrated under vacuum. The residue was subjected to column chromatography on silica gel eluting with 5% methanol in dichloromethane. Collection and concentration of appropriate fractions provided the titled compound.

¹HNMR (400 MHz, CDCl₃) δ 7.34 (dd, J=6.8, 2.0 Hz, 1H), 7.21-7.17 (m, 1H), 7.09 (t, J=8.8 Hz, 1H), 6.06 (br s, 1H), 4.64 (s, 2H), 4.06 (s, 3H), 3.53 (s, 3H), 3.34 (t, J=6.1 Hz, 2H), 2.55 (t, J=6.1 Hz, 2H), 1.45 (9H, s).

Step 2

N-[6-(3-Chloro-4-fluorobenzyl)-4-methoxy-2-methyl-3,5-dioxo-2,3,5,6,7,8-hexahydro-2,6-naphthyridin-1-yl]methanesulfonamide A mixture of tert-butyl-[6-(3-chloro-4-fluorobenzyl)-4-methoxy-2-methyl-3,5-dioxo-2,3,5,6,7,8-hexahydro-2,6-naphthyridin-1-yl]carbamate (0.49 g, 1.07 mol) and sodium hydride (54 mg, 1.34 mmol; 60% dispersion in oil) in anhydrous DMF (6 mL) was stirred at 0° C. for 30 minutes. Methanesulfonyl chloride (0.18 g, 1.61 mmol) was added, and the mixture was allowed to warm up slowly to room temperature. The reaction mixture was quenched with aqueous acid and diluted with dichloromethane. The organic extract was washed with brine, dried over anhydrous sodium sulfate, filtered, and concentrated under vacuum. The residue was subjected to column chromatograph on silica gel eluting with a mixture of 1% methanol in dichloromethane. Collection and concentration of appropriate fractions provided the intermediate tert-butyl-[6-(3-chloro-4-fluorobenzyl)-4-methoxy-2-methyl-3,5-dioxo-2,3,5,6,7,8-hexahydro-2,6-naphthyridin-1-yl](methylsulfonyl)carbamate (ES MS M+1=544). A solution of the above intermediate sulfonylcarbamate (281 mg, 0.52 mmol) and trifluoroacetic acid (5 mL) in anhydrous dichloromethane (5 mL) was stirred at room temperature for 10 minutes. The product mixture was concentrated under vacuum. The residue was partitioned between dichloromethane and aqueous acid. The organic extract was washed dried over anhydrous sodium sulfate, filtered, and concentrated under vacuum to provide the title compound. ES MS M+1=444

Step 3

N-[6-(3-Chloro-4-fluorobenzyl)-4-methoxy-2-methyl-3,5-dioxo-2,3,5,6,7,8-hexahydro-2,6-naphthyridin-1-yl]-N-methylmethane-sulfonamide A cold (0° C.) solution of N-[6-(3-chloro-4-fluorobenzyl)-4-methoxy-2-methyl-3,5-dioxo-2,3,5,6,7,8-hexahydro-2,6-naphthyridin-1-yl]methanesulfonamide (60 mg, 0.14 mmol) in anhydrous DMF (1 mL) was treated with sodium hydride (6.8 mg, 0.17 mmol; 60% dispersion in oil). The resultant mixture was stirred at the same temperature for 30 minutes, and treated with iodomethane (38 mg, 0.27 mmol). The reaction mixture was allowed to slowly warmed up to room temperature. The product mixture was concentrated under vacuum. The residue was partitioned between chloroform and brine. The organic extract was dried over anhydrous sodium sulfate, filtered, and concentrated under vacuum to provide the title compound. ES MS M+1=458

Step 4

N-[6-(3-Chloro-4-fluorobenzyl)-4-hydroxy-2-methyl-3,5-dioxo-2,3,5,6,7,8-hexahydro-2,6-naphthyridin-1-yl]-N-methylmethane-sulfonamide A solution of N-[6-(3-chloro-4-fluorobenzyl)-4-methoxy-2-methyl-3,5-dioxo-2,3,5,6,7,8-hexahydro-2,6-naphthyridin-1-yl]-N-methylmethane-sulfonamide (48 mg, 0.11 mmol) in 33% HBr in acetic acid (1 mL) was heated in an oil bath at 50° C. for 15 minutes. The product mixture was concentrated under vacuum, and the residue subject to preparative reverse phase HPLC purification. Collection and lyophilization of appropriate fractions afforded an oil. Trituration of the residual oil with diethyl ether provided the title compound as off white solid.

$^1$HNMR (400 MHz, CDCl$_3$) δ 7.36 (dd, J=1.8, 6.8 Hz, 1H), 7.20 (m, 1H), 7.14 (t, J=8.6 Hz, 1H), 4.68 (d, J=14.6 Hz, 1H), 4.63 (d, J=14.6 Hz, 1H), 3.58 (s, 3H), 3.48 (m, 2H), 3.18 (s, 6H), 3.10 (s, 3H), 2.92 (m, 1H), 2.74 (m, 1H). (ES MS M+1=444.0797)

The compounds in the following table were prepared in accordance with the procedure set forth in Example 73.

In a manner similar to that described for N-[6-(3-chloro-4-fluorobenzyl)-4-hydroxy-2-methyl-3,5-dioxo-2,3,5,6,7,8-hexahydro-2,6-naphthyridin-1-yl]-N-methylmethanesulfonamide (Example 73), substituting methanesulfonyl chloride with N,N-dimethylcarbamoyl chloride in step 2, the title compound was prepared.

$^1$HNMR (400 MHz, CDCl$_3$) δ 7.34 (dd, J=6.8, 2.0 Hz, 1H), 7.21-7.17 (m, 1H), 7.09 (t, J=8.8 Hz, 1H), 4.69 (s, 2H), 3.56 (s, 3H), 2.98 (s, 3H), 2.67 (s, 3H). ES MS M+1=437.

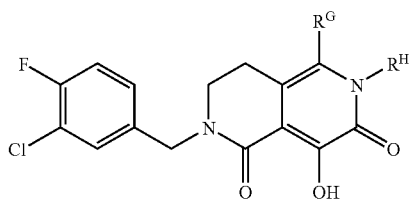

| Example | R$^G$ | R$^H$ | Name | ES MS (M + 1) |
|---|---|---|---|---|
| 74 | H$_3$C-N(-*)-S(=O)$_2$-CH$_2$CH$_3$ | CH$_3$ | N-[6-(3-chloro-4-fluorobenzyl)-4-hydroxy-2-methyl-3,5-dioxo-2,3,5,6,7,8-hexahydro-2,6-naphthyridin-1-yl]-N-methylethanesulfonamide | 458 |
| 75 | H$_3$C-N(-*)-S(=O)$_2$-CH$_3$ | isobutyl | N-[6-(3-chloro-4-fluorobenzyl)-4-hydroxy-2-isobutyl-3,5-dioxo-2,3,5,6,7,8-hexahydro-2,6-naphthyridin-1-yl]-N-methylmethanesulfonamide | 486 |
| 76 | H$_3$CCH$_2$-N(-*)-S(=O)$_2$-CH$_3$ | isobutyl | N-[6-(3-chloro-4-fluorobenzyl)-4-hydroxy-2-isobutyl-3,5-dioxo-2,3,5,6,7,8-hexahydro-2,6-naphthyridin-1-yl]-N-ethylmethanesulfonamide | 500 |

EXAMPLE 77

N-[6-(3-Chloro-4-fluorobenzyl)-4-hydroxy-2-methyl-3,5-dioxo-2,3,5,6,7,8-hexahydro-2,6-naphthyridin-1-yl]-N,N',N'-trimethylurea

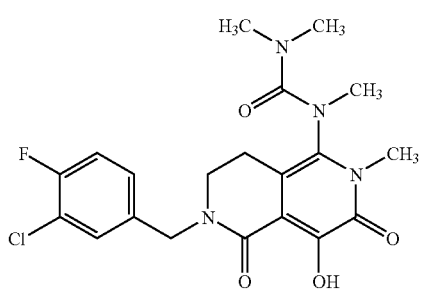

EXAMPLE 78

2-(3-Chloro-4-fluorobenzyl)-8-hydroxy-6-methyl-5-(5-methyl-1,3,4-oxadiazol-2-yl)-2,3,4,6-tetrahydro-2,6-naphthyridine-1,7-dione

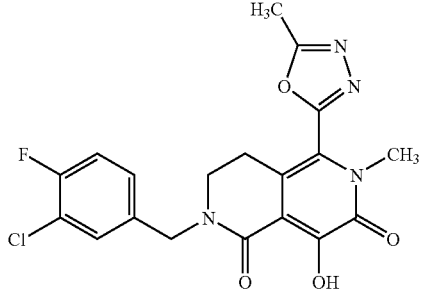

Step 1

N'-Acetyl-6-(3-Chloro-4-fluorobenzyl)-4-methoxy-2-methyl-3,5-dioxo-2,3,5,6,7,8-hexahydro-2,6-naphthyridine-1-carbohydrazide A suspension of 6-(3-chloro-4-fluorobenzyl)-4-methoxy-2-methyl-3,5-dioxo-2,3,5,6,7,8-hexahydro-2,6-naphthyridine-1-carboxylic acid (0.20 g, 0.51 mmol; Example 12, step 12) in anhydrous dichloromethane (5 mL) and anhydrous DMF (0.05 mL) at room temperature was treated with oxalyl chloride (0.09 mL, 1.01 mmol). The reaction mixture was stirred at room temperature for 3 hours and concentrated under vacuum. The residue was redissolved in anhydrous dichloromethane (5 mL), cooled to 0° C., and treated with a mixture of acetylhydrazide (56 mg, 0.76 mmol), triethylamine (0.26 g, 2.53 mmol), and DMAP (catalytic amount). The product mixture was stirred at room temperature overnight, diluted with dichloromethane and washed with water. The organic extract was dried over anhydrous sodium sulfate, filtered, concentrated under vacuum. The residue was subjected to column chromatography on silica gel eluting with 5% methanol in dichloromethane. Collection and concentration of appropriate fractions provided the titled compound. ES MS M+1=451

Step 2

2-(3-Chloro-4-fluorobenzyl)-8-hydroxy-6-methyl-5-(5-methyl-1,3,4-oxadiazol-2-yl)-2,3,4,6-tetrahydro-2,6-naphthyridine-1,7-dione A mixture of N'-acetyl-6-(3-chloro-4-fluorobenzyl)-4-methoxy-2-methyl-3,5-dioxo-2,3,5,6,7,8-hexahydro-2,6-naphthyridine-1-carbohydrazide (55 mg, 0.12 mmol) and Burgess reagent (116 mg, 0.49 mmol) in anhydrous THF (2 mL) was heated in a microwave oven at 120° C. for 15 minutes. The reaction mixture was concentrated under vacuum. The residue was subjected to column chromatography on silica gel eluting with 5% methanol in dichloromethane. Collection and concentration of appropriate fractions provided the intermediate oxazole. A solution of this intermediate (31 mg, 0.07 mmol) in 33% HBr in acetic acid (2 mL) was stirred at room temperature for 1 hour. The product mixture was concentrated under vacuum. The residue was partitioned between water and dichloromethane. The organic extract was dried over anhydrous magnesium sulfate, filtered, and concentrated under vacuum. The residue was triturated with anhydrous diethyl ether to provide the titled compound.

$^1$HNMR (400 MHz, CDCl$_3$) δ 7.33 (dd, J=6.8, 2.0 Hz, 1H), 7.21-7.17 (m, 1H), 7.11 (t, J=8.6 Hz, 1H), 4.66 (s, 2H), 3.42 (s, 3H), 3.40 (t, J=6.1 Hz, 2H), 2.72 (t, J=6.1 Hz, 2H), 2.63 (s, 3H). ES MS M+1=419

EXAMPLE 79

5-Bromo-2-(3-chloro-4-fluorobenzyl)-8-hydroxy-2,3,4,6-tetrahydro-2,6-naphthyridine-1,7-dione

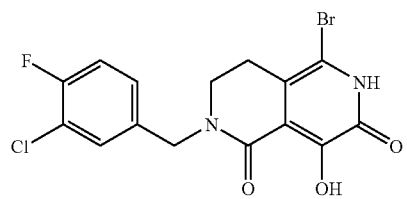

Step 1

5-Bromo-2-(3-chloro-4-fluorobenzyl)-8-methoxy-3,4-dihydro-2,6-naphthyridin-1(2H)-one A suspension of 6-(3-chloro-4-fluorobenzyl)-4-methoxy-2-methyl-3,5-dioxo-2,3,5,6,7,8-hexahydro-2,6-naphthyridine-1-carboxylic acid (3.5 g, 9.59 mmol; Example 12, step 12) in anhydrous dichloromethane (60 mL) and anhydrous DMF (0.45 mL) at room temperature was treated with oxalyl chloride (1.7 mL, 19.2 mmol). The reaction mixture was stirred at room temperature for 2 hours and concentrated under vacuum. A solution of the residue and AIBN (0.47 g, 2.88 mmol) in anhydrous dichloromethane (30 mL) was added portionwise to a solution of 2-pyridinethiol-N-oxide (2.4 g, 19.2 mmol) in a mixture of bromotrichloromethane (90 mL) and dichloroethane (30 mL) at 100° C. over a period of 20 minutes (Barton et al, *Tetrahedron Lett.*, 5939, 1985). The mixture was heated at the same temperature for 20 minutes, cooled to room temperature, and concentrated under vacuum. The residue was subjected to column chromatography on silica gel eluting with 2% methanol in dichloromethane. Collection and concentration of appropriate fractions provided the titled compound.

$^1$HNMR (400 MHz, CDCl$_3$) δ 8.14 (s, 1H), 7.38 (dd, J=6.9, 2.0 Hz, 1H), 7.22-7.19 (m, 1H), 7.10 (t, J=8.6 Hz, 1H), 4.66 (s, 2H), 4.03 (s, 3H), 3.48 (t, J=6.4 Hz, 2H), 2.94 (t, J=6.4 Hz, 2H). ES MS M+1=399, 401, 403.

Step 2

5-Bromo-2-(3-chloro-4-fluorobenzyl)-8-methoxy-2,3,4,6-tetrahydro-2,6-naphthyridine-1,7-dione 5-Bromo-2-(3-chloro-4-fluorobenzyl)-8-methoxy-2,3,4,6-tetrahydro-2,6-naphthyridine-1,7-dione was prepared in a manner similar to that described in Example 12, step 7 to 9, except the oxidation of 5-bromo-2-(3-chloro-4-fluorobenzyl)-8-methoxy-3,4-dihydro-2,6-naphthyridin-1(2H)-one to the corresponding pyridine N-oxide was oxidized with hydrogen peroxide urea complex (Caron et al., *Tetrahedron Lett.*, 2299, 2000).

$^1$HNMR (400 MHz, CDCl$_3$) δ 7.37 (dd, J=7.0, 2.0 Hz, 1H), 7.25-7.18 (m, 1H), 7.10 (t, J=8.6 Hz, 1H), 4.68 (s, 2H), 4.05 (s, 3H), 3.44 (t, J=6.2 Hz, 2H), 2.81 (t, J=6.2 Hz, 2H).

Step 3

5-Bromo-2-(3-chloro-4-fluorobenzyl)-8-hydroxy-2,3,4,6-tetrahydro-2,6-naphthyridine-1,7-dione A solution of 5-bromo-2-(3-chloro-4-fluorobenzyl)-8-methoxy-2,3,4,6-tetrahydro-2,6-naphthyridine-1,7-dione (1.40 g, 3.37 mmol) in 33% HBr in acetic acid (20 mL) was stirred at room temperature for 1 hour. The product mixture was concentrated under vacuum. The residue was dissolved in methanol, concentrated under vacuum, and triturated with anhydrous diethyl ether. The solid precipitated was filtered to provide the titled compound.
$^1$HNMR (400 MHz, CDCl$_3$) δ 9.03 (br s, 1H), 7.35 (dd, J=6.8, 2.0 Hz, 1H), 7.21-7.17 (m, 1H), 7.13 (t, J=8.6 Hz, 1H), 4.66 (s, 2H), 3.49 (t, J=6.2 Hz, 2H), 2.84 (t, J=6.2 Hz, 2H).

EXAMPLE 80

5-Bromo-2-(3-chloro-4-fluorobenzyl)-8-hydroxy-6-methyl-2,3,4,6-tetrahydro-2,6-naphthyridine-1,7-dione

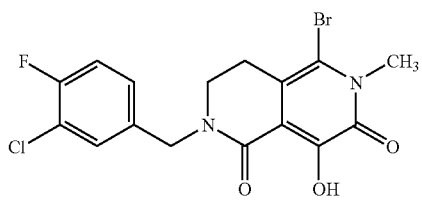

N-Methylation of 5-bromo-2-(3-chloro-4-fluorobenzyl)-8-hydroxy-2,3,4,6-tetrahydro-2,6-naphthyridine-1,7-dione (Example 79) was carried out as described in Example 12, step 10. The resultant reaction mixture was cooled to 0° C. and acidified with aqueous HCl. The resultant mixture was filtered and washed with diethyl ether to provide the titled compound as creamy white solid.
$^1$HNMR (400 MHz, CDCl$_3$) δ 7.34 (dd, J=7.0, 2.0 Hz, 1H), 7.24-7.18 (m, 1H), 7.14 (t, J=8.6 Hz, 1H), 4.65 (s, 2H), 3.77 (s, 3H), 3.44 (t, J=6.2 Hz, 2H), 2.84 (t, J=6.2 Hz, 2H).

EXAMPLE 81

2-(3-Chloro-4-fluorobenzyl)-8-hydroxy-2,3,4,6-tetrahydro-2,6-naphthyridine-1,7-dione

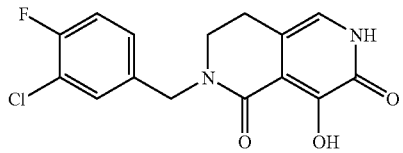

Step 1

6-(3-Chloro-4-fluorobenzyl)-4-hydroxy-3,5-dioxo-2,3,5,6,7,8-hexahydro-2,6-naphthyridine-1-carboxylic acid A solution of ethyl 3,4-bis(acetyloxy)-6-(3-chloro-4-fluorobenzyl)-5-oxo-5,6,7,8-hexahydro-2,6-naphthyridine-1-carboxylate (1.00 g, 2.09 mmol; Example 12, step 8) and lithium hydroxide (0.70 g, 16.70 mmol) in a mixture of THF-methanol-water (30 mL, 1:1:1 by volume) was heated under reflux in an oil bath at 90° C. overnight. The product mixture was acidified and concentrated under vacuum. The residue was triturated with diethyl ether. The solid precipitated was filtered and washed with ether to provide the titled compound. ES MS M+1=367.

Step 2

2-(3-Chloro-4-fluorobenzyl)-8-hydroxy-2,3,4,6-tetrahydro-2,6-naphthyridine-1,7-dione A mixture of 6-(3-chloro-4-fluorobenzyl)-4-hydroxy-3,5-dioxo-2,3,5,6,7,8-hexahydro-2,6-naphthyridine-1-carboxylic acid (0.30 g, 0.82 mmol) and quinoline (0.11 g, 0.82 mmol) was heated at 190° C. for 2.5 hours. The product mixture was cooled to room temperature and triturated with diethyl ether. The solid precipitated was filtered, and was subjected to preparative reverse phase HPLC purification. Collection and lyophilization of appropriate fractions provide the titled compound.
$^1$HNMR (400 MHz, CD$_3$OD) δ 7.49 (dd, J=6.8, 2.0 Hz, 1H), 7.36-7.32 (m, 1H), 7.22 (t, J=8.8 Hz, 1H), 6.66 (br s, 1H), 4.67 (s, 2H), 3.51 (t, J=6.1 Hz, 2H), 2.74 (t, J=6.1 Hz, 2H). ES MS M+1=323

EXAMPLE 82

2-(3-Chloro-4-fluorobenzyl)-8-hydroxy-6-methyl-2,3,4,6-tetrahydro-2,6-naphthyridine-1,7-dione

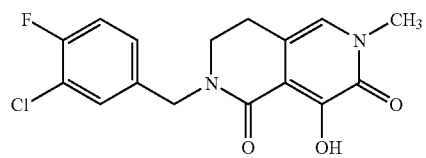

Step 1

2-(3-Chloro-4-fluorobenzyl)-8-methoxy-6-methyl-2,3,4,6-tetrahydro-2,6-naphthyridine-1,7-dione A solution of 2-(3-chloro-4-fluorobenzyl)-8-hydroxy-2,3,4,6-tetrahydro-2,6-naphthyridine-1,7-dione (0.40 g, 1.24 mmol; Example 81), methyl iodide (1.76 g, 12.4 mmol), and cesium carbonate (2.02 g, 6.20 mmol) in THF (50 mL) was heated under reflux overnight. The product mixture concentrated under vacuum. The residue was partitioned between water and ethyl acetate. The organic extract was dried over anhydrous sodium sulfate, filtered, and concentrated under vacuum. The residual oil was subjected to preparative reverse phase HPLC purification. Collection and lyophilization of appropriate fractions provide the titled compound.
$^1$HNMR (400 MHz, CDCl$_3$) δ 7.37 (dd, J=6.8, 2.0 Hz, 1H), 7.25-7.21 (m, 1H), 7.12 (t, J=8.8 Hz, 1H), 6.92 (s, 1H), 4.69 (s, 2H), 4.09 (s, 3H), 3.57 (s, 3H), 3.40 (t, J=6.1 Hz, 2H), 2.62 (t, J=6.1 Hz, 2H). ES MS M+1=351

Step 2

2-(3-Chloro-4-fluorobenzyl)-8-hydroxy-6-methyl-2,3,4,6-tetrahydro-2,6-naphthyridine-1,7-dione A solution of 2-(3-chloro-4-fluorobenzyl)-8-methoxy-6-methyl-2,3,4,6-tetrahydro-2,6-naphthyridine-1,7-dione (30 mg, 0.086 mmol) and 33% HBr in acetic acid (5 mL) in acetic acid (10 mL) was stirred at room temperature for 2 hours. The product mixture was concentrated under vacuum. The residue was subjected to preparative reverse phase HPLC purification. Collection and lyophilization of appropriate fractions provide the titled compound.
ES MS M+1=337

EXAMPLE 83

2-(3-Chloro-4-fluorobenzyl)-5-ethyl-8-hydroxy-6-methyl-2,3,4,6-tetrahydro-2,6-naphthyridine-1,7-dione

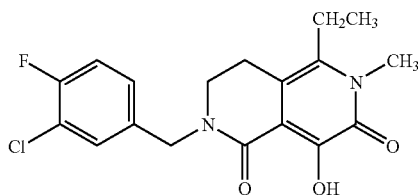

Step 1

5-Bromo-2-(3-chloro-4-fluorobenzyl)-8-methoxy-6-methyl-2,3,4,6-tetrahydro-2,6-naphthyridine-1,7-dione A solution of 5-bromo-2-(3-chloro-4-fluorobenzyl)-8-hydroxy-2,3,4,6-tetrahydro-2,6-naphthyridine-1,7-dione (8.00 g, 19.92 mmol; Example 79), methyl iodide (28.27 g, 199.19 mmol), and cesium carbonate (32.45 g, 99.59 mmol) in THF (100 mL) was heated under reflux overnight. The product mixture concentrated under vacuum. The residue was partitioned between water and ethyl acetate. The organic extract was dried over anhydrous sodium sulfate, filtered, and concentrated under vacuum. The residual oil was subjected to preparative reverse phase HPLC purification. Collection and lyophilization of appropriate fractions provide the titled compound.
ES MS M+1=429.

Step 2

2-(3-Chloro-4-fluorobenzyl)-5-ethyl-8-methoxy-6-methyl-2,3,4,6-tetrahydro-2,6-naphthyridine-1,7-dione A solution of 5-bromo-2-(3-chloro-4-fluorobenzyl)-8-methoxy-6-methyl-2,3,4,6-tetrahydro-2,6-naphthyridine-1,7-dione (0.40 g, 0.93 mmol), tri-n-butyl vinyl tin (0.38 g, 1.21 mmol), and bis(tri-phenylphosphine)palladium (II) chloride (65 mg, 0.093 mmol) in THF (30 mL) was heated under reflux for two hours. The product mixture concentrated under vacuum. The residue was subjected to preparative reverse phase HPLC purification. Collection and lyophilization of appropriate fractions provide the intermediate vinyl intermediate. ES MS M+1=377. A mixture of this vinyl intermediate (60 mg, 0.16 mmol) and 5% platinum on charcoal (50 mg) in ethanol (20 mL) was stirred under a balloon of hydrogen at room temperature for 30 minutes. The resultant mixture was filtered, and concentrated under vacuum to provide the titled compound.
$^1$HNMR (400 MHz, CDCl$_3$) δ 7.38 (dd, J=6.8, 2.0 Hz, 1H), 7.24-7.19 (m, 1H), 7.11 (t, J=8.8 Hz, 1H), 4.69 (s, 2H), 4.02 (s, 3H), 3.62 (s, 3H), 3.37 (t, J=6.1 Hz, 2H), 2.7-2.6 (m, 4H), 1.15 (t, J=7.3 Hz, 3H).
ES MS M+1=379.

Step 3

2-(3-Chloro-4-fluorobenzyl)-5-ethyl-8-hydroxy-6-methyl-2,3,4,6-tetrahydro-2,6-naphthyridine-1,7-dione A solution of 2-(3-chloro-4-fluorobenzyl)-5-ethyl-8-methoxy-6-methyl-2,3,4,6-tetrahydro-2,6-naphthyridine-1,7-dione (55 mg, 0.15 mmol) and 33% HBr in acetic acid (5 mL) in acetic acid (10 mL) was stirred at room temperature overnight. The product mixture was concentrated under vacuum. The residue was subjected to preparative reverse phase HPLC purification. Collection and lyophilization of appropriate fractions provide the titled compound.
$^1$HNMR (400 MHz, CDCl$_3$) δ 7.36 (dd, J=6.4, 2.0 Hz, 1H), 7.20 (m, 1H), 7.13 (t, J=8.4 Hz, 1H), 4.66 (s, 2H), 3.66 (s, 3H), 3.44 (t, J=6.1 Hz, 2H), 2.78 (t, J=6.1 Hz, 2H), 2.65 (q, J=7.3 Hz, 2H), 1.15 (t, J=7.3 Hz, 3H). ES MS M+1=365.

EXAMPLE 84

2-(3-Chloro-4-fluorobenzyl)-5-cyclopropyl-8-hydroxy-6-methyl-2,3,4,6-tetrahydro-2,6-naphthyridine-1,7-dione

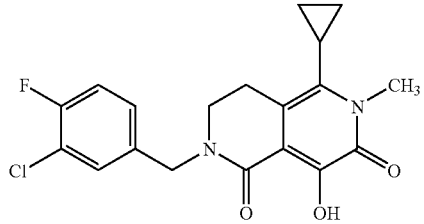

To a cold (0° C.) solution of 2-(3-chloro-4-fluorobenzyl)-5-vinyl-8-methoxy-6-methyl-2,3,4,6-tetrahydro-2,6-naphthyridine-1,7-dione (0.12 g, 0.32 mmol; Example 83, step 2) in diethyl ether (5 mL), a solution of diazomethane (~3 mmol) in diethyl ether was added. Catalytic amount of palladium (II) acetate was added and the mixture was stirred at the same temperature for 30 minutes. The product mixture was filtered and concentrated under vacuum. The residue was subjected to preparative reverse phase HPLC purification. Collection and lyophilization of appropriate fractions provide the cyclopropanation intermediate. Following the demethylation procedure described in Example 83, step 3, the above intermediate was converted to the titled compound.
$^1$HNMR (400 MHz, CDCl$_3$) δ 12.77 (s, 1H), 7.35 (dd, J=6.4, 2.0 Hz, 1H), 7.20 (m, 1H), 7.13 (t, J=8.4 Hz, 1H), 4.66 (s, 2H), 3.73 (s, 3H), 3.41 (t, J=6.0 Hz, 2H), 2.90 (t, J=6.0 Hz, 2H), 1.68 (m, 1H), 1.12 (q, J=8.2 Hz, 2H), 0.62 (q, J=8.2 Hz, 2H). ES MS M+1=377.

EXAMPLE 85

2-(3-Chloro-4-fluorobenzyl)-8-hydroxy-6-methyl-5-pyridin-3-yl-2,3,4,6-tetrahydro-2,6-naphthyridine-1,7-dione

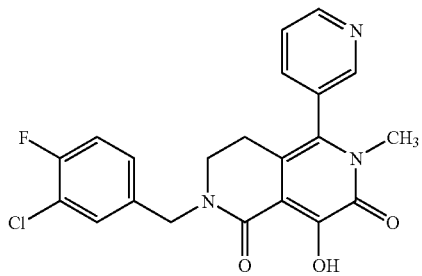

A mixture of 5-bromo-2-(3-chloro-4-fluorobenzyl)-8-hydroxy-6-methyl-2,3,4,6-tetrahydro-2,6-naphthyridine-1,7-dione (35 mg, 0.08 mmol; Example 80), tetrakis(triphenylphosphine)palladium(0) (5 mg), pyridine-3-boronic acid (15 mg, 0.13 mmol), aq sodium carbonate (2 M, 0.5 mL), and dioxane (1.5 mL) was heated in a microwave oven at 100° C. for 15 minutes. The product mixture was concentrated under vacuum, and the residue was partitioned between water and dichloromethane. The organic extract was separated, concentrated under vacuum. The residue was subjected to preparative reverse phase HPLC purification. Collection and lyophilization of appropriate fractions provide the titled compound.

$^1$HNMR (400 MHz, CDCl$_3$) δ 13.06 (br s, 1H), 8.74 (d, J=3.3 Hz, 1H), 8.51 (d, J=1.5 Hz, 1H), 7.58 (d, J=7.9 Hz, 1H), 7.46 (m, 1H), 7.34 (dd, J=6.8, 2.0 Hz, 1H), 7.21-7.18 (m, 1H), 7.12 (t, J=8.6 Hz, 1H), 4.70 (d, J=14.6 Hz, 1H), 4.61 (d, J=14.6 Hz, 1H), 3.34 (m, 2H), 2.43 (m, 2H).

ES MS M+1=414

The compounds in the following table were prepared in accordance with the procedure set forth in Example 85, using the appropriate reagents.

| Example | R$^G$ | Name | ES MS (M + 1) |
|---|---|---|---|
| 86 | | 2-(3-chloro-4-fluorobenzyl)-8-hydroxy-6-methyl-5-pyridin-4-yl-2,3,4,6-tetrahydro-2,6-naphthyridine-1,7-dione | 414 |
| 87 | | 2-(3-chloro-4-fluorobenzyl)-8-hydroxy-6-methyl-5-(2-furyl)-2,3,4,6-tetrahydro-2,6-naphthyridine-1,7-dione | 403 |

EXAMPLE 88

Oral Compositions

As a specific embodiment of an oral composition of a compound of this invention, 50 mg of compound of Example 1 is formulated with sufficient finely divided lactose to provide a total amount of 580 to 590 mg to fill a size O hard gelatin capsule. Encapsulated oral compositions containing any one of the compounds disclosed in the other examples can be similarly prepared.

EXAMPLE 89

HIV Integrase Assay: Strand Transfer Catalyzed by Recombinant Integrase

Assays for the strand transfer activity of integrase were conducted in accordance with WO 02/30930 for recombinant integrase. Representative compounds of the present invention exhibit inhibition of strand transfer activity in this assay. For example, the compounds in Examples 1-15, 17-71, and 73-87 were tested in the integrase assay and were found to have IC$_{50}$'s less than about 1 micromolar.

Further description on conducting the assay using preassembled complexes is found in Wolfe, A. L. et al., *J. Virol.* 1996, 70: 1424-1432, Hazuda et al., *J. Virol.* 1997, 71: 7005-7011; Hazuda et al., *Drug Design and Discovery* 1997, 15: 17-24; and Hazuda et al., *Science* 2000, 287: 646-650.

EXAMPLE 90

Assay for Inhibition of HIV Replication

Assays for the inhibition of acute HIV infection of T-lymphoid cells were conducted in accordance with Vacca, J. P. et al., *Proc. Natl. Acad. Sci. USA* 1994, 91: 4096. Representative compounds of the present invention exhibit inhibition of HIV replication in this assay. For example, the compounds in Examples 1-15, 17-71, and 73-87 were found to have IC$_{95}$'s equal to or less than about 10 micromolar in the present assay.

EXAMPLE 91

6-(3-Chloro-4-fluorobenzyl)-4-hydroxy-N,N,2-trimethyl-3,5-dioxo-2,3,5,6,7,8-hexahydro-2,6-naphthyridine-1-carboxamide

Step 1

1-(3-Chloro-4-fluorobenzyl)piperidin-2-one

Valerolactam (60 g) was dissolved in MTBE (1.5 L) at room temperature. To this solution was added Bu$_4$NSO$_4$ (4.9 g) as a phase transfer catalyst. The cloudy solution was stirred at room temperature for 5 minutes. Then, NaOH (50 wt %; 300 mL) was slowly added as to keep the internal temperature below 30° C. 3-Chloro-4-fluorobenzyl bromide (108.3 g) was then added slowly to this biphasic mixture, again as to keep the internal temperature under control. The reaction was then aged for 4 hours at room temperature. At this time LC showed the reaction to be complete. Water (500 mL) was then added. After phase cut, the organic layer was washed with brine (300 mL), dried under MgSO$_4$ followed by solvent switch to hep-

Step 2

Preparation of an Unsaturated Sulfide of Formula 1

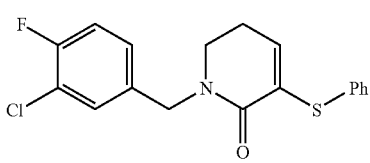

1-(3-Chloro-4-fluorobenzyl)piperidin-2-one (25 g) was dissolved in THF (250 mL) and cooled to −20 degrees C. under nitrogen atmosphere. LHMDS (204 mL, 1M in THF) was added over 40 minutes at −20 to −30° C. and aged for 1 hour at −20° C. Methyl benzene sulfinate (17.78 g) was added over 30 minutes, again keeping the internal temperature at −20° C. The reaction was aged for 30 minutes at −20° C. at which time LC showed the reaction to be complete. The reaction mixture was then quenched with water (100 mL) and diluted with EtOAc (300 mL). After phase cut, the organic layer was washed with HCl 2N (2×100 mL). The organic layer was then washed with brine (2×100 mL), dried under $MgSO_4$ followed by solvent switch to DCM (600 mL; final volume 400 mL). To this solution was added acetic anhydride (11.6 mL) and $MeSO_3H$ (3.07 mL). The solution was then aged at room temperature overnight. The reaction was quenched with water (300 mL) and cooled to 0° C. The slurry obtained was then carefully basified to pH=8 with solid $Na_2CO_3$. The organic layer obtained after phase cut was then washed with brine and dried under $MgSO_4$. After evaporation of solvents, the title unsaturated sulfide 1 was obtained as an oil which solidified on standing. The title sulfide 1 can be crystallized from MeOH.

Step 3

Preparation of a Vinyl Sulfoxide of Formula 2

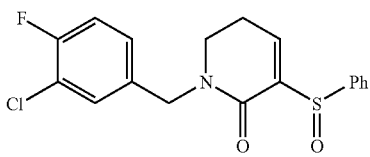

Unsaturated sulfide 1 (35.47 g) was dissolved in MeOH (200 mL) and water was added (50 mL) followed by the addition of solid $NaIO_4$ (39.82 g). The slurry obtained was stirred at room temperature for 3 days. The slurry was then filtered and the solid obtained was washed with EtOAc (200 mL). The filtrate was then evaporated until almost dryness and diluted with EtOAc (350 mL) and washed with $H_2O$ (200 mL). The organic layer was then washed with brine (200 mL) and dried under $MgSO_4$. The organic solvents were then removed to completion. The oil obtained was crystallized with a IPAc:Hexane (1:1.2) mixture and seeding to afford the title sulfoxide 2.

Step 4

Preparation of a Michael Adduct of Formula 3

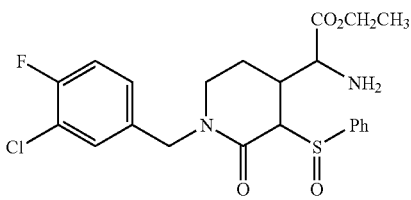

To a solution of vinyl sulfoxide 2 (5 g, 13.74 mmoles) in THF (70 mL) at 0° C. was added diphenylketimine glycine ethyl ester (4 g, 15.mmoles) followed by t-BuOLi (0.2 g, 2.5 mmoles). The mixture was stirred for 20 minutes at 0° C. then, HCl 2N (80 mL) was added. The resulting mixture was stirred at 20° C. for 20 minutes and MTBE (160 mL) was added. After phase separation, the aqueous layer was basified to pH=8-9 by addition of solid $Na_2CO_3$. The resulting aqueous layer was extracted twice with EtOAc (2×100 mL) and the solvent evaporated under reduced pressure to give the title adduct 3 as an oil.

Step 5

Preparation of an Oxamate of Formula 4

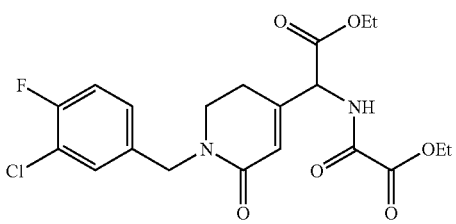

To a solution of adduct 3 (6.2 g, 13.28 mmoles) in THF (70 mL) at 0° C. was added triethylamine (2 mL, 14.6 mmoles) followed by dropwise addition of ethyloxalyl chloride (1.55 mL, 13.94 mmoles). The resulting slurry was stirred for 20 minutes at 0° C., then water (50 mL) was added. The mixture was extracted with EtOAc (2×1100 mL), then solvent switched to toluene (final volume: 80 mL). The toluene solution was heated to 90° C. for 30-45 minutes then passed through a plug of silica gel (50 g) using EtOAc/hexanes 1:1 (200 mL), then EtOAc as eluent. After evaporation of the solvents, the title oxamate 4 was obtained.

Step 6

Ethyl 6-(3-chloro-4-fluorobenzyl)-3,4-dihydroxy-5-oxo-5,6,7,8-tetrahydro-2,6-naphthyridine-1-carboxylate To a solution of oxamate 4 (2 g, 4.5 mmoles) in THF (35 mL) was added LiBr (1.2 g, 18.1 mmoles) followed by DABCO (0.76 g, 6.8 mmoles). The mixture was stirred for 18 hours at 20° C., then HCl 2N (50 mL) was added and the mixture was extracted with EtOAc (50 mL). Solvents were evaporated under reduced pressure to give the title compound as a pale yellow solid.

Alternative Route:

Ethyl 6-(3-chloro-4-fluorobenzyl)-3,4-dihydroxy-5-oxo-5,6,7,8-tetrahydro-2,6-naphthyridine-1-carboxylate To a stirred solution of ethyl 6-(3-chloro-4-fluorobenzyl)-4-hydroxy-5-oxo-5,6,7,8-tetrahydro-2,6-naphthyridine-1-carboxylate (5.0 g; see Example 12, Step 6) and sodium acetate (0.89 g) in acetic acid (90 mL) was added peracetic acid (28 mL). The mixture was then heated at 50° C. overnight. The mixture was cooled to 5° C. and saturated $NaHSO_4$ (17 mL) added, keeping the temperature at less than 25° C. The mixture was concentrated to 50% original volume and partitioned between tert-butyl methyl ether (100 mL) and water (50 mL). The organic phase collected and the volatiles evaporated. The residue was dissolved in toluene (50 mL) and volatiles evaporated, the residue dissolved in toluene (50 mL) and evaporation repeated. Finally the residue was dissolved in toluene (20 mL). Acetic anhydride (3.9 mL) was added and the mixture heated at reflux until complete by HPLC analysis. The mixture cooled to ambient temperature and sodium ethoxide in ethanol (20 mL) was added. The reaction mixture stirred overnight. 2N HCl (31 mL) was added and the title product isolated by filtration.

$^1$H NMR (400 MHz, $CDCl_3$) δ 9.6-9.5 (bs, 1H), 7.4 (dd, J=6.8. 2.4 Hz, 1H), 7.2 (m, 1H), 7.15 (t, J=8.4 Hz, 1H), 4.7 (s, 2H), 4.35 (q, J=7.2 Hz, 2H), 3.45 (t, J=6.4 Hz, 2H), 3.35 (t, J=6.4 Hz, 2H), 1.4 (t, J=7.2 Hz, 3H) ppm.

Step 7

Methyl 6-(3-chloro-4-fluorobenzyl)-4-hydroxy-2-methyl-3,5-dioxo-2,3,5,6,7,8-hexahydro-2,6-naphthyridine-1-carboxylate To a stirred suspension of ethyl 6-(3-chloro-4-fluorobenzyl)-3,4-dihydroxy-5-oxo-5,6,7,8-tetrahydro-2,6-naphthyridine-1-carboxylate (40 g) in DMF (200 mL) was added magnesium methoxide in methanol (100 mL). The mixture heated at 40-50° C. for 3 hours. The excess methanol distilled off, and methyl tosylate (18 mL) was added. The reaction mixture was heated at 50° C. overnight, then cooled to 25° C., and then quenched into 1N HCl (100 mL). The suspension stirred for 1 hour at ambient temperature. The product was isolated by filtration, and the filter cake washed with water (2×100 mL) and then dried on the filter under an atmosphere of nitrogen. The crude product was suspended in methanol (460 mL), heated at reflux temperature for 1 hour, and then allowed to cool to ambient temperature. The product was isolated by filtration and the filter cake washed with cold methanol (2×40 mL) and dried to give the title product.

$^1$H NMR (400 MHz, $CDCl_3$) δ 13.37 (s, 1H), 7.35 (dd, J=2.4, 6.9 Hz, 1H), 7.22-7.18 (m, 1H), 7.13 (t, J=8.4 Hz, 1H), 4.67 (s, 2H), 3.92 (s, 3H), 3.54 (s, 3H), 3.43 (t, J=6.4 Hz, 2H), 2.81 (t, J=6.4 Hz, 2H) ppm. (ES MS M+1=395.0)

Step 8

6-(3-Chloro-4-fluorobenzyl)-4-hydroxy-N,N,2-trimethyl-3,5-dioxo-2,3,5,6,7,8-hexahydro-2,6-naphthyridine-1-carboxamide To THF (80 mL) cooled to −10° C. was added iPrMgCl (2M in THF, 60 mL). Dimethylamine (2M in THF) was then added at −10 to 0° C., the mixture then stirred for 1 hour at −5 to −10° C. The resulting suspension of $ClMgNMe_2$ at −10° C. was allowed to warm to 0° C., and a solution of methyl 6-(3-chloro-4-fluorobenzyl)-4-hydroxy-2-methyl-3,5-dioxo-2,3,5,6,7,8-hexahydro-2,6-naphthyridine-1-carboxylate (10.0 g) in dichloromethane (100 mL) was added over 20 minutes at 0° C. The mixture was then stirred until reaction was complete by HPLC. The reaction mixture was quenched with 1N HCl (335 mL). The organic layer was collected and the aqueous layer extracted with $CH_2Cl_2$ (35 mL). The organic phases were then combined and washed with brine (35 mL). Volatiles were evaporated to give the title product as an amorphous solid.

$^1$H NMR (400 MHz, $CD_3OD$) δ 7.46 (dd, J=2.2, 7.14 Hz, 1H), 7.33-7.29 (m, 1H), 7.17 (t, J=9.0 Hz, 1H), 4.72 (d, J=14.8 Hz, 1H), 4.65 (d, J=14.8 Hz, 1H), 3.35 (s, 3H), 3.33-3.96 (m, 2H), 3.07 (s, 3H), 2.97 (s, 3H), 2.47 (dd, J=5.68, 11.36 Hz, 2H) ppm. (ES MS M+1=408.0)

EXAMPLE 92

6-(3-Chloro-4-fluorobenzyl)-4-hydroxy-2-isopropyl-N,N-dimethyl-3,5-dioxo-2,3,5,6,7,8-hexahydro-2,6-naphthyridine-1-carboxamide Step 1

Preparation of a Michael Adduct of Formula 5

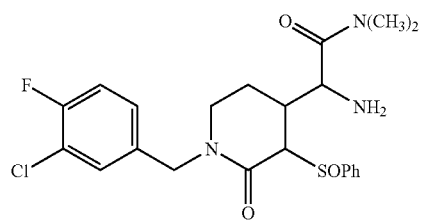

To a solution of vinyl sulfoxide 2 (5 g, 13.74 mmoles; Example 91, Step 3) in THF (70 mL) at 0° C. was added diphenylketimine glycine dimethyl amide (4 g, 15.mmoles) followed by t-BuOLi (0.2 g, 2.5 mmoles). The mixture was stirred for 20 minutes at 0° C., and then HCl 2N (80 mL) was added. The resulting mixture was stirred at 20° C. for 20 minutes and MTBE (160 mL) was added. After phase separation, the aqueous layer was basified to pH=8-9 by addition of solid $Na_2CO_3$. The resulting aqueous layer was extracted twice with EtOAc (2×100 mL) and the solvent evaporated under reduced pressure to give the title adduct as an oil.

Step 2

Preparation of an Isopropyl Amine of Formula 6

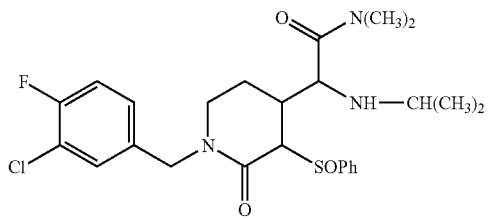

To a solution of adduct 5 (2.5 g, 5.35 mmoles) in MeOH (30 mL) was added acetone (0.8 mL, 10.7 mmoles) followed sodium triacetoxyborohydride (1.2 g, 5.9 mmoles). The mixture was stirred for 20 minutes, and then water (10 mL) and NaHCO$_3$ saturated (30 mL) were added. The resulting mixture was extracted twice with EtOAc (2×30 mL) and the solvent evaporated under reduced pressure to provide the crude title product.

Step 3

Preparation of an Oxamate of Formula 7

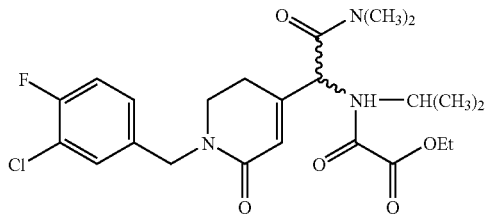

Crude amine 6 (5 mmol) is dissolved in THF (40 mL) at 0° C. and triethylamine (1.4 mL, 2.2 eq.) was added followed by dropwise addition of ethyloxalyl chloride (1 mL, 2.1 eq.). The resulting slurry was stirred for 20 minutes at 0° C., then water (30 mL) was added. The mixture was extracted with EtOAc (2×40 mL), then solvent switched to toluene (final volume: 20 mL). The toluene solution was heated at 90° C. for 3045 minutes then passed through a plug of silica gel (20 g) using EtOAc/hexanes 1:1 (200 mL), then EtOAc as eluant. The title oxamate 7 was obtained after evaporation of the solvents.

Step 4

6-(3-Chloro-4-fluorobenzyl)-4-hydroxy-2-isopropyl-N,N-dimethyl-3,5-dioxo-2,3,5,6,7,8-hexahydro-2,6-naphthyridine-1-carboxamide To a solution of oxamate 7 (160 mg) in THF (3 mL) was added LiBr (110 mg, 4 eq.) followed by DABCO (56 mg, 1.5 eq.). The mixture was stirred for 10 minutes at room temperature, then HCl 2N (5 mL) was added and the mixture was extracted with EtOAc (5 mL). The solvents were evaporated under reduced pressure to give the title compound.

EXAMPLE 93

Crystalline sodium salt of 6-(3-chloro-4-fluorobenzyl)-4-hydroxy-2-isopropyl-N,N-dimethyl-3,5-dioxo-2,3,5,6,7,8-hexahydro-2,6-naphthyridine-1-carboxamide Part A: Preparation MeOH (10 mL) and MTBE (50 mL) were added to 6-(3-chloro-4-fluorobenzyl)-4-hydroxy-2-isopropyl-N,N-dimethyl-3,5-dioxo-2,3,5,6,7,8-hexahydro-2,6-naphthyridine-1-carboxamide (6.94 g). NaOH/MeOH (1 N, 15.95 mL) was then charged thereto, and the admixture stirred until the carboxamide dissolved. The solution was filtered and additional MTBE (65 mL) was added to the filtrate. The filtrate was concentrated by removal of MeOH under vacuum (190 mm Hg at 40° C.). The resulting concentrate (140 mL) was seeded, heated to 40° C., and aged overnight. The aged concentrate was then cooled to room temperature, and the resulting solids were separated by filtration, washed with 10% MeOH/MTBE, and vacuum dried at room temperature to afford a crystalline sodium salt.

Part B: Characterization

An XRPD pattern of a Na salt prepared in the manner described in Part A was generated on a Philips Analytical X'Pert Pro X-ray powder diffractometer using a continuous scan from 2.5 to 40 degrees 2 Θ. Copper K-Alpha 1 ($K_{\alpha 1}$) and K-Alpha 2 ($K_{\alpha 2}$) radiation was used as the source. The experiment was run under ambient conditions. 2Θ values and the corresponding d-spacings in the XRPD pattern include the following:

| Peak No. | d-spacing (Å) | 2 Theta |
| --- | --- | --- |
| 1 | 15.0 | 5.9 |
| 2 | 8.1 | 10.9 |
| 3 | 7.1 | 12.5 |
| 4 | 6.6 | 13.3 |
| 5 | 5.7 | 15.5 |
| 6 | 5.0 | 17.6 |
| 7 | 4.7 | 18.7 |
| 8 | 4.2 | 21.3 |
| 9 | 3.7 | 23.9 |

A Na salt prepared in the manner described in Part A was also analyzed by a TA Instruments DSC 2910 differential scanning calorimeter at a heating rate of 10° C./min from room temperature to 250° C. in a closed pan in a nitrogen atmosphere. The DSC curve exhibited an endotherm with a peak temperature of 220° C. and an associated heat of fusion of 27 J/gm. The endotherm is believed to be due to melting.

A thermogravimetric analysis was performed with a Perkin-Elmer Model TGA 7 under nitrogen at a heating rate of 10° C./min from room temperature to 250° C. The TG curve showed a 1.1% weight loss from 20 to 220° C.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A compound of Formula I, or a pharmaceutically acceptable salt thereof:

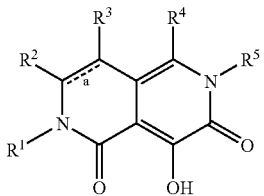

(I)

wherein:
bond

"‐‐‐ a ‐‐‐"

in the ring is a single bond or a double bond;
R$^1$ is —C$_{1-6}$ alkyl substituted with R$^J$, wherein R$^J$ is:
(A) (i) aryl or (ii) aryl fused to a 5- or 6-membered heteroaromatic ring containing from 1 to 4 heteroatoms independently selected from N, O and S, wherein the aryl or fused aryl is:
(a) optionally substituted with from 1 to 5 substituents each of which is independently:
(1) —C$_{1-6}$ alkyl optionally substituted with —OH, —O—C$_{1-6}$ alkyl, —O—C$_{1-6}$ haloalkyl, —CN, —NO$_2$, —N(R$^a$)R$^b$, —C(=O)N(R$^a$)R$^b$, —C(=O)R$^a$, —CO$_2$R$^a$, —S(O)$_n$R$^a$, —SO$_2$N(R$^a$)R$^b$, —N(R$^a$)C(=O)R$^b$, —N(R$^a$)CO$_2$R$^b$, —N(R$^a$)SO$_2$R$^b$, —N(R$^a$)SO$_2$N(R$^a$)R$^b$, —OC(=O)N(R$^a$)R$^b$, or —N(R$^a$)C(=O)N(R$^a$)R$^b$,
(2) —O—C$_{1-6}$ alkyl,
(3) —C$_{1-6}$ haloalkyl,
(4) —O—C$_{1-6}$ haloalkyl,
(5) —OH,
(6) halogen,
(7) —CN,
(8) —NO$_2$,
(9) —N(R$^a$)R$^b$,
(10) —C(=O)N(R$^a$)R$^b$,
(11) —C(=O)R$^a$,
(12) —CO$_2$R$^a$,
(13) —SR$^a$,
(14) —S(=O)R$^a$,
(15) —SO$_2$R$^a$,
(16) —SO$_2$N(R$^a$)R$^b$,
(17) —N(R$^a$)SO$_2$R$^b$,
(18) —N(R$^a$)SO$_2$N(R$^a$)R$^b$,
(19) —N(R$^a$)C(=O)R$^b$,
(20) —N(R$^a$)C(=O)—C(=O)N(R$^a$)R$^b$, or
(21) —N(R$^a$)CO$_2$R$^b$, and
(b) optionally substituted with 1 or 2 substituents each of which is independently:
(1) phenyl,
(2) benzyl,
(3) —HetA,
(4) —C(=O)—HetA, or
(5) —HetB;
wherein each HetA is independently a C$_{4-7}$ azacycloalkyl or a C$_{3-6}$ diazacycloalkyl, either of which is optionally substituted with from 1 to 4 substituents each of which is independently oxo or C$_{1-6}$ alkyl; and wherein each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, C$_{1-6}$ alkyl, C$_{1-6}$ haloalkyl, O—C$_{1-6}$ alkyl, O—C$_{1-6}$ haloalkyl, or hydroxy; or
(B) a 5- or 6-membered heteroaromatic ring containing from 1 to 4 heteroatoms independently selected from N, O and S, wherein the heteroaromatic ring is:
(i) optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or hydroxy; and
(ii) optionally substituted with 1 or 2 substituents each of which is independently aryl or —C$_{1-6}$ alkyl substituted with aryl;
R$^2$ and R$^3$ are each independently —H or —C$_{1-6}$ alkyl;
R$^4$ is:
(1) —H,
(2) —C$_{1-6}$ alkyl,
(3) —C$_{1-6}$ haloalkyl,
(4) —C$_{1-6}$ alkyl substituted with —OH, —O—C$_{1-6}$ alkyl, —O—C$_{1-6}$ haloalkyl, —CN, —N(R$^a$)R$^b$, —C(=O)N(R$^a$)R$^b$, —C(=O)R$^a$, —CO$_2$R$^a$, —C(=O)—N(R$^a$)—C$_{1-6}$ alkylene-OR$^b$ with the proviso that the —N(R$^a$)— moiety and the —OR$^b$ moiety are not both attached to the same carbon of the —C$_{1-6}$ alkylene-moiety, —S(O)$_n$R$^a$, —SO$_2$N(R$^a$)R$^b$, —N(R$^a$)C(=O)—R$^b$, —N(R$^a$)CO$_2$R$^b$, —N(R$^a$)SO$_2$R$^b$, —N(R$^a$)SO$_2$N(R$^a$)R$^b$, —N(R$^a$)C(=O)N(R$^a$)R$^b$, or —OC(=O)N(R$^a$)R$^b$,
(5) —C(=O)R$^a$,
(6) —CO$_2$R$^a$,
(7) —C(=O)N(R$^a$)R$^b$,
(8) —C(=O)—N(R$^a$)—C$_{1-6}$ alkylene-OR$^b$ with the proviso that the —N(R$^a$)— moiety and the —OR$^b$ moiety are not both attached to the same carbon of the —C$_{1-6}$ alkylene-moiety,
(9) —N(R$^a$)—C(=O)—R$^b$,
(10) —N(R$^a$)—C(=O)—C(=O)N(R$^a$)R$^b$,
(11) —N(R$^a$)SO$_2$R$^b$,
(12) —N(R$^a$)SO$_2$N(R$^a$)R$^b$,
(13) —N(R$^a$)C(=O)N(R$^a$)R$^b$,
(14) —OC(=O)N(R$^a$)R$^b$,
(15) —R$^K$,
(16) —C(=O)—R$^K$,
(17) —C(=O)N(R$^a$)—R$^K$,
(18) —C(=O)N(R$^a$)—C$_{1-6}$ alkylene-R$^K$,
(19) —C$_{1-6}$ alkyl substituted with —R$^K$,
(20) —C$_{1-6}$ alkyl substituted with —C(=O)—R$^K$,
(21) —C$_{1-6}$ alkyl substituted with —C(=O)N(R$^a$)—R$^K$, or
(22) —C$_{1-6}$ alkyl substituted with —C(=O)N(R$^a$)—C$_{1-6}$ alkylene-R$^K$,
wherein R$^K$ is
(i) C$_{3-8}$ cycloalkyl which is optionally substituted with from 1 to 4 substituents each of which is independently halogen, —OH, —C$_{1-6}$ alkyl, —C$_{1-6}$ haloalkyl, —O—C$_{1-6}$ alkyl, or —O—C$_{1-6}$ haloalkyl,
(ii) aryl, which is optionally substituted with from 1 to 5 substituents each of which is independently —C$_{1-6}$ alkyl, —C$_{1-6}$ alkylene-OH, —C$_{1-6}$ alkylene-O—C$_{1-6}$ alkyl, —C$_{1-6}$ alkylene-O—C$_{1-6}$ haloalkyl, —C$_{1-6}$ alkylene-N(R$^a$)R$^b$, —C$_{1-6}$ alkylene-C(=O)N(R$^a$)R$^b$, —C$_{1-6}$ alkylene-C(=O)R$^a$, —C$_{1-6}$ alkylene-CO$_2$R$^a$, —C$_{1-6}$ alkylene-S(O)$_n$R$^a$, —O—C$_{1-6}$ alkyl, —C$_{1-6}$ haloalkyl, —O—C$_{1-6}$ haloalkyl, —OH, halogen, —N(R$^a$)R$^b$, —C(=O)N(R$^a$)R$^b$, —C(=O)R$^a$, —CO$_2$R$^a$, —S(O)$_n$R$^a$, or —SO$_2$N(R$^a$)R$^b$, (iii) HetK, which is a 4- to 7-membered saturated heterocyclic ring containing at least one carbon atom and from 1 to 4 heteroatoms independently selected from N, O and S, wherein the heterocyclic ring is:
  (a) optionally substituted with from 1 to 6 substituents each of which is independently halogen, —C$_{1-6}$ alkyl, —C$_{1-6}$ haloalkyl, —O—C$_{1-6}$ alkyl, —O—C$_{1-6}$ haloalkyl, oxo; and
  (b) optionally substituted with aryl or HetC; wherein HetC is a 5- or 6-membered heteroaromatic ring containing from 1 to 4 heteroatoms independently selected from N, O and S, wherein the heteroaromatic ring is optionally fused with a benzene ring, and the optionally fused heteroaromatic ring is optionally substituted with from 1 to 4 substituents each of which is independently —C$_{1-6}$ alkyl, —C$_{1-6}$ haloalkyl, —O—C$_{1-6}$ alkyl, —O—C$_{1-6}$ haloalkyl, or hydroxy; or (iv) —HetL, which is a 5- or 6-membered heteroaromatic ring containing from 1 to 4 heteroatoms independently selected from N, O and S, wherein the heteroaromatic ring is optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or hydroxy;

R$^5$ is:
(1) —H,
(2) —C$_{1-6}$alkyl,
(3) —C$_{3-8}$ cycloalkyl optionally substituted with from 1 to 4 substituents each of which is independently halogen,—OH, C$_{1-6}$ alkyl, —C$_{1-6}$ haloalkyl, —O—C$_{1-6}$ alkyl, —O—C$_{1-6}$ haloalkyl,
(4) —C$_{1-6}$ alkyl substituted with C$_{3-8}$ cycloalkyl, wherein the cycloalkyl is optionally substituted with from 1 to 4 substituents each of which is independently halogen, —OH, —C$_{1-6}$ alkyl, —C$_{1-6}$ haloalkyl, —O—C$_{1-6}$ alkyl, or —O—C$_{1-6}$ haloalkyl,
(5) —C$_{1-6}$ alkyl substituted with aryl, wherein the aryl is optionally substituted with from 1 to 5 substituents each of which is independently —C$_{1-6}$ alkyl, —C$_{1-6}$ alkylene-OH, —C$_{1-6}$ alkylene- O—C$_{1-6}$ alkyl, —C$_{1-6}$ alkylene-O—C$_{1-6}$ haloalkyl, —C$_{1-6}$ alkylene-N(R$^a$)R$^b$, —C$_{1-6}$ alkylene-C(=O)N(R$^a$)R$^b$, —C$_{1-6}$ alkylene-C(=O)R$^a$, —C$_{1-6}$ alkylene-CO$_2$R$^a$, —C$_{1-6}$ alkylene-S(O)$_n$R$^a$, —O—C$_{1-6}$ alkyl, —C$_{1-6}$ haloalkyl, —O—C$_{1-6}$ haloalkyl, —OH, halogen, —N(R$^a$)R$^b$, —C(=O)N(R$^a$)R$^b$, —C(=O)R$^a$, —CO$_2$R$^a$, —S(O)$_n$R$^a$, or —SO$_2$N(R$^a$)R$^b$, or
(6) —C$_{1-6}$ alkyl substituted with HetD, wherein HetD is:
  (i) a 4- to 7-membered saturated heterocyclic ring containing at least one carbon atom and from 1 to 4 heteroatoms independently selected from N, O and S, wherein the heterocyclic ring is optionally substituted with from 1 to 5 substituents each of which is independently halogen, —C$_{1-6}$ alkyl, —C$_{1-6}$ haloalkyl, —O—C$_{1-6}$ alkyl, —O—C$_{1-6}$ haloalkyl, or oxo; or
  (ii) a 5- or 6-membered heteroaromatic ring containing from 1 to 4 heteroatoms independently selected from N, O and S, wherein the heteroaromatic ring is optionally substituted with from 1 to 4 substituents each of which is independently —C$_{1-6}$ alkyl, —C$_{1-6}$ haloalkyl, —O—C$_{1-6}$ alkyl, —O—C$_{1-6}$ haloalkyl, or hydroxy;

each aryl is independently phenyl, naphthyl, or indenyl;
each R$^a$ is independently H or C$_{1-6}$ alkyl;
each R$^b$ is independently H or C$_{1-6}$ alkyl; and
each n is independently an integer equal to zero, 1, or 2.

2. A compound according to claim 1 which is a compound of Formula II, or a pharmaceutically acceptable salt thereof:

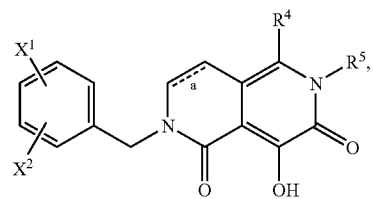

wherein:
X$^1$ and X$^2$ are each independently:
(1) —H,
(2) —C$_{1-6}$alkyl,
(3) —O—C$_{1-6}$ alkyl,
(4) —C$_{1-6}$ haloalkyl,
(5) —O—C$_{1-6}$ haloalkyl,
(6) halogen,
(7) —CN,
(8) —N(R$^a$)R$^b$,
(9) —C(=O)N(R$^a$)R$^b$,
(10) —SR$^a$,
(11) —S(O)R$^a$,
(12) —SO$_2$R$^a$,
(13) —N(R$^a$)SO$_2$R$^b$,
(14) —N(R$^a$)SO$_2$N(R$^a$)R$^b$,
(15) —N(R$^a$)C(=O)R$^b$,
(16) —N(R$^a$)C(=O)—C(=O)N(R$^a$)R$^b$,
(17) —HetA,
(18) —C(=O)—HetA, or
(19) HetB;
  wherein each HetA is independently a C$_{4-5}$ azacycloalkyl or a C$_{3-4}$ diazacycloalkyl, either of which is optionally substituted with 1 or 2 substituents each of which is independently oxo or C$_{1-6}$ alkyl; and with the proviso that when HetA is attached to the rest of the compound via the —C(=O)— moiety, the HetA is attached to the —C(=O)— via a ring N atom; and
  each HetB is independently a 5- or 6-membered heteroaromatic ring containing from 1 to 4 heteroatoms independently selected from N, O and S, wherein the heteroaromatic ring is optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or hydroxy;

R$^4$ is:
(1) —CO$_2$R$^a$,
(2) —C(=O)N(R$^a$)R$^b$,
(3) —C(=O)—N(R$^a$)—(CH$_2$)$_{2-3}$—OR$^b$,
(4) —N(R$^a$)C(=O)R$^b$, (5) —N(R$^a$)SO$_2$R$^b$,
(6) —HetK,
(7) —C(=O)—HetK,
(8) —C(=O)N(R$^a$)—(CH$_2$)$_{0-2}$—(C$_{3-6}$ cycloalkyl), wherein the cycloalkyl is optionally substituted with from 1 to 4 substituents each of which is independently halogen, —C$_{1-6}$ alkyl, —CF$_3$, —O—C$_{1-6}$ alkyl, or —OCF$_3$, or
(9) —C(=O)N(R$^a$)—CH$_2$-phenyl, wherein the phenyl is optionally substituted with from 1 to 4 substituents each of which is independently —C$_{1-6}$ alkyl, —O—C$_{1-6}$ alkyl, —CF$_3$, —OCF$_3$, or halogen;
wherein HetK is a 5- or 6-membered saturated heterocyclic ring containing a total of from 1 to 4 heteroatoms independently selected from 1 to 4 N atoms, from 0 to 2 O atoms, and from 0 to 2 S atoms, wherein the heterocyclic ring is optionally substituted with (i) from 1 to 4 substituents each of which is independently —C$_{1-6}$ alkyl, oxo; and with the proviso that when HetK is attached to the rest of the compound via the —C(=O)— moiety, the HetK is attached to the —C(=O)— via a ring N atom;

R$^5$ is:
(1) —H,
(2) —C$_{1-6}$ alkyl,
(3) —C$_{3-6}$ cycloalkyl,
(4) —(CH$_2$)$_{1-2}$—C$_{3-6}$ cycloalkyl, or
(5) —CH$_2$-phenyl;
each R$^a$ is independently H or C$_{1-6}$ alkyl; and
each R$^b$ is independently H or C$_{1-6}$.

3. The compound according to claim 2, or a pharmaceutically acceptable salt thereof, wherein:
X$^1$ and X$^2$ are each independently:
(1) —H,
(2) —C$_{1-4}$ alkyl,
(3) —C$_{1-4}$ haloalkyl,
(4) —O—C$_{1-4}$ alkyl,
(5) halogen,
(6) —CN,
(7) —C(=O)NH$_2$,
(8) —C(=O)NH(—C$_{1-4}$ alkyl),
(9) —C(=O)N(—C$_{1-4}$ alkyl)$_2$, or
(10) —SO$_2$—C$_{1-4}$ alkyl;

R$^4$ is:
(1) —CO$_2$H,
(2) —C(=O)—O—C$_{1-4}$ alkyl,
(3) —C(=O)NH$_2$,
(4) —C(=O)NH—C$_{1-4}$ alkyl,
(5) —C(=O)N(C$_{1-4}$ alkyl)$_2$,
(6) —C(=O)—NH—(CH$_2$)$_{2-3}$—O—C$_{1-4}$ alkyl,
(7) —C(=O)—N(C$_{1-4}$ alkyl)—(CH$_2$)$_{2-3}$—O—C$_{1-4}$ alkyl,
(8) —NHC(=O)—C$_{1-4}$ alkyl,
(9) —N(C$_{1-4}$ alkyl)C(=O)—C$_{1-4}$ alkyl,
(10) —NHSO$_2$—C$_{1-4}$ alkyl,
(11) —N(C$_{1-4}$ alkyl)SO$_2$—C$_{1-4}$ alkyl,
(12) —C(=O)—HetK, wherein HetK is:

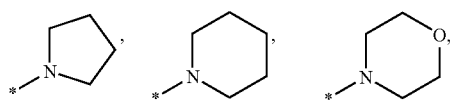

-continued

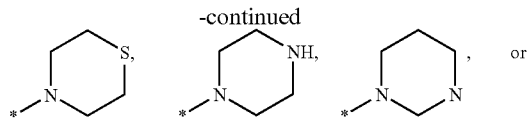

wherein the asterisk * denotes the point of attachment to the rest of the compound,
(13) —C(=O)NH—(CH$_2$)$_{0-1}$—(C$_{3-6}$ cycloalkyl),
(14) —C(=O)N(C$_{1-4}$ alkyl)-(CH$_2$)$_{0-1}$—(C$_{3-6}$ cycloalkyl),
(15) —C(=O)NH—CH$_2$-phenyl, or
(16) —C(=O)N(C$_{1-4}$ alkyl)-CH$_2$-phenyl; and R$^5$ is:
(1) —H,
(2) —C$_{1-4}$ alkyl,
(3) —C$_{3-6}$ cycloalkyl, or
(4) —CH$_2$—C$_{3-6}$ cycloalkyl, or
(5) —CH$_2$-phenyl.

4. The compound according to claim 2, or a pharmaceutically acceptable salt thereof, which is a compound of Formula III:

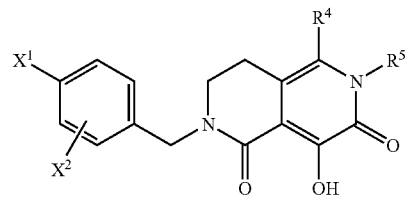

(III)

wherein:
X$^1$ is:
(1) —H,
(2) bromo,
(3) chloro,
(4) fluoro, or
(5) methoxy;
X$^2$ is:
(1) —H,
(2) bromo,
(3) chloro,
(4) fluoro,
(5) methoxy,
(6) —C$_{1-4}$ alkyl,
(7) —CF$_3$,
(8) —OCF$_3$,
(9) —CN, or
(10) —SO$_2$(C$_{1-4}$ alkyl);

R$^4$ is:
(1) —CO$_2$H,
(2) —C(=O)—O—C$_{1-4}$ alkyl,
(3) —C(=O)NH$_2$,
(4) —C(=O)NH—C$_{1-4}$ alkyl,
(5) —C(=O)N(C$_{1-4}$ alkyl)$_2$,
(6) —C(=O)—NH—(CH$_2$)$_{2-3}$—O—C$_{1-4}$ alkyl,
(7) —C(=O)—N(C$_{1-4}$ alkyl)-(CH$_2$)$_{2-3}$—O—C$_{1-4}$ alkyl,
(8) —NHC(=O)—C$_{1-4}$ alkyl,
(9) —N(C$_{1-4}$ alkyl)C(=O)—C$_{1-4}$ alkyl,
(10) —NHSO$_2$—C$_{1-4}$ alkyl,
(11) —N(C$_{1-4}$ alkyl)SO$_2$—C$_{1-4}$alkyl,
(12) —C(=O)—HetK, wherein HetK is:

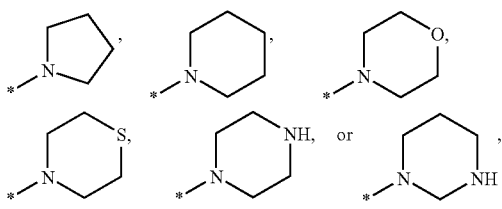

wherein the asterisk * denotes the point of attachment to the rest of the compound,
(13) —C(=O)NH—(CH$_2$)$_{0-1}$—(C$_{3-6}$ cycloalkyl),
(14) —C(=O)N(C$_{1-4}$ alkyl)-(CH$_2$)$_{0-1}$—(C$_{3-6}$ cycloalkyl),
(15) —C(=O)NH—CH$_2$-phenyl, or
(16) —C(=O)N(C$_{1-4}$ alkyl)-CH$_2$-phenyl; and
R$^5$ is:
(1) —H,
(2) —C$_{1-4}$ alkyl,
(3) cyclopropyl,
(4) cyclobutyl,
(5) —CH$_2$-cyclopropyl,
(6) —CH$_2$-cyclobutyl, or
(7) —CH$_2$-phenyl.

5. A pharmaceutical composition comprising an effective amount of a compound according to claim 1, or a pharmaceutically acceptable salt thereof, and a pharmaceutically acceptable carrier.

6. A method for treating infection by HIV or for treating AIDS in a subject in need thereof which comprises administering to the subject an effective amount of the compound according to claim 1, or a pharmaceutically acceptable salt thereof.

7. A process for preparing a compound of Formula IV:

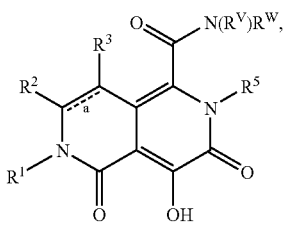

which comprises:
(B) contacting a compound of Formula V:

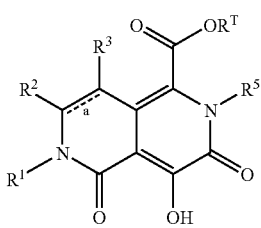

with a Grignard salt of an amine of Formula VI:

HN(R$^V$)R$^W$      (VI)

to obtain Compound IV; wherein:

bond

"- - -$^a$- - -"

in the ring is a single bond or a double bond;
R$^1$ is —C$_{1-6}$ alkyl substituted with R$^J$, wherein R$^J$ is:
(A) aryl or aryl fused to a 5- or 6-membered heteroaromatic ring containing from 1 to 4 heteroatoms independently selected from N, O and S, wherein the aryl or fused aryl is:
(a) optionally substituted with from 1 to 5 substituents each of which is independently:
(1) —C$_{1-6}$ alkyl,
(2) —C$_{1-6}$ alkyl substituted with —O—C$_{1-6}$ alkyl, —O—C$_{1-6}$ haloalkyl, —NO$_2$, —N(R$^a$)R$^b$, or —S(O)$_n$R$^a$,
(3) —C$_{1-6}$haloalkyl,
(4) —O—C$_{1-6}$ alkyl,
(5) halogen,
(6) C(=O)N(R$^a$)R$^b$, or
(7) —SO$_2$R$^a$, and
(b) optionally substituted with 1 or 2 substituents each of which is independently:
(1) phenyl,
(2) benzyl, or
(3) -HetB;
wherein each HetB is a 5- or 6-membered heteroaromatic ring containing from 1 to 4 heteroatoms independently selected from N, O and S, wherein the heteroaromatic ring is optionally substituted with from 1 to 4 substituents each of which is independently halogen, —C$_{1-6}$ alkyl, —C$_{1-6}$ haloalkyl, —O—C$_{1-6}$ alkyl, or —O—C$_{1-6}$ haloalkyl; or
(B) a 5- or 6-membered heteroaromatic ring containing from 1 to 4 heteroatoms independently selected from N, O and S; wherein the heteroaromatic ring is
(i) optionally substituted with from 1 to 4 substituents each of which is independently halogen, —C$_{1-6}$ alkyl, —C$_{1-6}$ haloalkyl, —O—C$_{1-6}$ alkyl, or —O—C$_{1-6}$ haloalkyl, and
(ii) optionally substituted with 1 or 2 substituents each of which is independently aryl or —C$_{1-6}$ alkyl substituted with aryl;
R$^2$ and R$^3$ are each independently —H or —C$_{1-6}$ alkyl;
R$^5$ is:
(1) —C$_{1-6}$ alkyl,
(2) —C$_{3-8}$ cycloalkyl optionally substituted with from 1 to 4 substituents each of which is independently —C$_{1-6}$ alkyl or —O—C$_{1-6}$ alkyl,
(3) —C$_{1-6}$ alkyl substituted with C$_{3-8}$ cycloalkyl, wherein the cycloalkyl is optionally substituted with from 1 to 4 substituents each of which is independently —C$_{1-6}$ alkyl or —O—C$_{1-6}$ alkyl,
(4) —C$_{1-6}$ alkyl substituted with aryl, wherein the aryl is optionally substituted with from 1 to 5 substituents each of which is independently —C$_{1-6}$ alkyl, —C$_{1-6}$ alkylene-O—C$_{1-6}$ alkyl, or halogen, or
(5) —C$_{1-6}$ alkyl substituted with a 5- or 6-membered heteroaromatic ring containing from 1 to 4 heteroatoms independently selected from N, O and S, wherein the heteroaromatic ring is optionally substituted with from 1 to 4 substituents each of which is independently —C$_{1-6}$ alkyl;

$R^T$ is —$C_{1-6}$ alkyl;

$R^V$ and $R^W$ are each independently —$C_{1-6}$ alkyl or $R^V$ and $R^W$ together with the N atom to which they are both attached form a 4- to 6-membered saturated heterocyclic ring optionally containing a heteroatom in addition to the nitrogen attached to $R^V$ and $R^W$ selected from N, O, and S, where the S is optionally oxidized to S(O) or S(O)$_2$, and wherein the saturated heterocyclic ring is optionally substituted with 1 or 2 substituents each of which is independently a $C_{1-6}$ alkyl group;

each aryl is independently phenyl, naphthyl, or indenyl;

each $R^a$ is independently H or $C_{1-6}$ alkyl; and each $R^b$ is independently H or $C_{1-6}$ alkyl.

8. The process according to claim 7, wherein the process further comprises:

(A) treating a compound of Formula IX:

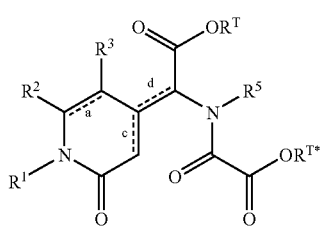

(IX)

with (i) a tertiary amine base in the presence of a lithium salt or (ii) an alkoxide base, to obtain a compound of Formula V; wherein one of bonds " ----c---- "

and

" ----d---- "

is a single bond and the other is a double bond; and $R^{T*}$ is $C_{1-6}$ alkyl.

9. A process for preparing a compound of Formula IV:

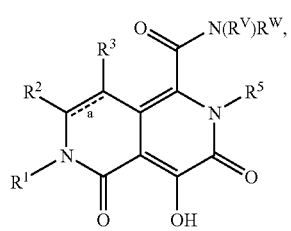

(IV)

which comprises treating a compound of Formula X:

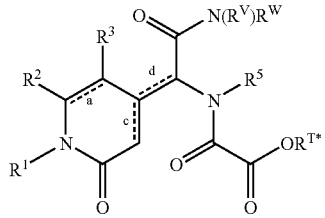

(X)

with (i) a tertiary amine base in the presence of a lithium salt or (ii) an alkoxide base, to obtain a compound of Formula IV, wherein:

bond

" ----a---- "

in the ring is a single bond or a double bond;

$R^1$ is —$C_{1-6}$ alkyl substituted with $R^J$, wherein $R^J$ is:

(A) aryl or aryl fused to a 5- or 6-membered heteroaromatic ring containing from 1 to 4 heteroatoms independently selected from N, O and S, wherein the aryl or fused aryl is:

(a) optionally substituted with from 1 to 5 substituents each of which is independently:

(1) —$C_{1-6}$ alkyl, (2) —$C_{1-6}$ alkyl substituted with —O—$C_{1-6}$ alkyl, —O—$C_{1-6}$ haloalkyl, —NO$_2$, —N(R$^a$)R$^b$, or —S(O)$_n$R$^a$, (3) —$C_{1-6}$ haloalkyl, (4) —O—$C_{1-6}$ alkyl, (5) halogen, (6) C(=O)N(R$^a$)R$^b$, or (7) —SO$_2$R$^a$, and (b) optionally substituted with 1 or 2 substituents each of which is independently:

(1) phenyl, (2) benzyl, or (3) -HetB;

wherein each HetB is a 5- or 6-membered heteroaromatic ring containing from 1 to 4 heteroatoms independently selected from N, O and S, wherein the heteroaromatic ring is optionally substituted with from 1 to 4 substituents each of which is independently halogen, —$C_{1-6}$ alkyl, —$C_{1-6}$ haloalkyl, —O—$C_{1-6}$ alkyl, or —O—$C_{1-6}$ haloalkyl; or (B) a 5- or 6-membered heteroaromatic ring containing from 1 to 4 heteroatoms independently selected from N, O and S; wherein the heteroaromatic ring is (i) optionally substituted with from 1 to 4 substituents each of which is independently halogen, —$C_{1-6}$ alkyl, —$C_{1-6}$ haloalkyl, —O—$C_{1-6}$ alkyl, or —O—$C_{1-6}$ haloalkyl, and (ii) optionally substituted with 1 or 2 substituents each of which is independently aryl or —$C_{1-6}$ alkyl substituted with aryl;

$R^2$ and $R^3$ are each independently —H or —$C_{1-6}$ alkyl;
$R^5$ is:
(1) —$C_{1-6}$ alkyl,
(2) —$C_{3-8}$ cycloalkyl optionally substituted with from 1 to 4 substituents each of which is independently —$C_{1-6}$ alkyl or —O—$C_{1-6}$ alkyl,
(3) —$C_{1-6}$ alkyl substituted with $C_{3-8}$ cycloalkyl, wherein the cycloalkyl is optionally substituted with from 1 to 4 substituents each of which is independently —$C_{1-6}$ alkyl or —O—$C_{1-6}$ alkyl,
(4) —$C_{1-6}$ alkyl substituted with aryl, wherein the aryl is optionally substituted with from 1 to 5 substituents each of which is independently —$C_{1-6}$ alkyl, —$C_{1-6}$ alkylene-O—$C_{1-6}$ alkyl, or halogen, or
(5) —$C_{1-6}$ alkyl substituted with a 5- or 6-membered heteroaromatic ring containing from 1 to 4 heteroatoms independently selected from N, O and S, wherein the heteroaromatic ring is optionally substituted with from 1 to 4 substituents each of which is independently —$C_{1-6}$ alkyl;
$R^V$ and $R^W$ are each independently —$C_{1-6}$ alkyl or $R^V$ and $R^W$ together with the N atom to which they are both attached form a 4- to 6-membered saturated heterocyclic ring optionally containing a heteroatom in addition to the nitrogen attached to $R^V$ and $R^W$ selected from N, O, and S, where the S is optionally oxidized to S(O) or S(O)$_2$, and wherein the saturated heterocyclic ring is optionally substituted with 1 or 2 substituents each of which is independently a $C_{1-6}$ alkyl group;
each aryl is independently phenyl, naphthyl, or indenyl;
each $R^a$ is independently H or $C_{1-6}$ alkyl;
each $R^b$ is independently H or $C_{1-6}$ alkyl;
one of bonds "----c----"

and

"----d----"

is a single bond and the other is a double bond; and
$R^{T*}$ is $C_{1-6}$ alkyl.

10. A process for preparing a compound of Formula VII:

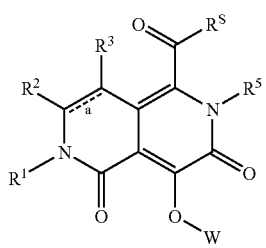

(VII)

which comprises reacting an alkylating agent of formula $R^5$-Z with a compound of Formula VIII:

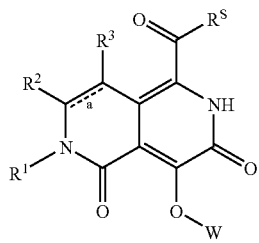

(VIII)

in a polar aprotic solvent and in the presence of a base selected from a magnesium base and a calcium base; wherein:
bond "----a----"

in the ring is a single bond or a double bond;
W is —H or —$C_{1-6}$ alkyl;
Z is halogen or —SO$_3$-Q wherein Q is (i) $C_{1-6}$ alkyl or (ii) phenyl optionally substituted with 1 or 2 substituents each of which is independently a $C_{1-6}$ alkyl;
$R^S$ is —O—$C_{1-6}$ alkyl or N($R^V$)$R^W$ wherein $R^V$ and $R^W$ are each independently —$C_{1-6}$ alkyl or $R^V$ and $R^W$ together with the N atom to which they are both attached form a 4- to 6-membered saturated heterocyclic ring optionally containing a heteroatom in addition to the nitrogen attached to $R^V$ and $R^W$ selected from N, O, and S, where the S is optionally oxidized to S(O) or S(O)$_2$, and wherein the saturated heterocyclic ring is optionally substituted with 1 or 2 substituents each of which is independently a $C_{1-6}$ alkyl group;
$R^1$ is —$C_{1-6}$ alkyl substituted with $R^J$, wherein $R^J$ is:
(A) aryl or aryl fused to a 5- or 6-membered heteroaromatic ring containing from 1 to 4 heteroatoms independently selected from N, O and S, wherein the aryl or fused aryl is:
(a) optionally substituted with from 1 to 5 substituents each of which is independently:
(1) —$C_{1-6}$ alkyl optionally substituted with —OH, —O—$C_{1-6}$ alkyl, —O—$C_{1-6}$ haloalkyl, —CN, —NO$_2$, —N($R^a$)$R^b$, —C(=O)N($R^a$)$R^b$, —C(=O)$R^a$, —CO$_2$$R^a$, —S(O)$_n$$R^a$, —SO$_2$N($R^a$)$R^b$, —N($R^a$)C(=O)$R^b$, —N($R^a$)CO$_2$$R^b$, —N($R^a$)SO$_2$$R^b$, —N($R^a$)SO$_2$N($R^a$)$R^b$, —OC(=O)N($R^a$)$R^b$, or —N($R^a$)C(=O)N($R^a$)$R^b$,
(2) —O—$C_{1-6}$ alkyl,
(3) —$C_{1-6}$ haloalkyl,
(4) —O—$C_{1-6}$ haloalkyl,
(5) —OH,
(6) halogen,
(7) —CN,
(8) —NO$_2$,
(9) —N($R^a$)$R^b$,
(10) —C(=O)N($R^a$)$R^b$,
(11) —C(=O)$R^a$,
(12) —CO$_2$$R^a$,
(13) —SR$^a$,
(14) —S(=O)$R^a$,
(15) —SO$_2$$R^a$,
(16) —SO$_2$N($R^a$)$R^b$,
(17) —N($R^a$)SO$_2$$R^b$,
(18) —N($R^a$)SO$_2$N($R^a$)$R^b$,

(19) —N(R$^a$)C(=O)R$^b$,
(20) —N(R$^a$)C(=O)—C(=O)N(R$^a$)R$^b$, or
(21) —N(R$^a$)CO$_2$R$^b$, and (b) optionally substituted with 1 or 2 substituents each of which is independently:
(1) phenyl,
(2) benzyl,
(3) —HetA,
(4) —C(=O)—HetA, or
(5) —HetB;
wherein each HetA is independently a C$_{4-7}$ azacycloalkyl or a C$_{3-6}$ diazacycloalkyl, either of which is optionally substituted with from 1 to 4 substituents each of which is independently oxo or C$_{1-6}$ alkyl; and
wherein each HetB is a 5- or 6-membered heteroaromatic ring containing from 1 to 4 heteroatoms independently selected from N, O and S, wherein the heteroaromatic ring is optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or hydroxy; or (B) a 5- or 6-membered heteroaromatic ring containing from 1 to 4 heteroatoms independently selected from N, O and S; wherein the heteroaromatic ring is
(i) optionally substituted with from 1 to 4 substituents each of which is independently halogen, —C$_{1-6}$ alkyl, —C$_{1-6}$ haloalkyl, —O—C$_{1-6}$ alkyl, —O—C$_{1-6}$ haloalkyl, or hydroxy, and
(ii) optionally substituted with 1 or 2 substituents each of which is independently aryl or —C$_{1-6}$ alkyl substituted with aryl;

R$^2$ and R$^3$ are each independently —H or —C$_{1-6}$ alkyl;
R$^5$ is:
(1) —C$_{1-6}$alkyl,
(2) —C$_{3-8}$ cycloalkyl optionally substituted with from 1 to 4 substituents each of which is independently —C$_{1-6}$ alkyl or —O—C$_{1-6}$ alkyl,
(3) —C$_{1-6}$ alkyl substituted with C$_{3-8}$ cycloalkyl, wherein the cycloalkyl is optionally substituted with from 1 to 4 substituents each of which is independently —C$_{1-6}$ alkyl or —O—C$_{1-6}$ alkyl,
(4) —C$_{1-6}$ alkyl substituted with aryl, wherein the aryl is optionally substituted with from 1 to 5 substituents each of which is independently —C$_{1-6}$ alkyl, —C$_{1-6}$ alkylene-O—C$_{1-6}$ alkyl, or halogen, or
(5) —C$_{1-6}$ alkyl substituted with a 5- or 6-membered heteroaromatic ring containing from 1 to 4 heteroatoms independently selected from N, O and S, wherein the heteroaromatic ring is optionally substituted with from 1 to 4 substituents each of which is independently —C$_{1-6}$ alkyl;

each aryl is independently phenyl, naphthyl, or indenyl;
each R$^a$ is independently H or C$_{1-6}$ alkyl;
each R$^b$ is independently H or C$_{1-6}$ alkyl; and
each n is independently an integer equal to zero, 1, or 2.

11. A compound according to claim 1, or a pharmaceutically acceptable salt thereof, wherein the compound is selected from the group consisting of:
methyl 6-(4-fluorobenzyl)-4-hydroxy-3, 5-dioxo-2, 3,5,6, 7, 8-hexahydro-2,6-naphthyridine- 1 -carboxylate;
6-(4-fluorobenzyl)-4-hydroxy-N,N-dimethyl-3, 5 -dioxo-2,3, 5, 6,7,8-hexahydro-2,6-naphthyridine- 1 -carboxamide;
N-cyclobutyl-6-(4-fluorobenzyl)-4-hydroxy-3, 5 -dioxo-2,3, 5, 6,7,8-hexahydro-2,6-naphthyridine- 1 -carboxamide;
N-cyclopropyl-6-(4-fluorobenzyl)-4-hydroxy-3, 5 -dioxo-2,3, 5, 6,7,8-hexahydro-2,6-naphthyridine- 1 -carboxamide;
6-(4-fluorobenzyl)-4-hydroxy-N-isopropyl-3, 5 -dioxo-2,3, 5, 6,7,8-hexahydro-2,6-naphthyridine- 1 -carboxamide;
6-(4-fluorobenzyl)-4-hydroxy-N-methyl-3, 5 -dioxo-2,3, 5, 6,7,8 -hexahydro-2,6-naphthyridine- 1 -carboxamide;
6-(4-fluorobenzyl)-4-hydroxy-3, 5 -dioxo-2,3, 5, 6,7, 8-hexahydro-2,6-naphthyridine- 1 -carboxylic acid;
N- [6-(4-fluorobenzyl)-3, 4-dihydroxy-5 -oxo-5, 6,7, 8-tetrahydro-2,6-naphthyridin-1 -yl]-N-methylmethanesulfonamide;
N- [6-(4-fluorobenzyl)-4-hydroxy-2-methyl-3, 5 -dioxo-2,3, 5, 6,7, 8-hexahydro-2,6-naphthyridin- 1 -yl]-N-methylacetamide;
6-(4-fluorobenzyl)-4-hydroxy-N, N, 2-trimethyl-3,5-dioxo-2, 3,5,6,7, 8-hexahydro-2,6-naphthyridine- 1 -carboxamide;
6-(3 -chloro-4-fluorobenzyl)-4-hydroxy-N,N,2-trimethyl-3, 5 -dioxo-2,3, 5, 6,7, 8-hexahydro-2,6-naphthyridine-1 -carboxamide; and
6-(4-fluorobenzyl)-4-hydroxy-N,N,2-trimethyl-3, 5 -dioxo-2,3, 5, 6-tetrahydro-2,6-naphthyridine- 1 -carboxamide.

* * * * *